(12) United States Patent
Wong et al.

(10) Patent No.: US 10,842,846 B2
(45) Date of Patent: *Nov. 24, 2020

(54) THERAPEUTIC INHIBITOR FOR EBV-ASSOCIATED TUMOR WITH TAILOR RESPONSIVE OPTICAL IMAGING

(71) Applicant: Hong Kong Baptist University, Hong Kong (HK)

(72) Inventors: Ka Leung Wong, Hong Kong (HK); Nai Ki Mak, Hong Kong (HK); Lijun Jiang, Hong Kong (HK)

(73) Assignee: Hong Kong Baptist University, Hong Kong (CN)

( * ) Notice: Subject to any disclaimer, the term of this patent is extended or adjusted under 35 U.S.C. 154(b) by 18 days.

This patent is subject to a terminal disclaimer.

(21) Appl. No.: 16/170,165

(22) Filed: Oct. 25, 2018

(65) Prior Publication Data

US 2019/0060394 A1 Feb. 28, 2019

Related U.S. Application Data

(63) Continuation-in-part of application No. 15/495,971, filed on Apr. 24, 2017, now Pat. No. 10,137,115.

(60) Provisional application No. 62/327,504, filed on Apr. 26, 2016, provisional application No. 62/406,927, filed on Oct. 11, 2016.

(51) Int. Cl.
| | | |
|---|---|---|
| *A61K 49/00* | (2006.01) | |
| *A61K 38/10* | (2006.01) | |
| *A61K 51/08* | (2006.01) | |
| *A61K 38/00* | (2006.01) | |
| *C07K 7/08* | (2006.01) | |
| *A61K 47/54* | (2017.01) | |
| *A61N 5/10* | (2006.01) | |

(52) U.S. Cl.
CPC ............ *A61K 38/10* (2013.01); *A61K 47/547* (2017.08); *A61K 49/0021* (2013.01); *A61K 49/0032* (2013.01); *A61K 49/0056* (2013.01); *A61K 51/088* (2013.01); *A61N 5/1039* (2013.01); *C07K 7/08* (2013.01); *A61K 38/00* (2013.01); *A61K 2123/00* (2013.01)

(58) Field of Classification Search
CPC .... A61K 38/10; A61K 2123/00; A61K 49/00; A61K 38/00; A61K 49/032; A61K 51/00; A61K 51/08; A61K 51/088; A61K 47/00; A61K 47/547; A61K 49/0056; A61K 49/0021; C07K 7/08; A61N 5/1039
USPC .......... 424/1.11, 1.65, 1.69, 1.81, 1.85, 1.89, 424/9.1, 9.2, 9.3, 9.4, 9.5, 9.6; 514/1, 514/1.1, 19.2, 19.3, 19.4, 19.5, 19.6, 21.5, 514/21.6; 530/300, 327

See application file for complete search history.

(56) References Cited

U.S. PATENT DOCUMENTS 10,137,115 B2 * 11/2018 Wong ...................... A61P 31/22

* cited by examiner

*Primary Examiner* — D. L. Jones

(74) *Attorney, Agent, or Firm* — Spruson & Ferguson (Hong Kong) Limited

(57) ABSTRACT

The present disclosure provides peptides useful as inhibitors of the dimerization interface of EBNA1. The present disclosure also provides methods for treating and imaging EBV-associated cancers.

12 Claims, 197 Drawing Sheets

Specification includes a Sequence Listing.

KGGWFGKHRGQGGSNPKFENIAEGLRALLARSHVERTTDEGTWAGVFVYGGSKTSLYN
LRRGTALAIPQCRLTPLSRLPFGMAPGPGPQPGPLRESIVCYFMVFLQTHIFAEVLKDA
IKQLVMTKPAPTCNIRVTVCSFQQGVQLP

Figure 15A

L2P3
L2CAhx-RrRKGGYFMVF
GB= -60.7 kcal/mol
PB= -53.4 kcal/mol

P4
YFMVFGGRrRK
GB= -41.8 kcal/mol
PB= -44.7 kcal/mol

L2P4
L2CAhx-YFMVFGGRrRK
GB= -62.6 kcal/mol
PB= -63.6 kcal/mol

J-GdL3P4

J-GdL3P5 P5(YFIVF)

J-GaL₃P₂

J-GaL₃P₃

J-GaL₃P₄

J-GaL₃P₅ P₅(YFIVF)

```
                        SEQUENCE LISTING

<160> NUMBER OF SEQ ID NOS: 4

<210> SEQ ID NO 1
<211> LENGTH: 5
<212> TYPE: PRT
<213> ORGANISM: Artificial sequence
<220> FEATURE:
<223> OTHER INFORMATION: The sequence is synthesized

<400> SEQUENCE: 1

Tyr Phe Met Val Phe
1               5

<210> SEQ ID NO 2
<211> LENGTH: 13
<212> TYPE: PRT
<213> ORGANISM: Artificial sequence
<220> FEATURE:
<223> OTHER INFORMATION: The sequence is synthesized
<220> FEATURE:
<221> NAME/KEY: PEPTIDE
<222> LOCATION: (2)..(2)
<223> OTHER INFORMATION: X is 6-aminohexanoic acid
<220> FEATURE:
<221> NAME/KEY: PEPTIDE
<222> LOCATION: (3)..(3)
<223> OTHER INFORMATION: R is L-arginine
<220> FEATURE:
<221> NAME/KEY: PEPTIDE
<222> LOCATION: (4)..(4)
<223> OTHER INFORMATION: X is D-arginine
<220> FEATURE:
<221> NAME/KEY: PEPTIDE
<222> LOCATION: (5)..(5)
<223> OTHER INFORMATION: R is L-arginine

<400> SEQUENCE: 2

Cys Xaa Arg Xaa Arg Lys Gly Gly Tyr Phe Met Val Phe
1               5                   10

<210> SEQ ID NO 3
<211> LENGTH: 13
```

```
<212> TYPE: PRT
<213> ORGANISM: Artificial sequence
<220> FEATURE:
<223> OTHER INFORMATION: The sequence is synthesized
<220> FEATURE:
<221> NAME/KEY: PEPTIDE
<222> LOCATION: (2)..(2)
<223> OTHER INFORMATION: X is 6-aminohexanoic acid
<220> FEATURE:
<221> NAME/KEY: PEPTIDE
<222> LOCATION: (10)..(10)
<223> OTHER INFORMATION: R is L-arginine
<220> FEATURE:
<221> NAME/KEY: PEPTIDE
<222> LOCATION: (11)..(11)
<223> OTHER INFORMATION: X is D-arginine
<220> FEATURE:
<221> NAME/KEY: PEPTIDE
<222> LOCATION: (12)..(12)
<223> OTHER INFORMATION: R is L-arginine

<400> SEQUENCE: 3

Cys Xaa Tyr Phe Met Val Phe Gly Gly Arg Xaa Arg Lys
1               5                   10

<210> SEQ ID NO 4
<211> LENGTH: 147
<212> TYPE: PRT
<213> ORGANISM: Human Gamma Herpes Virus 4

<400> SEQUENCE: 4

Lys Gly Gly Trp Phe Gly Lys His Arg Gly Gln Gly Gly Ser Asn Pro
1               5                   10                  15

Lys Phe Glu Asn Ile Ala Glu Gly Leu Arg Ala Leu Leu Ala Arg Ser
                20                  25                  30

His Val Glu Arg Thr Thr Asp Glu Gly Thr Trp Val Ala Gly Val Phe
            35                  40                  45

Val Tyr Gly Gly Ser Lys Thr Ser Leu Tyr Asn Leu Arg Arg Gly Thr
        50                  55                  60

Ala Leu Ala Ile Pro Gln Cys Arg Leu Thr Pro Leu Ser Arg Leu Pro
65                  70                  75                  80

Phe Gly Met Ala Pro Gly Pro Gly Pro Gln Pro Gly Pro Leu Arg Glu
                85                  90                  95

Ser Ile Val Cys Tyr Phe Met Val Phe Leu Gln Thr His Ile Phe Ala
            100                 105                 110

Glu Val Leu Lys Asp Ala Ile Lys Asp Leu Val Met Thr Lys Pro Ala
        115                 120                 125

Pro Thr Cys Asn Ile Arg Val Thr Val Cys Ser Phe Asp Asp Gly Val
    130                 135                 140

Asp Leu Pro
145
```

THERAPEUTIC INHIBITOR FOR EBV-ASSOCIATED TUMOR WITH TAILOR RESPONSIVE OPTICAL IMAGING

CROSS-REFERENCE TO RELATED APPLICATIONS

This application is a continuation in part of U.S. patent application Ser. No. 15/495,971 filed on Apr. 24, 2017, which claims priority to U.S. Provisional Patent Application Ser. No. 62/327,504 filed on Apr. 26, 2016 and from U.S. Provisional Patent Application Ser. No. 62/406,927 filed on Oct. 11, 2016, the content of which being incorporated by reference in their entirety.

FIELD OF INVENTION

This invention is in the field of pharmaceuticals and chemical. The present invention relates to a nucleus-permeable small-molecule inhibitor, synthesis thereof and the use of said molecule for cancer treatment and imaging.

BACKGROUND OF INVENTION

Epstein-Barr virus (EBV) is a ubiquitous human herpes virus, which causes both infectious mononucleosis and lymphoproliferative diseases. The oncogenic development of other cancers (e.g. nasopharyngeal carcinoma and a subgroup of EBV-positive gastric cancer) is also associated with the latent infection of EBV virus. EBV's life cycle processes, like viral DNA replication and segregation, a viral protein, Epstein-Barr nuclear antigen 1 (EBNA1) is critical. Considering the indispensable homodimerization criteria for EBNA1 to function properly, specifically blocking the dimer formation presents a way to treat latently EBV-infected tumor. Recently, several of EBNA1 specific inhibitors have been reported. A small molecule named Eikl has been developed through high-throughput screening to target the EBNA1 amino acid sequence 459-607 of the dimerization domain, while some peptide-based inhibitors have been reported to similarly work in the region of 560-574. However, the lack of specific subcellular localization and no responsive binding limit these existing EBNA1 inhibitors' effectiveness on imaging and inhibition of EBNA1 dimerization, furthermore hindering the efficacy of selective inhibition of cancer cells with EBV latent infection.

Literature reveals that EBNA1 is broadly distributed in the nucleus of EBV-infected cells. The process of EBNA1 tethering to host cell chromosomes is critical to efficient replication of EBV-derived plasmids. The development of responsive target-specific bioprobes for in vitro microscopic studies of EBNA1 at the nucleus is still rare. Accordingly, it is an objective of the present invention to provide nucleus permeable and EBNA1-specific molecules.

Citation or identification of any reference in this section or any other section of this application shall not be construed as an admission that such reference is available as prior art for the present application.

SUMMARY OF INVENTION

Accordingly, the present invention provides a peptide comprising SEQ ID NO. 2 or SEQ ID NO. 3, and a peptide conjugate comprising SEQ ID NO. 3, which effectively target the dimerization interface of EBNA1, methods of synthesizing said peptide conjugate, and methods of inhibiting growth of EBV and treating EBV-associated tumors. The present invention also provides methods of imaging EBV-associated tumors.

In a first aspect, provided herein is a peptide comprising the sequence CAhxRrRKGGYFMVF (SEQ ID NO. 2) or the sequence CAhxYFMVFGGRrRK (SEQ ID NO. 3).

In a first embodiment of the first aspect, provided herein is the peptide of the first aspect, wherein the peptide comprises SEQ ID NO. 2.

In a second embodiment of the first aspect, provided herein is the peptide of the first aspect, wherein the peptide consists of SEQ ID NO. 2.

In a third embodiment of the first aspect, provided herein is the peptide of the first aspect, wherein the peptide comprises SEQ ID NO. 3.

In a fourth embodiment of the first aspect, provided herein is the peptide of the first aspect, wherein the peptide consists of SEQ ID NO. 3.

In a fifth embodiment of the first aspect, provided herein is a peptide conjugate comprising 4-(4-(diethylamino)styryl)-N-carboxymethylpyridinium coupled to the peptide of the first aspect through an amide bond as shown below:

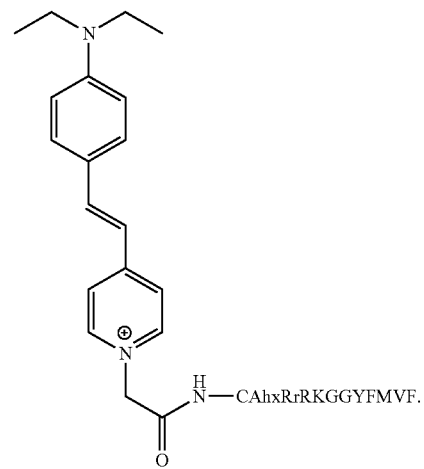

In a second aspect, provided herein is a method for imaging Epstein-Barr virus-infected cells comprising introducing the peptide of the fifth embodiment of the first aspect to the Epstein-Barr virus-infected cells; radiating the Epstein-Barr virus-infected cells at an appropriate absorption band; and detecting resulting emission bands from the radiated Epstein-Barr virus-infected cells using fluorescence imaging.

In a first embodiment of the second aspect, provided herein is the method of the second aspect, wherein the appropriate absorption bands of the Epstein-Barr virus-infected cells are at 274 nm and ~500 nm.

In a second embodiment of the second aspect, provided herein is the method of the second aspect, wherein the fluorescence imaging detects resulting emission bands at 560 nm and ~625 nm.

In a third aspect, provided herein is a method for treating cancer in a subject in need thereof comprising the step of administering the peptide of the fifth embodiment of the first aspect to the subject, wherein cells the cancer is infected by Epstein-Barr virus.

In a first embodiment of the third aspect, provided herein is the method of the third aspect, wherein the peptide is administered by intra-tumoral injection.

In a fourth aspect, provided herein is a method of preparing the peptide of the fifth embodiment of the first aspect, wherein the method comprises the steps:

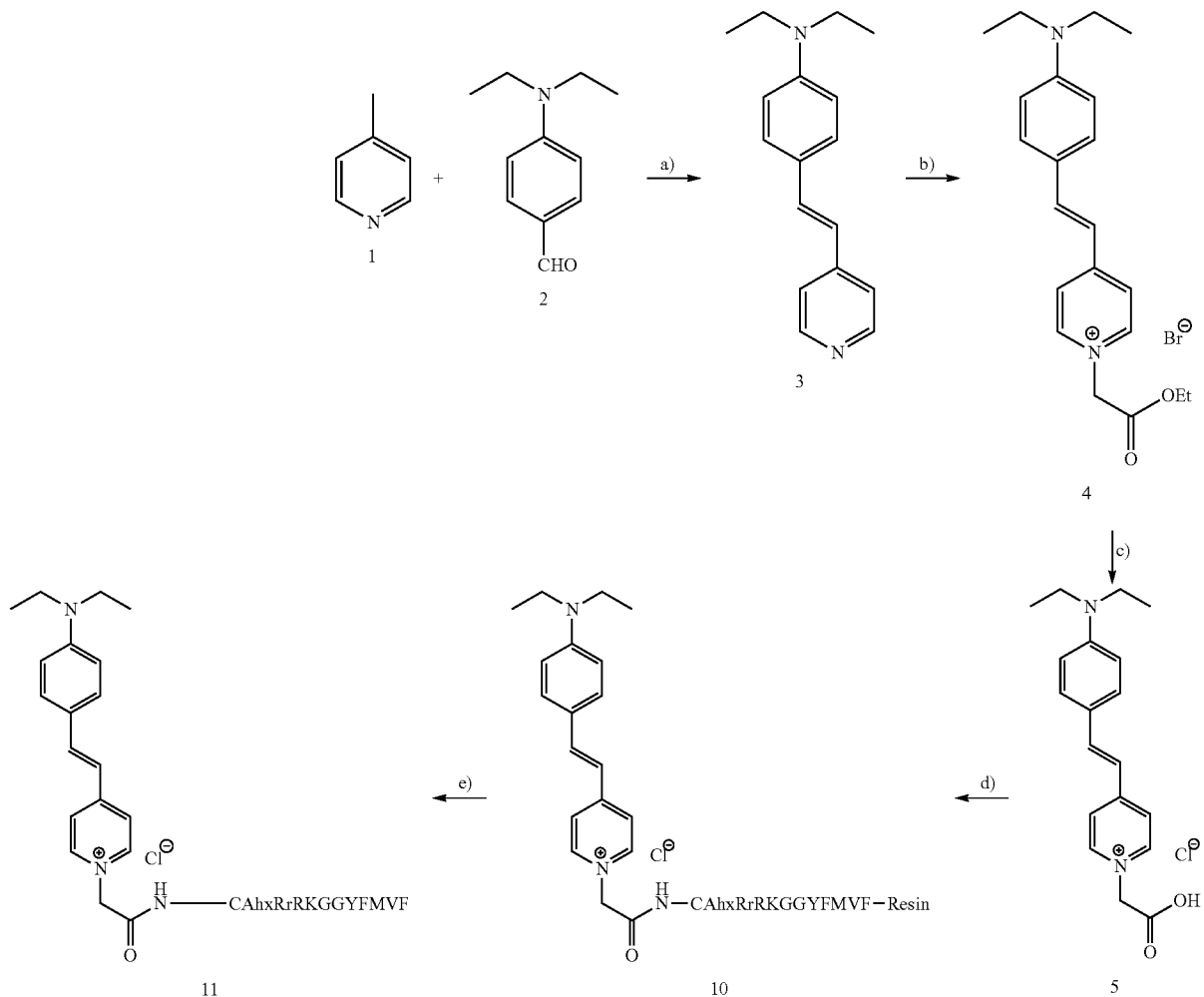

a) reacting compound 1 (4-methylpyridine) and compound 2 (4-diethylaminobenzaldehyde) in the presence of NaH dispersed in mineral oil and dimethylformide (DMF) at about 60° C. to produce compound 3 (N,N'-diethyl-4-(2-(pyridine-4-yl)vinyl) aniline);

b) reacting compound 3 with ethyl bromoacetate in the presence of acetonitrile (MeCN) at about 85° C. to obtain compound 4 (4-(4-(diethylamino)styryl)-1-(2-ethoxy-2-oxoethyl)pyridine-1-ium bromide); c) hydrolyzing compound 4 with 0.4M NaOH in the presence of dioxane at room temperature to obtain compound 5 (4-(4-(diethylamino)styryl)-N-carboxymethylpyridinium chloride);

d) coupling compound 5 with CAhxRrRKGGYFMVF-resin in the presence of diisopropylethylamine (DIPEA), benzotriazol-1-yl-oxytri pyrrolidinophosphonium hexafluorophosphate (PyBOP) and DMF at room temperature to obtain compound 10; and e) cleaving the resin of compound 10 in the presence of trifluoroacetic acid (TFA), triisopropylsilane (TIS) and water at room temperature to obtain the peptide of the fifth embodiment of the first aspect.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which:

FIG. 15A shows the major structural motifs in the protein sequence of EBNA1 DBD domain (Protein database ID: 1B3T, chain A, residue 461-607).

FIG. 28C shows the plot (emission vs absorbance of $L_2P_4$ in water in the presence of saturated WT-EBNA1 for the emission quantum yield determination ($\lambda_{ex}$=480 nm. By comparative method using rhodamine 6G, the quantum yields of $L_2P_4$+WT EBNA1 is 22.9%).

FIG. 29A shows the emission spectra of $L_2P_2$ upon addition of WT-EBNA1 in PBS buffer for the binding constant determination (Conc.: 2 µM).

FIG. 29B shows the emission spectra of $L_2P_3$ upon addition of WT-EBNA1 in PBS buffer for the binding constant determination (Conc.: 2 µM).

FIG. 29C shows the double logarithm regression curve of $L_2P_3$ upon addition of WT-EBNA1 in PBS buffer for the binding constant determination (Conc.: 2 µM. The values for log $K_a$ is 5.50 calculated from double logarithm regression and the binding ratio is 1:1 was found for $L_2P_3$ to WT-EBNA1).

FIG. 29D shows the emission spectra of $L_2P_4$ upon addition of WT-EBNA1 in PBS buffer for the binding constant determination (Conc.: 2 µM).

FIG. 29E shows the double logarithm regression curve of $L_2P_4$ upon addition of WT-EBNA1 in PBS buffer for the binding constant determination (Conc.: 2 µM. The value for log $K_a$ is 6.82 calculated from double logarithm regression and the binding ratio is 1:1 was found for $L_2P_4$ to WT-EBNA1).

FIG. 30A shows the changes in emission spectra for $L_2P_3$ (2 µM in PBS buffer), following internal addition of $ZnCl_2$.

FIG. 30B shows the changes in emission spectra for $L_2P_3$ (2 µM in PBS buffer), following internal addition of $NaHCO_3$.

FIG. 30C shows the changes in emission spectra for $L_2P_3$ (2 µM in PBS buffer), following internal addition of $CuCl_2$.

FIG. 30D shows the changes in emission spectra for $L_2P_3$ (2 µM in PBS buffer), following internal addition of citrates.

FIG. 30E shows the changes in emission spectra for $L_2P_3$ (2 µM in PBS buffer), following internal addition of BSA. The result demonstrated that $L_2P_3$ was selective towards WT-EBNA1.

FIG. 30F shows a comparison on the emission enhancement induced by the addition of two different proteins, WT-EBNA1 and BSA. The result demonstrated that $L_2P_3$ was selective towards WT-EBNA1.

Figure 31A:
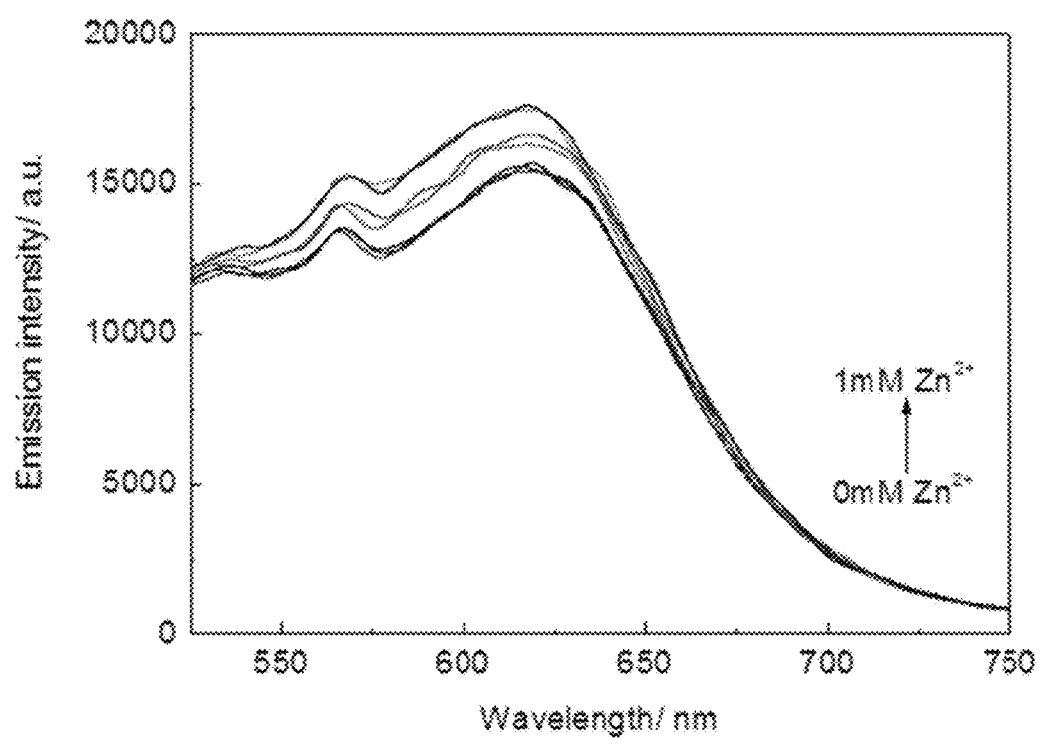

FIG. 31A shows the changes on emission spectra for $L_2P_4$ (2 µM in PBS buffer), following internal addition of $ZnCl_2$.

Figure 31B:
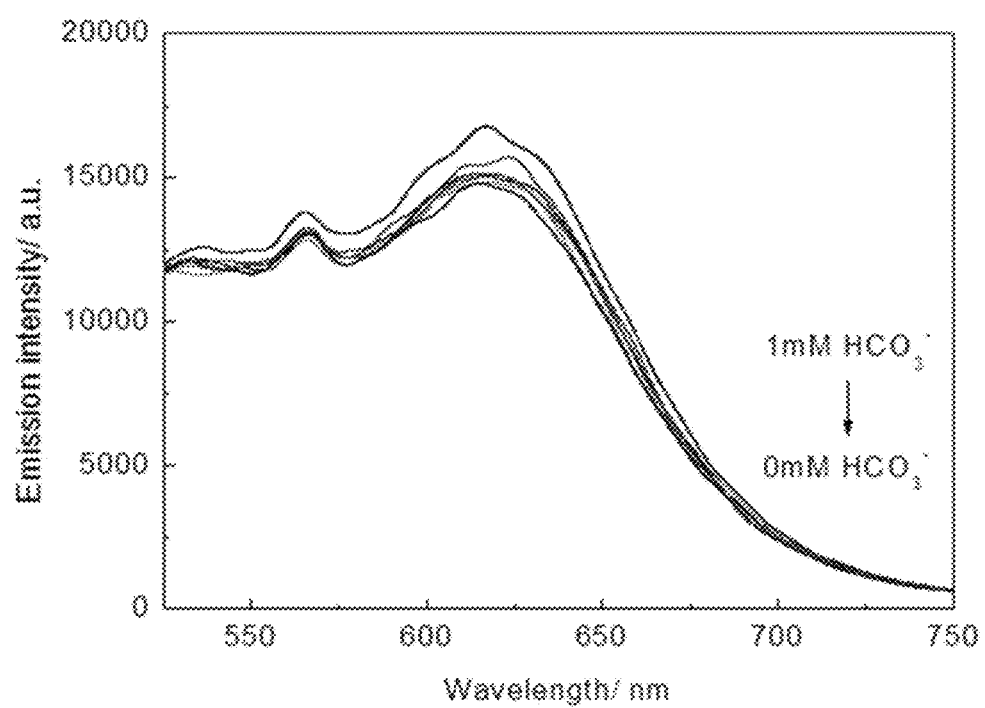

FIG. 31B shows the changes on emission spectra for $L_2P_4$ (2 µM in PBS buffer), following internal addition of $NaHCO_3$.

Figure 31C:
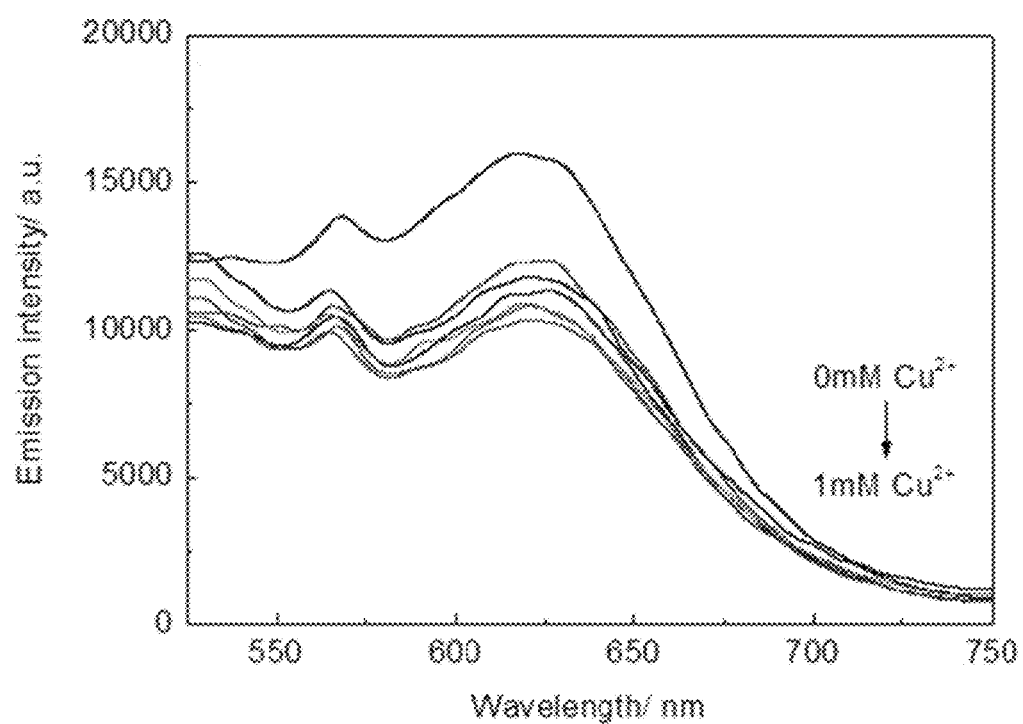

FIG. 31C shows the changes on emission spectra for $L_2P_4$ (2 µM in PBS buffer), following internal addition of $CuCl_2$.

Figure 31D:
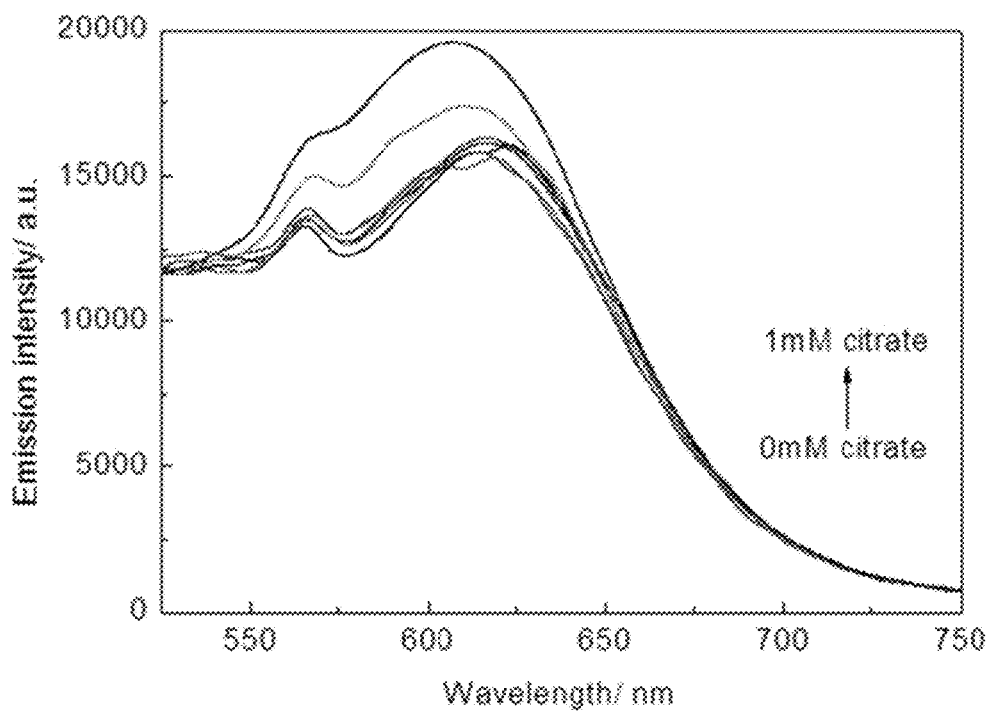

FIG. 31D shows the changes on emission spectra for $L_2P_4$ (2 µM in PBS buffer), following internal addition of citrates.

Figure 31E:
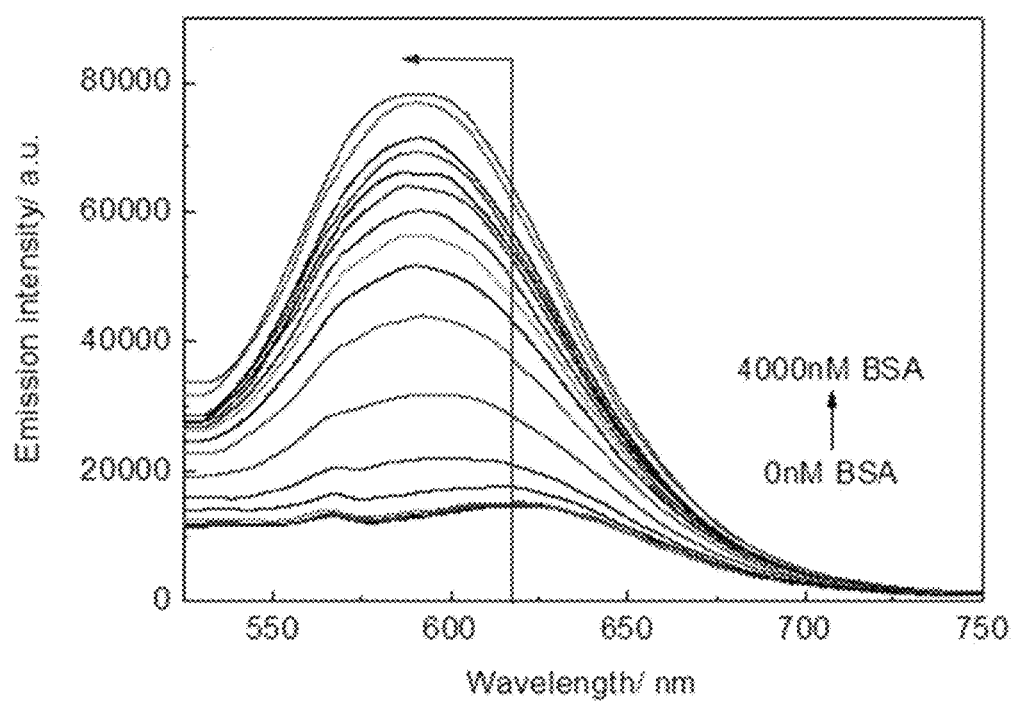

FIG. 31E shows the changes on emission spectra for $L_2P_4$ (2 µM in PBS buffer), following internal addition of BSA. The result demonstrated the selectivity of $L_2P_4$ towards WT-EBNA1 was higher than $L_2P_3$.

Figure 31F:
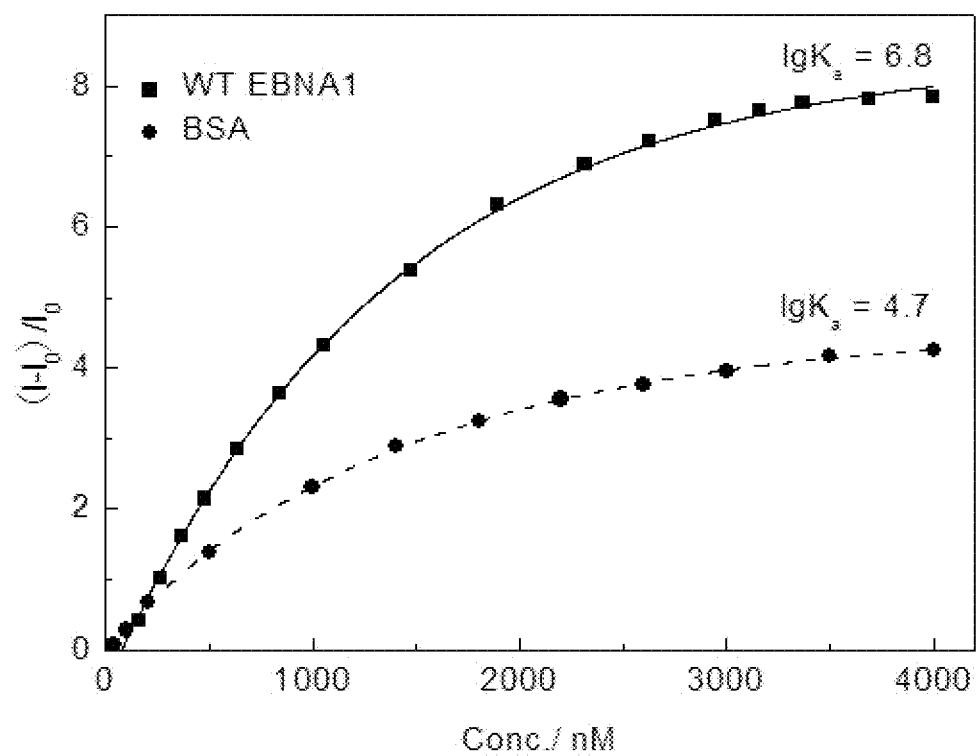

FIG. 31F shows a comparison on the emission enhancement induced by the addition of two different proteins, WT-EBNA1 and BSA. The result demonstrated the selectivity of $L_2P_4$ towards WT-EBNA1 was higher than $L_2P_3$.

Figure 32:
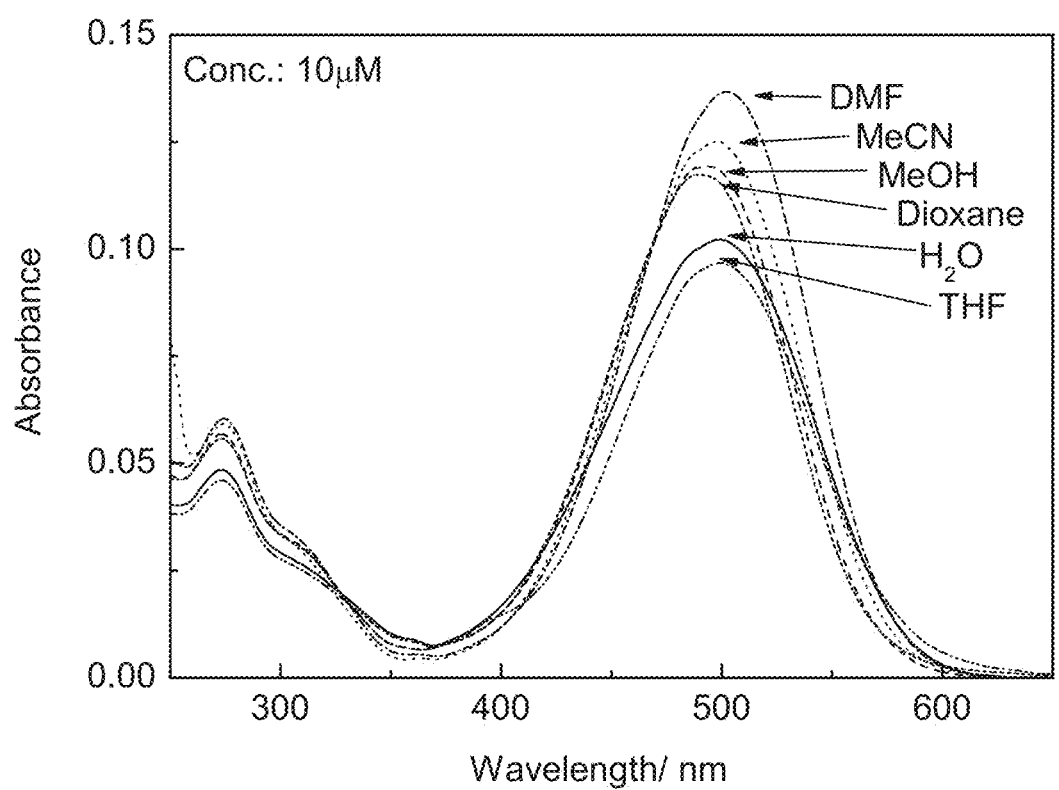

FIG. 32 shows the absorption spectra of $L_2P_4$ in different solvents (Concentration: 10 µM).

Figure 33A:
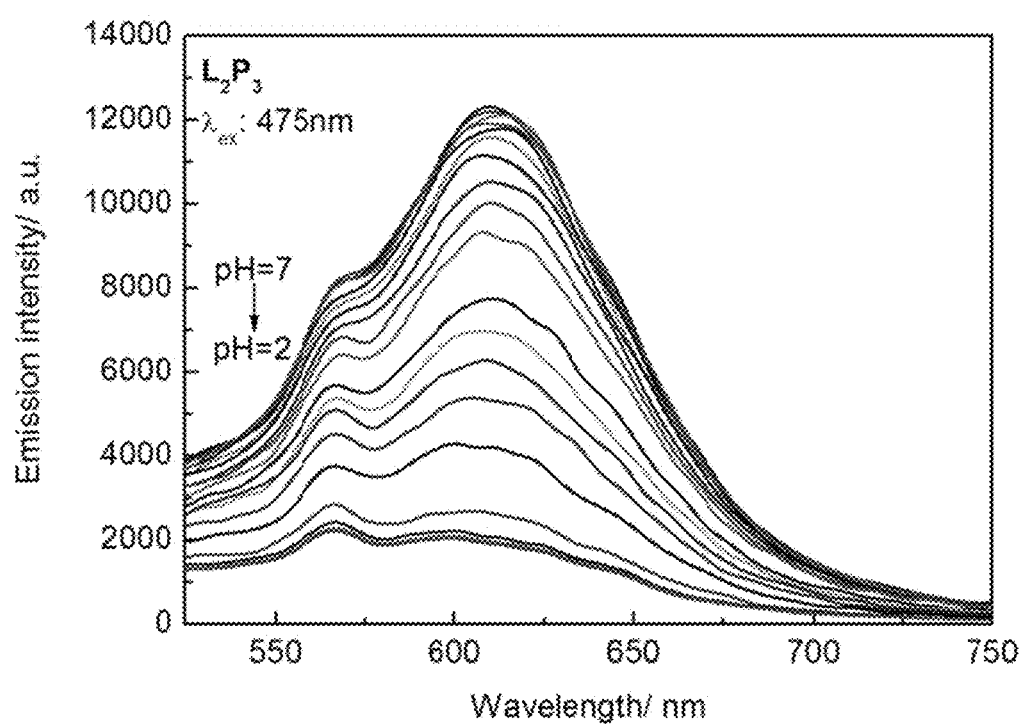

FIG. 33A shows the emission spectra of $L_2P_3$ in PBS buffer, for the investigation of pH effects on emission spectra and the determination of $pK_a$ value.

Figure 33B:
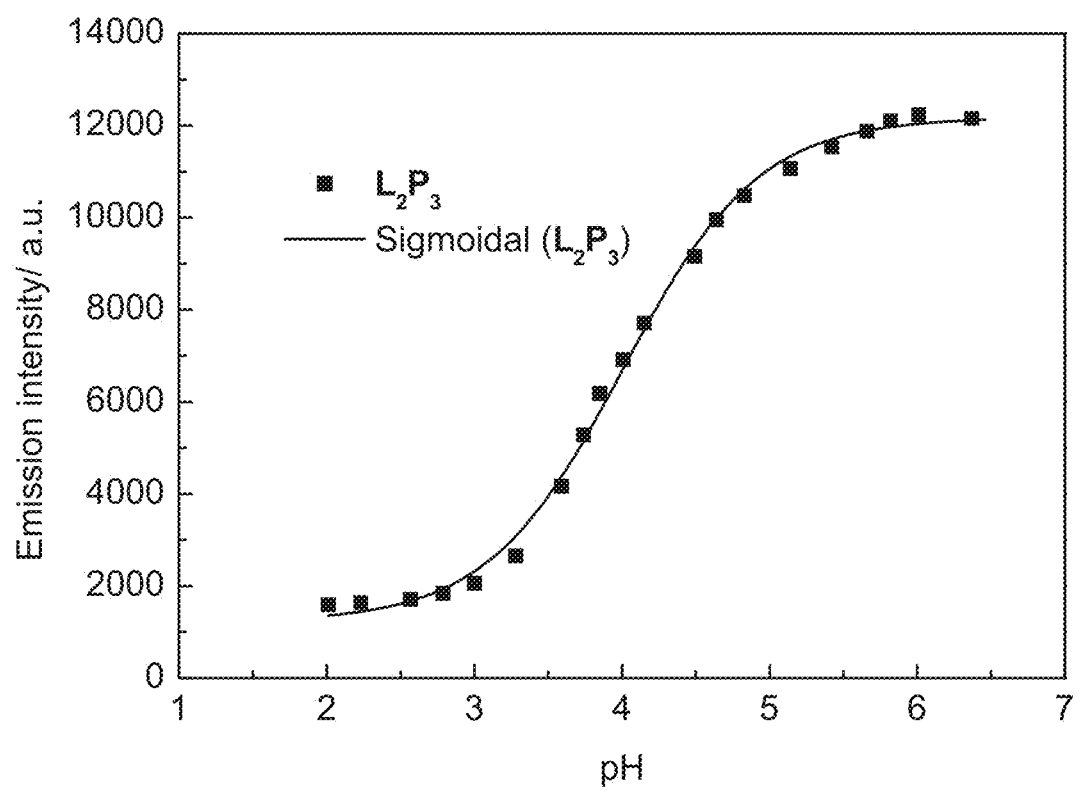

FIG. 33B shows the plot (emission vs pH) of $L_2P_3$ in PBS buffer, for the investigation of pH effects on emission spectra and the determination of $pK_a$ value.

Figure 33C:
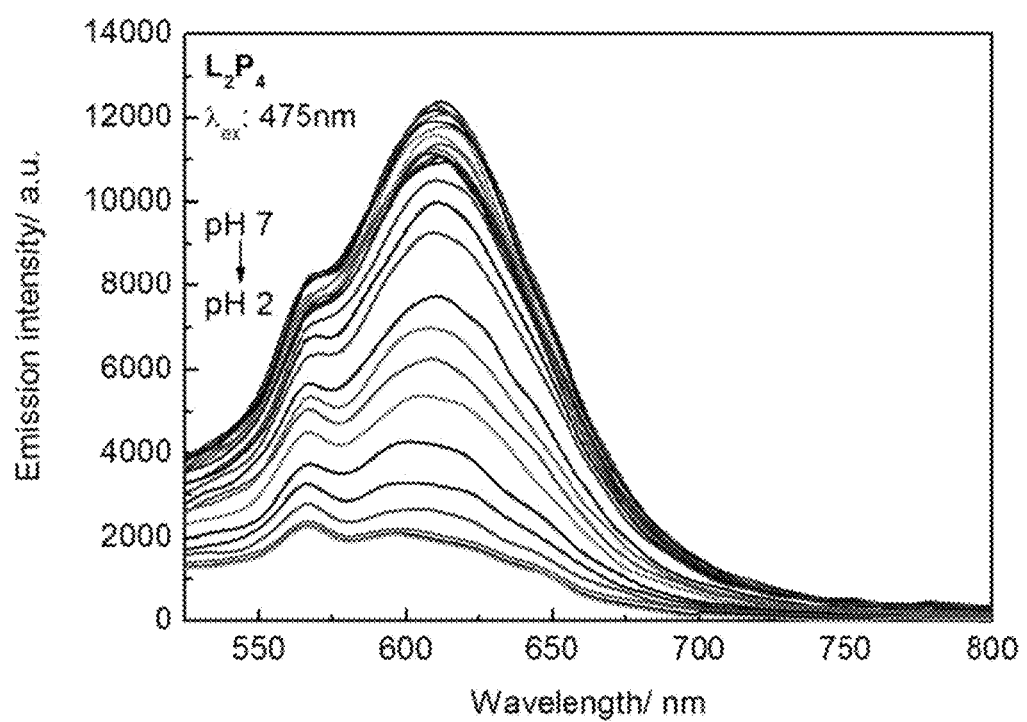

FIG. 33C shows the emission spectra of $L_2P_4$ in PBS buffer, for the investigation of pH effects on emission spectra and the determination of $pK_a$ value.

Figure 33D:
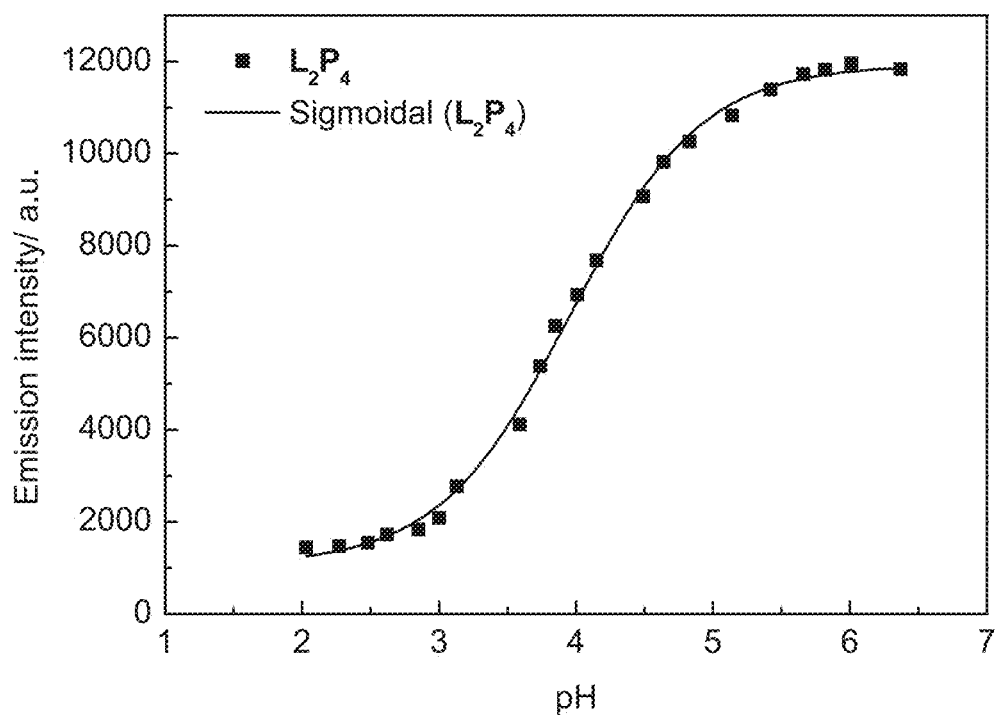

FIG. 33D shows the plot (emission vs pH) of $L_2P_4$ in PBS buffer, for the investigation of pH effects on emission spectra and the determination of $pK_a$ value.

Figure 34:
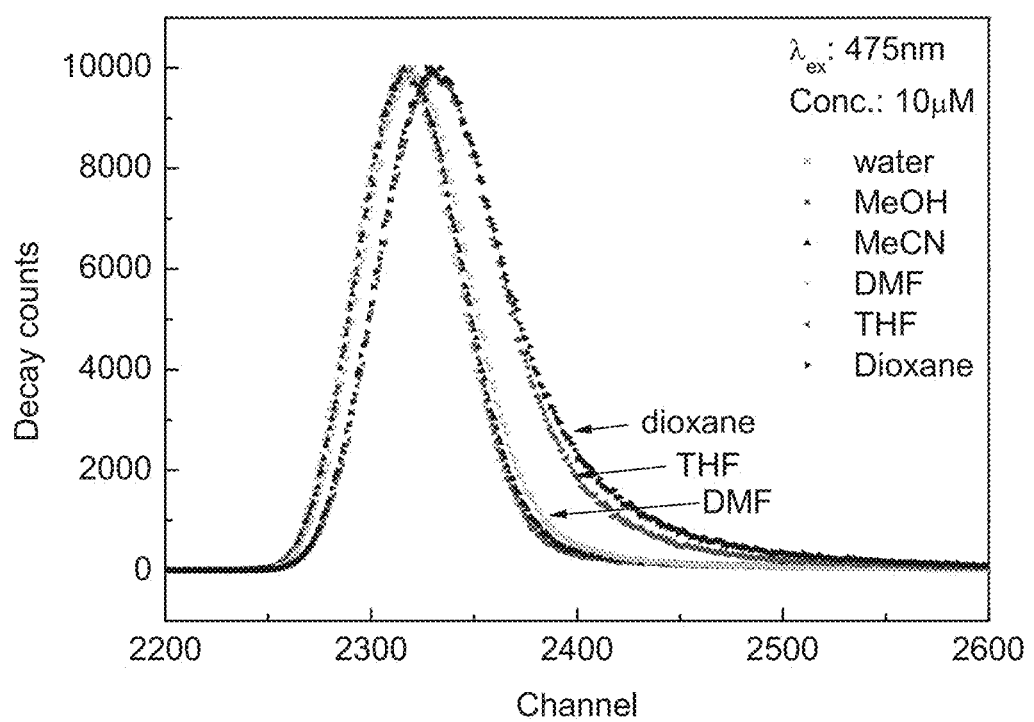

FIG. 34 shows the emission lifetime decay of $L_2P_4$ in different solvents (light source: 460 nm nanoLED, Concentration: 10 μM).

Figure 35A:
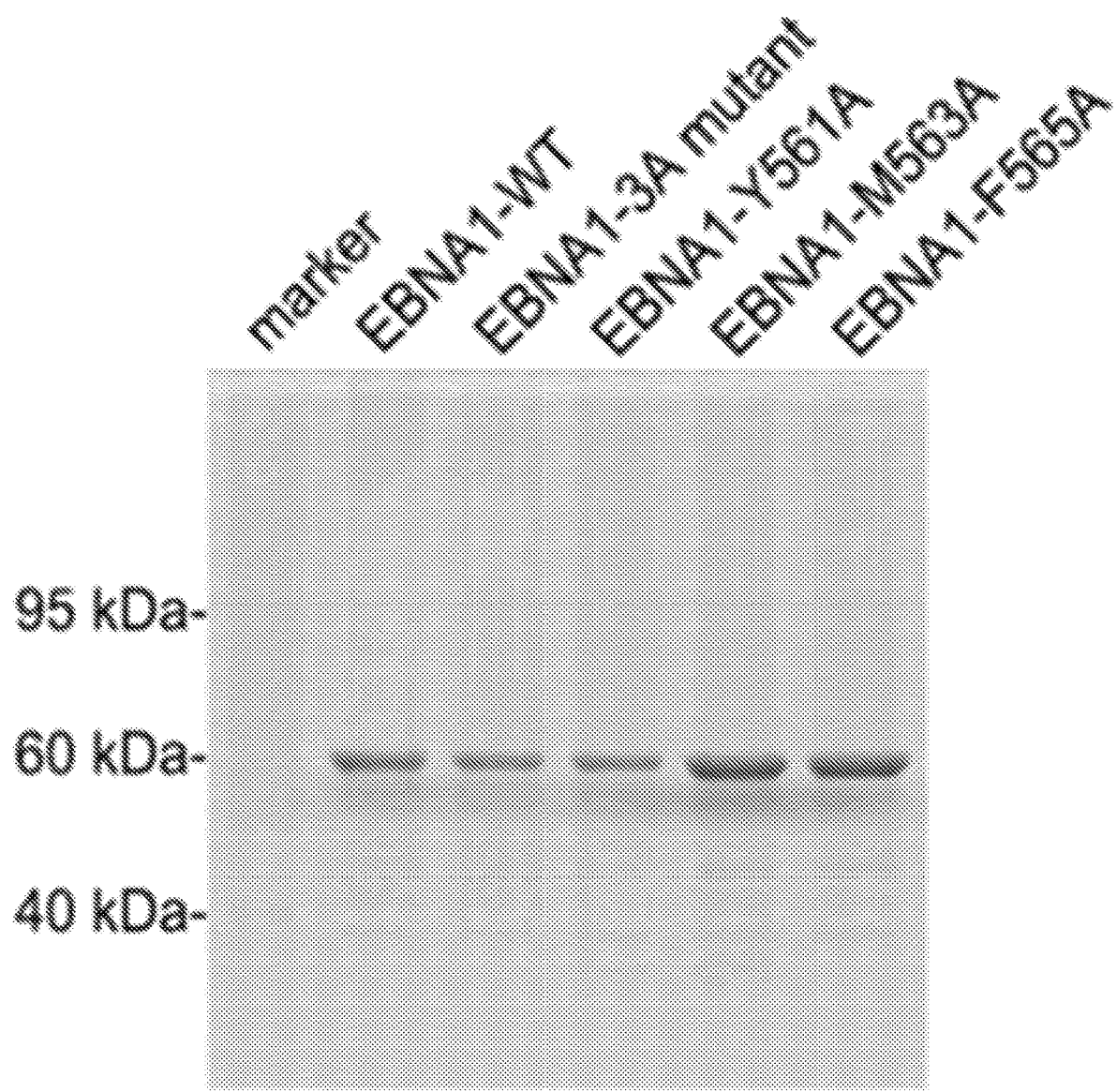

FIG. 35A shows the purified EBNA1 proteins. EBNA1 protein (379-641 a.a.) fusion with glutathione S-transferase (GST) was expressed in *Escherichia. coil* (BL21) and purified by glutathione sepharose 4B rinse (GE Healthcare Dharmacon). The residues YFMVF of WT-EBNA1 was mutated to FFAVA yielding EBNA1-3A mutant protein, or single amino acid mutation yielding $Y_{561}A$, $M_{563}A$ and $F_{565}A$.

Figure 35B:
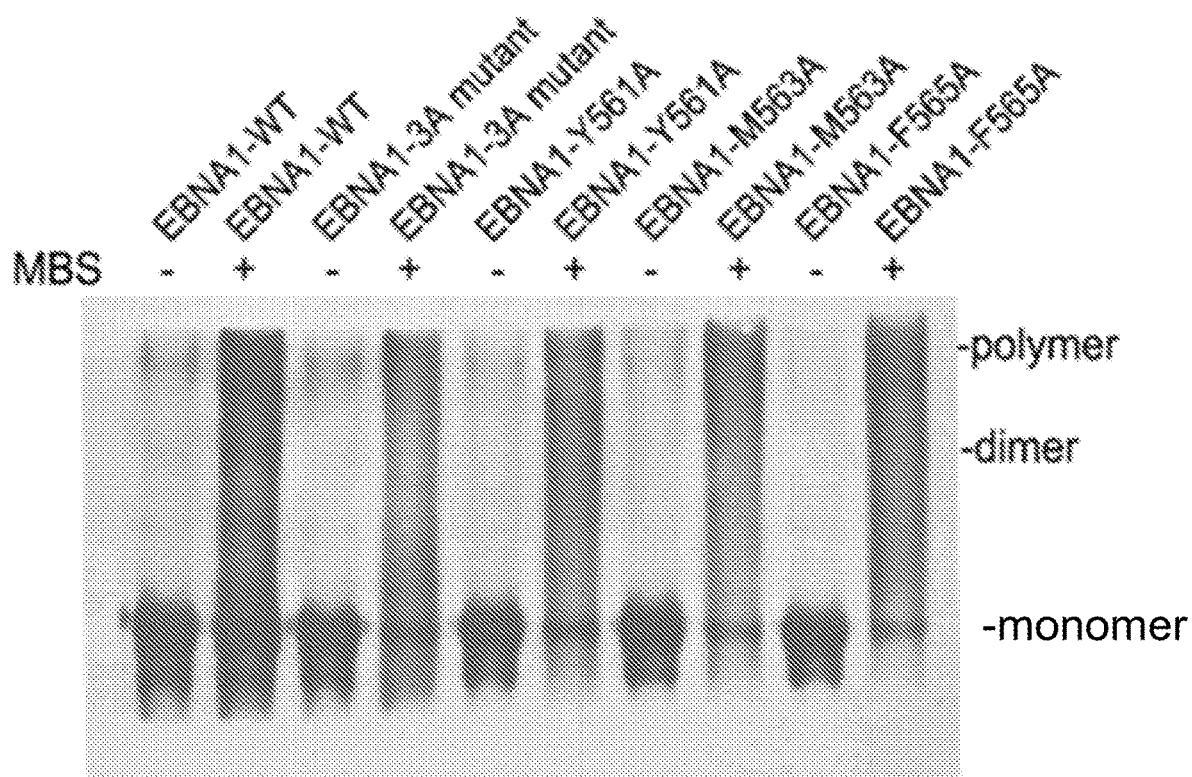

FIG. 35B WT and EBNA1 mutants were analysed for dimerization, they differently impairs the capability of EBNA1 dimerization.

Figure 35C:
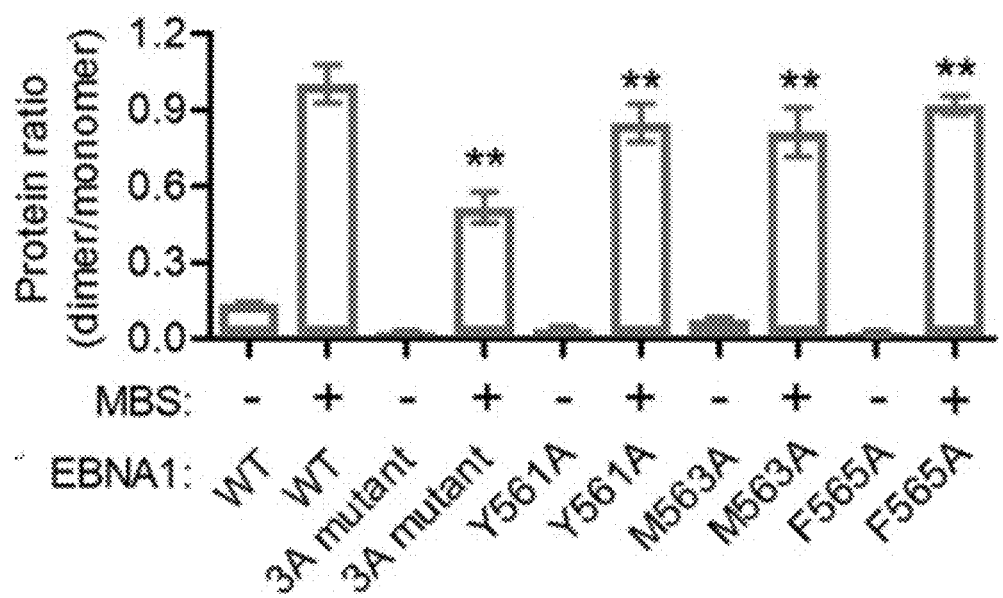

FIG. 35C EBNA1 homodimerization efficiency (**, P<0.01). WT and EBNA1 mutants differently impair the capability of EBNA1 dimerization.

Figure 36A:
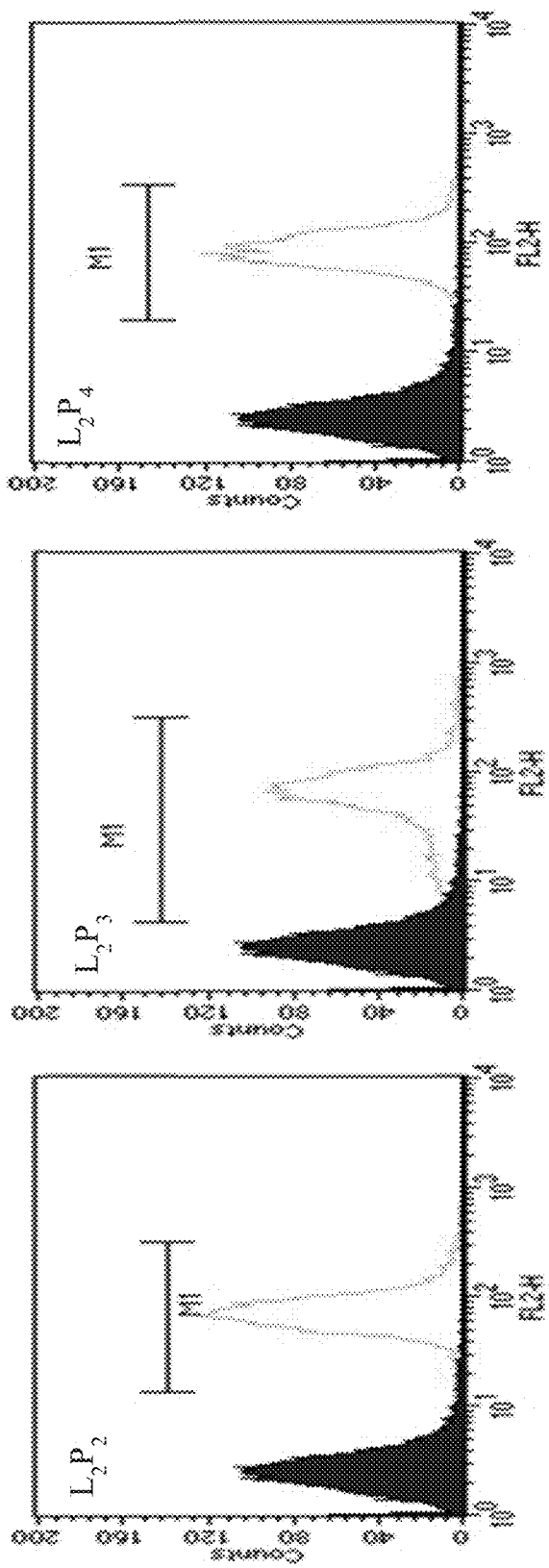

FIG. 36A shows the cellular uptake of $L_2P_2$, $L_2P_3$ and $L_2P_4$ in EBV-negative human cervical carcinoma HeLa cells.

Figure 36B:
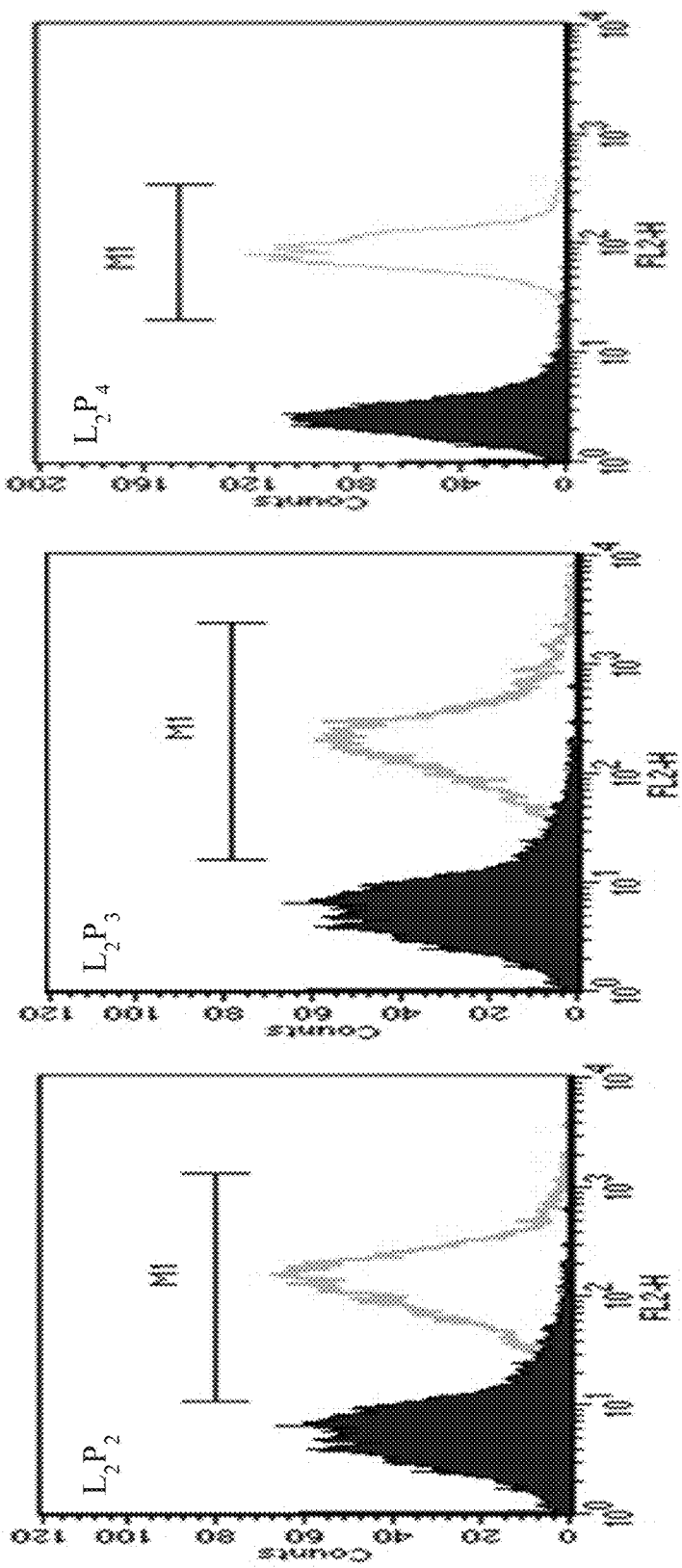

FIG. 36B shows the cellular uptake of $L_2P_2$, $L_2P_3$ and $L_2P_4$ in EBV-positive nasopharyngeal carcinoma C666-1 cells.

Figure 36C:
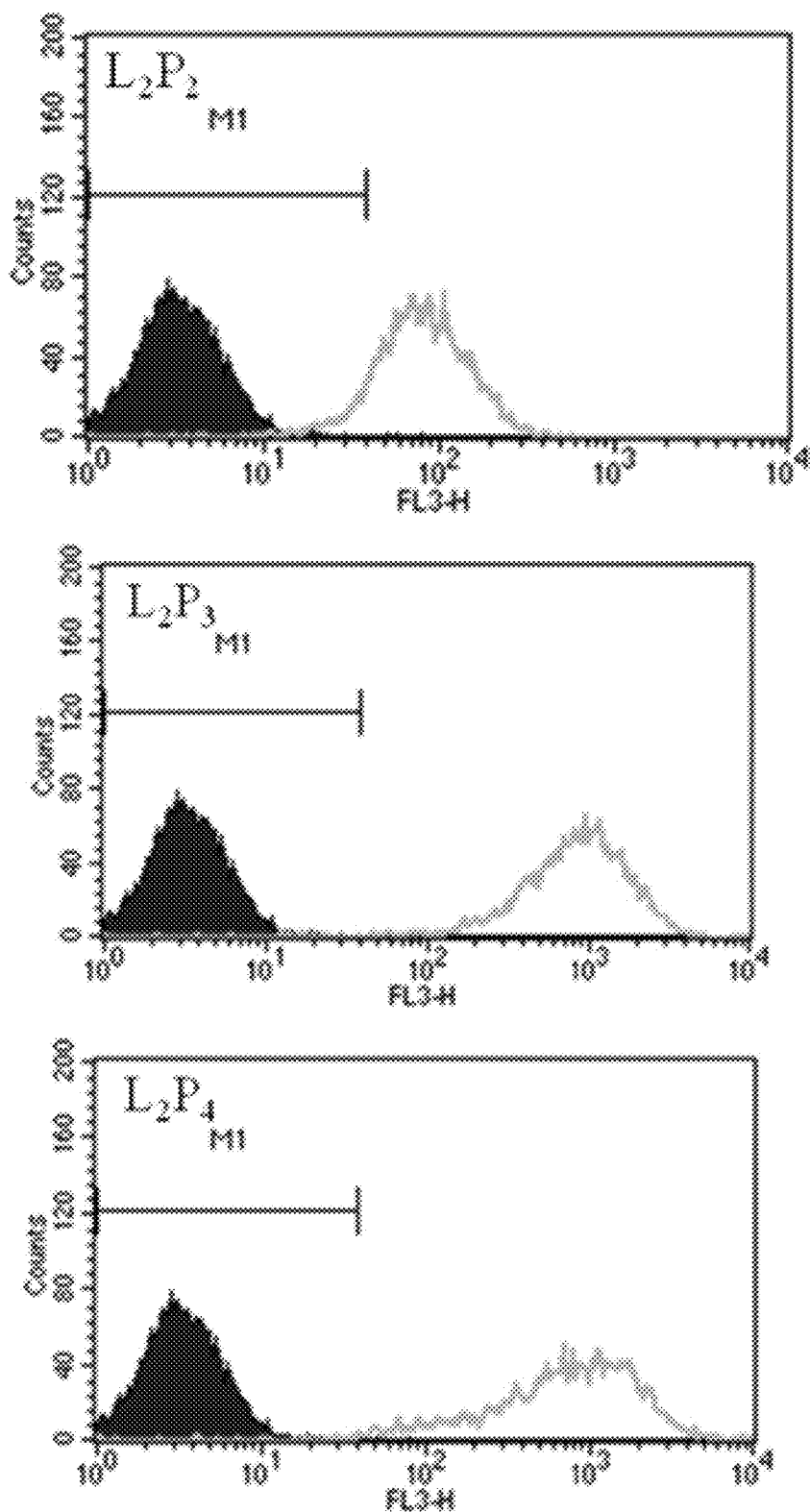

FIG. 36C shows the cellular uptake of $L_2P_2$, $L_2P_3$ and $L_2P_4$ in EBV-positive nasopharyngeal carcinoma NPC43 cells.

Figure 37A:
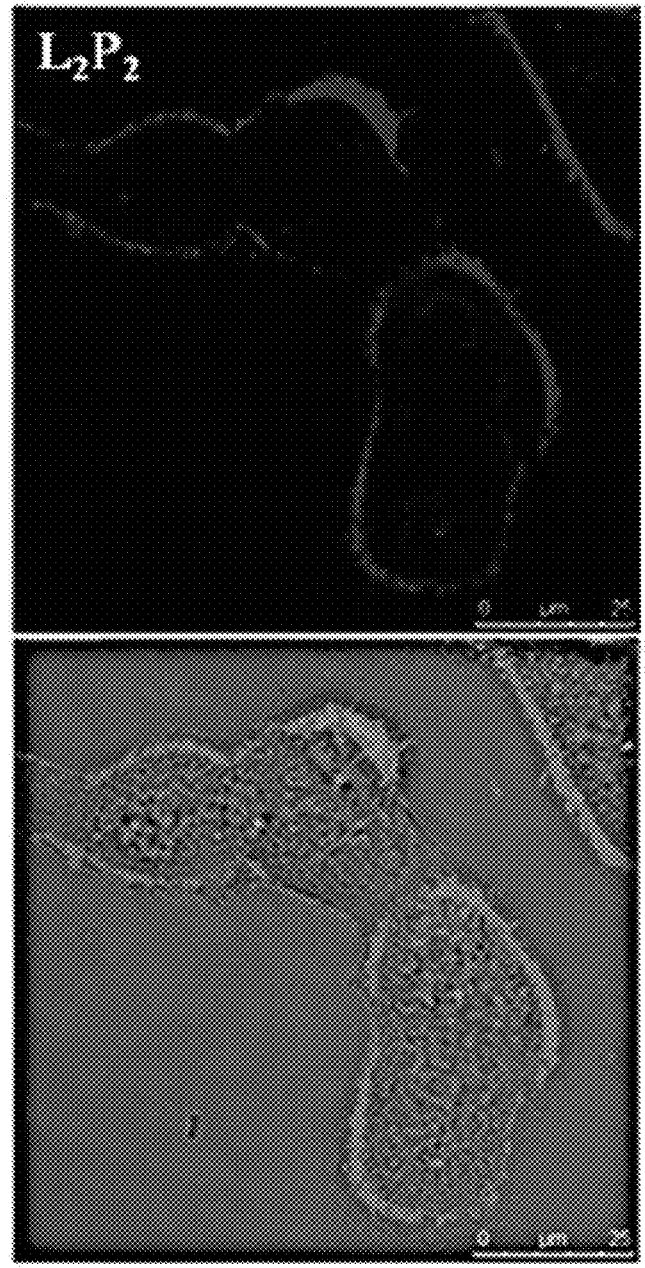

FIG. 37A shows the in vitro imaging of $L_2P_2$ in EBV-negative human cervical carcinoma HeLa cells ($\lambda_{ex}$=488 nm, $\lambda_{em}$=500-650 nm, Filter=BP500).

Figure 37B:
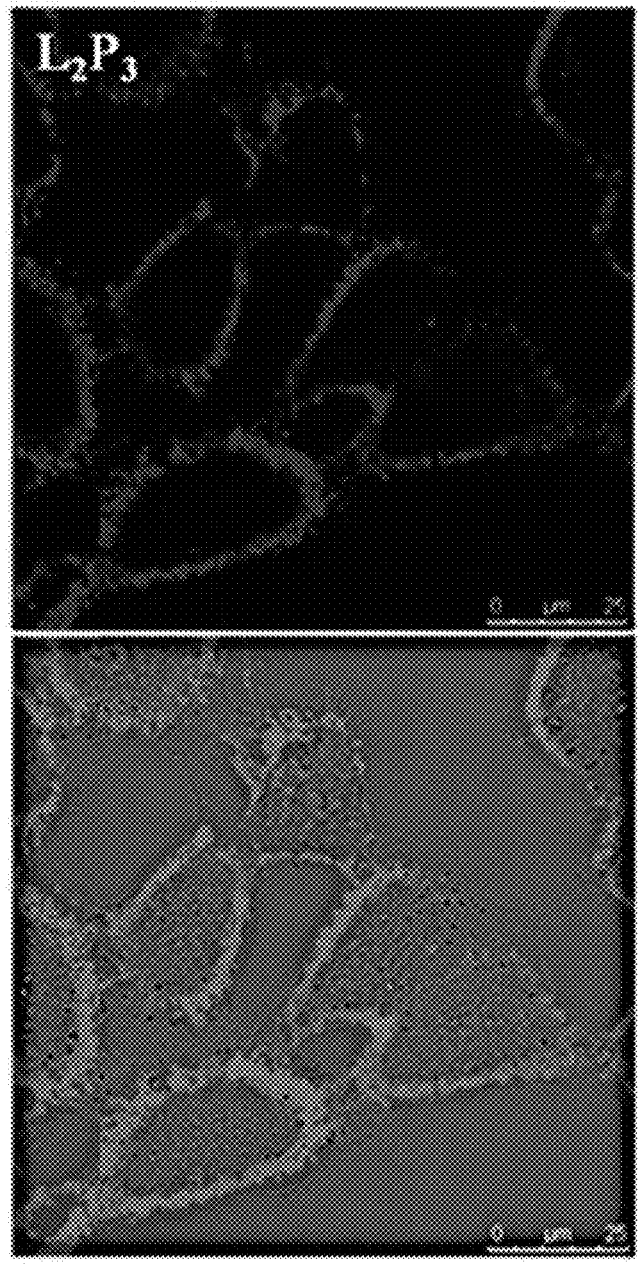

FIG. 37B shows the in vitro imaging of $L_2P_3$ in EBV-negative human cervical carcinoma HeLa cells ($\lambda_{ex}$=488 nm, $\lambda_{em}$=500-650 nm, Filter=BP500).

Figure 37C:
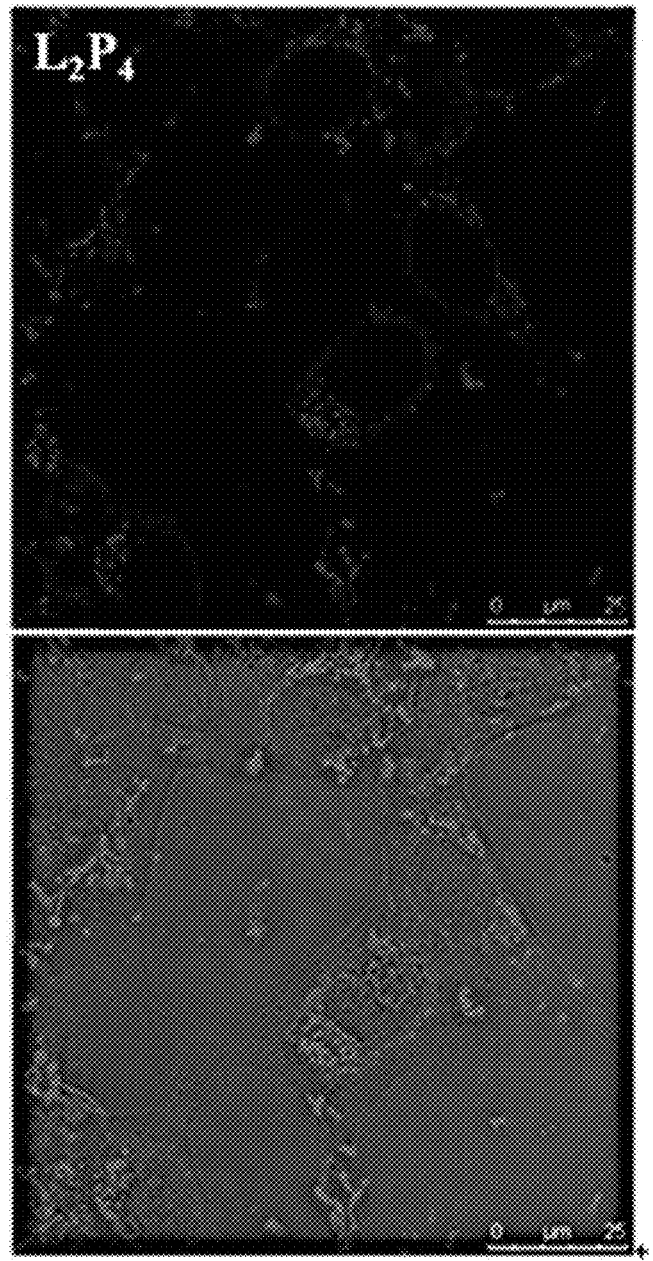

FIG. 37C shows the in vitro imaging of $L_2P_4$ in EBV-negative human cervical carcinoma HeLa cells ($\lambda_{ex}$=488 nm, $\lambda_{em}$=500-650 nm, Filter=BP500).

Figure 37D:
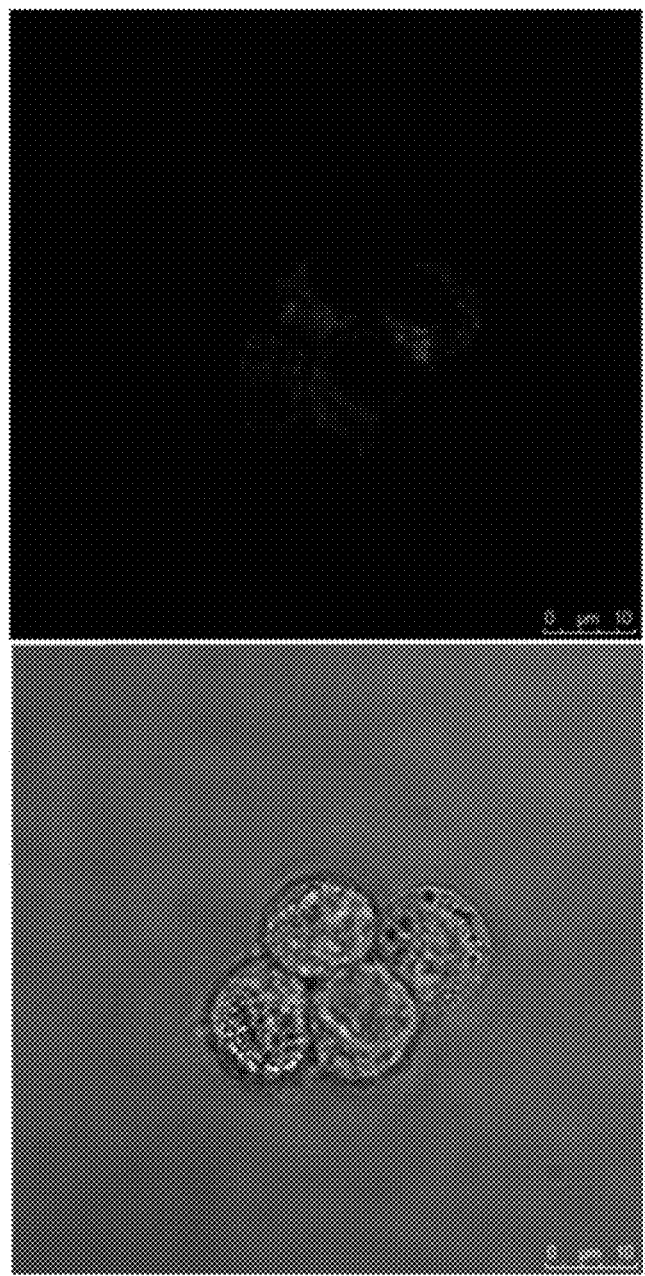

FIG. 37D shows the in vitro imaging of $L_2P_2$ in EBV-positive nasopharyngeal carcinoma C666-1 cells ($\lambda_{ex}$=488 nm, $\lambda_{em}$=500-650 nm, Filter=BP500).

Figure 37E:
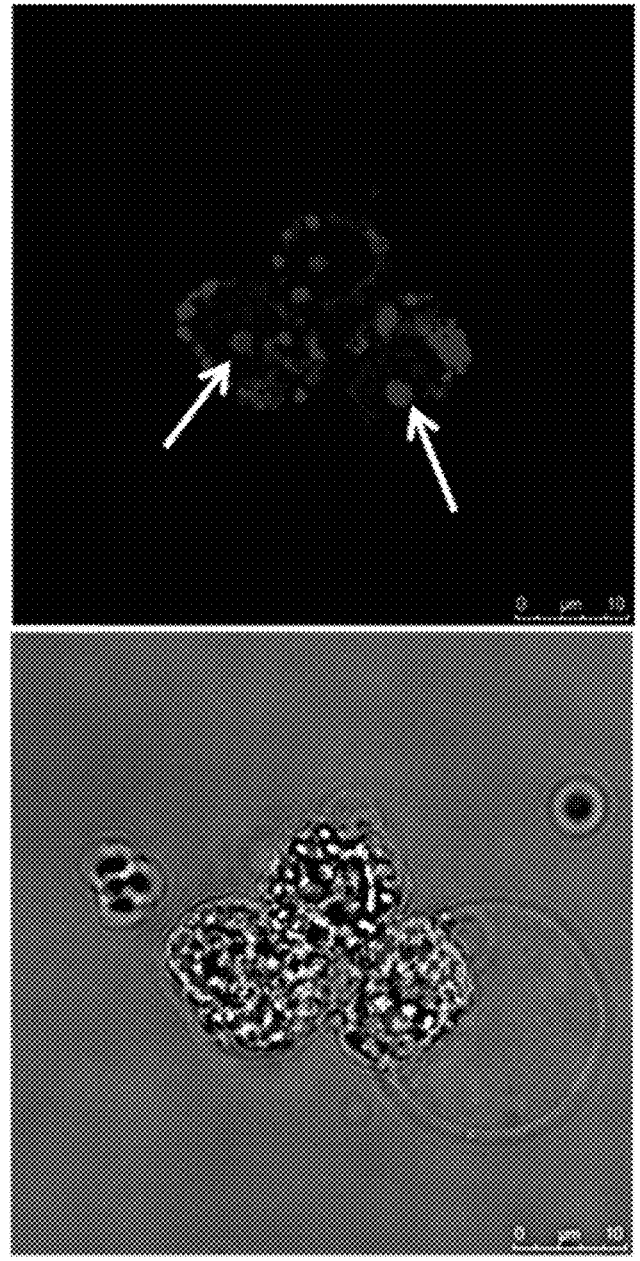

FIG. 37E shows the in vitro imaging of $L_2P_3$ in EBV-positive nasopharyngeal carcinoma C666-1 cells ($\lambda_{ex}$=488 nm, $\lambda_{em}$=500-650 nm, Filter=BP500).

Figure 37F:
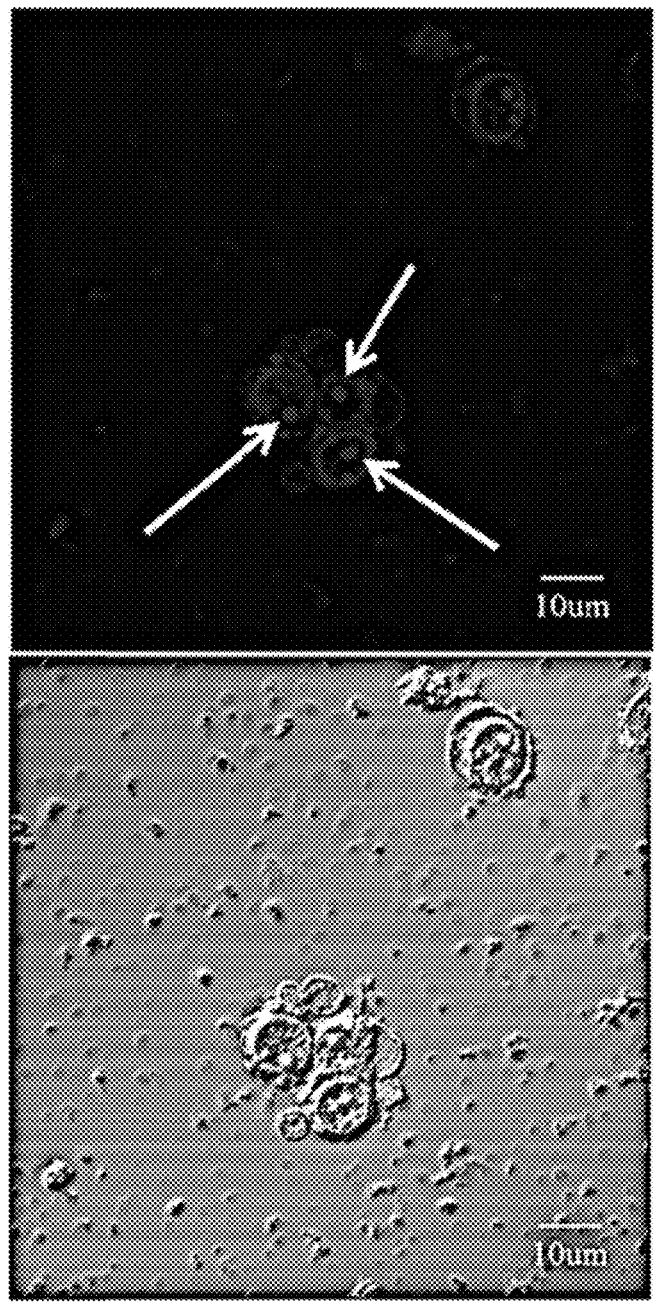

FIG. 37F shows the in vitro imaging of $L_2P_4$ in EBV-positive nasopharyngeal carcinoma C666-1 cells ($\lambda_{ex}$=488 nm, $\lambda_{em}$=500-650 nm, Filter=BP500). Different location can be found for the probes, that is, $L_2P_2$ demonstrated cytoplasm location only, while the $L_2P_3$ and $L_2P_4$ can goes into C666-1 cell nucleus with the help of NLS sequence (RrRK).

Figure 38A:
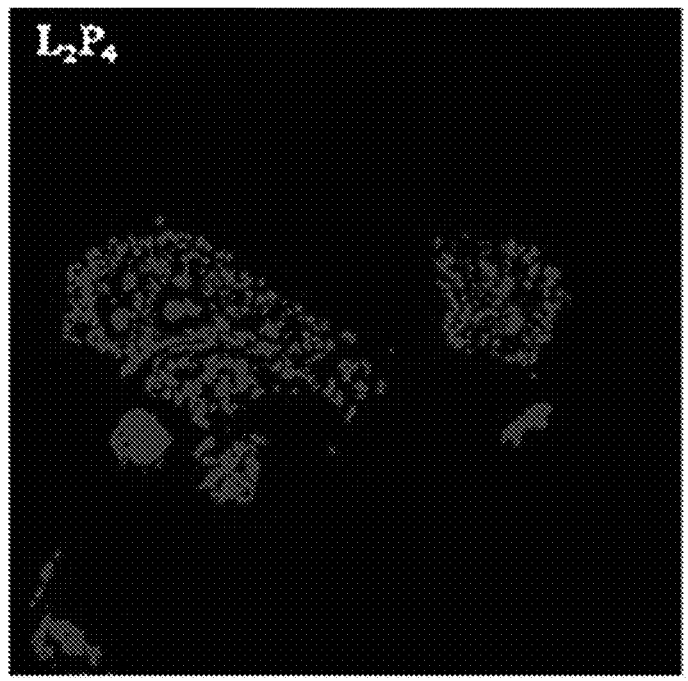

FIG. 38A shows the co-staining of $L_2P_4$ in C666-1 cells with lyso Green DND-26 tracker) (the cells were treated with 10 μM $L_2P_4$, it was then incubated for 6 hours, afterwards the cells were treated with 1 nM lyso tracker with 1 hour incubation). Here shows the emission from $L_2P_4$.

Figure 38B:
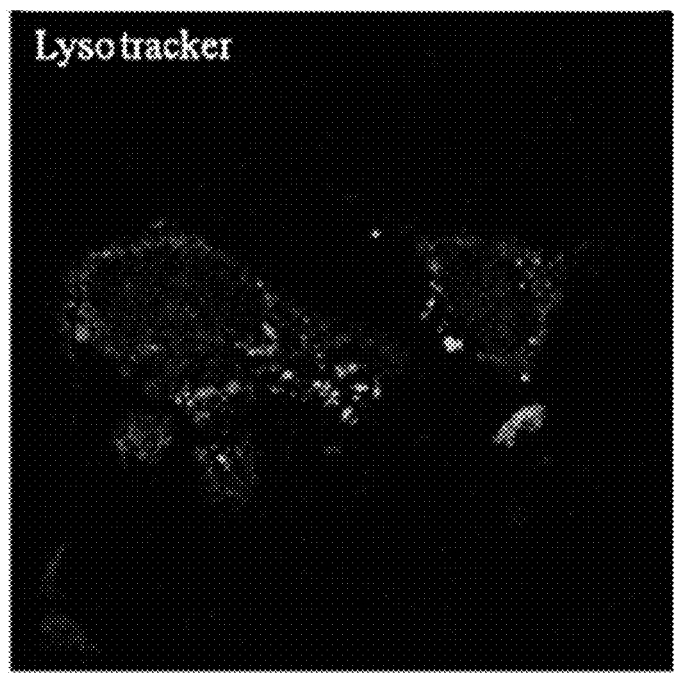

FIG. 38B shows the co-staining of $L_2P_4$ in C666-1 cells with lyso Green DND-26 tracker (the cells were treated with 10 μM $L_2P_4$, it was then incubated for 6 hours, afterwards the cells were treated with 1 nM lyso/tracker with 1 hour incubation). Here shows the emission from the lyso tracker.

Figure 38C:
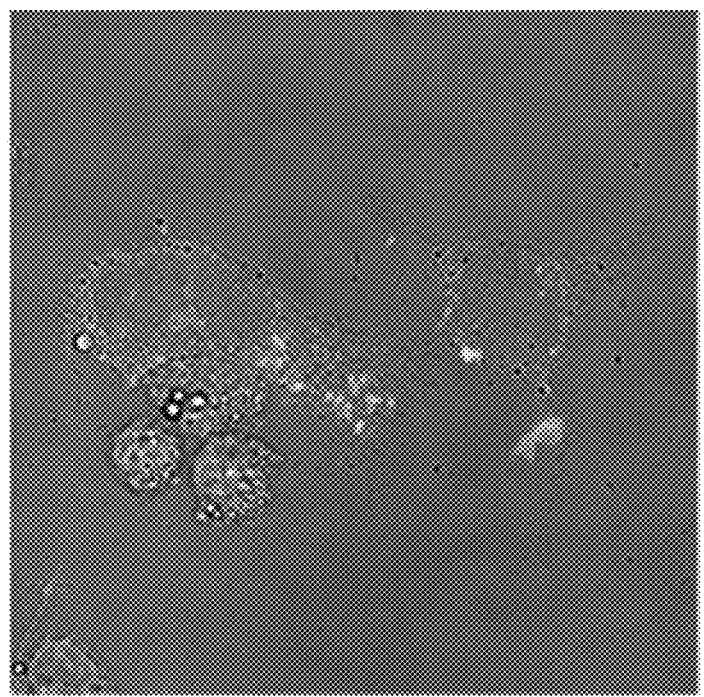

FIG. 38C shows the co-staining of $L_2P_4$ in C666-1 cells with lyso Green DND-26 tracker (the cells were treated with 10 μM $L_2P_4$, it was then incubated for 6 hours, afterwards the cells were treated with 1 nM mito tracker with 1 hour incubation). Almost no location on lysosome can be observed.

Figure 38D:
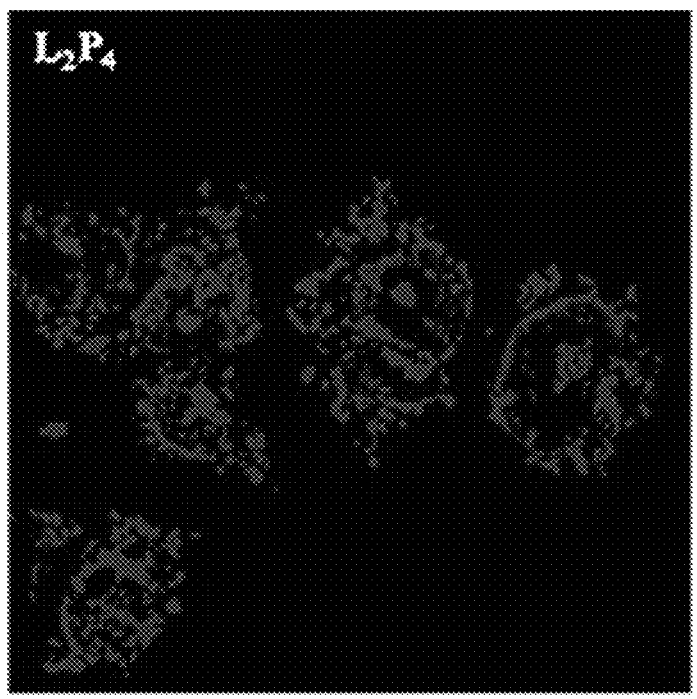

FIG. 38D shows the co-staining of $L_2P_4$ in C666-1 cells with mito Green FM M7514 tracker (the cells were treated with 10 μM $L_2P_4$, it was then incubated for 6 hours, afterwards the cells were treated with 1 nM mito tracker with 1 hour incubation). Here shows the emission from $L_2P_4$.

Figure 38E:
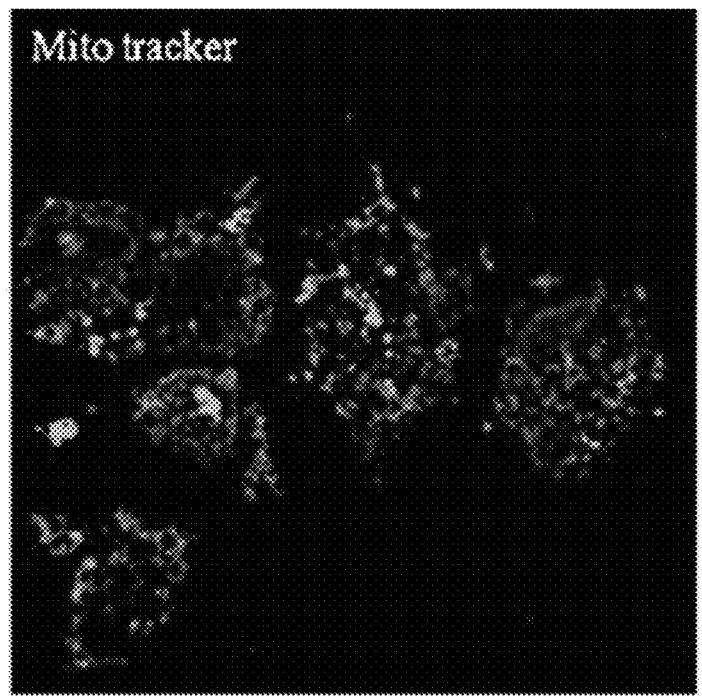

FIG. 38E shows the co-staining of $L_2P_4$ in C666-1 cells with mito Green FM M7514 tracker (the cells were treated with 10 μM $L_2P_4$, it was then incubated for 6 hours, afterwards the cells were treated with 1 nM mito tracker with 1 hour incubation). Here shows the emission from the mito tracker.

Figure 38F:
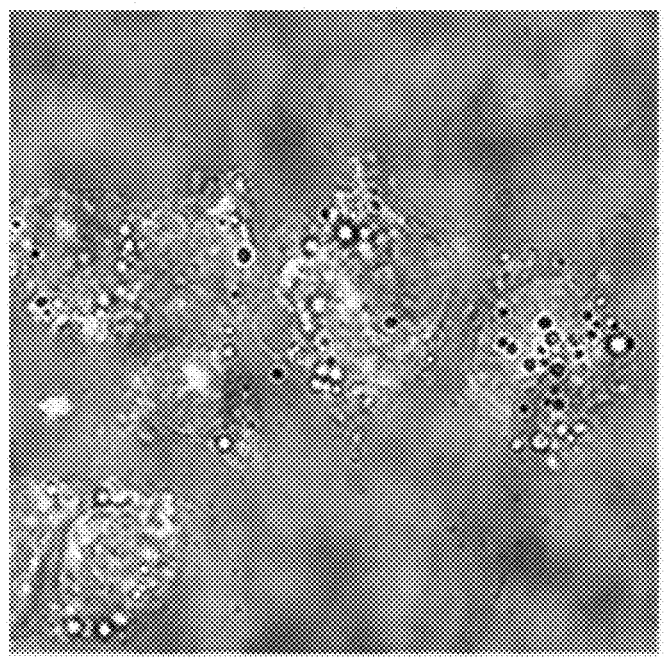

FIG. 38F shows the co-staining of $L_2P_4$ in C666-1 cells with mito Green FM M7514 tracker (the cells were treated with 10 μM $L_2P_4$, it was then incubated for 6 hours, afterwards the cells were treated with 1 nM mito tracker with 1 hour incubation). It showed location on mitochondria due to $L_2$ itself normally located on mitochondria.

Figure 39A:
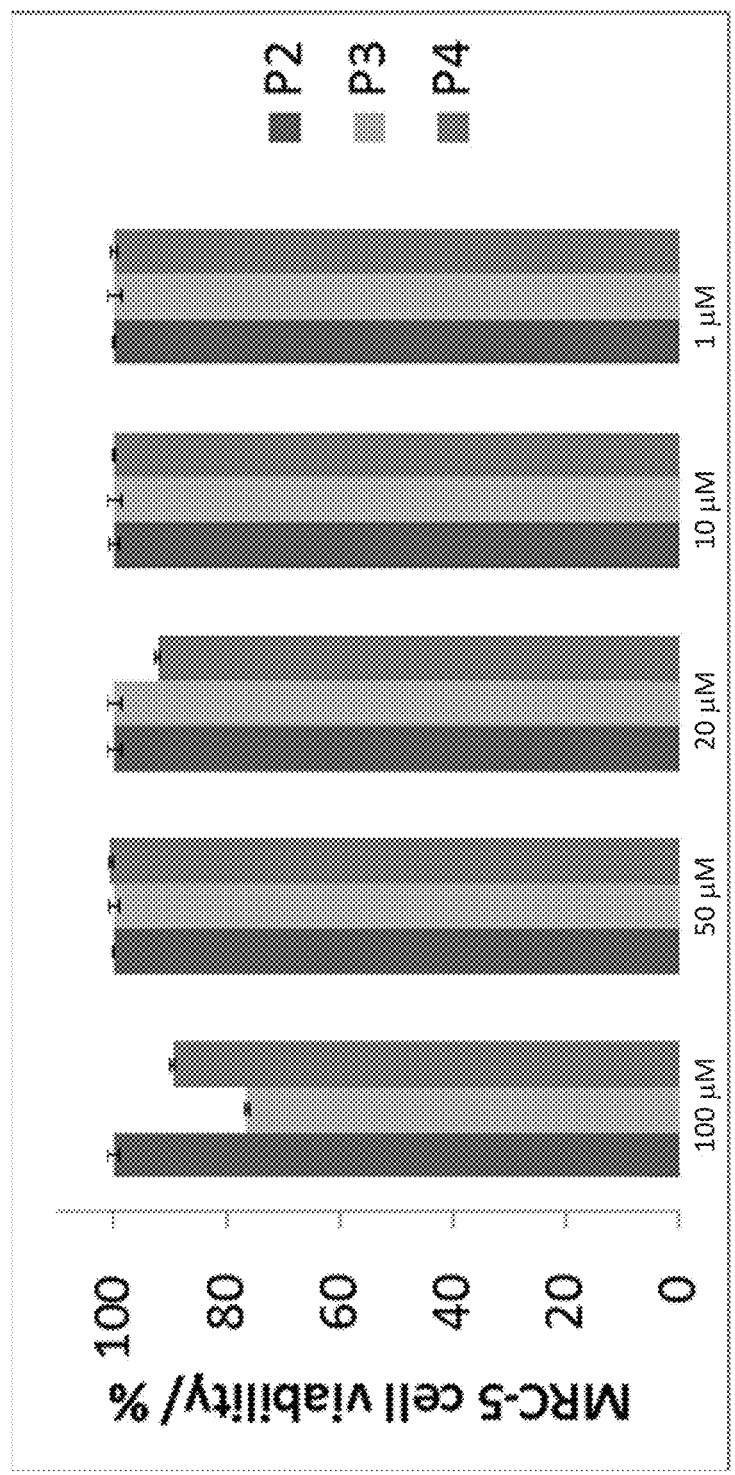

FIG. 39A shows the cytotoxicity assay results of $P_n$ (n=2, 3, 4) on EBV-negative human lung fibroblast normal MRC-5 cells (incubation time: 24 hours).

Figure 39B:
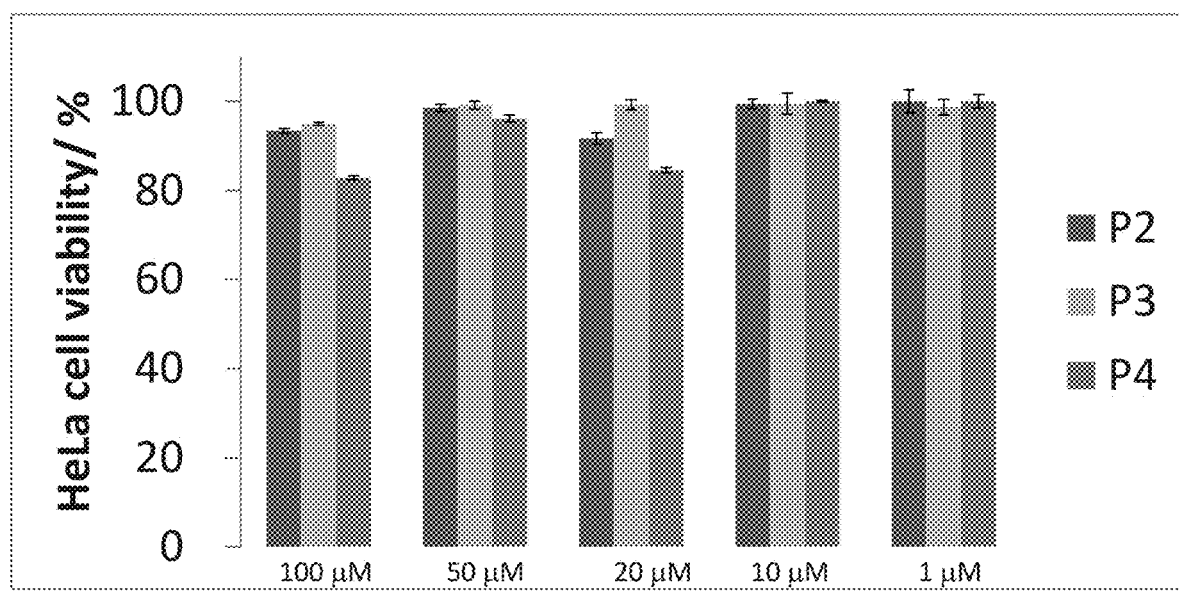

FIG. 39B shows the cytotoxicity assay results of $P_n$ (n=2, 3, 4) on EBV-negative human cervical carcinoma HeLa cells (incubation time: 24 hours).

Figure 39C:
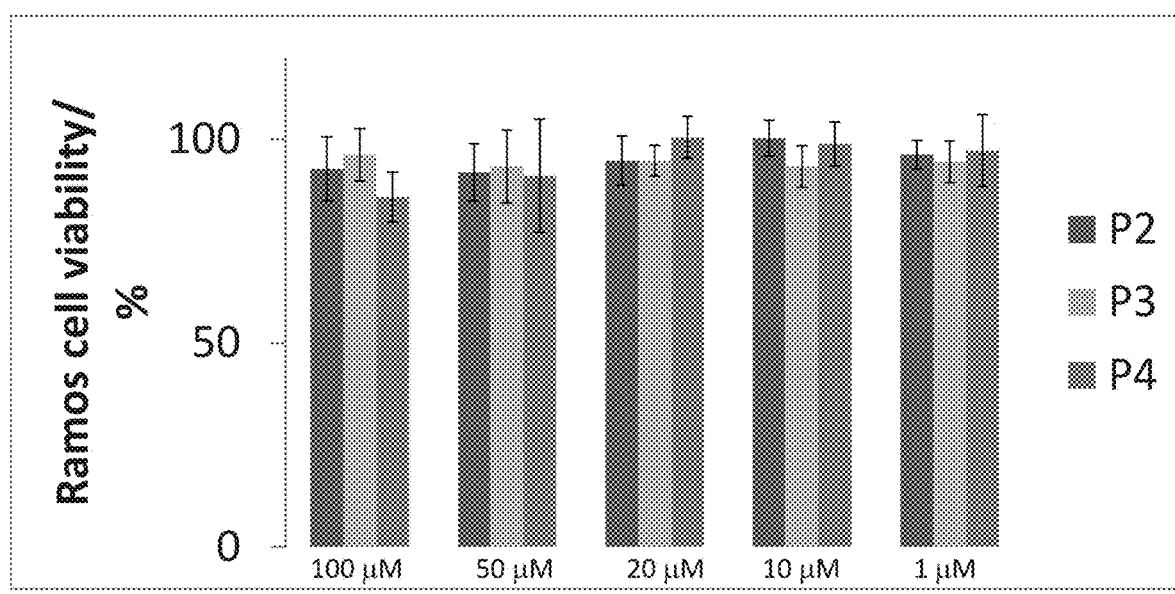

FIG. 39C shows the cytotoxicity assay results of $P_n$ (n=2, 3, 4) on EBV-negative Burkitt's lymphoma Ramos cells (incubation time: 24 hours).

Figure 39D:
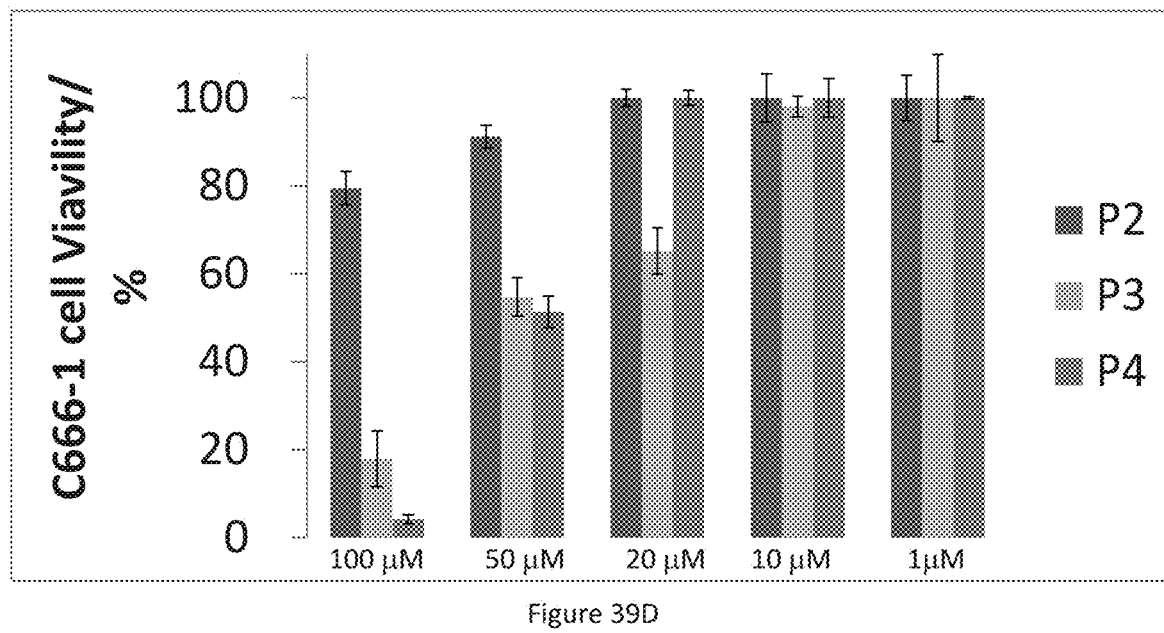

FIG. 39D shows the cytotoxicity assay results of $P_n$ (n=2, 3, 4) on EBV-positive nasopharyngeal carcinoma C666-1 cells (incubation time: 24 hours).

Figure 39E:
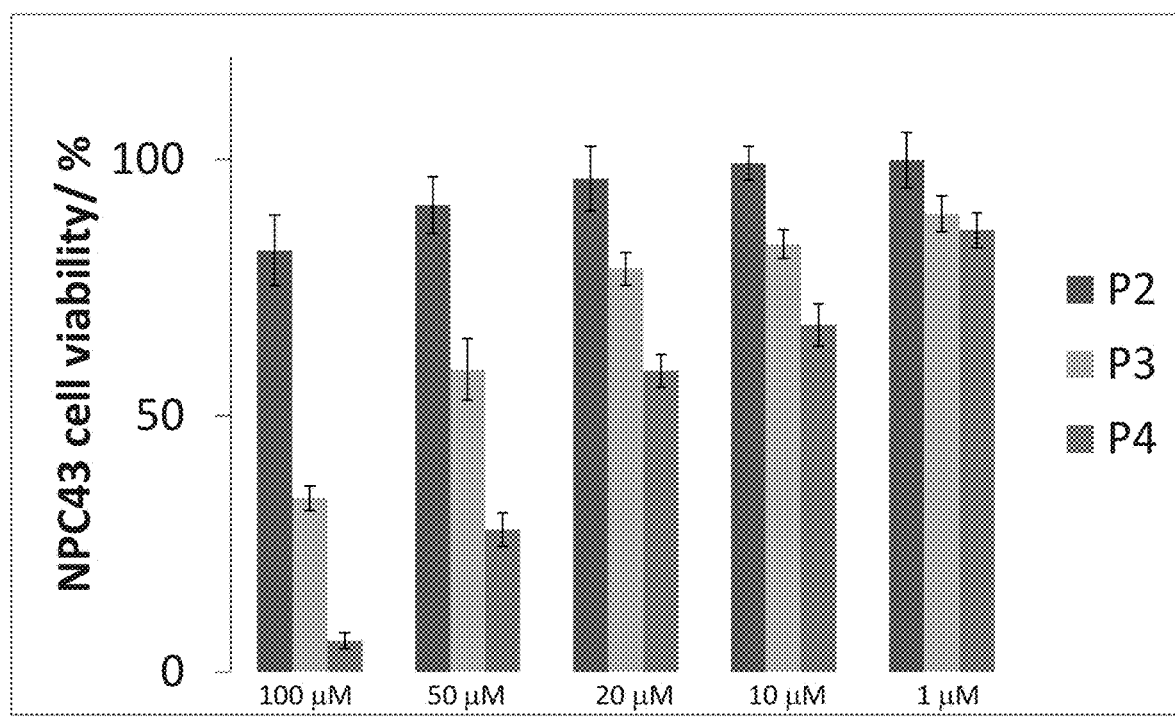

FIG. 39E shows the cytotoxicity assay results of $P_n$ (n=2, 3, 4) on newly derived EBV-positive nasopharyngeal carcinoma NPC43 cells (incubation time: 24 hours).

Figure 39F:
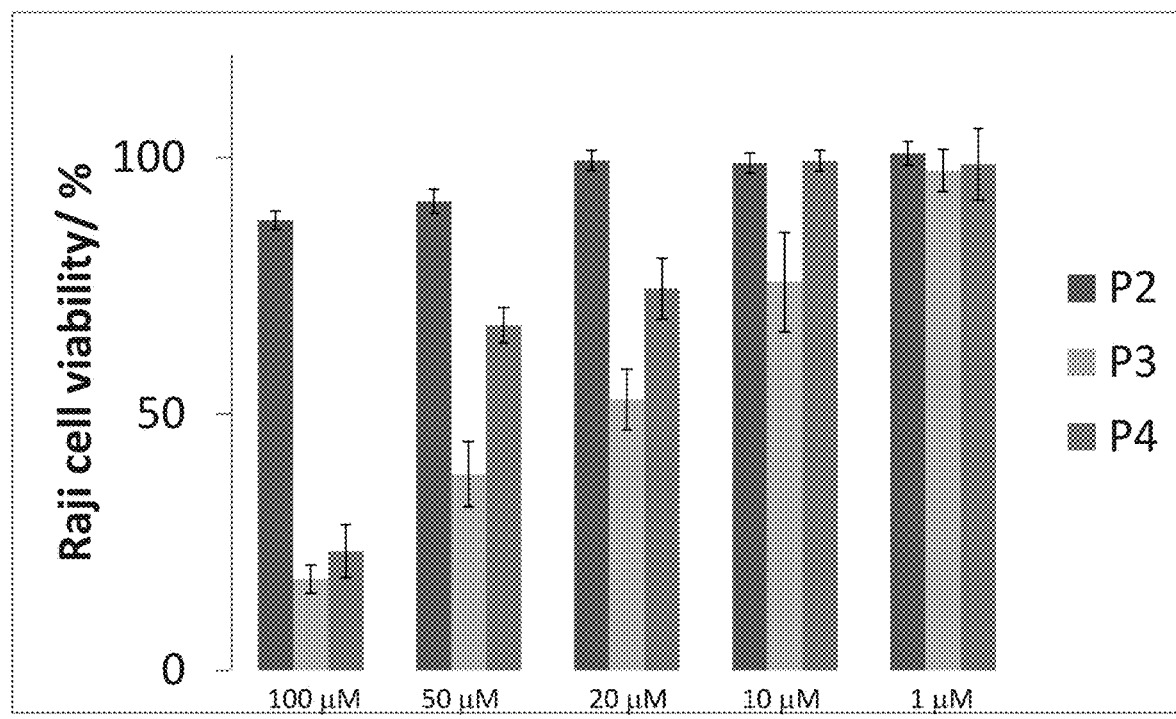

FIG. 39F shows the cytotoxicity assay results of $P_n$ (n=2, 3, 4) on EBV-positive Burkitt's lymphoma Raji cells (incubation time: 24 hours).

Figure 40:
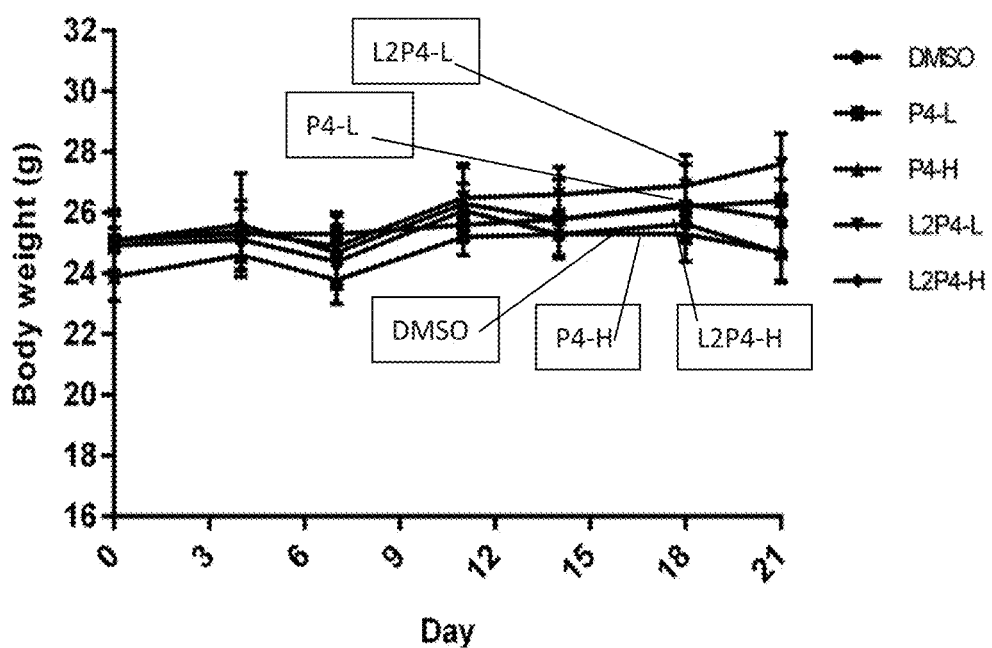

FIG. 40 shows the body weights of mice after treated with intra-tumoral injections of $P_4$, $L_2P_4$ (low or high dose) or DMSO twice weekly for 21 days.

Figure 41A:
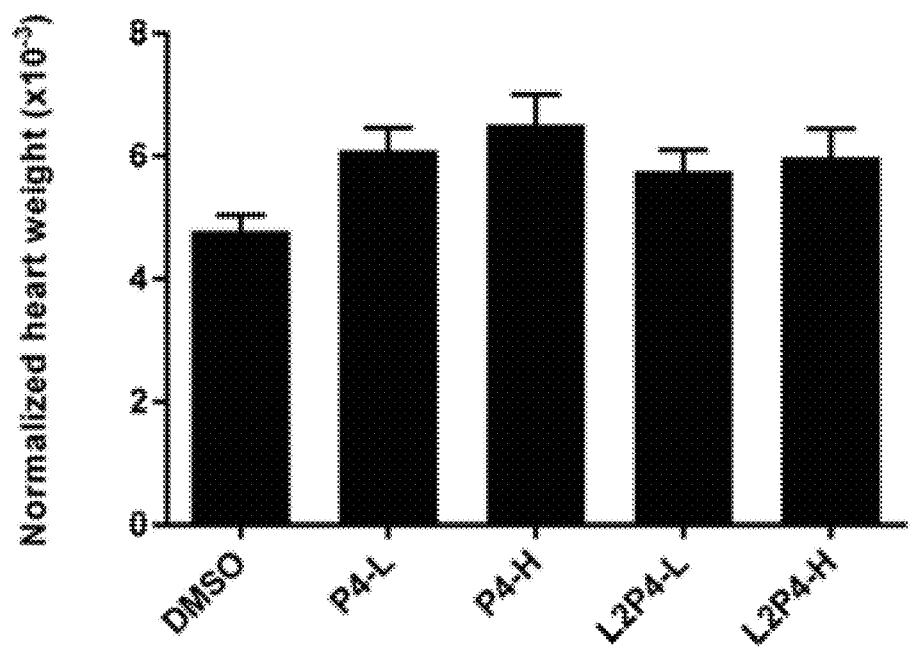

FIG. 41A shows the vital organ weights (heart) of mice after treated with different drugs in 21 days.

Figure 41B:
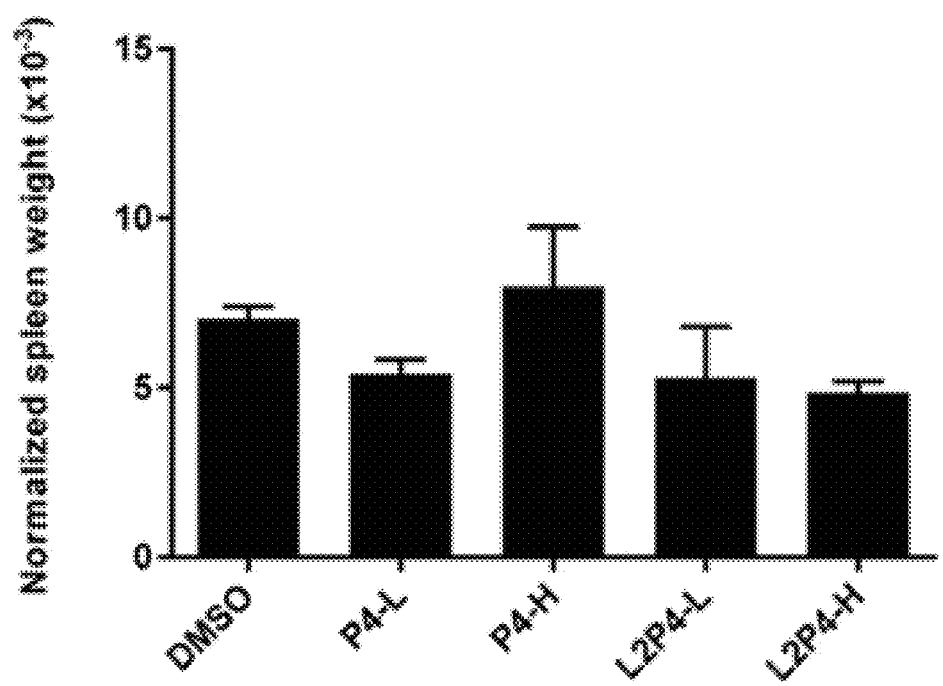

FIG. 41B shows the vital organ weights (spleen) of mice after treated with different drugs in 21 days.

Figure 41C:
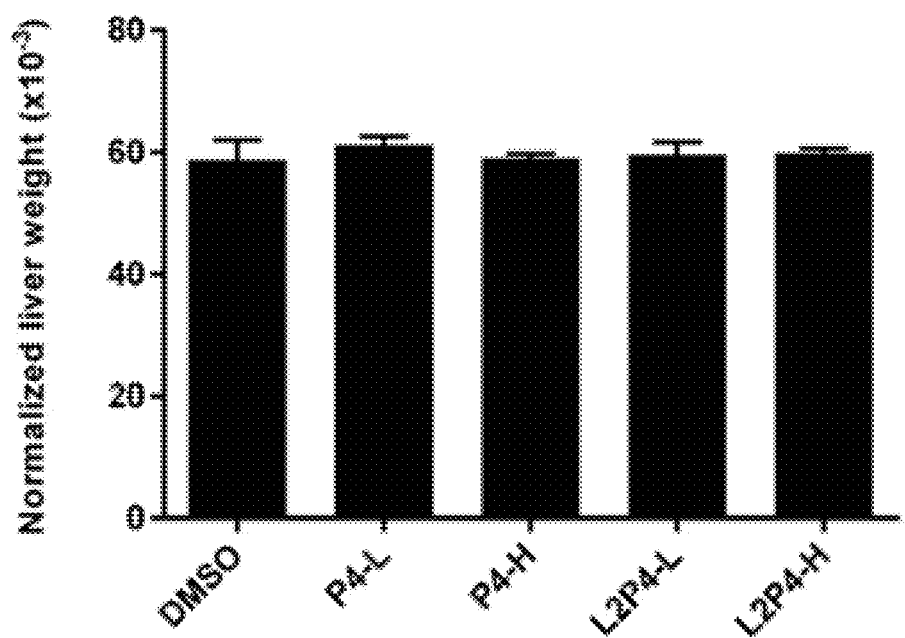

FIG. 41C shows the vital organ weights (liver) of mice after treated with different drugs in 21 days.

Figure 41D:
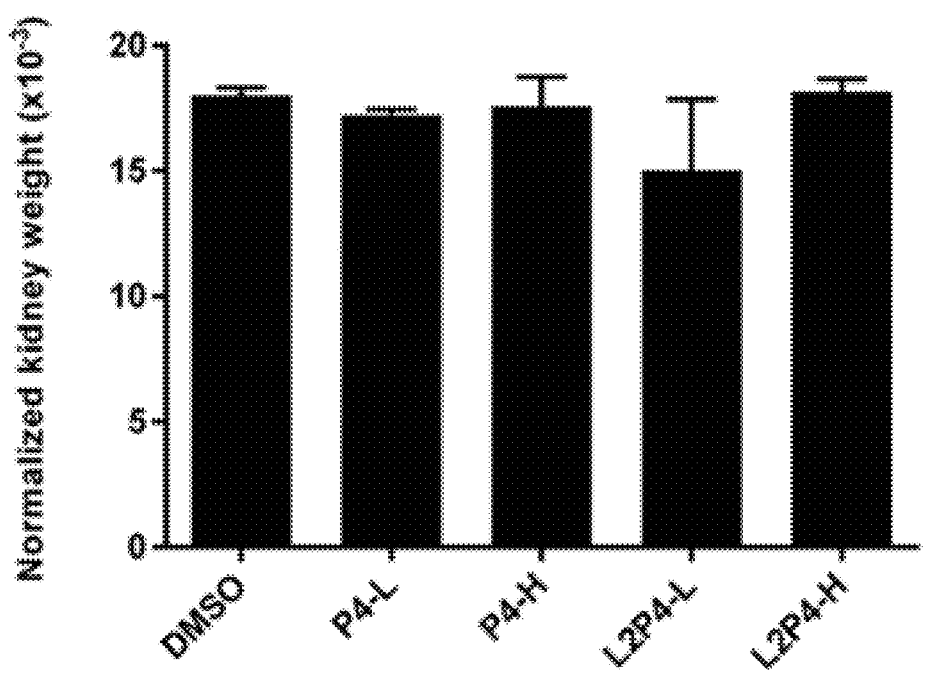

FIG. 41D shows the vital organ weights (kidney) of mice after treated with different drugs in 21 days.

Figure 41E:
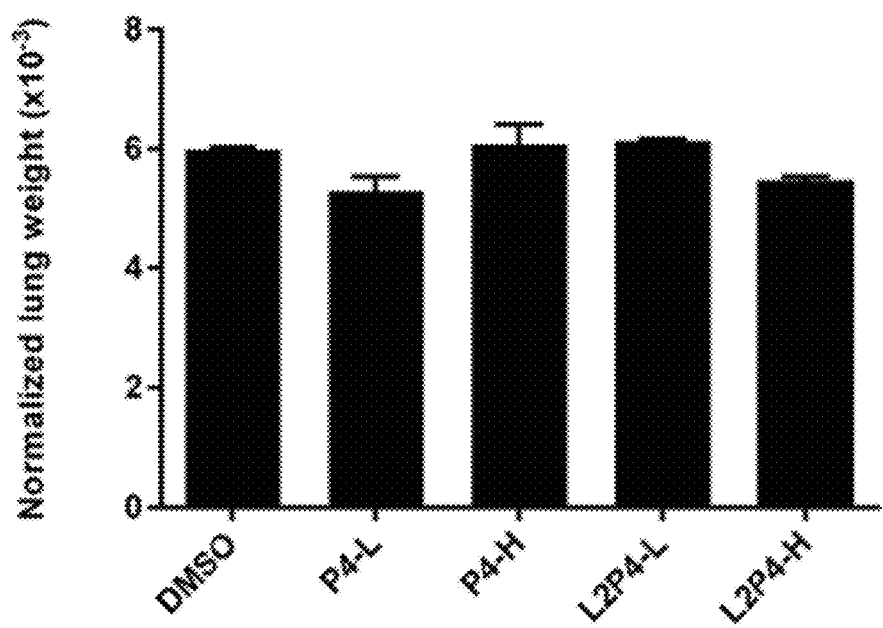

FIG. 41E shows the vital organ weights (lung) of mice after treated with different drugs in 21 days.

Figure 42A:
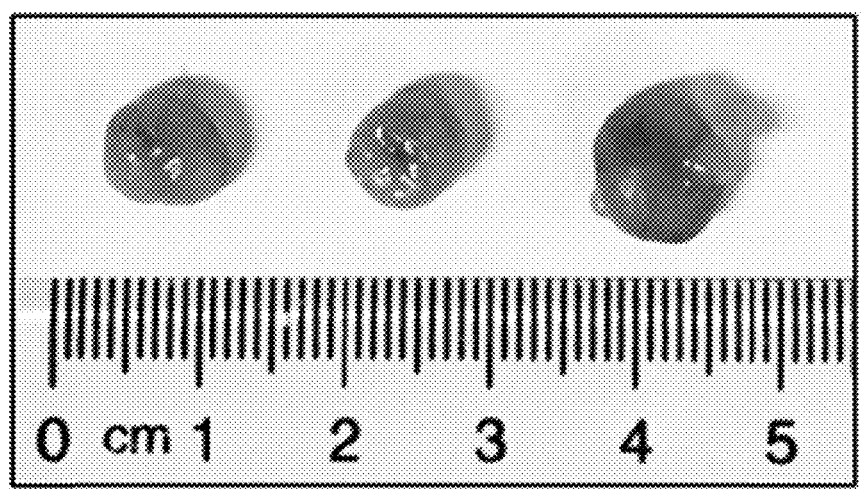

FIG. 42A shows the tumor sizes of mice after treated with $P_4$-L (low dosage of $P_4$, 2 μg/tumor).

Figure 42B:
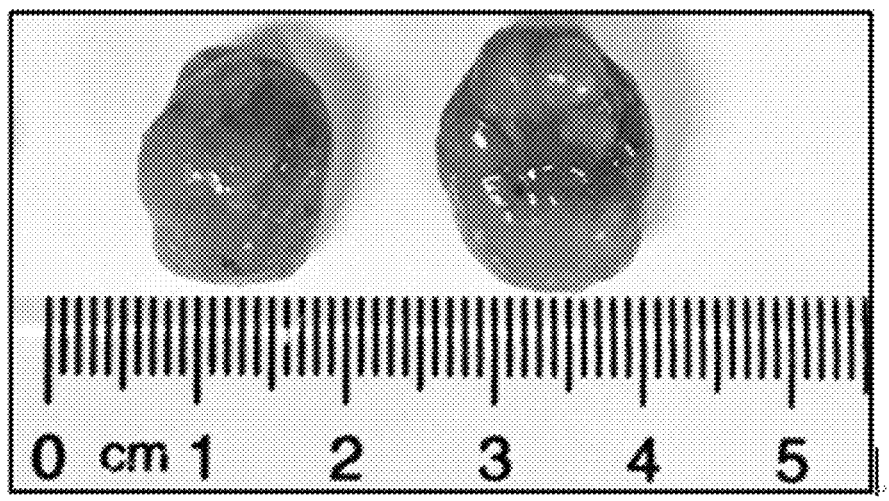

FIG. 42B shows the tumor sizes of mice after treated with $L_2P_4$-L (low dosage of $L_2P_4$, 2 μg/tumor).

Figure 43A:
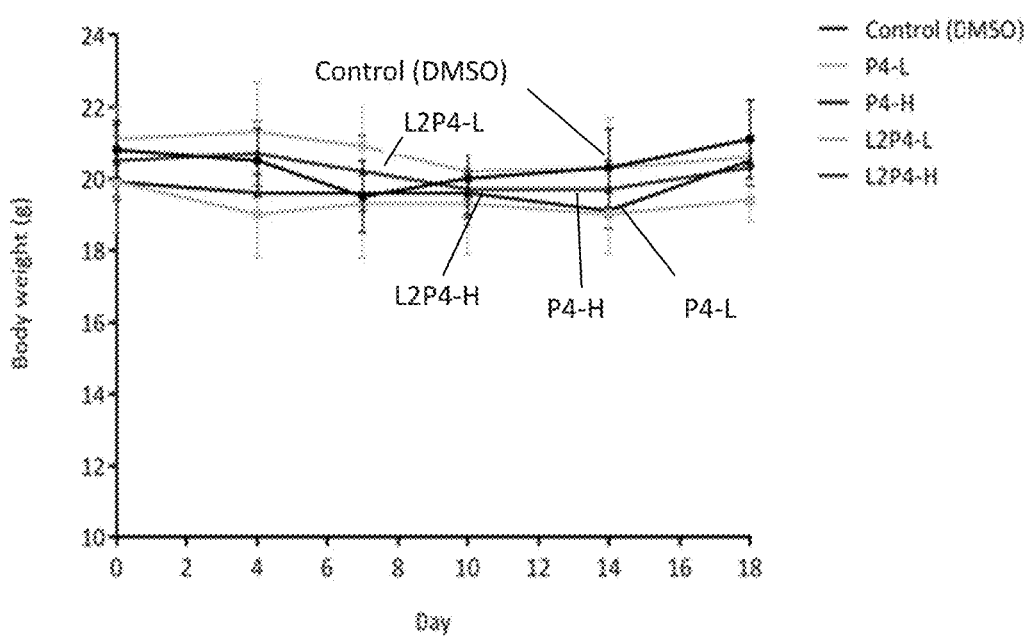

FIG. 43A shows the body weights of mice carrying HeLa xenografts after treated with intra-tumoral injections of $P_4$, $L_2P_4$ (low or high dose) or DMSO twice weekly for 18 days.

Figure 43B:
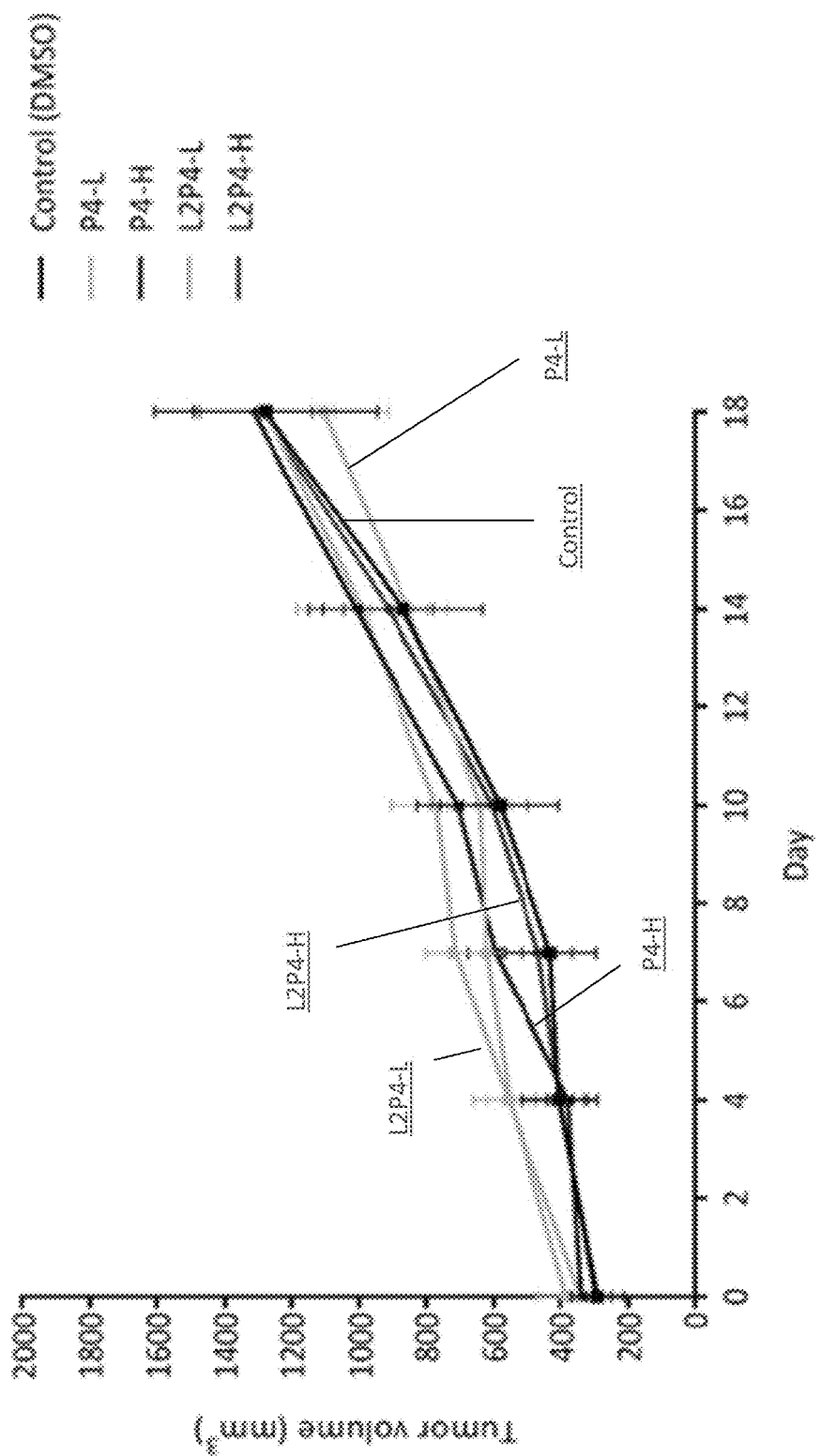

FIG. 43B shows tumor volume of mice carrying HeLa xenografts after treated with intra-tumoral injections of $P_4$, $L_2P_4$ (low or high dose) or DMSO twice weekly for 18 days.

Figure 43C:
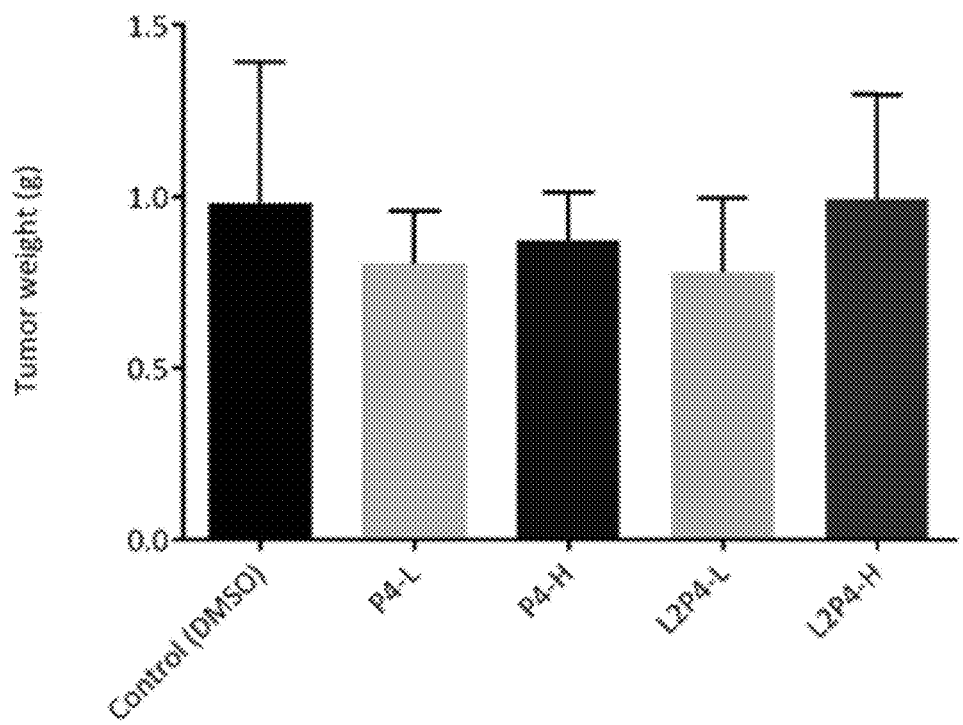

FIG. 43C shows tumor weights of mice carrying HeLa xenografts after treated with intra-tumoral injections of $P_4$, $L_2P_4$ (low or high dose) or DMSO twice weekly for 18 days. At the experimental endpoint, tumors were excised and weighed. Average tumor weights of tumors from each group in grams ±SEM.

Figure 44:
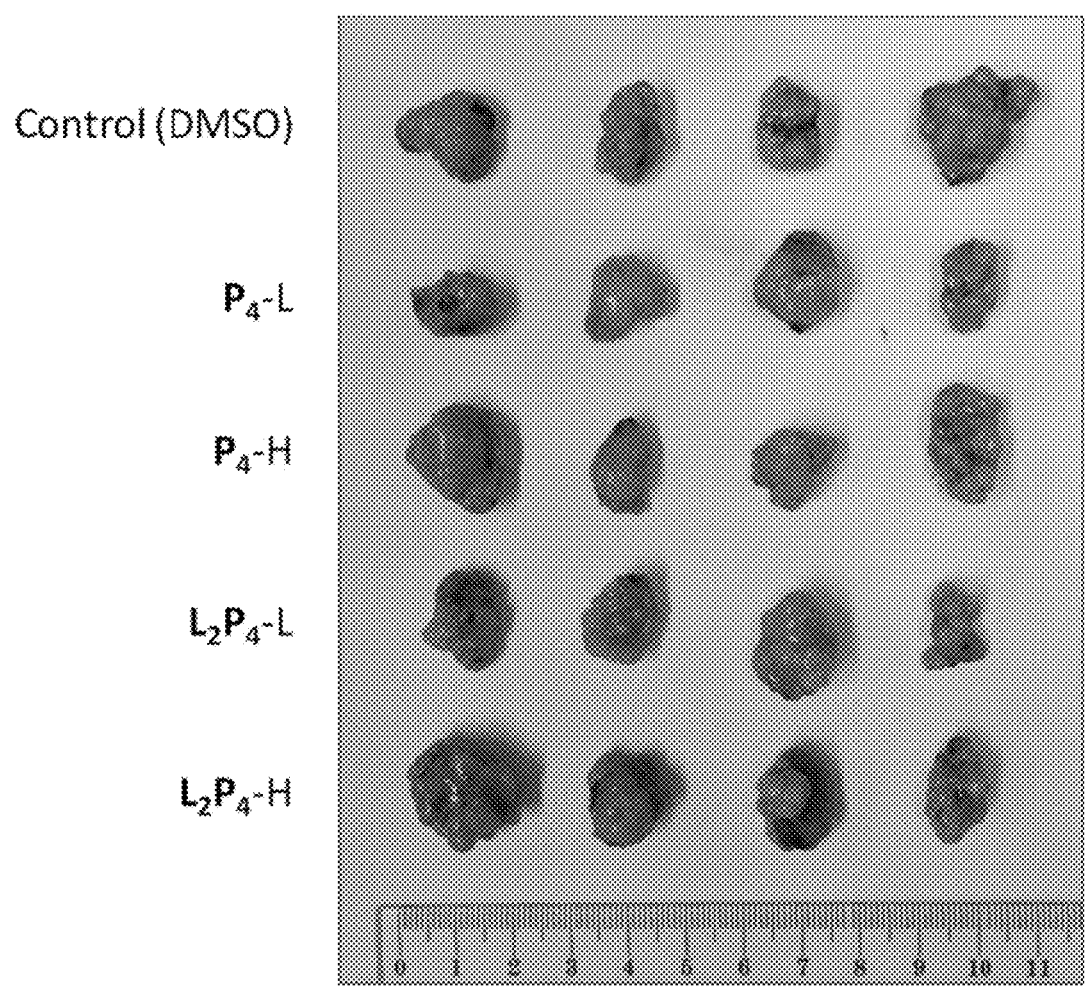

FIG. 44 shows the images of tumors from mice carrying HeLa xenografts after treated with intra-tumoral injections of $P_4$, $L_2P_4$ (low or high dose) or DMSO twice weekly after 18 days. Tumors were excised upon mice sacrifice and photographed. Images show representative tumors from each group.

Figure 9:
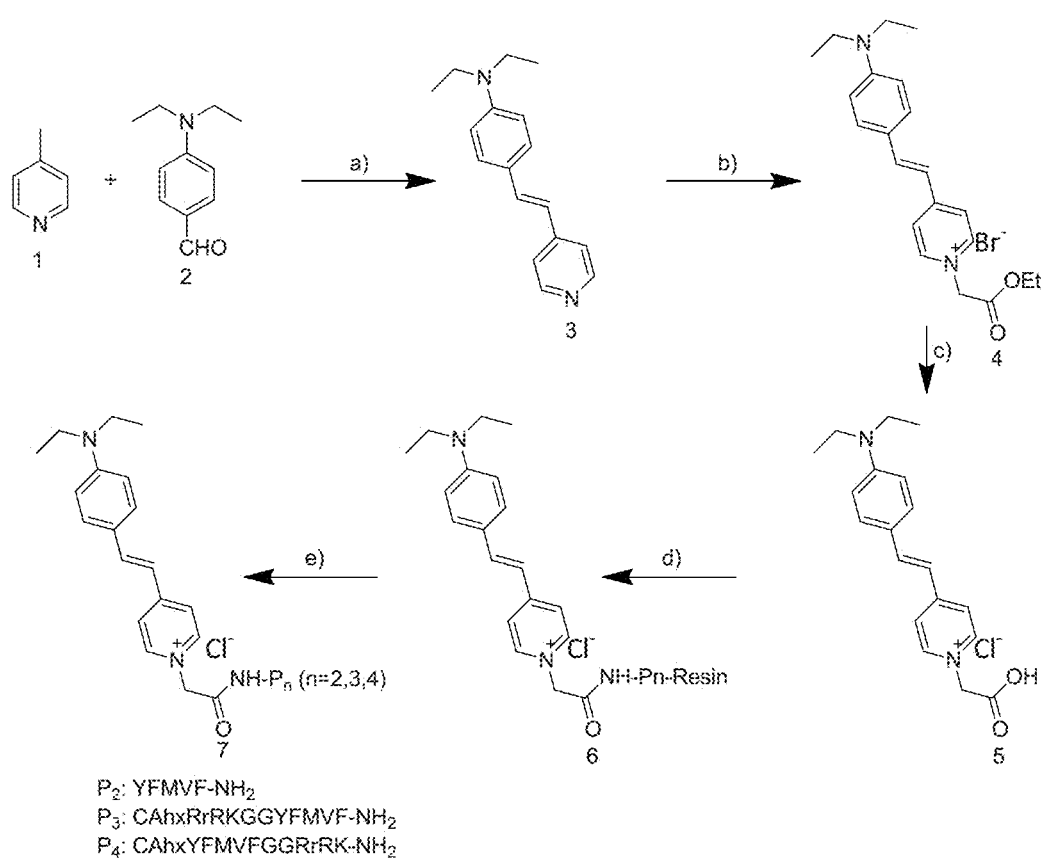
FIG. 9 shows the synthetic routes of $L_2P_2$, $L_2P_3$ and $L_2P_4$.
Figure 45:
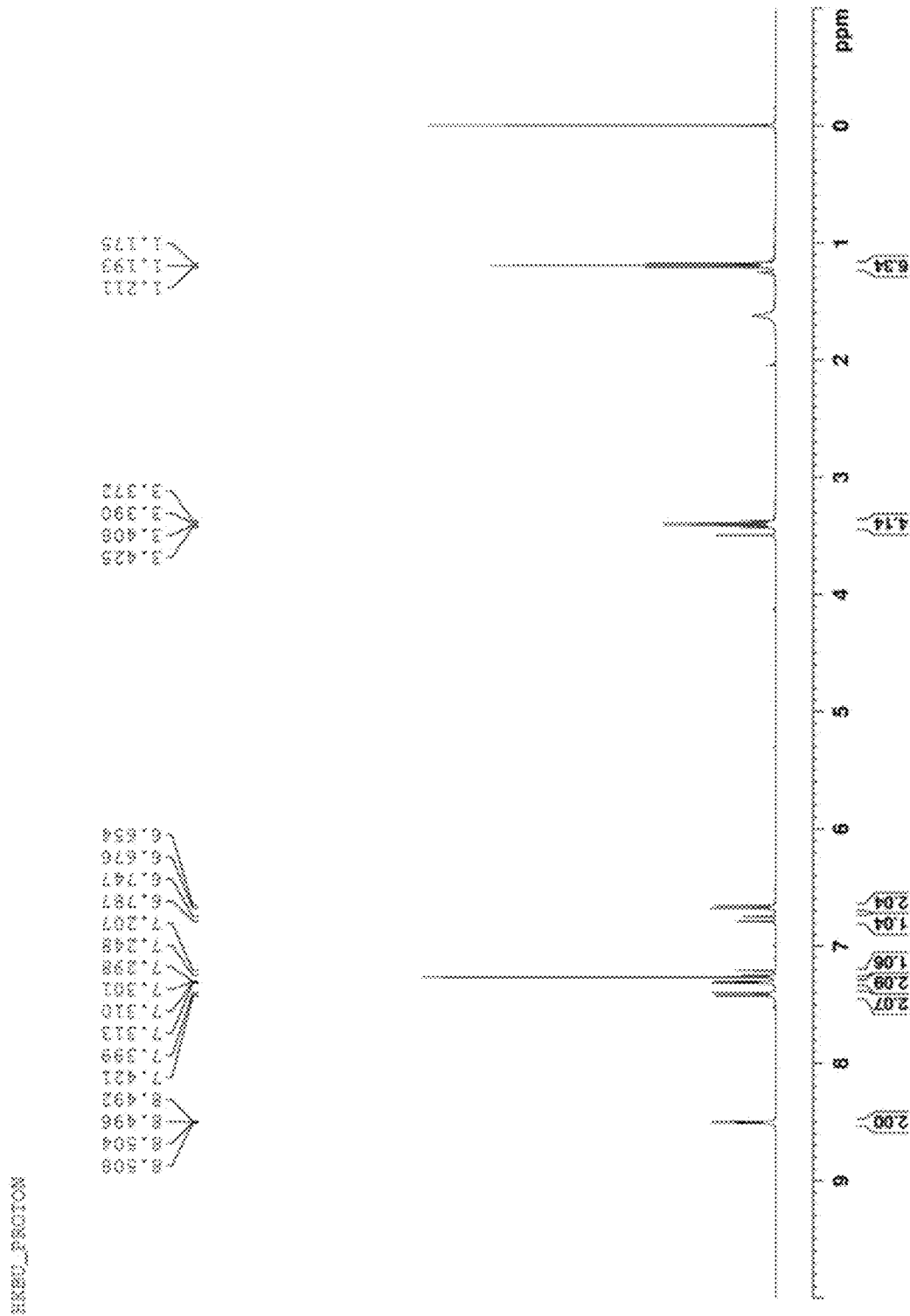

FIG. 45 shows the 400 MHz-$^1$H-NMR (CDCl$_3$) spectrum of compound 3 in FIG. 9.

Figure 46:
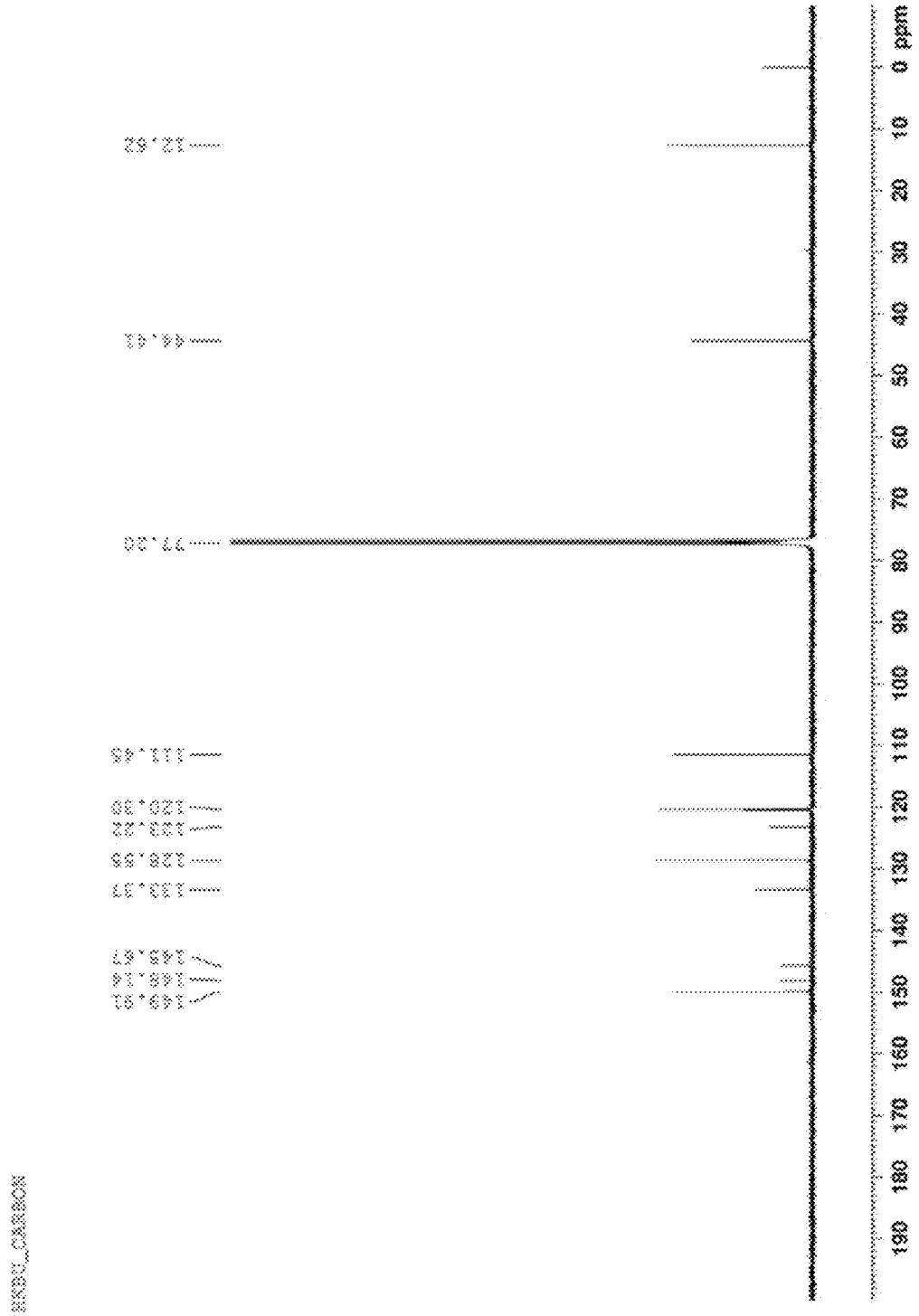

FIG. 46 shows the 100 MHz-$^{13}$C-NMR (CDCl$_3$) spectrum of compound 3 in FIG. 9.

Figure 47:
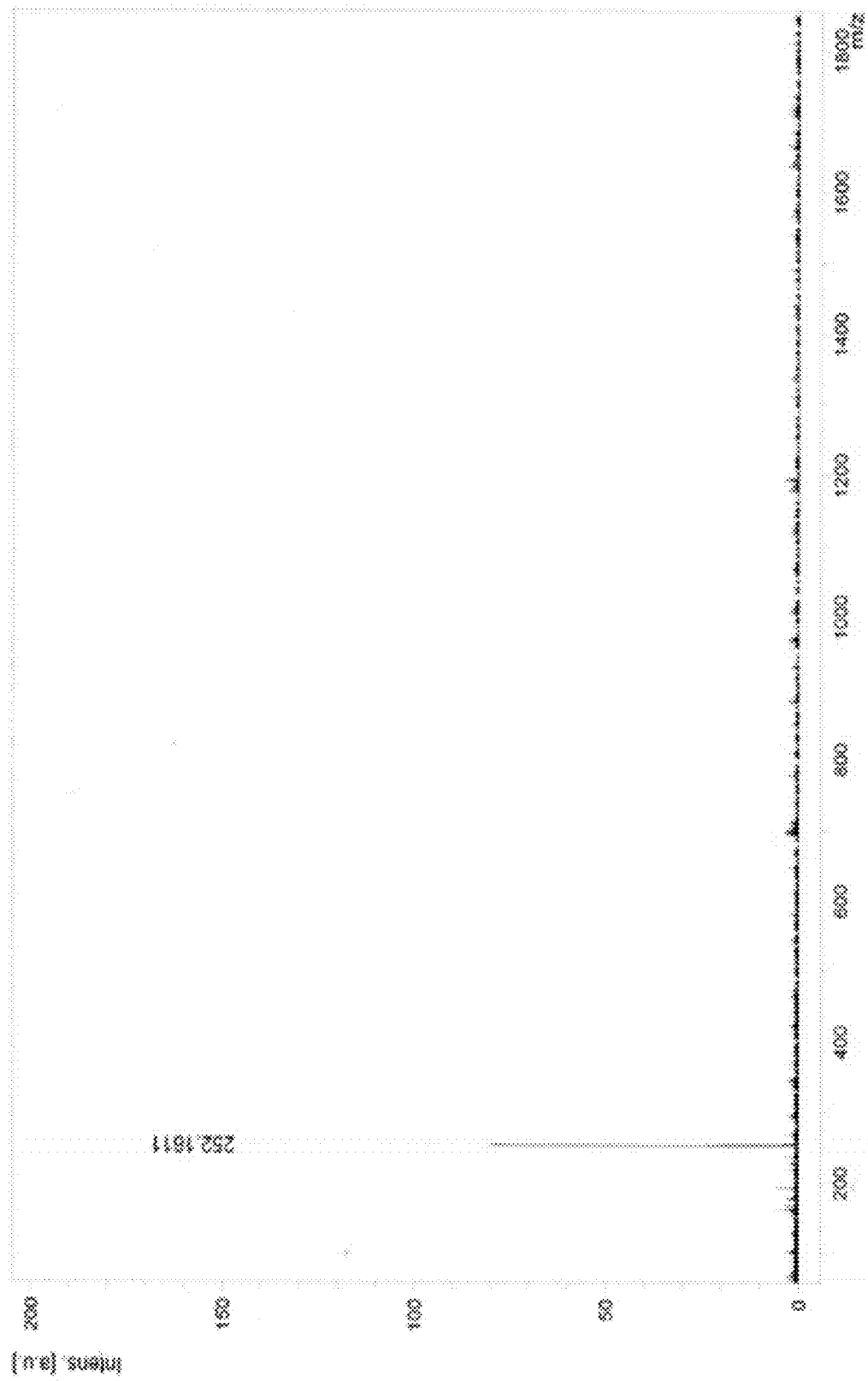

FIG. 47 shows the MALDI-TOF spectrum of compound 3 in FIG. 9, HRMS (m/z): [M]$^+$ calculated for C$_{17}$H$_{20}$N$_2$, 252.1626; found, 252.1611; error, −6 ppm.

Figure 48:
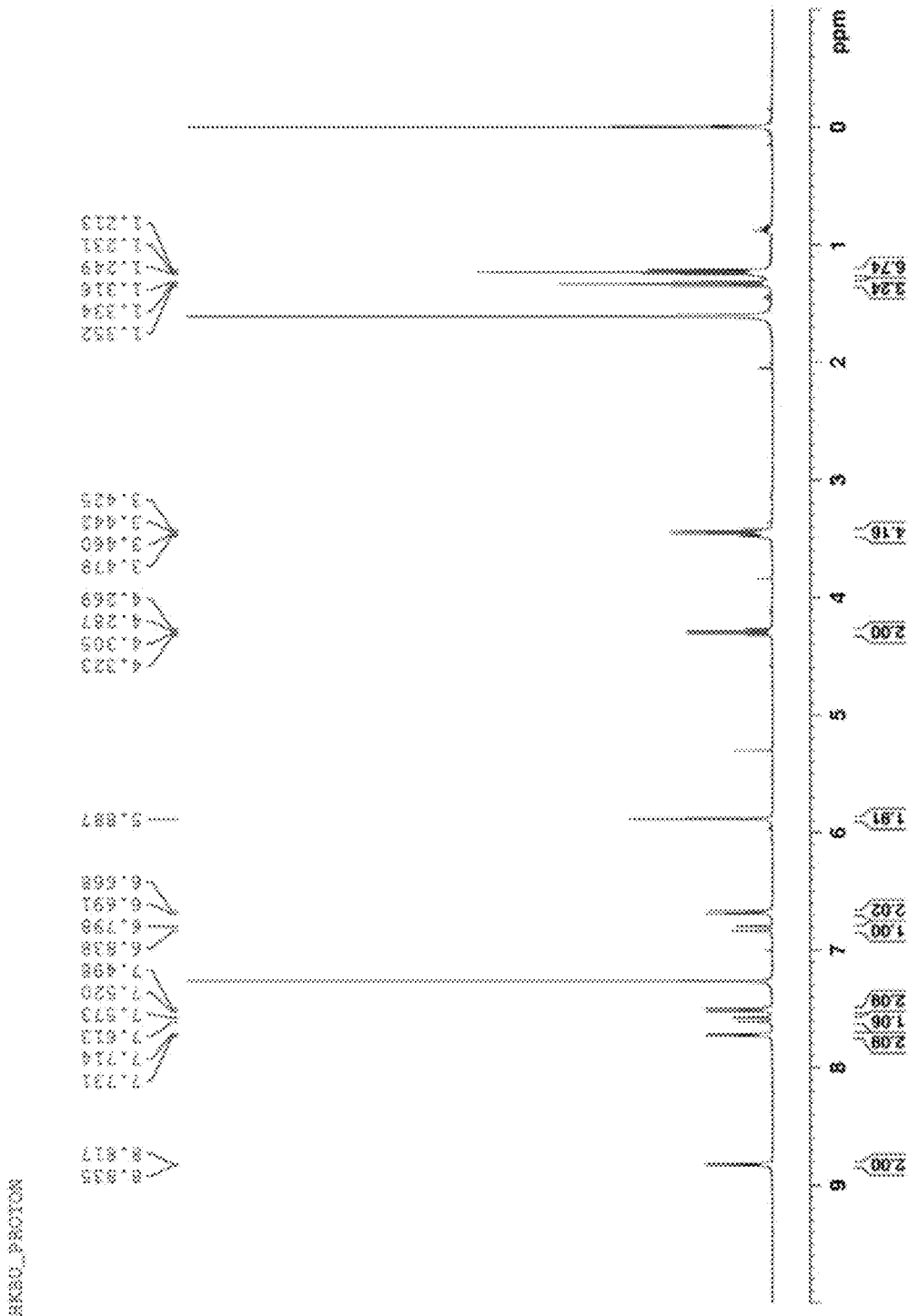

FIG. 48 shows the 400 MHz-$^1$H-NMR (CDCl$_3$) spectrum of compound 4 in FIG. 9.

Figure 49:
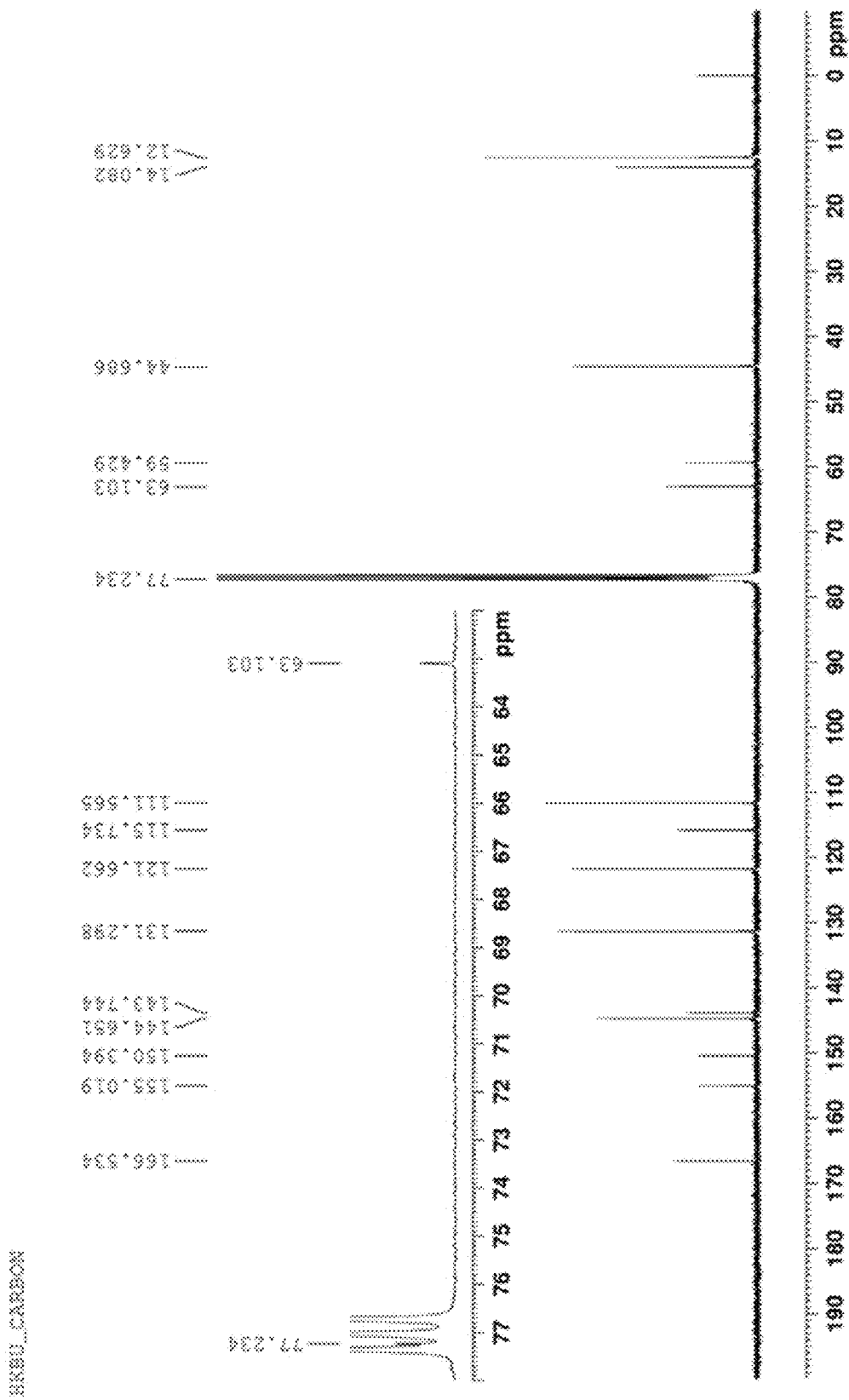

FIG. 49 shows the 100 MHz-$^{13}$C-NMR (CDCl$_3$) spectrum of compound 4 in FIG. 9.

Figure 50:
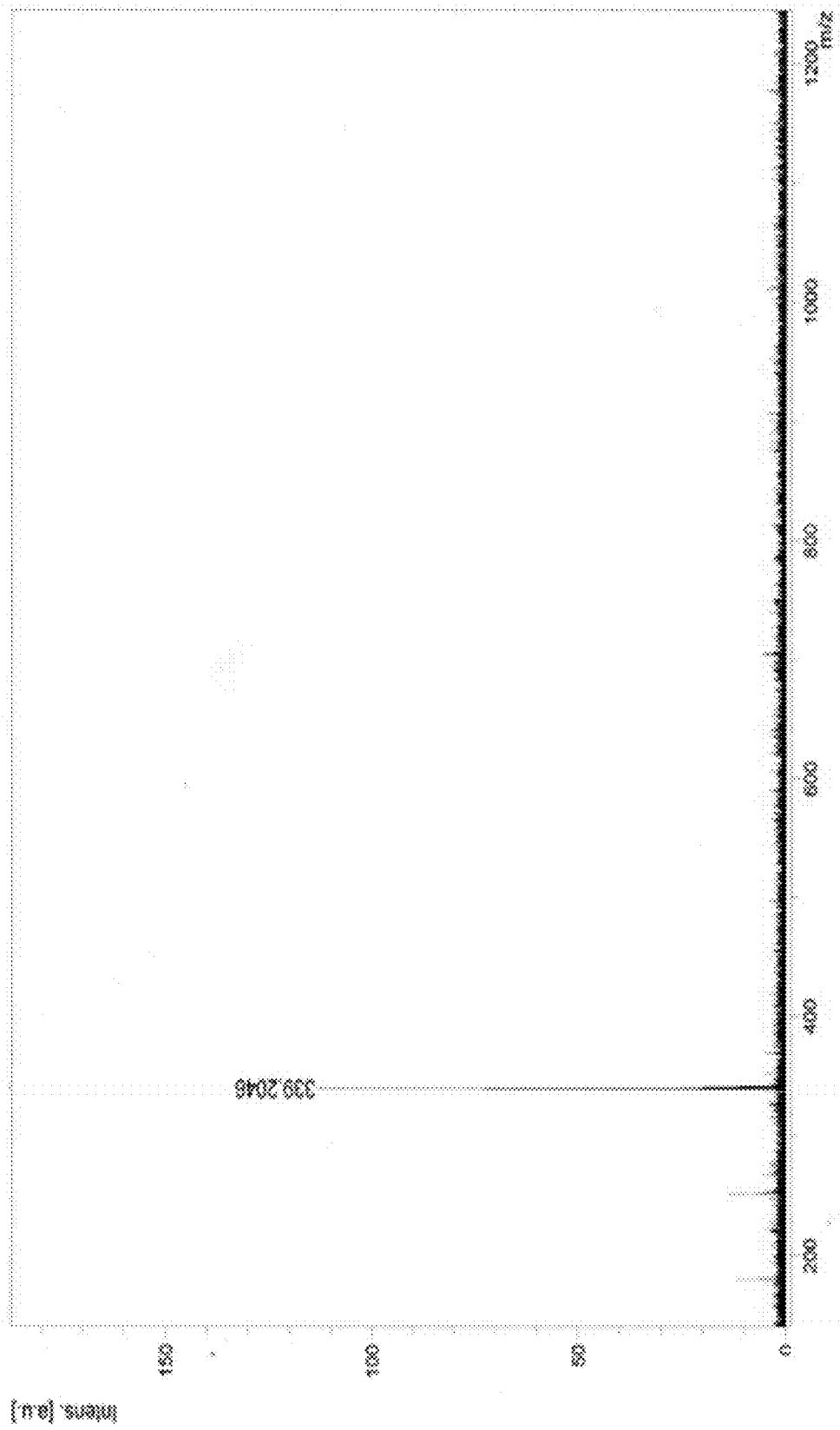

FIG. 50 shows the MALDI-TOF spectrum of compound 4 in FIG. 9, HRMS (m/z): [M]$^+$ calculated for C$_{21}$H$_{27}$N$_2$O$_2^+$, 339.2067; found, 339.2046; error: −6 ppm.

Figure 51:
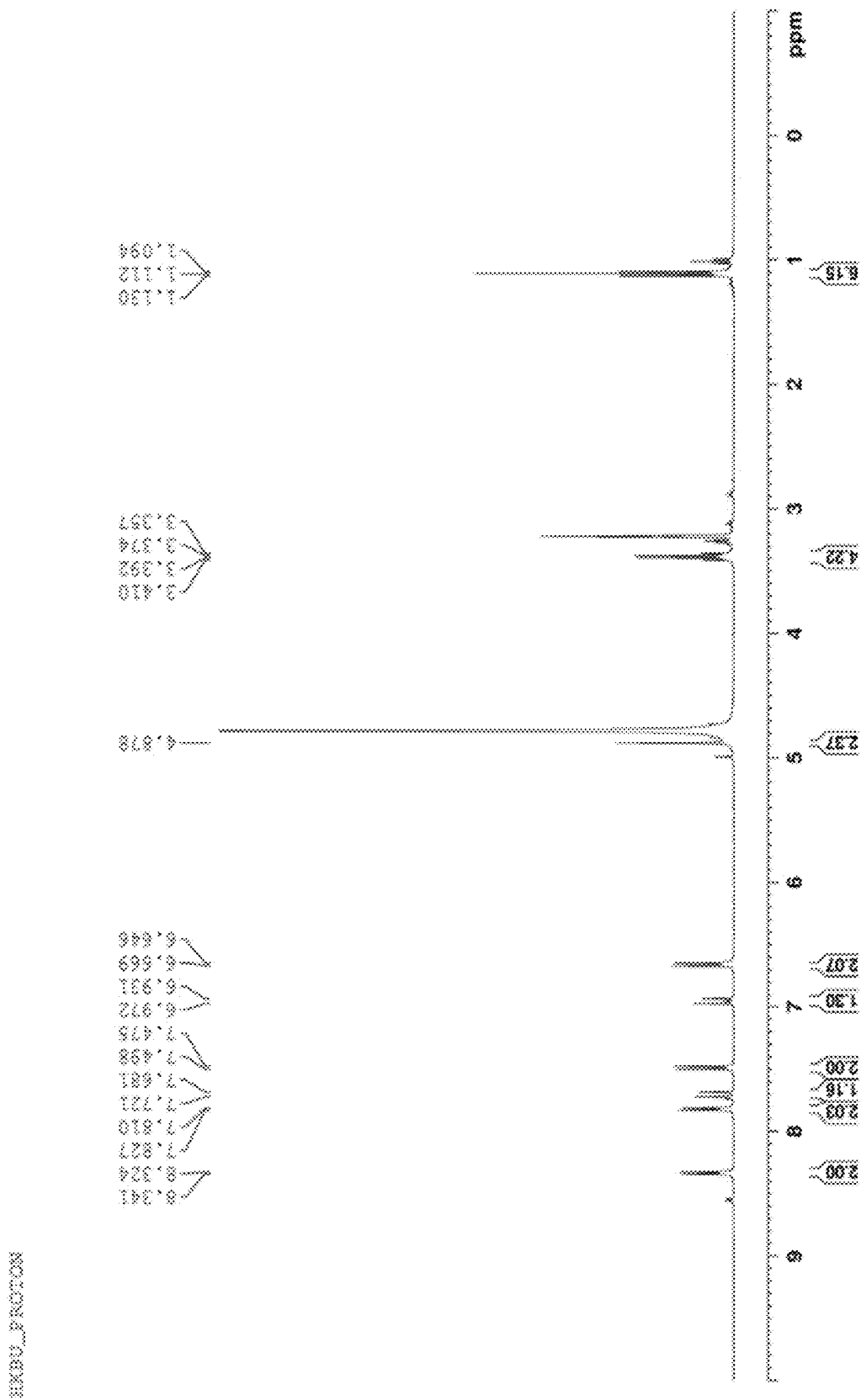

FIG. 51 shows the 400 MHz-$^1$H-NMR (MeOD) spectrum of compound 5 in FIG. 9.

Figure 52:
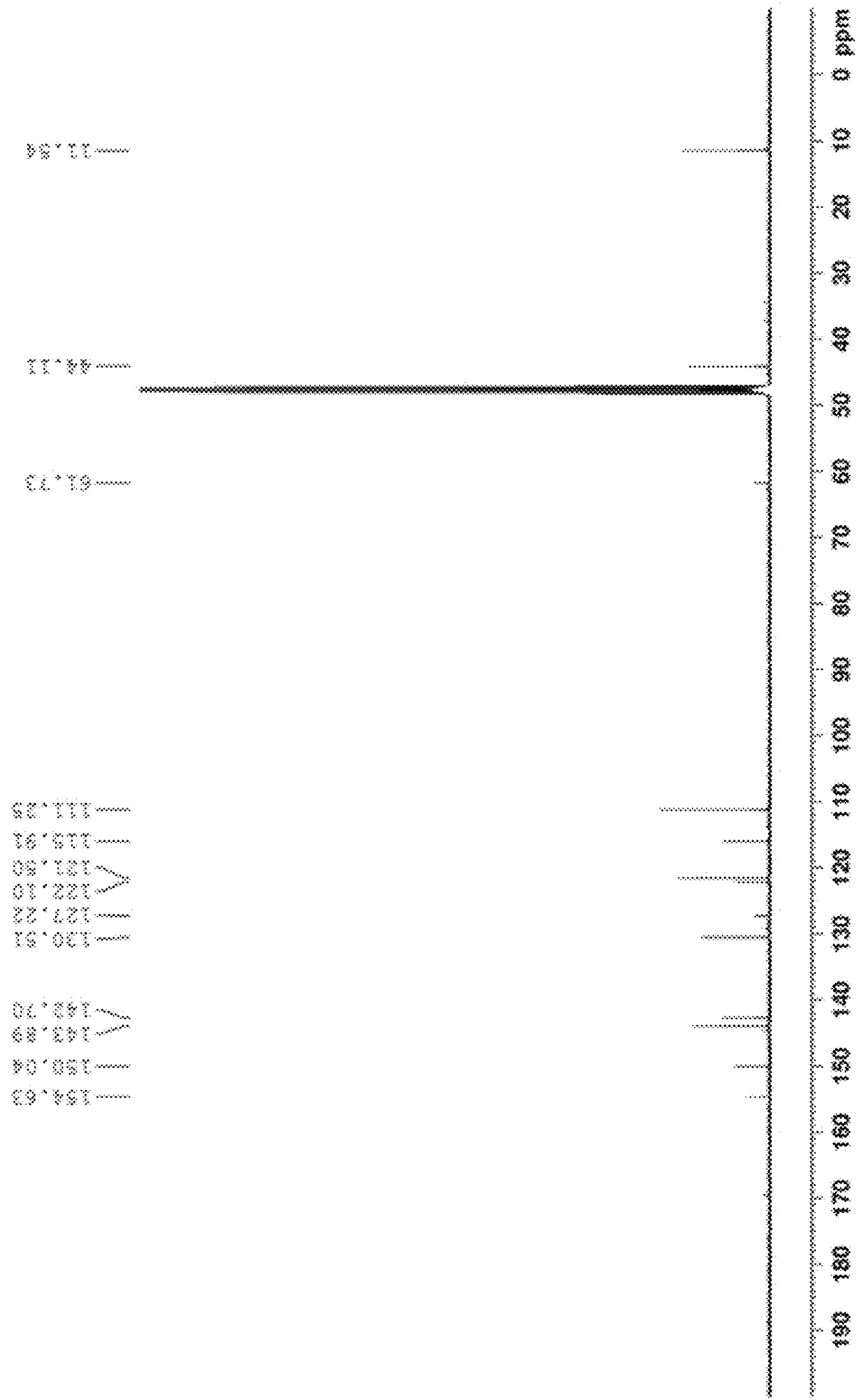

FIG. 52 shows the 100 MHz-$^{13}$C-NMR (MeOD) spectrum of compound 5 in FIG. 9.

Figure 53:
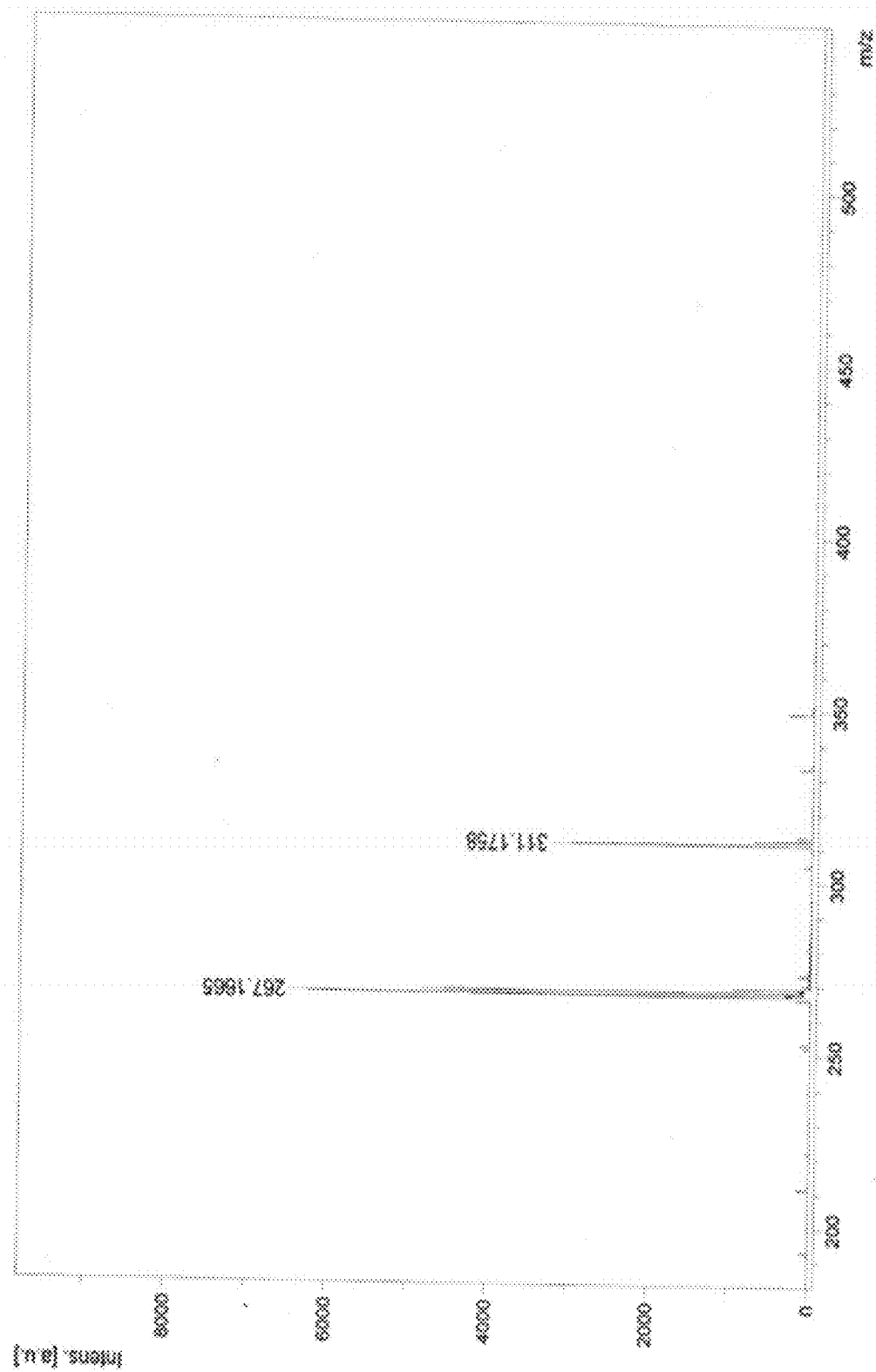

FIG. 53 shows the MALDI-TOF spectrum of compound 5 in FIG. 9, HRMS (m/z): [M]$^+$ calculated for C$_{19}$H$_{23}$N$_2$O$_2^+$, 311.1754; found, 311.1758; error: 1 ppm.

Figure 54:
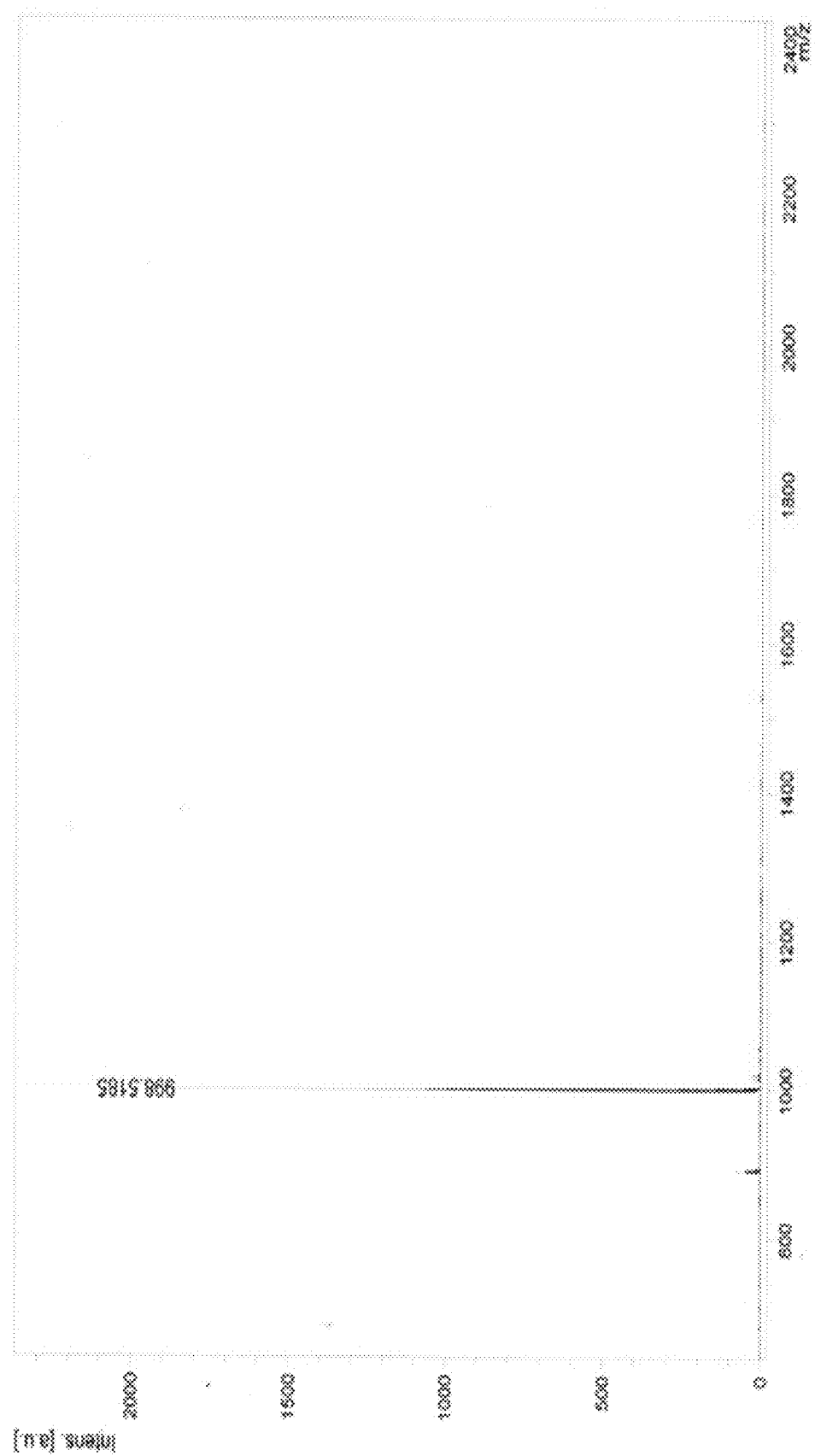

FIG. 54 shows the MALDI-TOF spectrum of L$_2$P$_2$, HRMS (m/z): [M]$^+$ calculated for C$_{56}$H$_{69}$N$_8$O$_7$S$^+$, 998.5083; found, 998.5185; error: 10 ppm.

Figure 55:
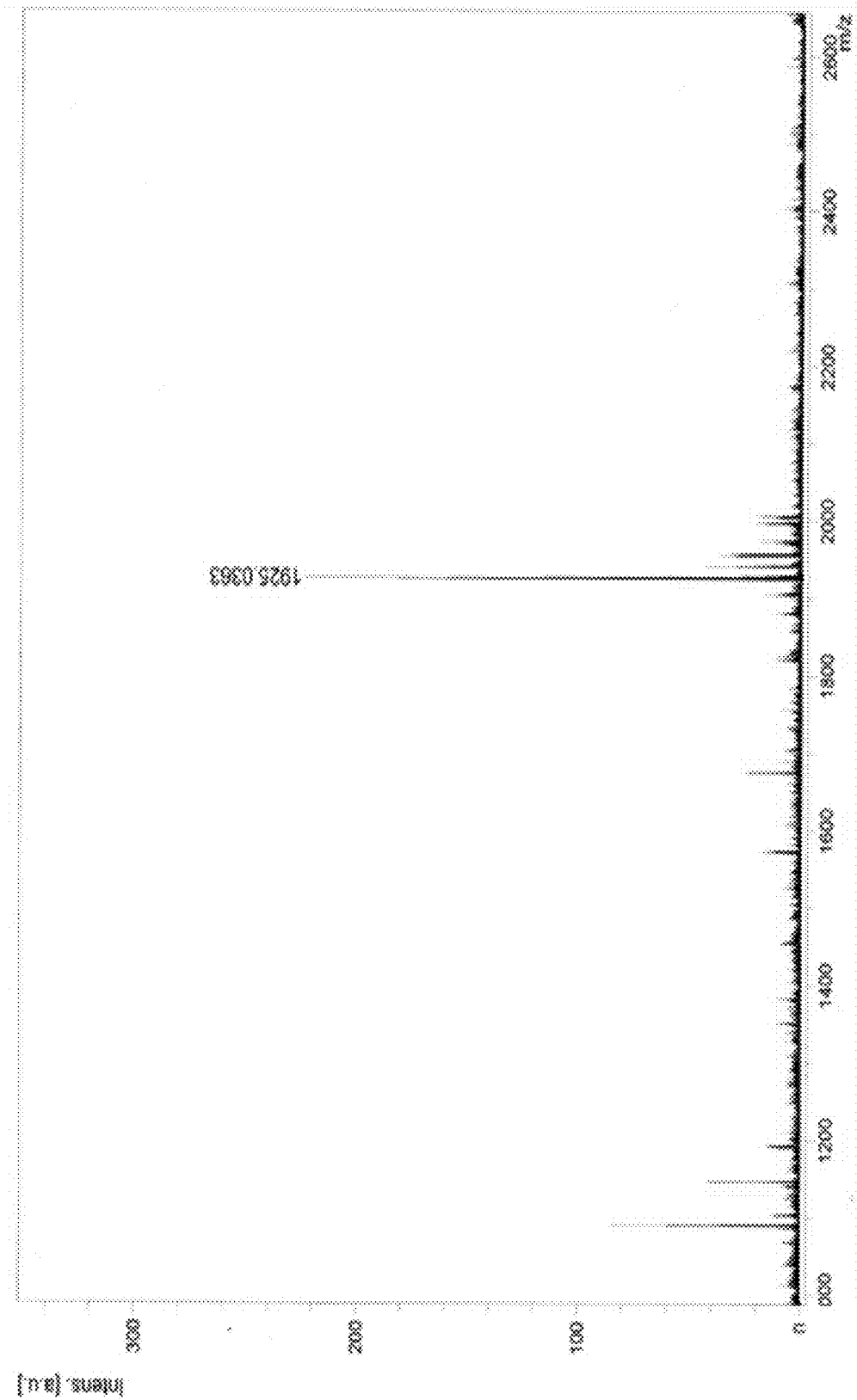

FIG. 55 shows the MALDI-TOF spectrum of L$_2$P$_3$, HRMS (m/z): [M+H]$^+$ calculated for C$_{93}$H$_{140}$N$_{26}$O$_{15}$S$_2^+$, 1925.0427; found, 1925.0363; error: −3 ppm.

Figure 56:
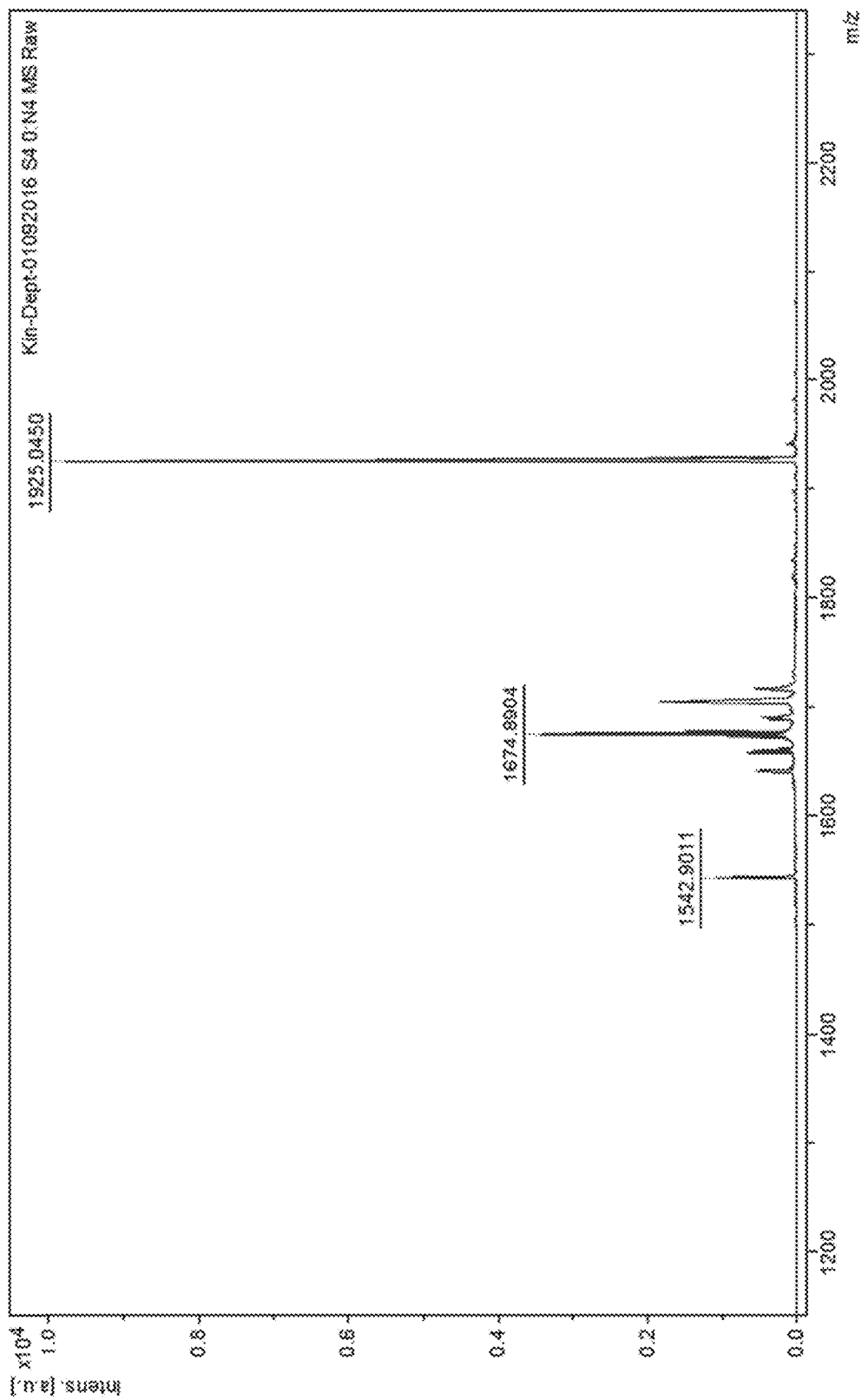

FIG. 56 shows the MALDI-TOF spectrum of L$_2$P$_4$, HRMS (m/z): [M+H]$^+$ calculated for C$_{93}$H$_{140}$N$_{26}$O$_{15}$S$_2^+$, 1925.0427; found, 1925.0450; error: 1 ppm.

Figure 57:
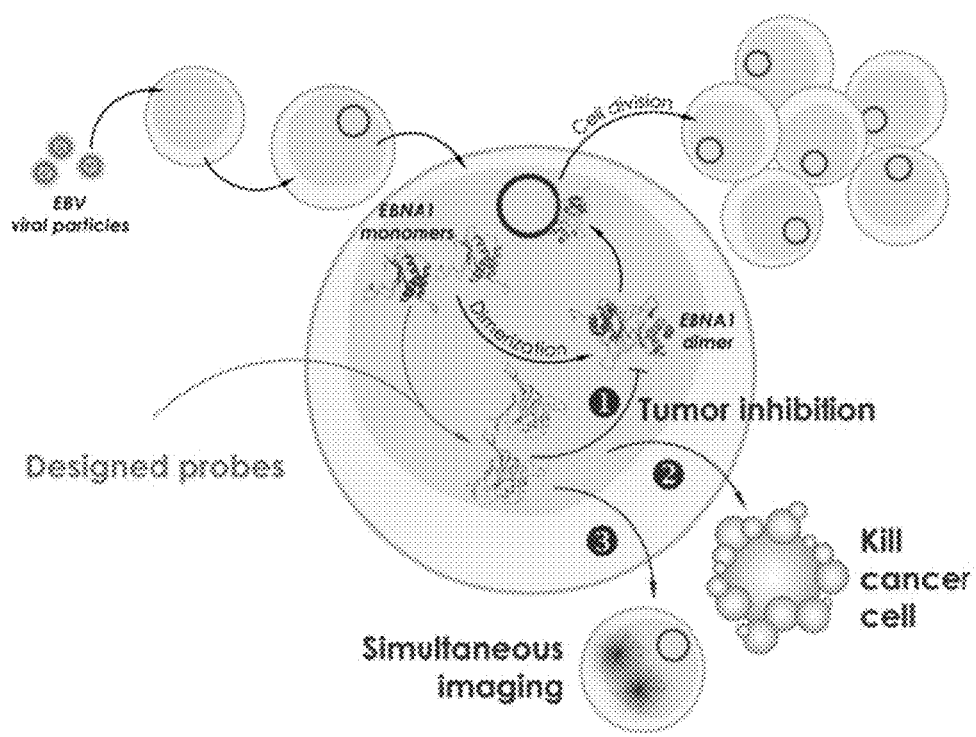

FIG. 57 shows illustrations of the peptide conjugates of the present invention and the use of the designed probes to kill cancer cell and imaging.

Figure 58:
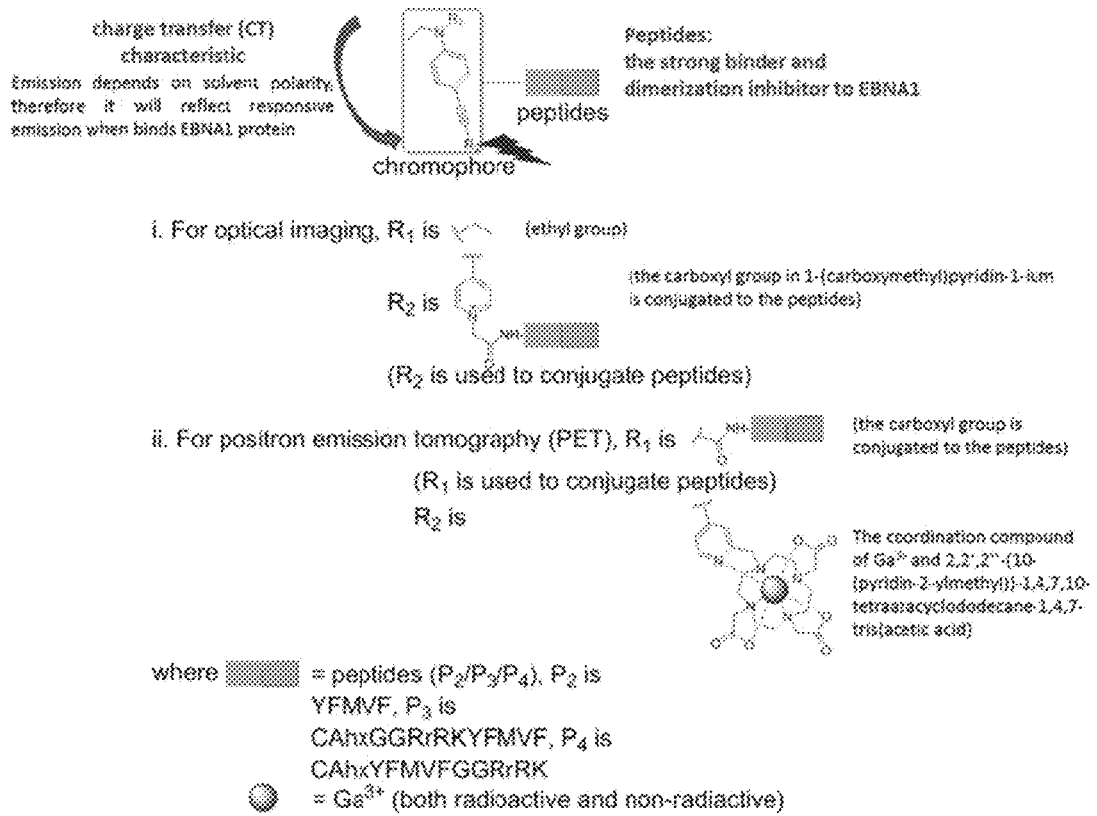

FIG. 58 shows the different synthesis pathways from the same L$_2$ structure family for L$_2$P$_4$ and L$_2$ with PET imaging.

Figure 59:
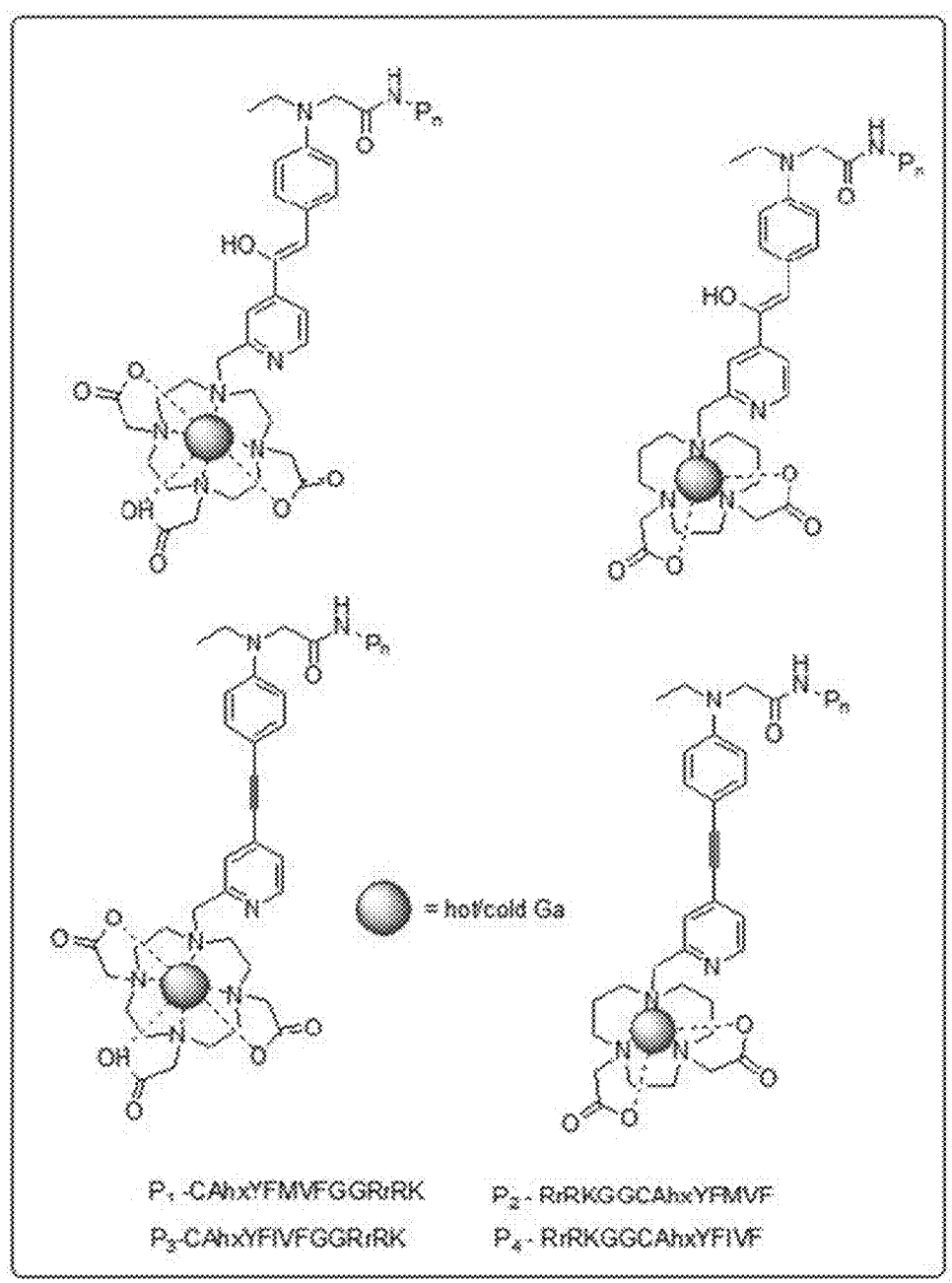

FIG. 59 shows successful synthesis of the peptide conjugated with particular PET available ligands.

Figure 60:
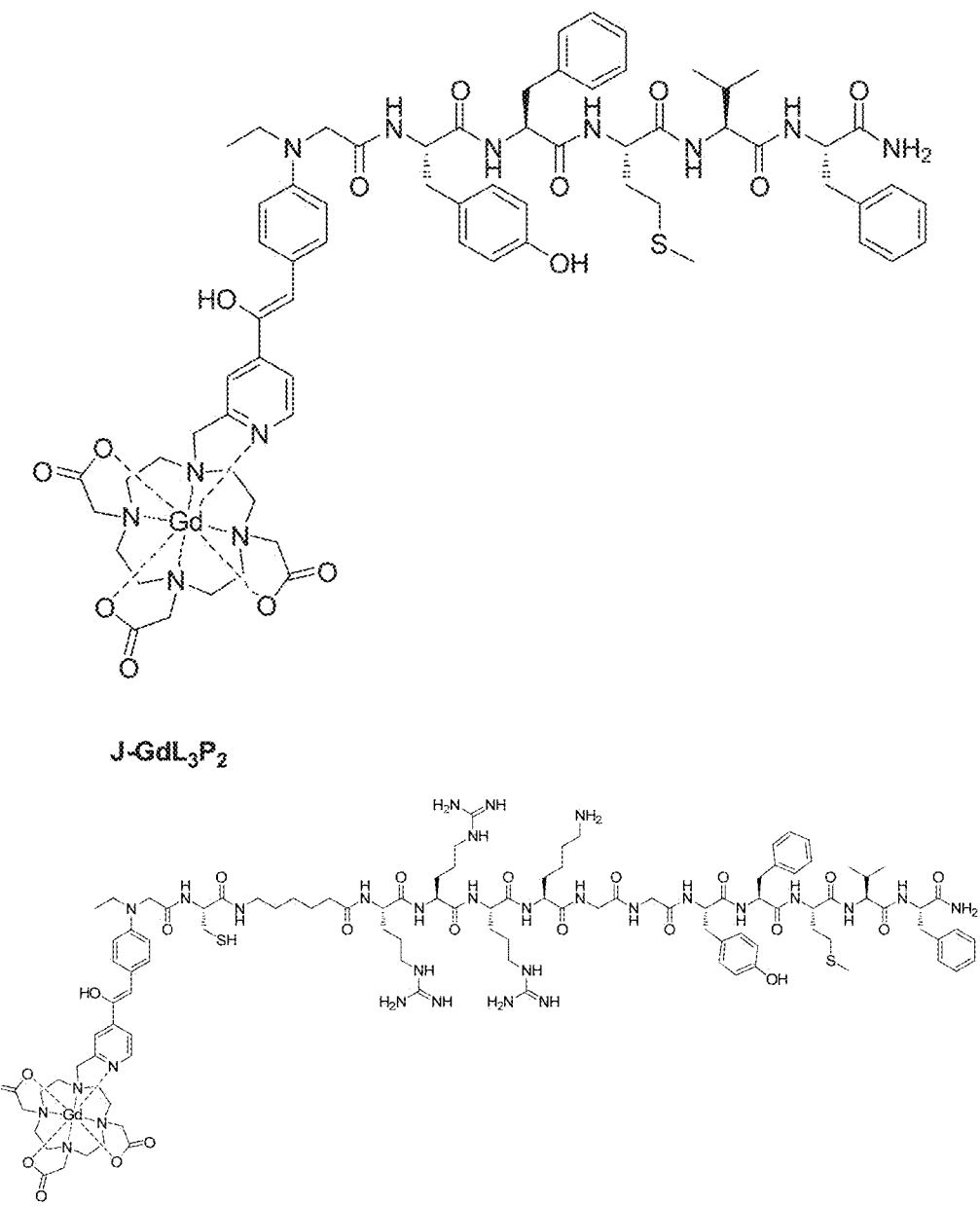
Figure 60:
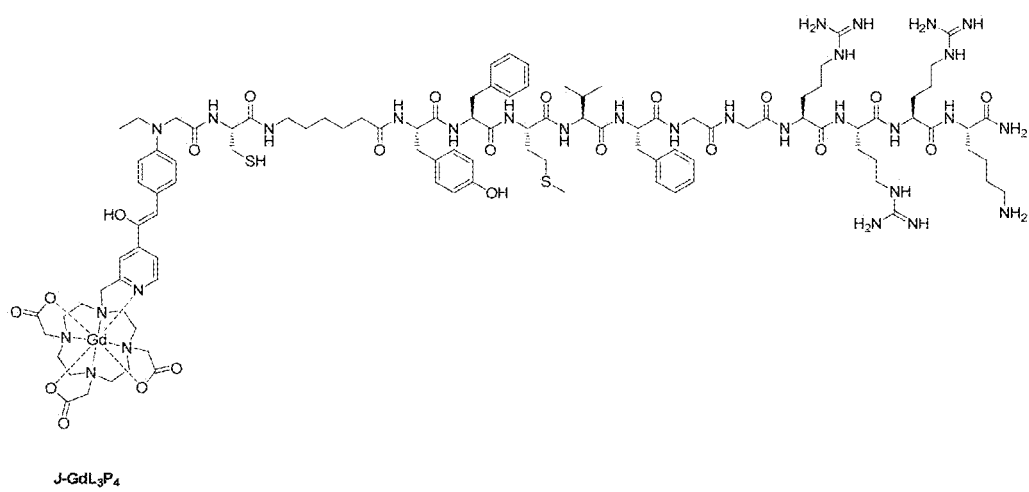
Figure 60:
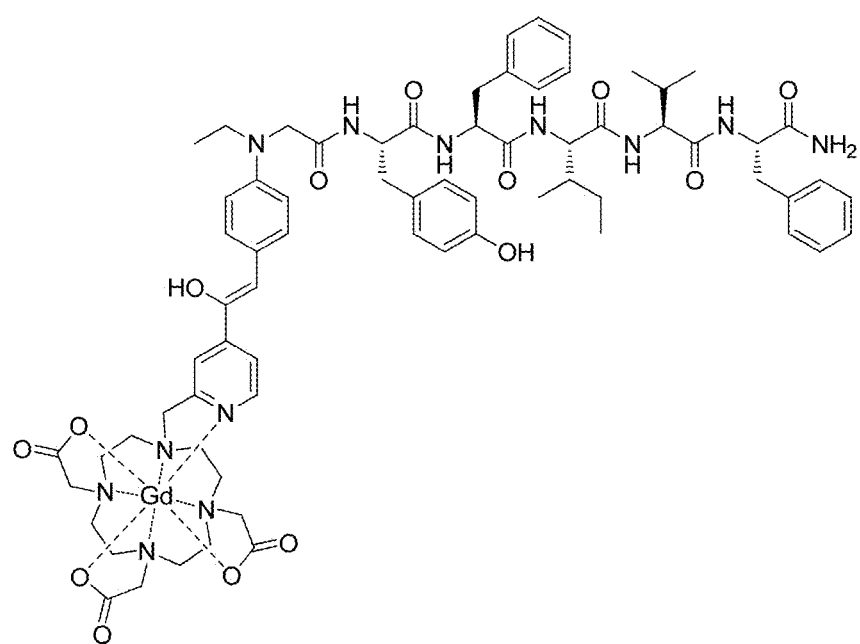

FIG. 60 shows embodiments of the present invention with MRI available ligands.

Figure 61:
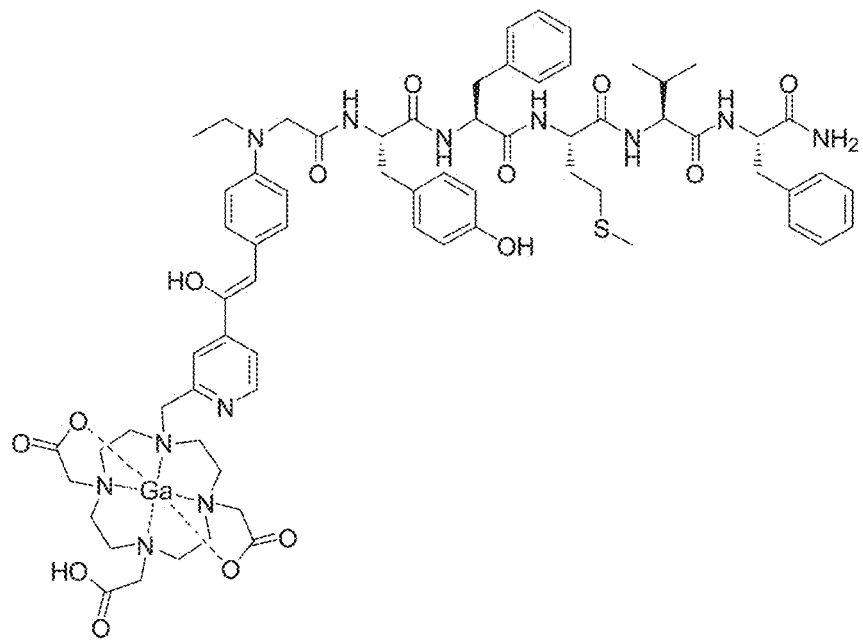
Figure 61:
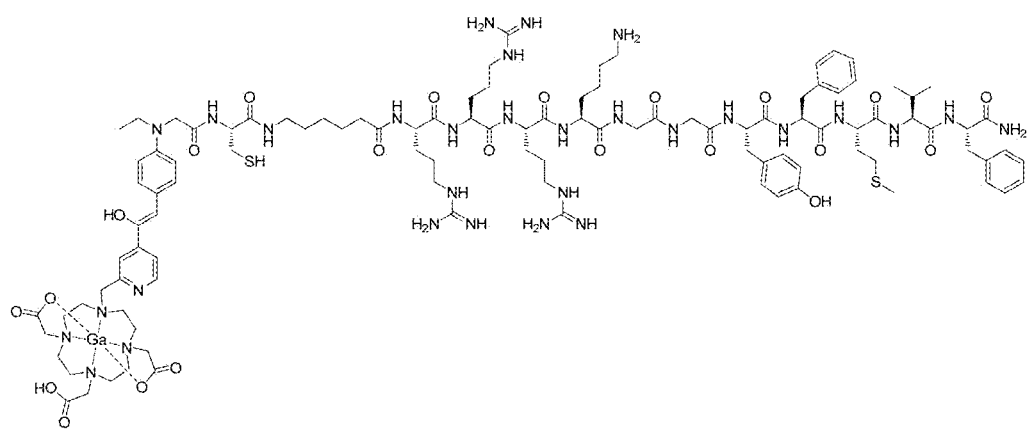
Figure 61:
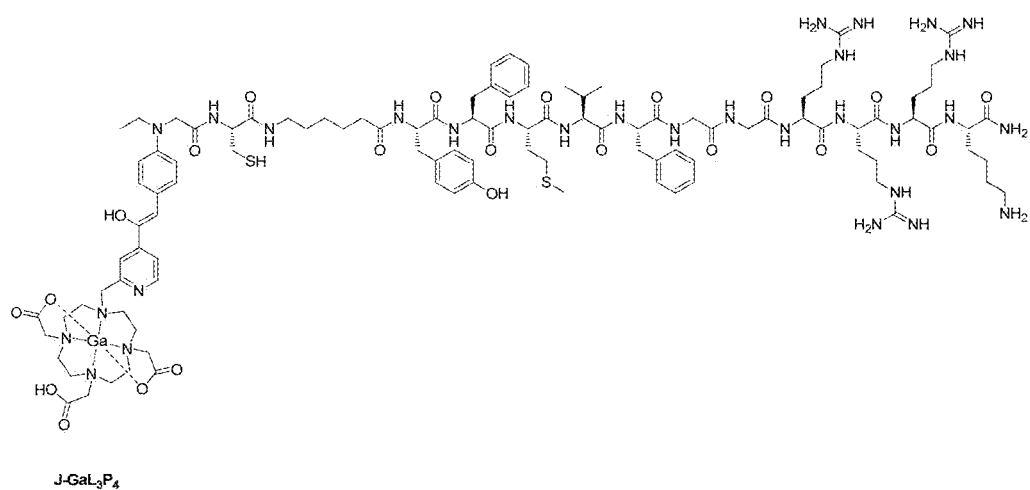
Figure 61:
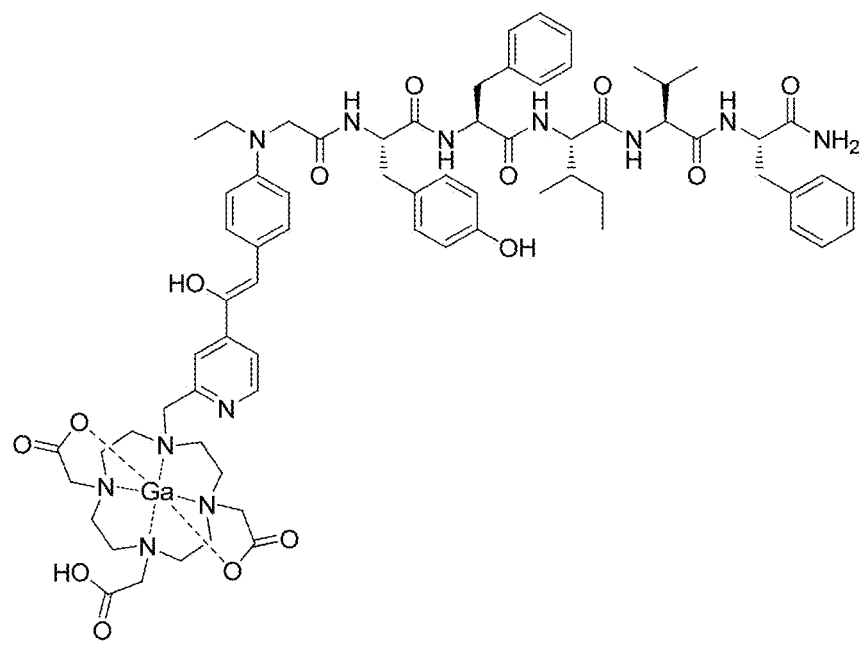

FIG. 61 shows embodiments of the present invention with PET ligands.

DETAILED DESCRIPTION OF INVENTION

The present invention is not to be limited in scope by any of the specific embodiments described herein. The following embodiments are presented for exemplification only.

The Epstein-Barr virus (EBV) is a ubiquitous human herpes virus that causes both infectious mononucleosis and lymphoproliferative diseases, but the virus is well controlled by the immune system once it establishes latent infection in human hosts. Epstein-Barr nuclear antigen 1 (EBNA1) is the only oncoprotein expressed in all EBV-positive tumors and it plays critical roles in maintenance, replication and transcription of the EBV genome. Furthermore, EBNA1 can influence cellular gene transcription, which is fundamental to the development of EBV-related tumors. Given these key biological functions, EBNA1 has become an attractive target for therapeutic intervention.

Considering that homodimerization of EBNA1 is essential for EBNA1 to function, inhibitors that can specifically prevent the dimerization process offer a novel avenue to target and kill the EBV-positive cells. Several EBNA1 inhibitors have been reported to efficiently block EBNA1 homodimerization, including the small molecule, EiK1, and a short EBNA1-derived peptide, P$_{85}$. Eikl was identified via high-throughput screening, and it's capable of targeting the dimeric interface of EBNA1 (residues 459-607). P$_{85}$, which contains a short EBNA1-derived β3 sheet (residues 560-566), also targets this region (residues 560-574). However, most of the EBNA1-targeting compounds that have been reported to date cannot be easily imaged (in vitro) and they have low bioavailability. Both the aforementioned issues present major challenges to the field and hamper the further development of EBNA1-targeting therapeutics. In the art, there is also a hybrid bioconjugate, JLP2, which contains a charged, water-soluble chromophore and an EBNA-1 specific peptide. While JLP2 made specific imaging and inhibition of EBNA1 in vitro possible, JLP2 lacks specific subcellular localization and displayed no responsive binding, which limited its further development as a tool for cellular imaging, and as a selective therapeutic agent for the treatment of EBV cancers.

It is also worth noting that EBNA1 is primarily localized in the nucleus of EBV-positive cells, and EBNA1 acts as a bridge between mitotic chromosomes and origin of replication (oriP) of plasmids. One factor that has limited the success of cancer therapies is the challenge of specifically targeting a desired cell type. A direct and sensitive system for visualizing EBNA1 in the nucleus and monitoring its effect on EBNA1 homodimerization is not currently available. To address this problem, there is a need to provide a nucleus-penetrating EBNA1-specific dual-probe for selective EBV cancer imaging and inhibition in vitro and in vivo. The development of responsive nucleus-permeable bioprobes for in vitro microscopic studies of EBNA1 and in vivo selective inhibition of EBV-positive tumor have not yet been explored in detail. To this end, the present invention provides peptide conjugate that are useful for responsive-emission imaging in EBV-positive cells and provides highly selective and efficient in vitro/vivo cytotoxicity to EBV-positive cells and tumors.

Figure 1A:
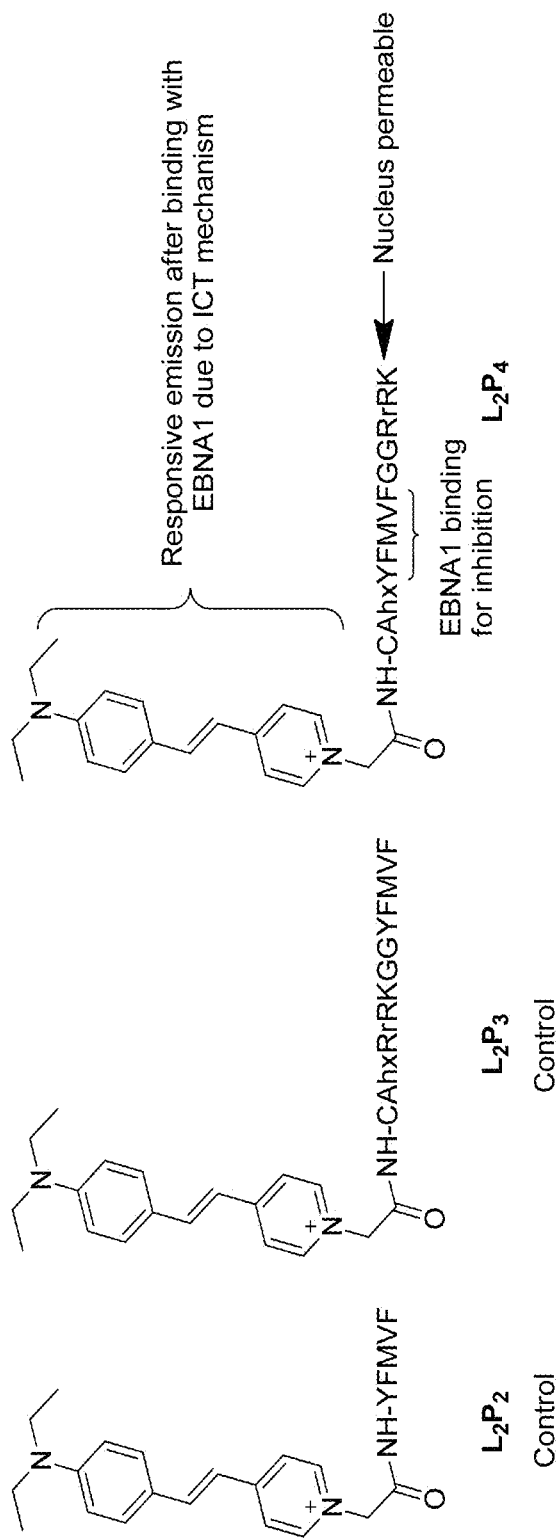
FIG. 1A shows the chemical structures of peptide conjugates $L_2P_2$, $L_2P_3$ and $L_2P_4$ of the present invention. $P_2$ (YFMVF) is a peptide derived from β4 of EBNA1 and it is EBNA1-specific. The $P_3$ (CAhxRrRKGGYFMVF, where Ahx is 6-aminohexanoic acid; R is L-arginine and r is D-arginine) and $P_4$ (CAhxYFMVFGGRrRK, where Ahx is 6-aminohexanoic acid) peptides are EBNA1-specific and nucleus-penetrating (due to addition of the RrRK motif in the middle ($P_3$) or at the C-terminus ($P_4$) of the sequence).

The dual-function peptide-conjugate probes, L$_2$P$_2$, L$_2$P$_3$ and L$_2$P$_4$, of the present application are shown in FIG. 1A and their synthesis is outlined in FIG. 9. L$_2$ is 4-(4-(Diethylamino)styryl)-N-carboxymethylpyridinium chloride and P$_2$, P$_3$ and P$_4$ are peptides of amino acid SEQ ID NO. 1, 2 and 3, respectively. P$_2$ (YFMVF) is a peptide derived from β4 of EBNA1 and it is EBNA1-specific. The P$_3$ (CAhxR-rRKGGYFMVF, where Ahx is 6-aminohexanoic acid; R is L-arginine and r is D-arginine) and P$_4$ (CAhxYFMVFGGR-rRK, where Ahx is 6-aminohexanoic acid) The characterization (including $^1$HNMR, $^{13}$CNMR and mass spectrometry) of the intermediates (compounds 3-5 in FIG. 9) and L$_2$P$_2$, L$_2$P$_3$ and L$_2$P$_4$ are shown in FIGS. 45-56. The peptide conjugates are purified via high-performance liquid chromatography; the purification and characterization procedures are provided in FIGS. 10A-14B. The L$_2$P$_4$ (where L$_2$ is 4-(4-(Diethylamino)styryl)-N-carboxymethylpyridinium chloride and P$_4$ is the amino acid sequence CAhxYFMVF-GGRrRK (SEQ ID No. 3) and they were coupled through an amide bond) interacts strongly with wild-type EBNA1 (WT-EBNA1) as confirmed by an 8.8-fold increase in its emission intensity upon binding with WT-EBNA1 (binding constant=6.7). L$_2$P$_4$ has a formula of (I) wherein formula (I) is

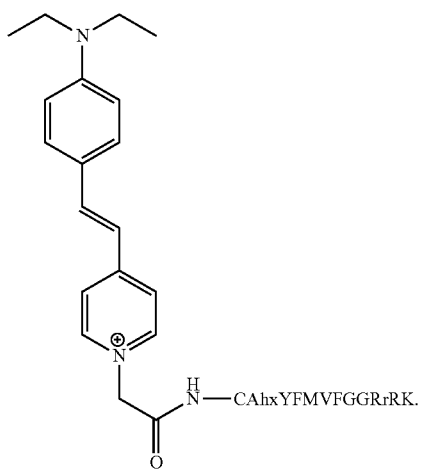

$L_2P_4$ responds significantly on binding with WT-EBNA1, and the responsive signal is found to be induced by intermolecular charge transfer (ICT) mechanism. Simultaneous imaging and inhibition of EBV-positive tumors are demonstrated by the dual-function fluorescent peptide-conjugate probes of the present invention through selective interference with EBNA1 homodimerization. $L_2P_4$ is highly cytotoxicity for EBV-positive cells (half-maximum inhibitory concentration, $IC_{50}=15$ μM), but has little or no cytotoxicity for EBV-negative cells, even at high doses (50 μM, $IC_{50}>0.5$ mM). Furthermore, $L_2P_4$ exhibits strong in vivo toxicity against EBV-positive tumors (intra-tumor injection of 4 μg resulted in 92.8% growth inhibition). Both the in vitro and in vivo studies described herein demonstrate the effectiveness of $L_2P_4$ as a dual EBV tumor-selective cancer targeting agent and imaging probe. The peptide conjugates of the present invention are useful to treat EBV-associated cancers (such as Burkitt's lymphoma, Hodgkin lymphoma, nasopharyngeal carcinoma and gastric carcinoma). The peptide conjugates of the present invention are also useful to image EBV-positive cells and tumors, thereby elucidating the function of EBNA1 in the replication of EBV inside the nucleus. The use of the peptide conjugates of the present invention in cancer treatment and cancer cell imaging is illustrated in FIG. 57.

Results and Discussion.

a. Rational Design and MD Simulations of the Peptide or Peptide Conjugates to EBNA1 Dimeric Interface—

Figure 1B:
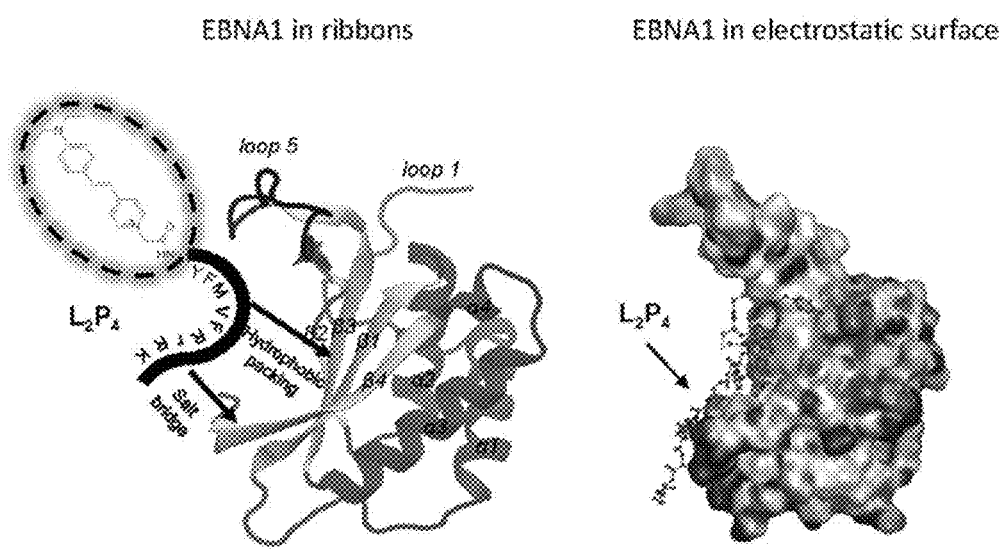
FIG. 1B shows the interactions between $L_2P_4$ and the putative monomer structure of the EBNA1 DNA-binding domain by MD simulations; EBNA1 is shown as ribbons (left) and as an electrostatic surface (right). The putative structure is generated from the isolation of the X-ray crystal structure of the EBNA1-DNA complex (protein database ID: 1B3T). The simulation shows $L_2P_4$ binds to EBNA1 dimeric interface primarily via hydrophobic interactions with the YFMVF motif, and that such interactions can be enhanced by further electrostatic interactions with the RrRK motif. The dashed oval denotes the red emissive ligand ($L_2$).

The X-ray crystal structure of EBNA1's DNA-binding domain (SEQ ID NO. 4) (protein database ID, 1B3T; chain A; residue 461 to 607) is an α/β mixed fold comprised of four alpha-helix and four beta-sheet motifs that are linked by several loops (FIG. 1B, left). Different structural motifs (the beta sheets, β1-β4) contribute to its distinct functional regions that drive formation of the dimer via hydrophobic packing; the alpha helices, α1 and α2, interact with DNA via electrostatic interaction, while α3 and α4 stabilize the beta sheets; the positively charged loop 1 mediates DNA binding; and the flexible loop 5 is involved in dimerization.

Figure 16A:
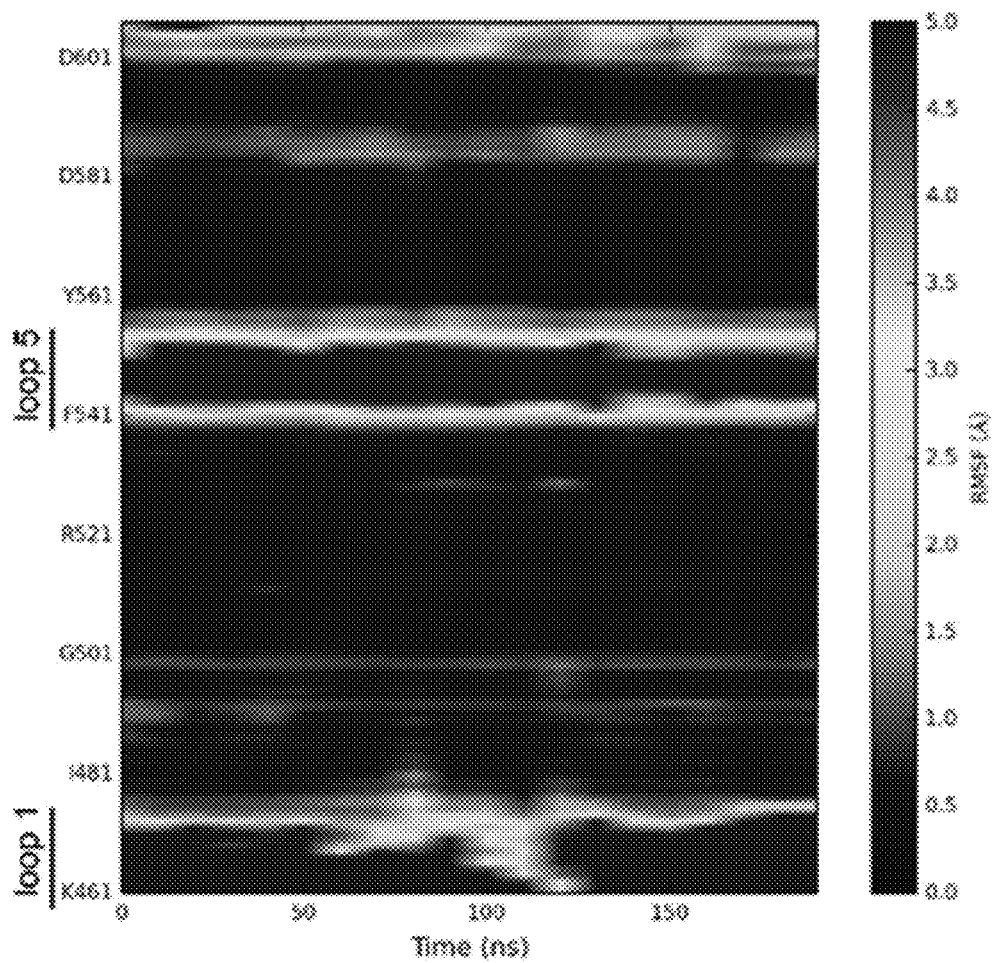
FIG. 16A shows the $C_\alpha$ RMSF of all residues in the putative structure of EBNA1 DBD monomer for the MD simulations of EBNA1 monomer (461-607).
Figure 16B:
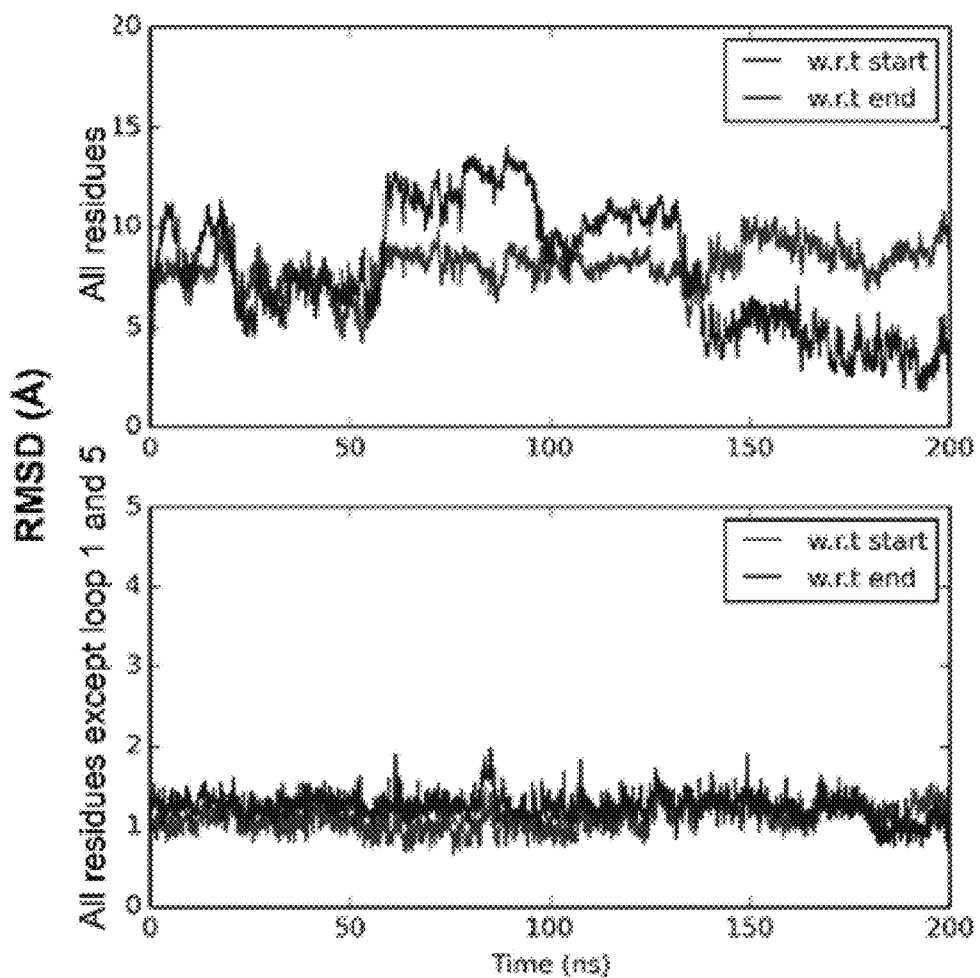
FIG. 16B shows the $C_\alpha$ RMSD of all residues in EBNA1 (upper) and the $C_\alpha$ RMSD of all residues except the highly dynamic loop 1 and 5 (lower).
Figure 16C:
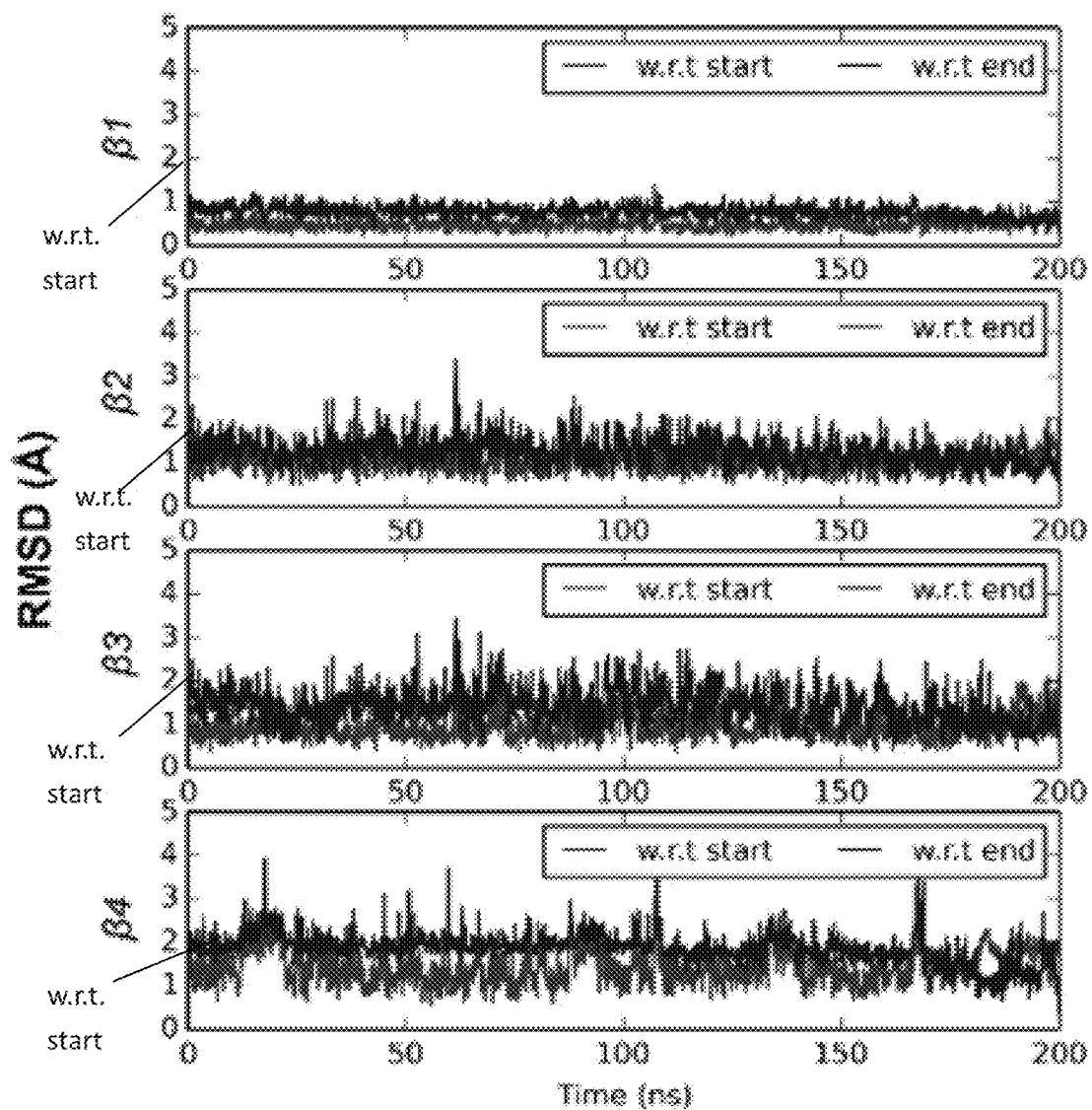
FIG. 16C shows the $C_\alpha$ RMSD of the four beta sheet motifs ($\beta$1: 503-511, $\beta$2: 532-540, $\beta$3: 556-566 and $\beta$4: 593-604) which comprise the dimerization interface.
Figure 16D:
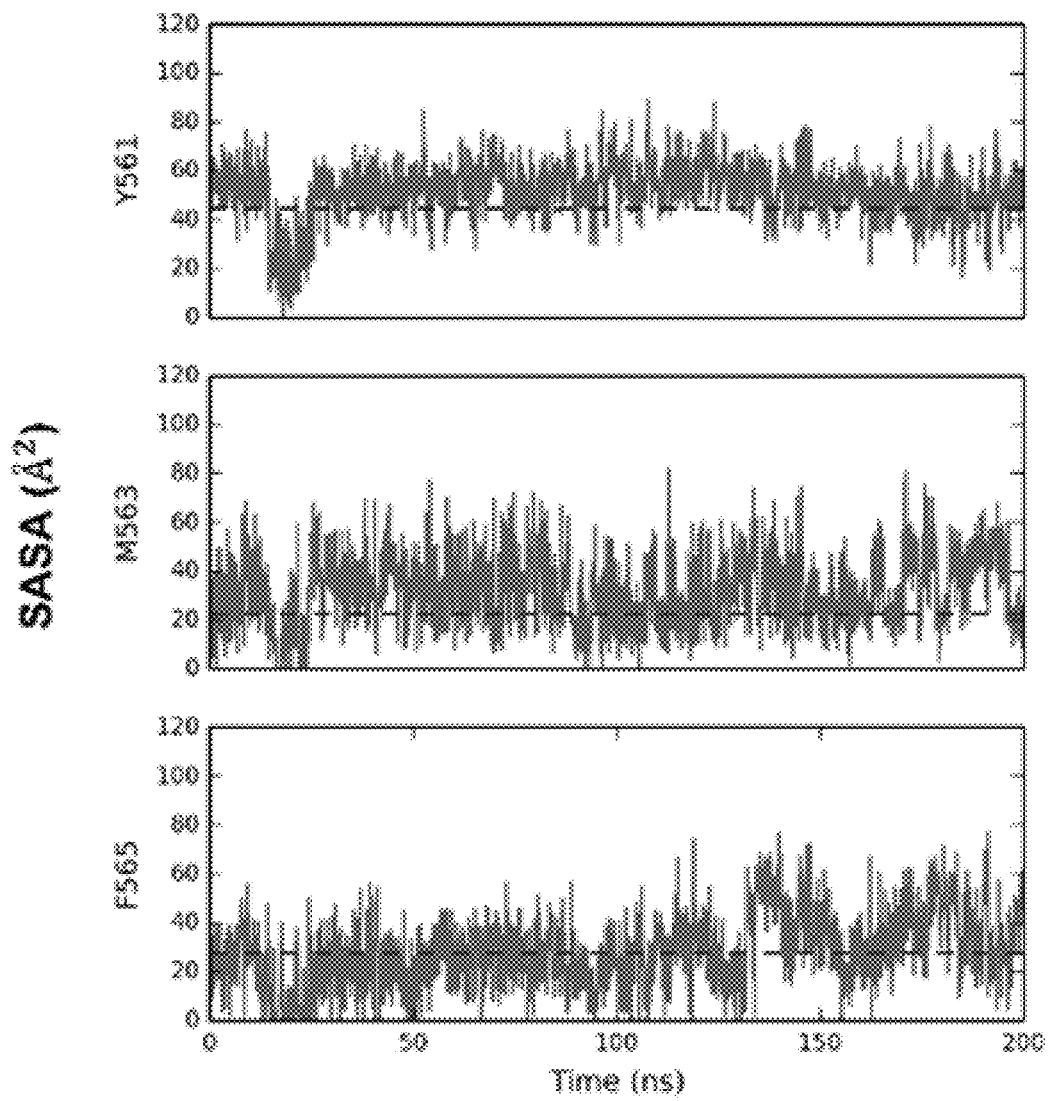
FIG. 16D shows the SASA of key residues on dimerization interface, including $Y_{561}$, $M_{563}$ and $F_{565}$. The referential value of each residue has been calculated and shown in dashed black line. For $Y_{561}$, the value is 44.7 Å$^2$; for $M_{563}$, it is 22.7 Å$^2$; and for $F_{565}$, it is 27.6 Å$^2$.
Figure 16E:
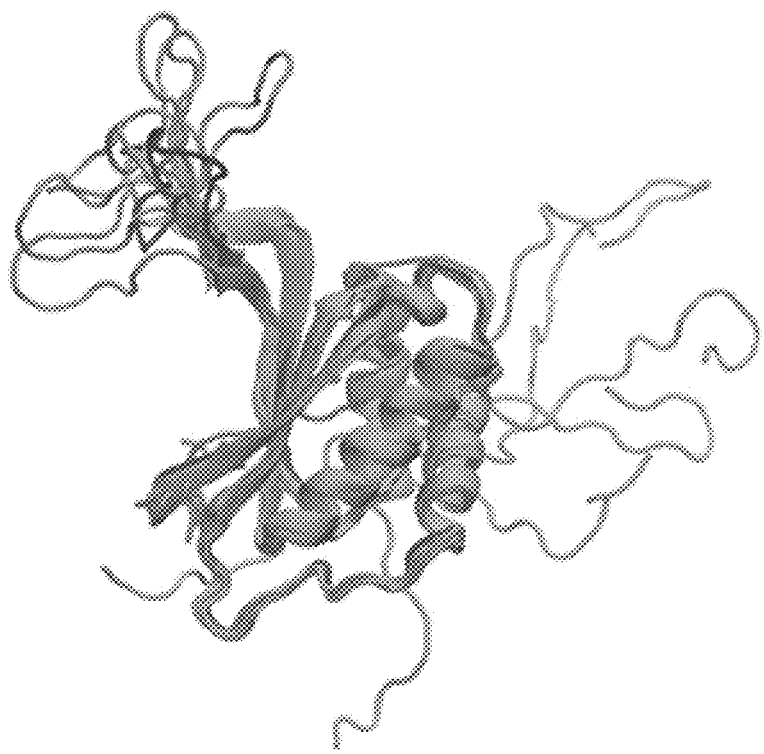
FIG. 16E shows the representative EBNA1 monomer conformations of major clusters (population>5%) calculated from 200 ns MD simulations.
Figure 16F:
FIG. 16F shows the representative structure of the largest cluster of EBNA1 monomer, and is chosen for docking study.
Figure 17A:
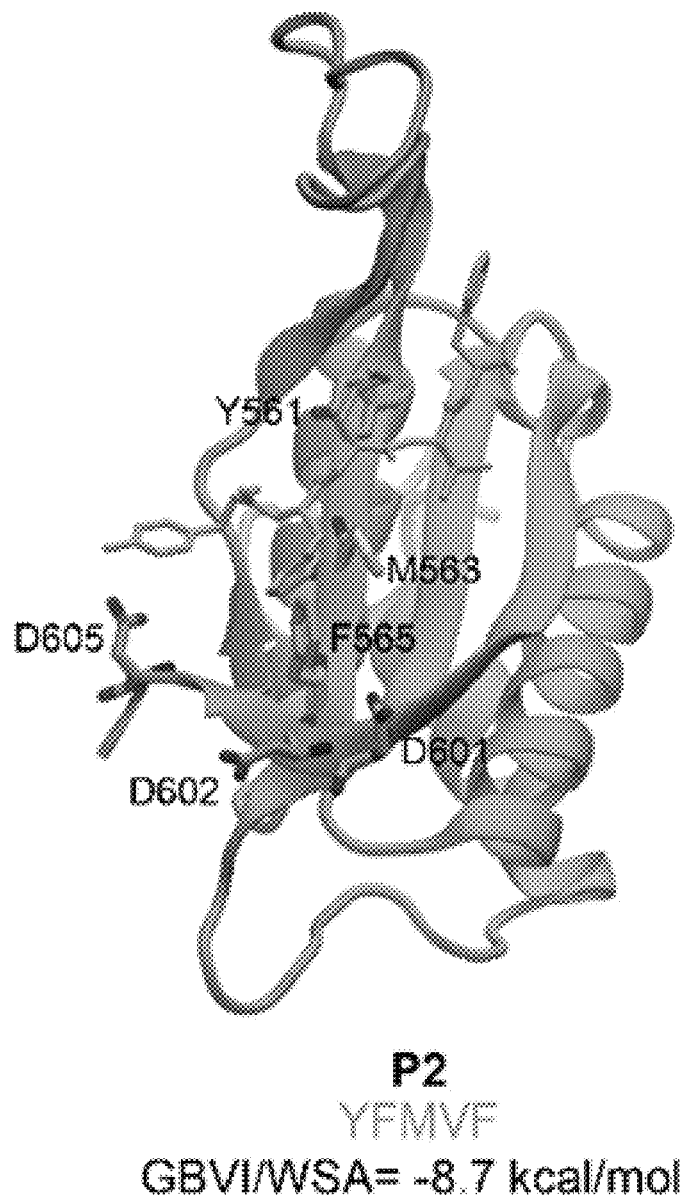
FIG. 17A shows the chosen pose of $P_2$-EBNA1 complex for the 200 ns MD simulations. The peptide sequence and docking energy has been marked in the figure. EBNA1 is rendered in ribbon, and the major binding sites in EBNA1 are rendered in stick mode in the 3D structure, including $Y_{561}$, $M_{563}$, $F_{565}$, $D_{601}$, $D_{602}$, and $D_{605}$.
Figure 17B:
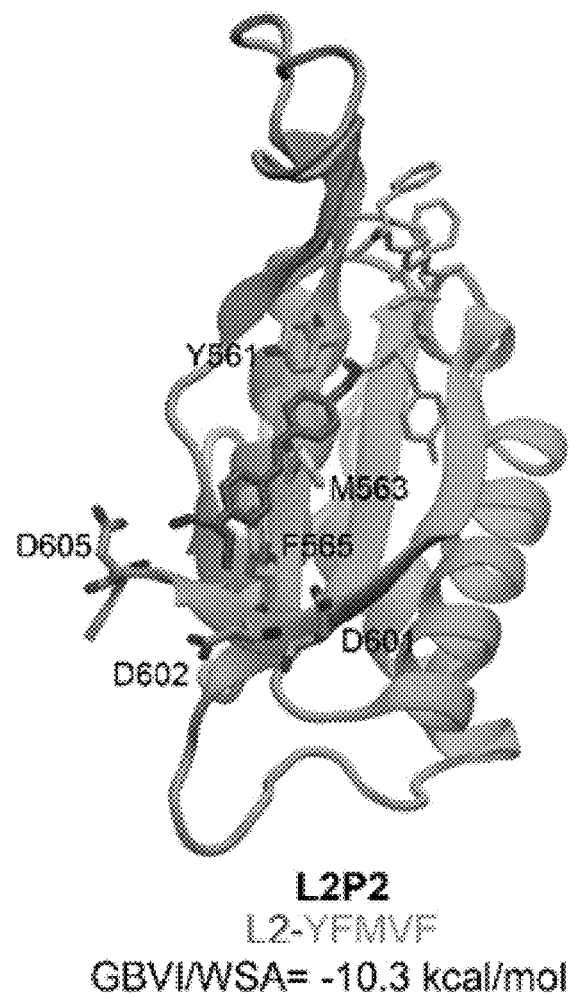
FIG. 17B shows the chosen pose of $L_2P_2$-EBNA1 complex for the 200 ns MD simulations. The peptide sequence and docking energy has been marked in the figure. EBNA1 is rendered in ribbon, and the major binding sites in EBNA1 are rendered in stick mode in the 3D structure, including $Y_{561}$, $M_{563}$, $F_{565}$, $D_{601}$, $D_{602}$, and $D_{605}$.
Figure 17C:
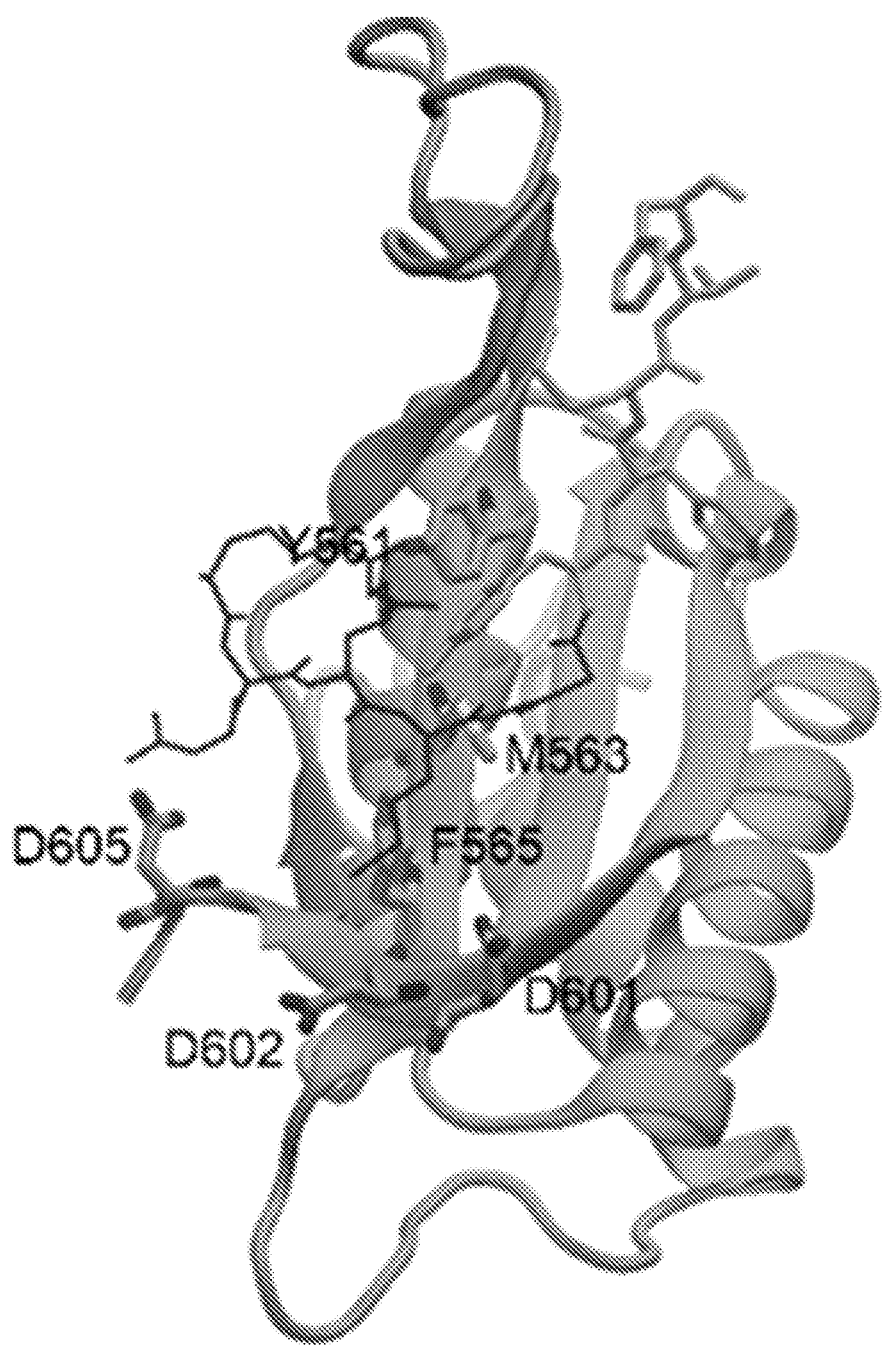
FIG. 17C shows the chosen pose of $P_3$-EBNA1 complex for the 200 ns MD simulations. The peptide sequence and docking energy has been marked in the figure. EBNA1 is rendered in ribbon, and the major binding sites in EBNA1 are rendered in stick mode in the 3D structure, including $Y_{561}$, $M_{563}$, $F_{565}$, $D_{601}$, $D_{602}$, and $D_{605}$.
Figure 17D:
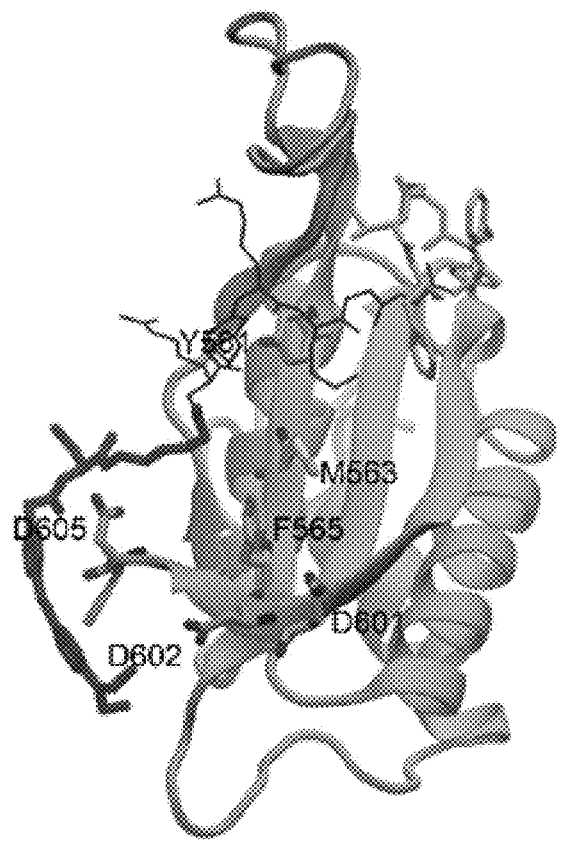
FIG. 17D shows the chosen pose of $L_2P_3$-EBNA1 complex for the 200 ns MD simulations. The peptide sequence and docking energy has been marked in the figure. EBNA1 is rendered in ribbon, and the major binding sites in EBNA1 are rendered in stick mode in the 3D structure, including $Y_{561}$, $M_{563}$, $F_{565}$, $D_{601}$, $D_{602}$, and $D_{605}$.
Figure 17E:
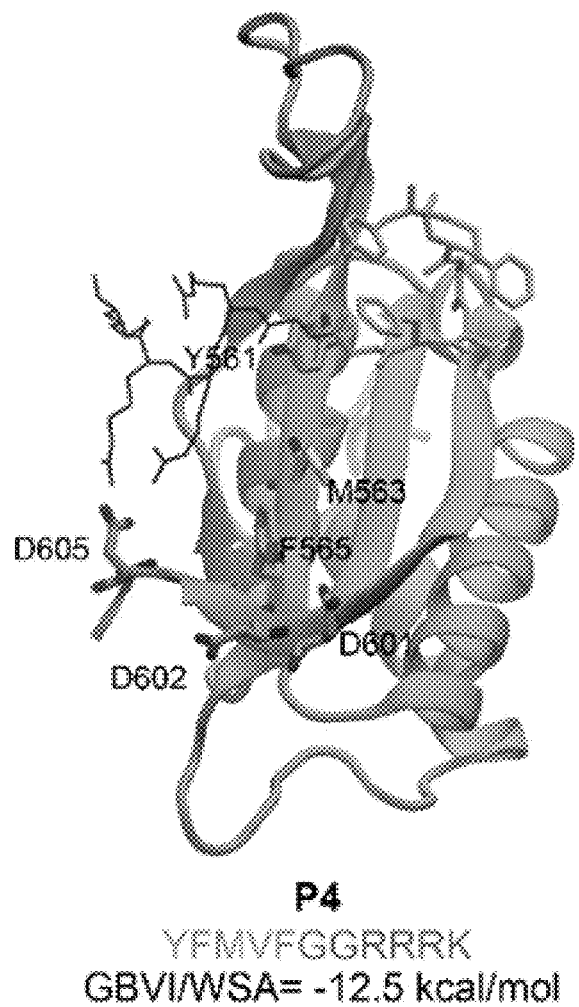
FIG. 17E shows the chosen pose of $P_4$-EBNA1 complex for the 200 ns MD simulations. The peptide sequence and docking energy has been marked in the figure. EBNA1 is rendered in ribbon, and the major binding sites in EBNA1 are rendered in stick mode in the 3D structure, including $Y_{561}$, $M_{563}$, $F_{565}$, $D_{601}$, $D_{602}$, and $D_{605}$.
Figure 17F:
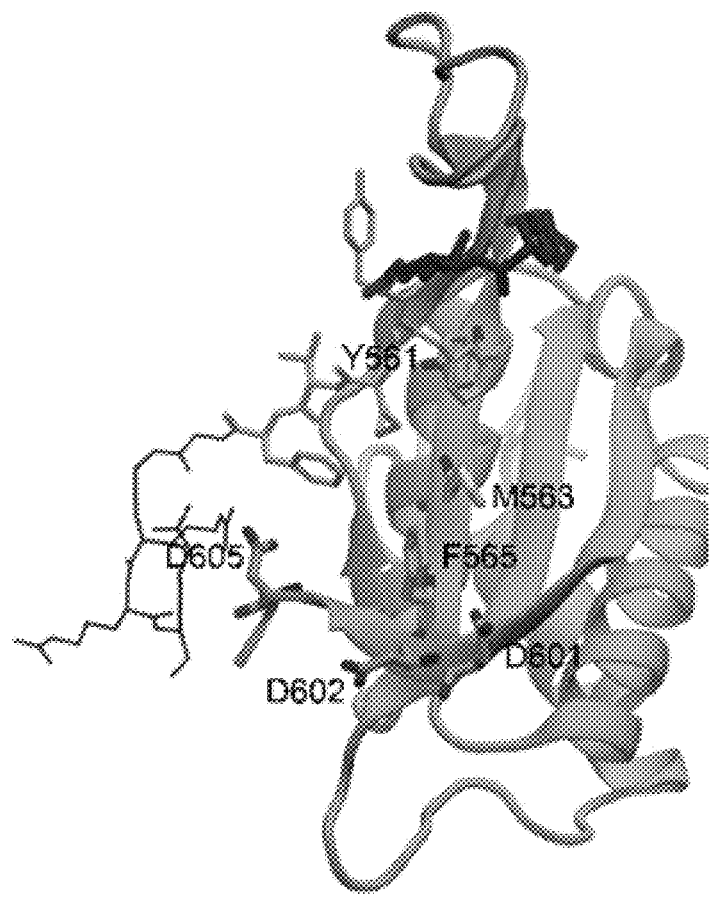
FIG. 17F shows the chosen pose of $L_2P_4$-EBNA1 complex for the 200 ns MD simulations. The peptide sequence and docking energy has been marked in the figure. EBNA1 is rendered in ribbon, and the major binding sites in EBNA1 are rendered in stick mode in the 3D structure, including $Y_{561}$, $M_{563}$, $F_{565}$, $D_{601}$, $D_{602}$, and $D_{605}$.

The structure of the EBNA1 DNA-binding domain monomer is generated from the X-ray crystal structure of its homodimer, and it is used to perform 200 ns all-atom explicit-solvent MD simulations in AMBER 14. The EBNA1 structure exhibits good stability and maintains the original conformation during the simulation, except for the highly dynamic loops 1 and 5 (FIGS. 16A and 16B), which make no contribution to the homodimerization of EBNA1. The 4 beta sheets which comprise the dimeric interface also exhibited reasonable stability (FIG. 16C). Moreover, the four beta sheets that make up the dimeric interface are also found to exhibit good stability. The accessibility of the dimeric interface in the putative structure is examined, the solvent-accessible surface area (SASA) calculation has been performed. and the results show that the key residues ($Y_{561}$, $M_{563}$ and $F_{565}$) on the dimeric interface can be accessed by extrinsic probes (FIG. 16D). After checking the stability and accessibility of this putative structure, a representative conformation is selected and a docking study is carried out to identify the docked poses for each ligand-EBNA1 complex (FIGS. 16E and 16F). The ligand is selected from $P_2$, $P_3$, $P_4$, $L_2P_2$, $L_2P_3$ and $L_2P_4$. All docked poses are then ranked using a scoring function to choose the final poses for each complex. It is found that most selected poses shared some similarities; for example, the interaction of the key residues in EBNA1 with a YFMVF motif appeared in all complexes (FIGS. 17A-17F). Furthermore, unexpected salt-bridging is found between the positively charged tetrapeptide RrRK and the aspartate-rich tail in EBNA1, demonstrating a secondary role for this nuclear localization sequence.

Figure 18A:
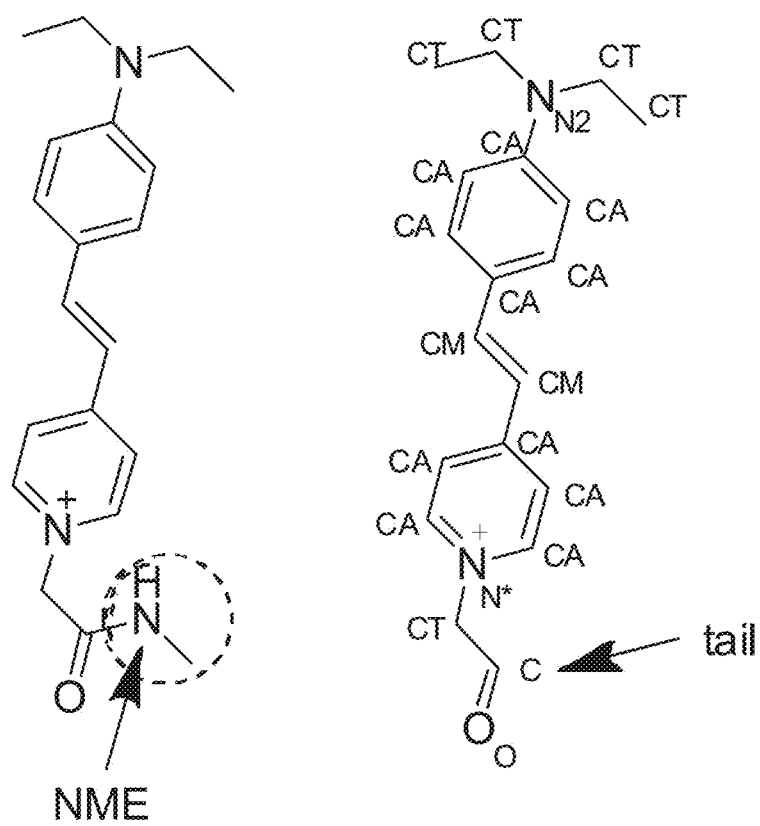
FIG. 18A shows the chemical structures (left) and AMBER atom types (right) of $L_2$. The putative structure is used to calculate Restrained Electrostatic Potential (RESP) charge and the Assisted Model Building with Energy Refinement (AMBER) atom types are shown.
Figure 18B:
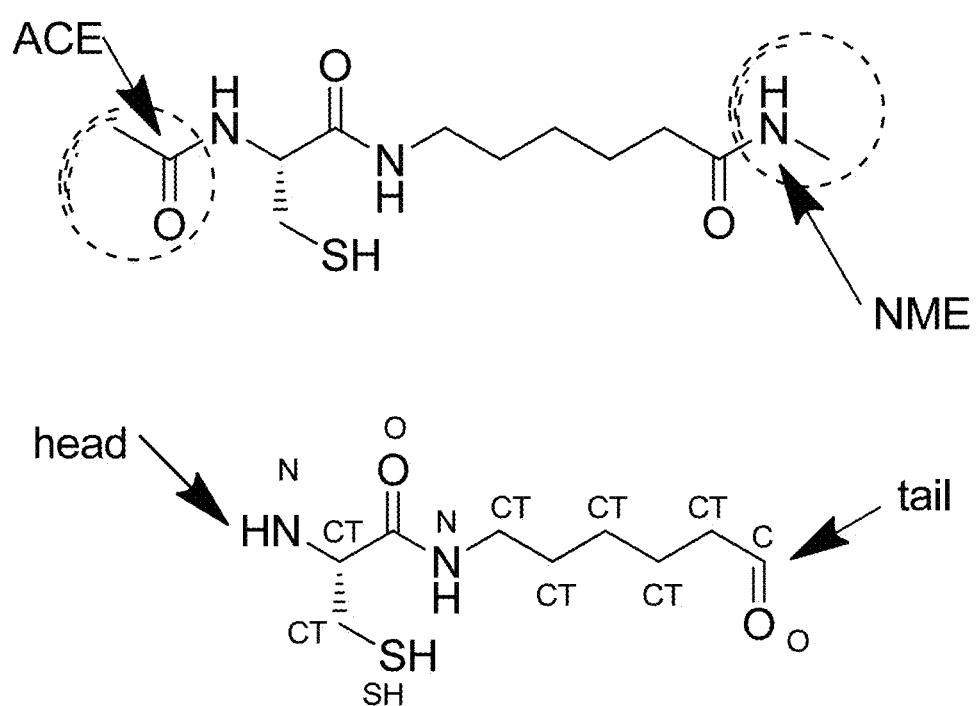
FIG. 18B shows the chemical structures and AMBER atom types of LIN. The putative structure is used to calculate Restrained Electrostatic Potential (RESP) charge and the Assisted Model Building with Energy Refinement (AMBER) atom types are shown in the figure.
Figure 19A:
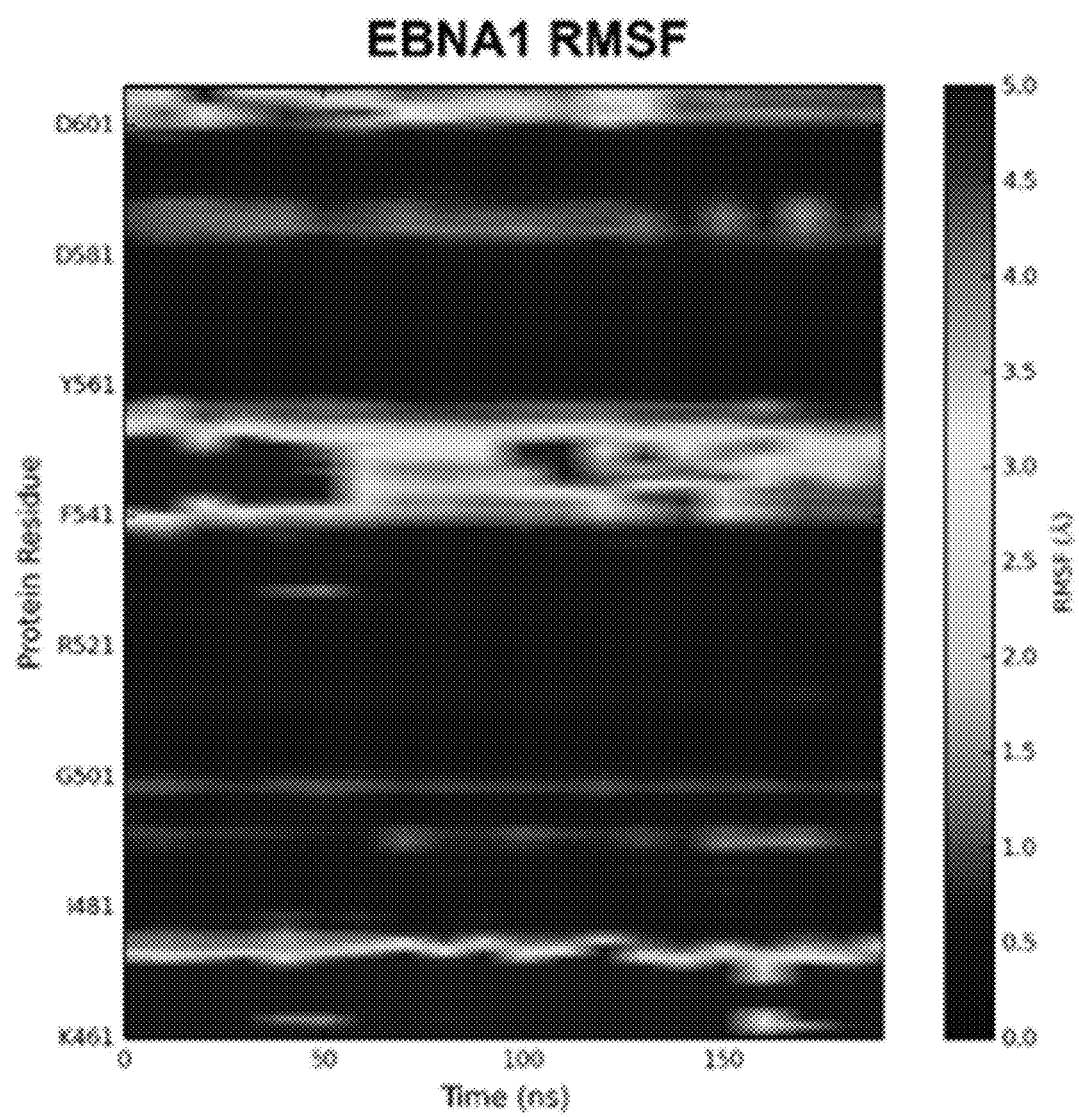
FIG. 19A shows the $C_\alpha$ RMSF of all residues in EBNA1 in the MD simulation of $P_2$-EBNA1 complex.
Figure 19B:
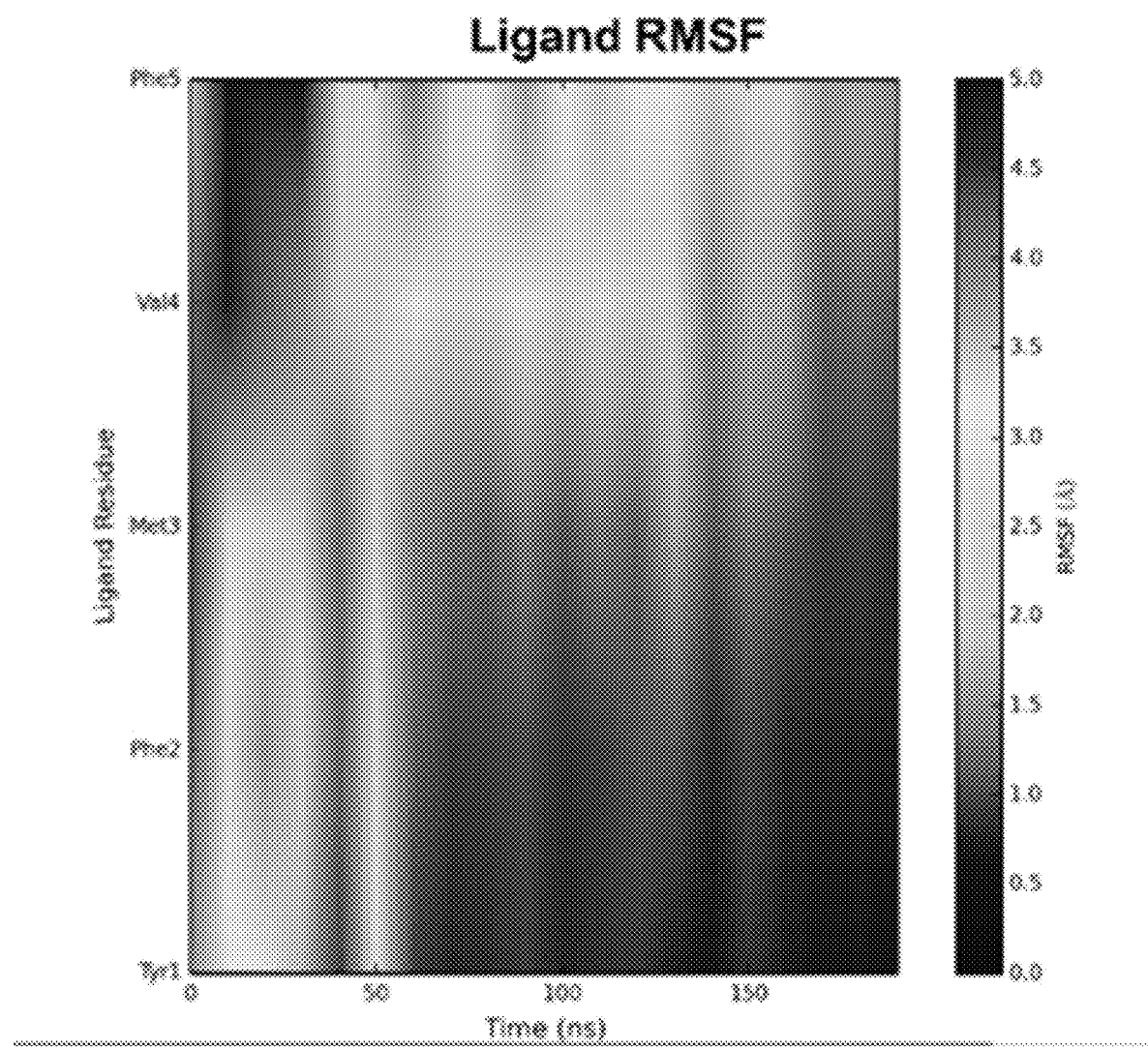
FIG. 19B shows the $C_\alpha$ RMSF of $P_2$ in the MD simulation of $P_2$-EBNA1 complex.
Figure 19C:
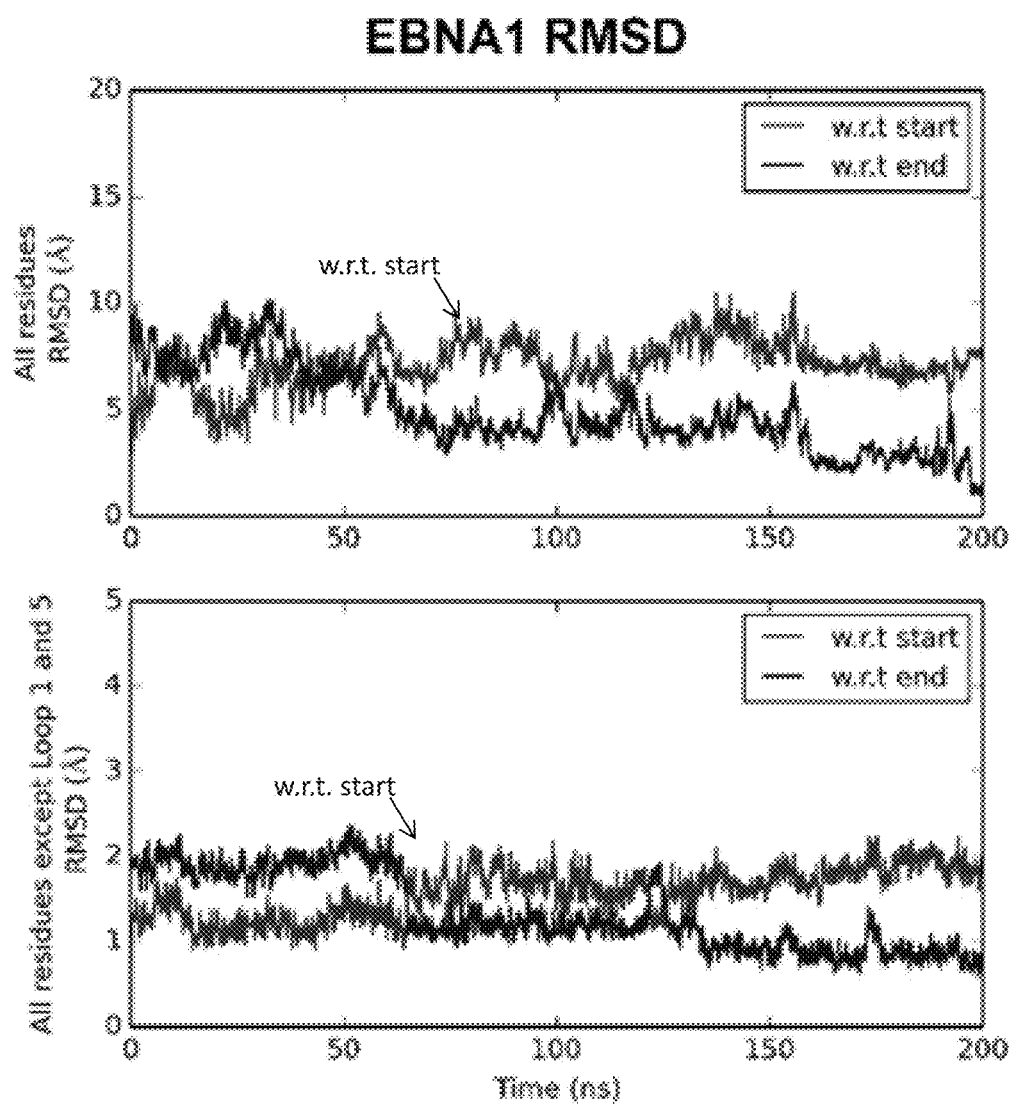
FIG. 19C shows the $C_\alpha$ RMSD evolution with all residues (upper) and all residues except the highly dynamic loop 1 and 5 (lower) of EBNA1 with regard to start or end conformation in the MD simulation of $P_2$-EBNA1 complex.
Figure 19D:
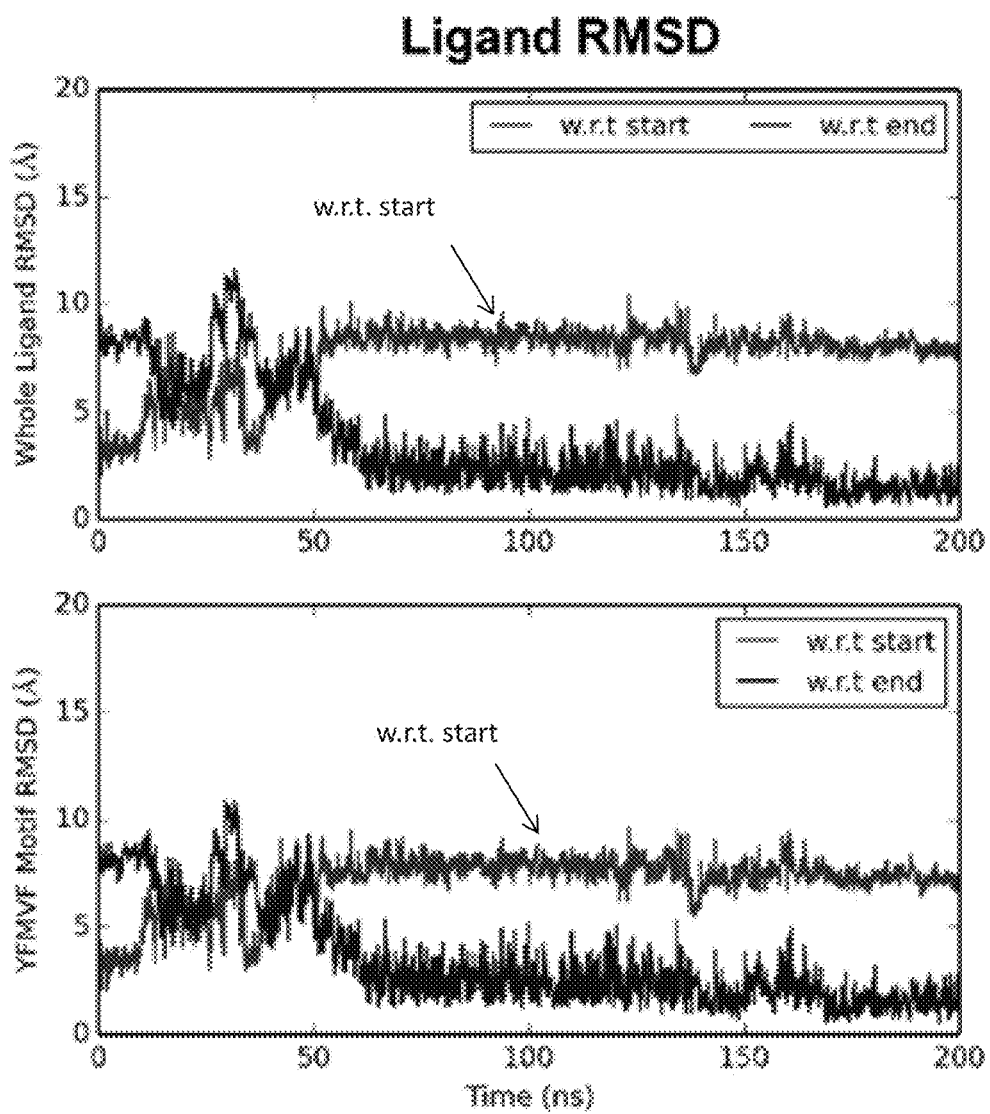
FIG. 19D shows the $C_\alpha$ RMSD evolution of all residues in $P_2$ (upper) and the $C_\alpha$ RMSD for YFMVF motif (lower) with regard to the start or end conformation in the MD simulation of $P_2$-EBNA1 complex.
Figure 19E:
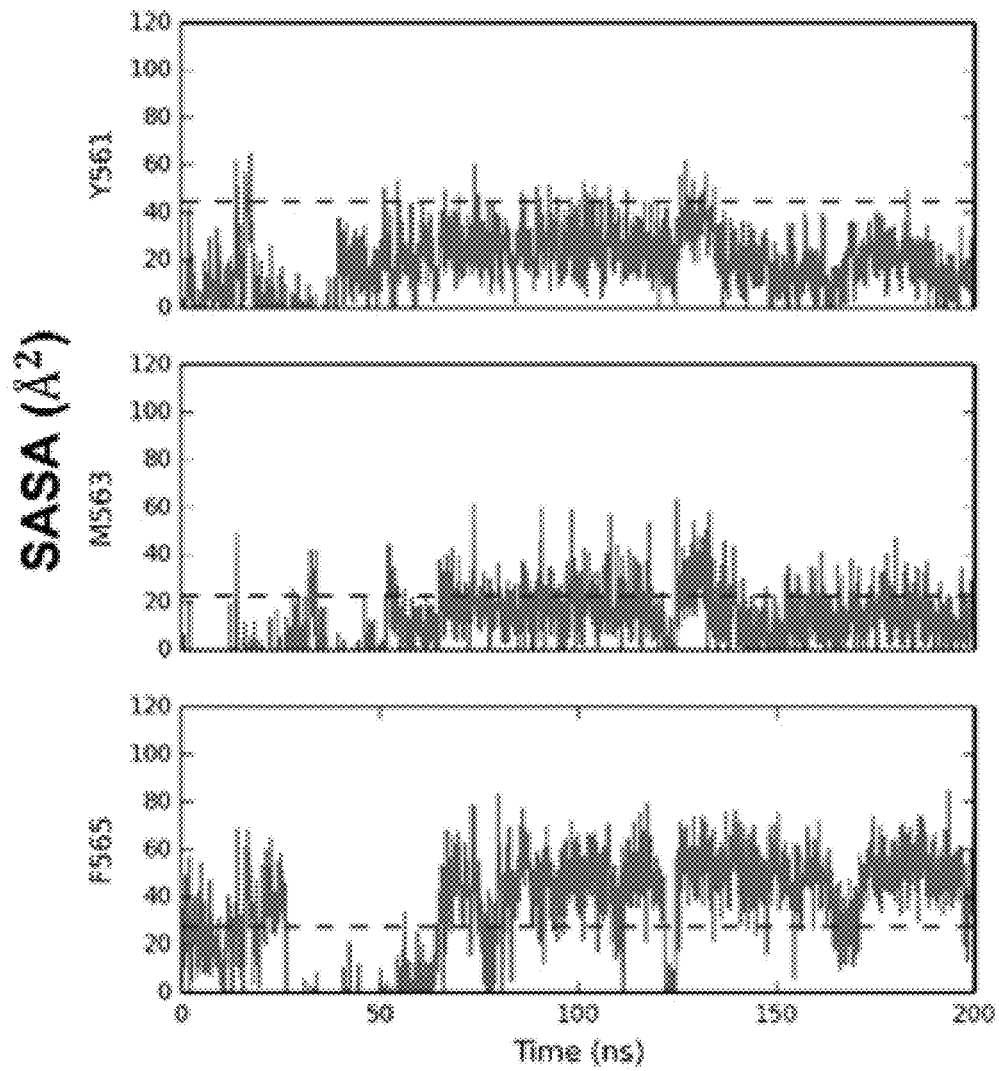
FIG. 19E shows the key residues on dimerization interface ($Y_{561}$, $M_{563}$ and $F_{565}$) involved in probe-receptor hydrophobic contacts in the MD simulation of $P_2$-EBNA1 complex. Observations are made by calculating the SASA of each residue during the simulation and compared with its referential value (dashed line) in free-accessible status. If the SASA is smaller than the referential one, it suggests that the intra- or inter-chain hydrophobic contacts may be formed within that residue.
Figure 20A:
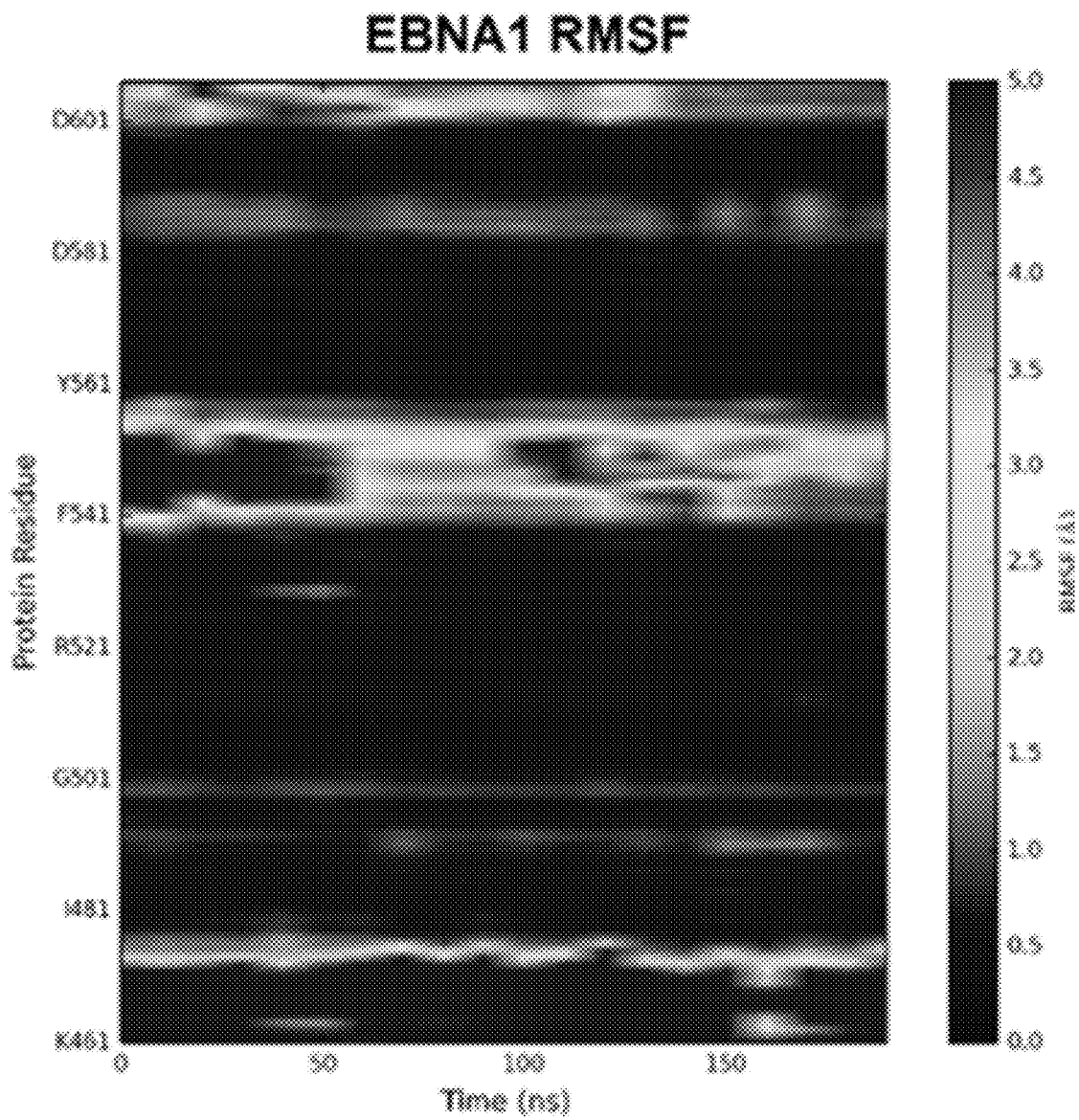
FIG. 20A shows the $C_\alpha$ RMSF of all residues in EBNA1 in the MD simulation of $L_2P_2$-EBNA1 complex.
Figure 20B:
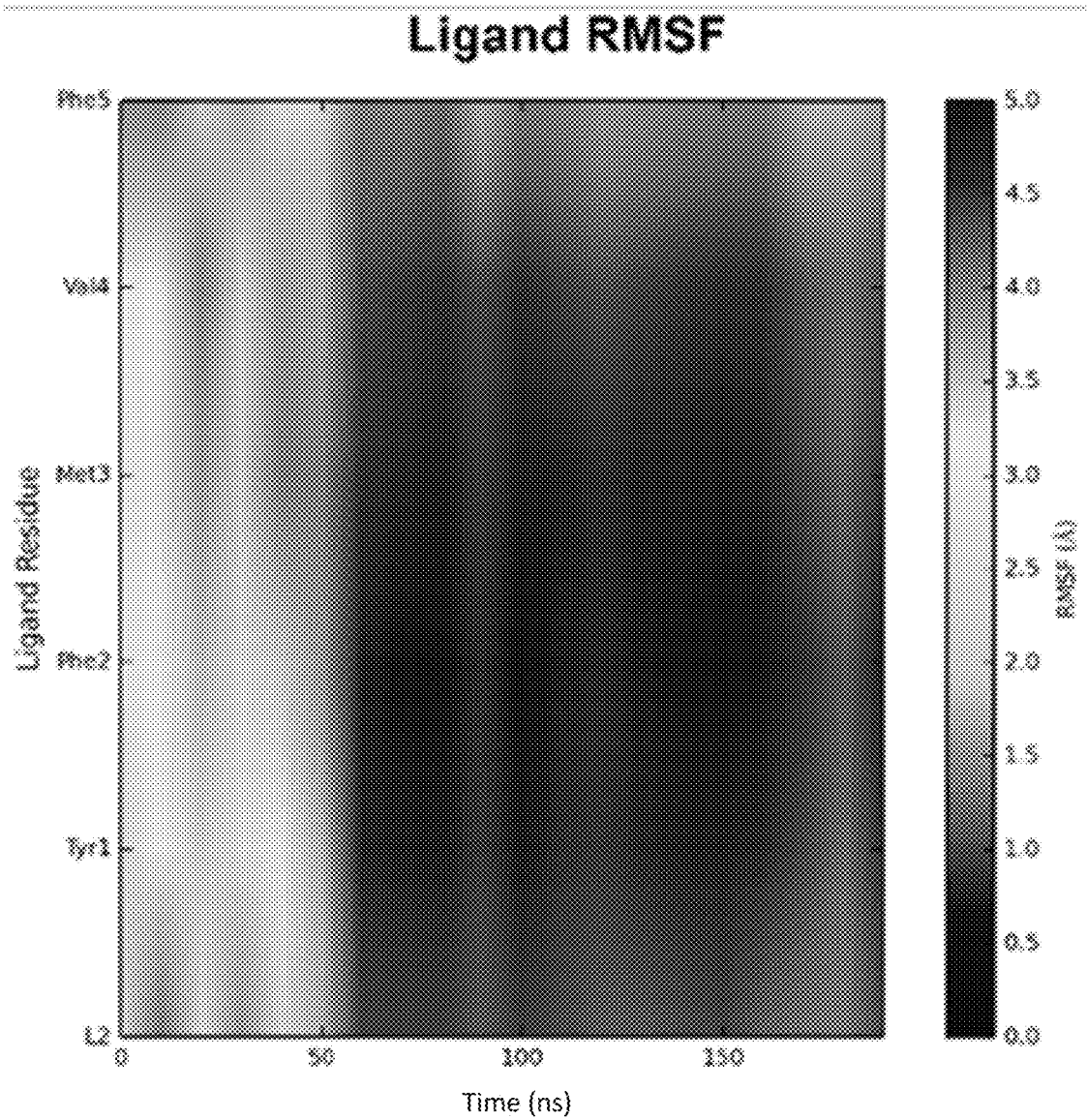
FIG. 20B shows the $C_\alpha$ RMSF of $L_2P_2$ in the MD simulation of $L_2P_2$-EBNA1 complex.
Figure 20C:
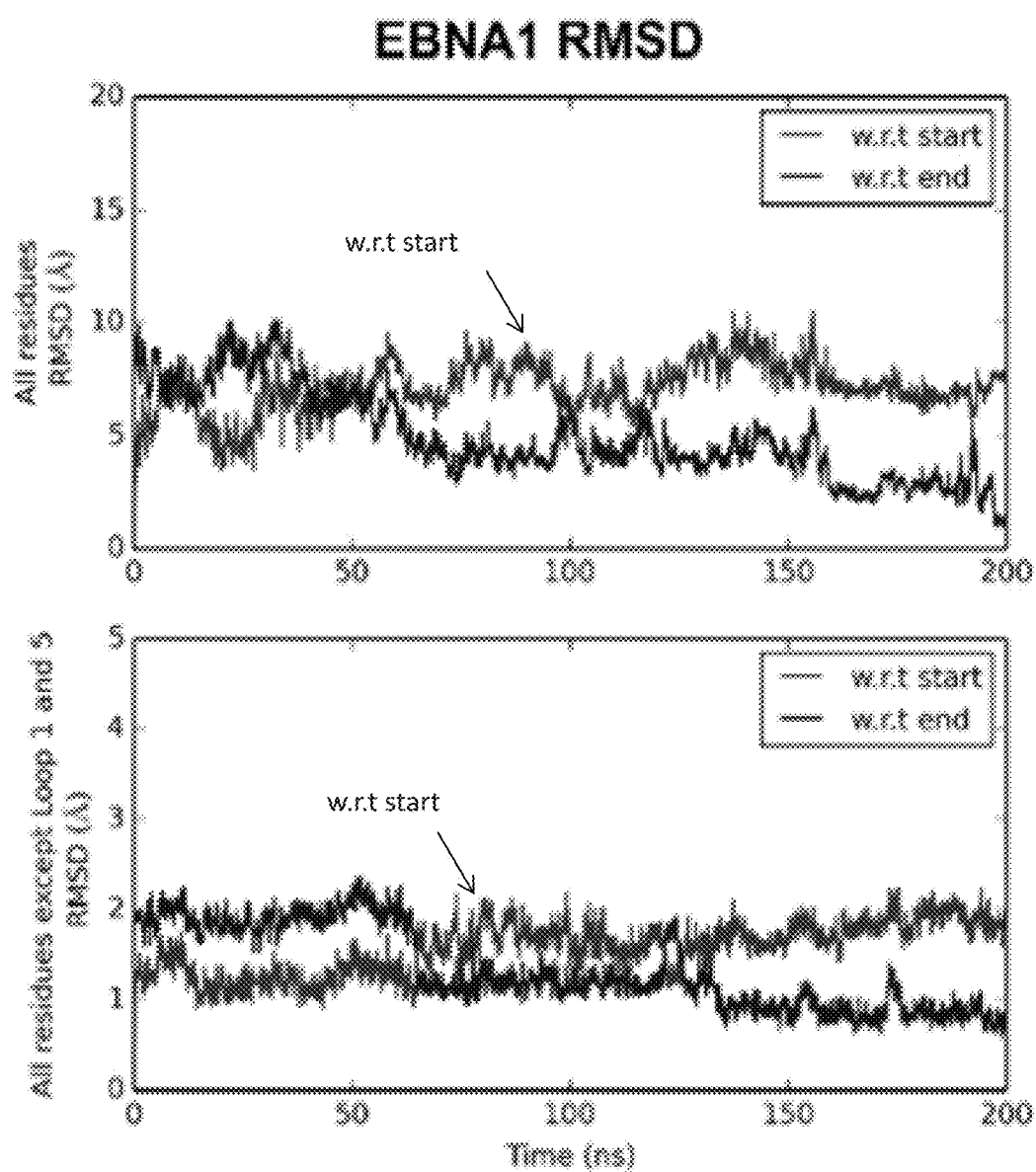
FIG. 20C shows the $C_\alpha$ RMSD evolution with all residues (upper) and all residues except the highly dynamic loop 1 and 5 (lower) of EBNA1 with regard to start or end conformation in the MD simulation of $L_2P_2$-EBNA1 complex.
Figure 20D:
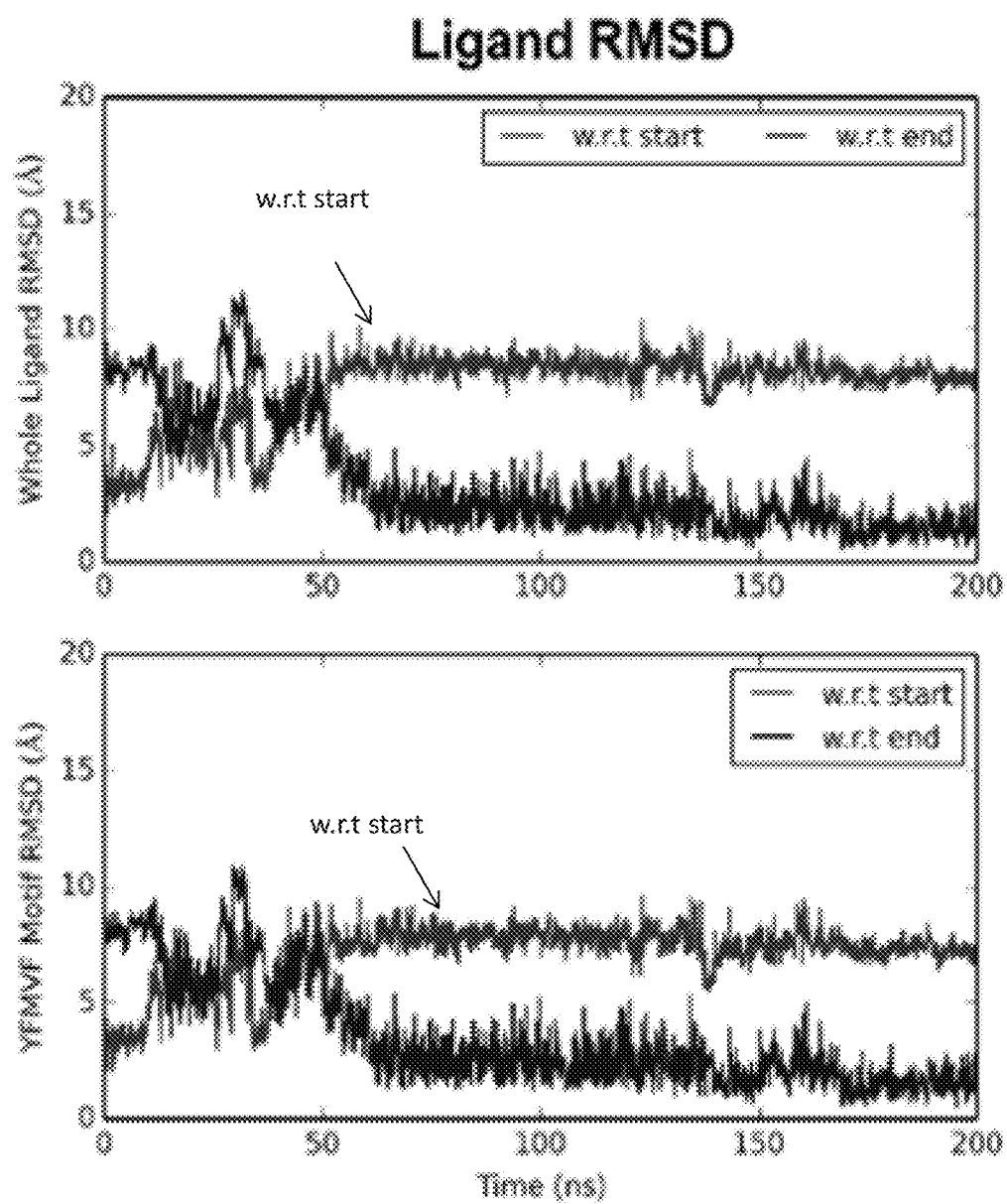
FIG. 20D shows the $C_\alpha$ RMSD evolution of $L_2P_2$ (upper) and the $C_\alpha$ RMSD for YFMVF motif (lower) with regard to the start or end conformation in the MD simulation of $L_2P_2$-EBNA1 complex.
Figure 20E:
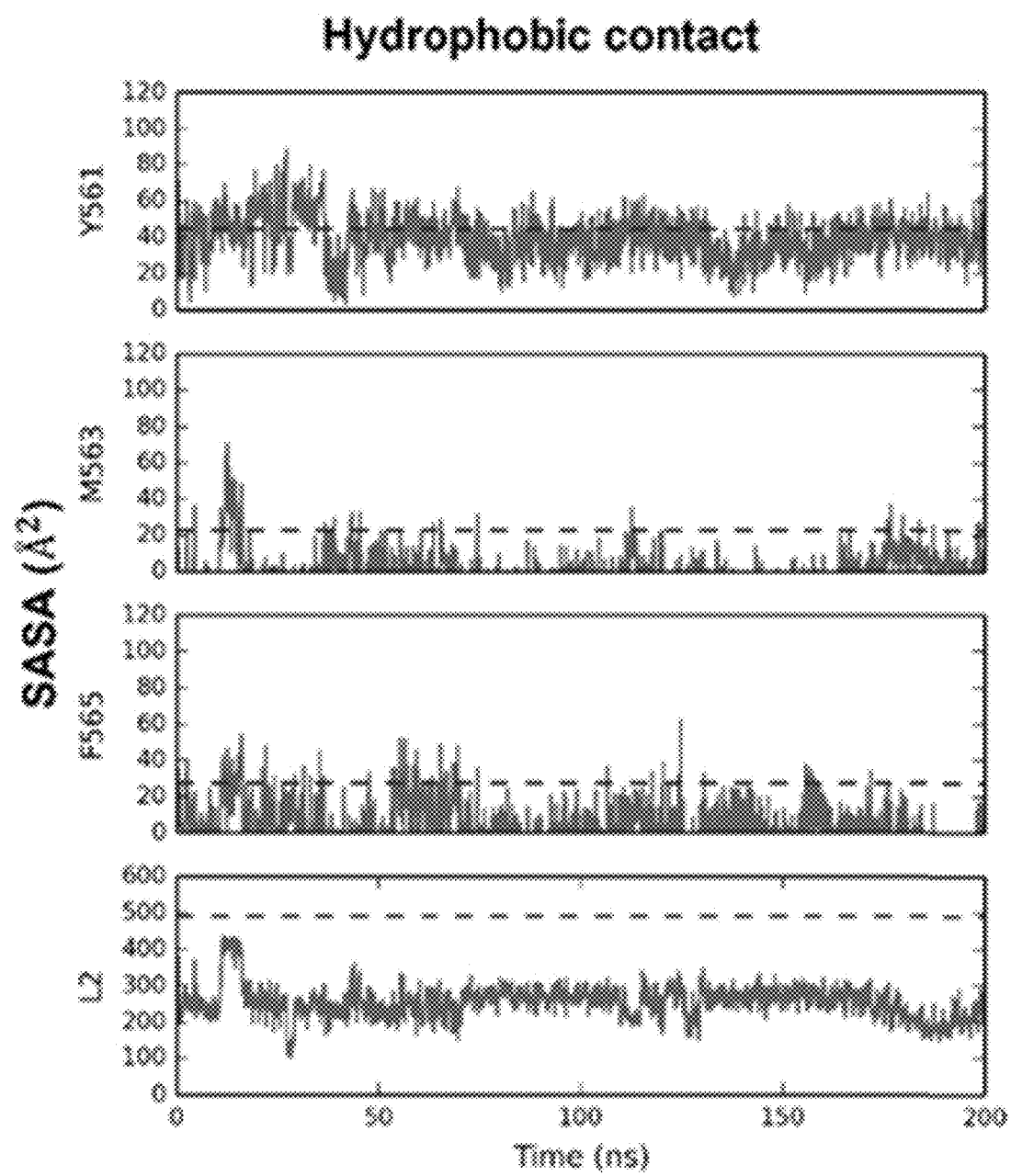
FIG. 20E shows the key residues on dimerization interface ($Y_{561}$, $M_{563}$ and $F_{565}$) involved in probe-receptor hydrophobic contacts in the MD simulation of $L_2P_2$-EBNA1 complex. Observations are made by calculating the SASA of each residue during the simulation and compared with its referential value (dashed line) in free-accessible status. If the SASA is smaller than the referential one, it suggests that the intra- or inter-chain hydrophobic contacts may be formed within that residue.
Figure 21A:
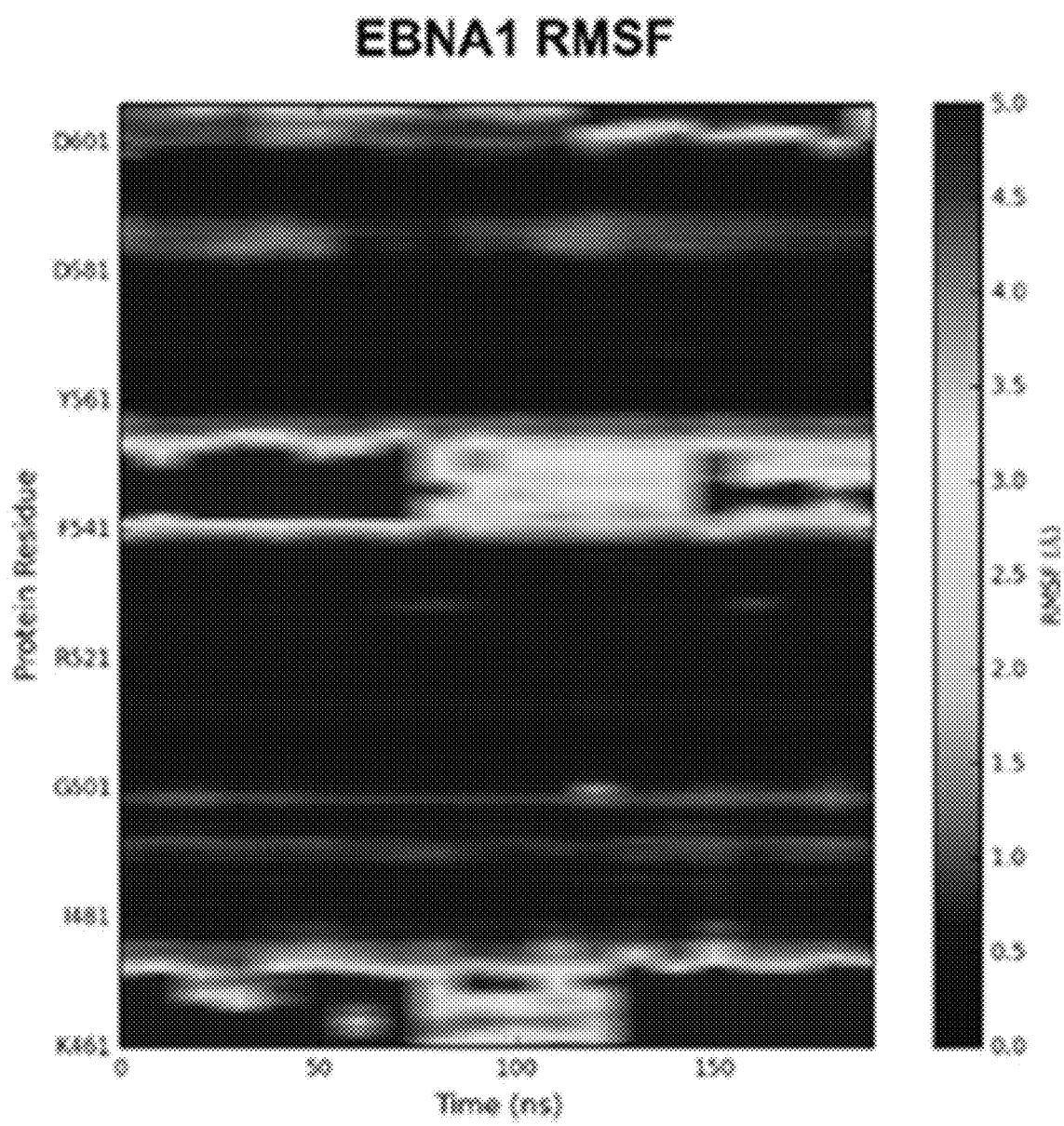
FIG. 21A shows the $C_\alpha$ RMSF of all residues in EBNA1 in the MD simulation of $P_3$-EBNA1 complex.
Figure 21B:
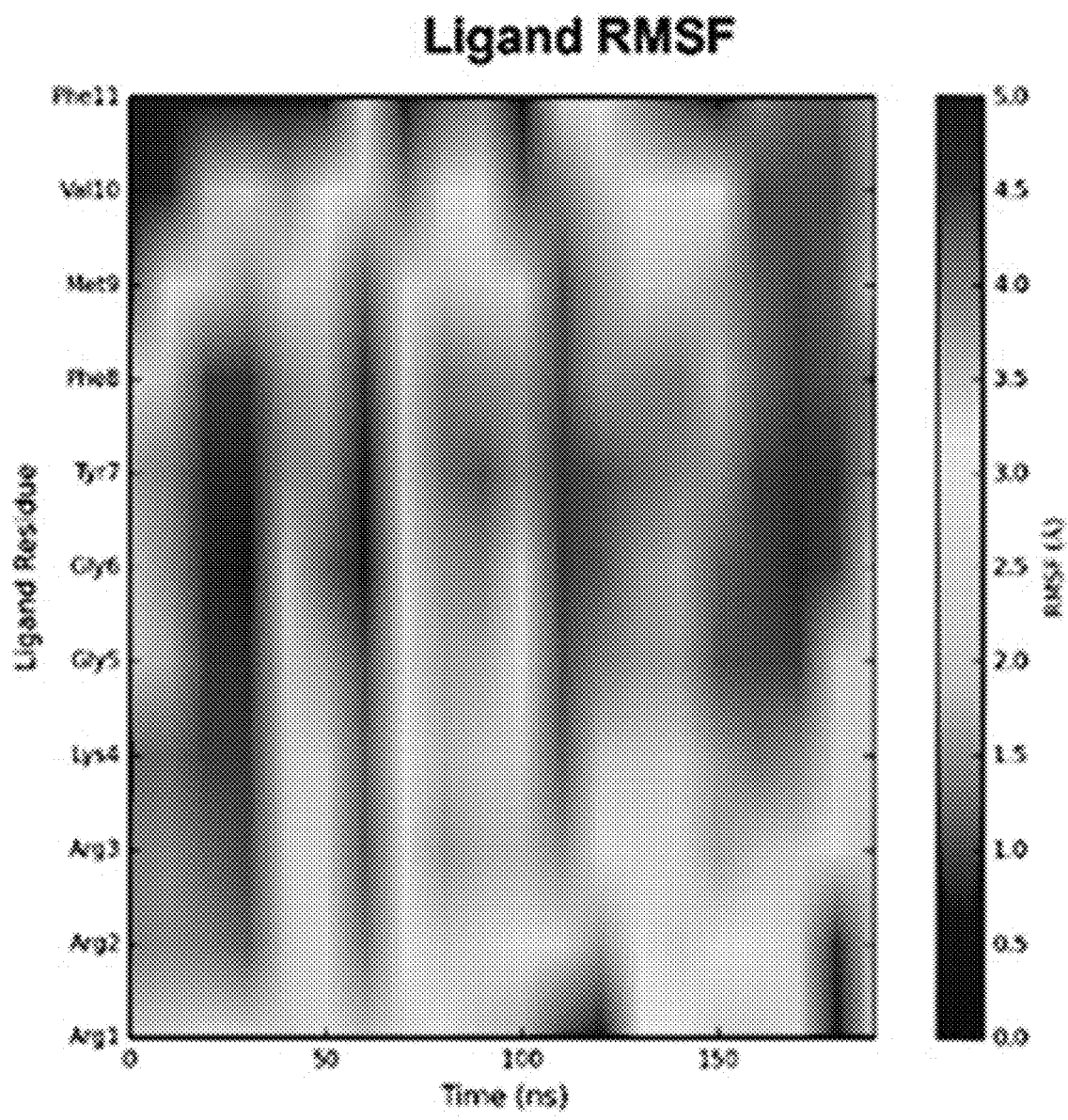
FIG. 21B shows the $C_\alpha$ RMSF of $P_3$ in the MD simulation of $P_3$-EBNA1 complex.
Figure 21C:
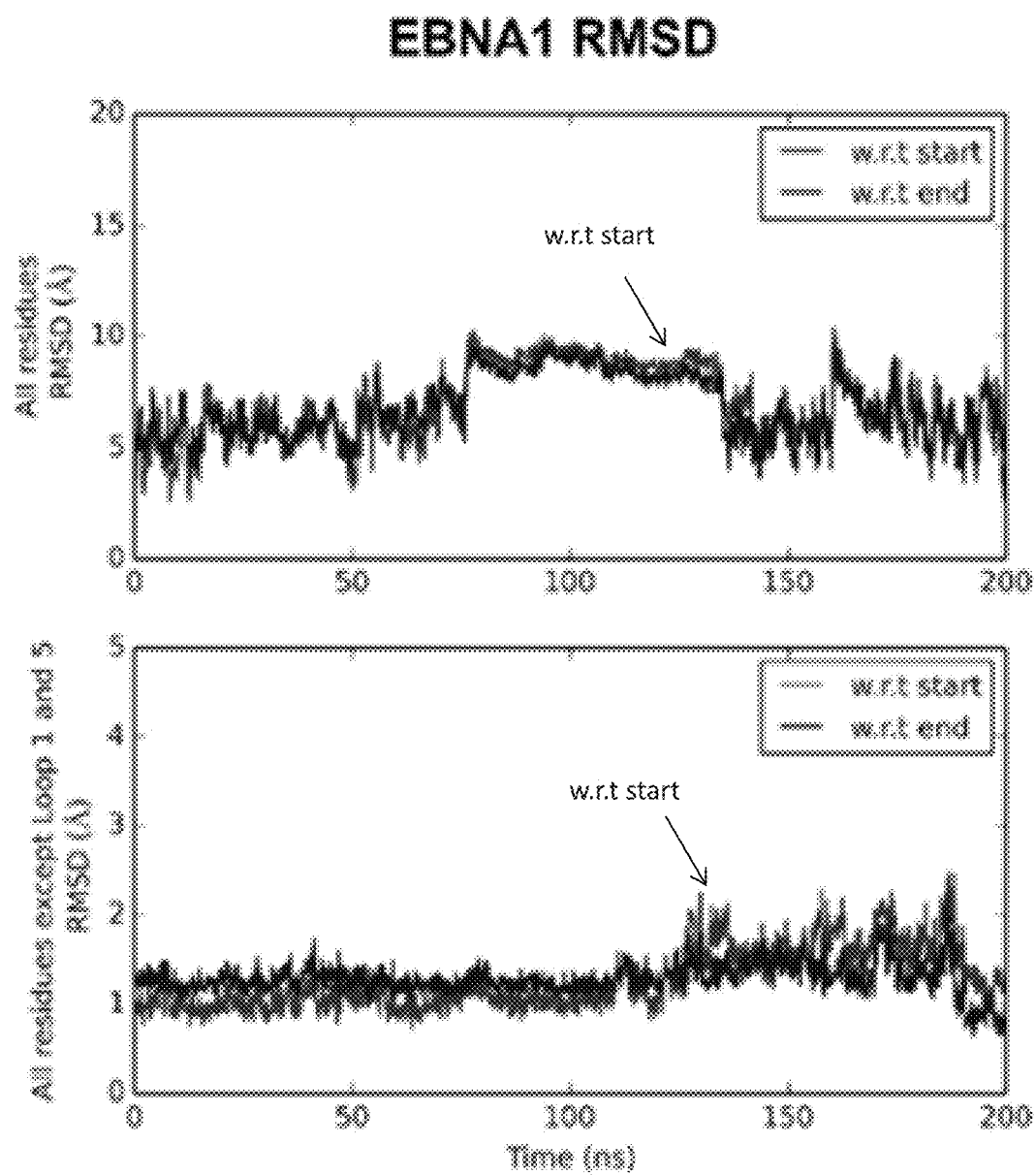
FIG. 21C shows the $C_\alpha$ RMSD evolution with all residues (upper) and all residues except the highly dynamic loop 1 and 5 (lower) of EBNA1 with regard to start or end conformation in the MD simulation of $P_3$-EBNA1 complex.
Figure 21D:
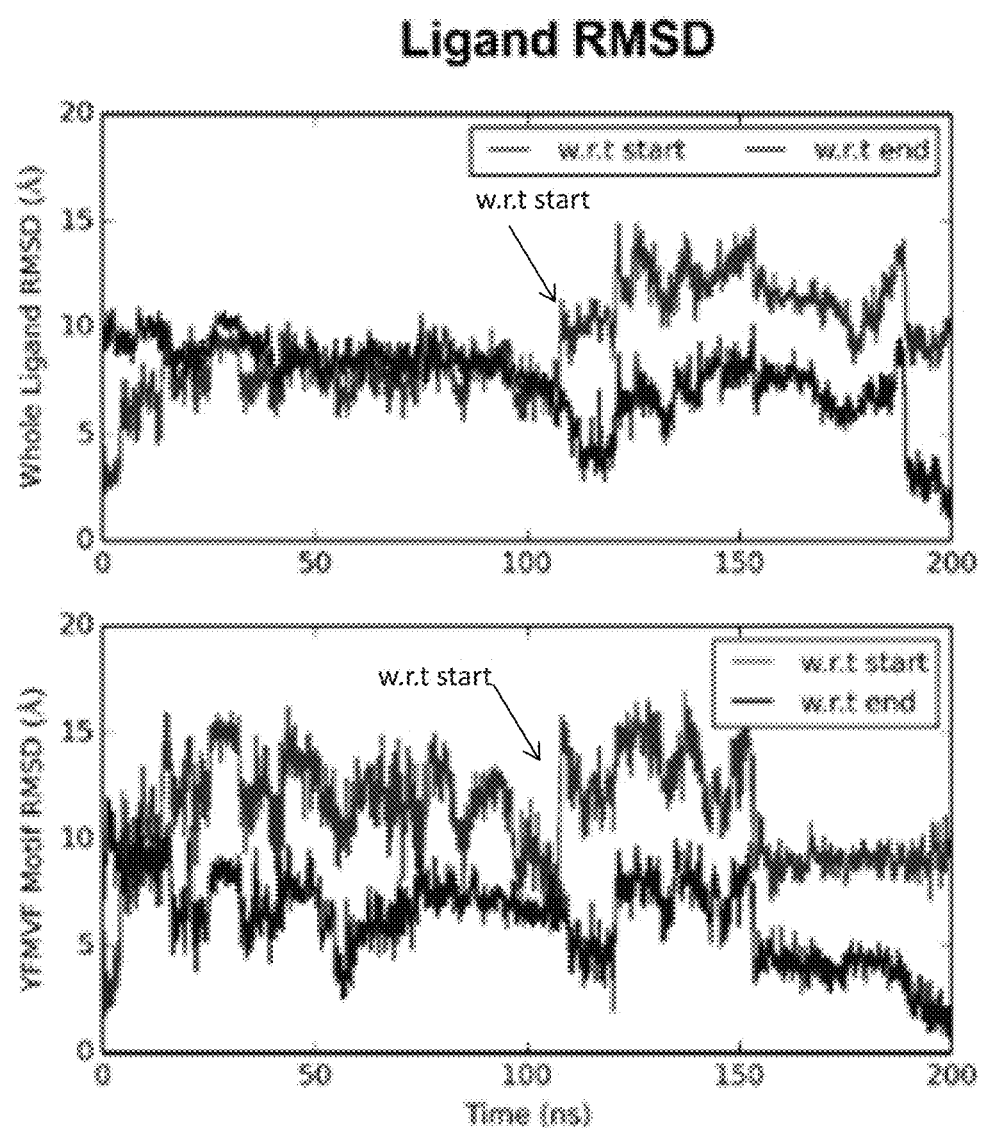
FIG. 21D shows the $C_\alpha$ RMSD evolution of all residues in $P_3$ (upper) and the $C_\alpha$ RMSD for YFMVF motif (lower) with regard to the start or end conformation in the MD simulation of $P_3$-EBNA1 complex.
Figure 21E:
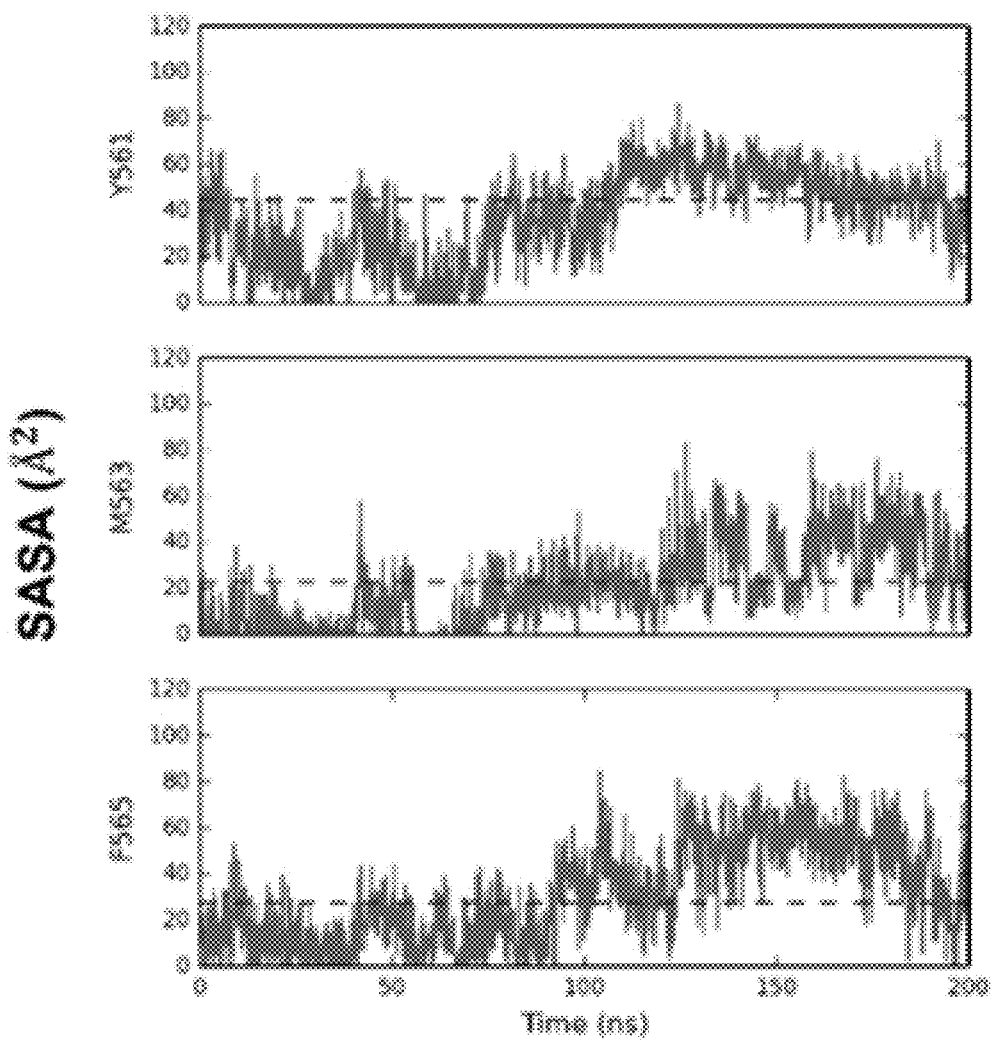
FIG. 21E shows the key residues on dimerization interface ($Y_{561}$, $M_{563}$ and $F_{565}$) involved in probe-receptor hydrophobic contacts in the MD simulation of $P_3$-EBNA1 complex. Observations were made by calculating the SASA of each residue during the simulation and compared with its referential (dashed line) in free-accessible status. If the SASA is smaller than the referential one, it suggests that the intra- or inter-chain hydrophobic contacts may be formed within that residue.
Figure 21F:
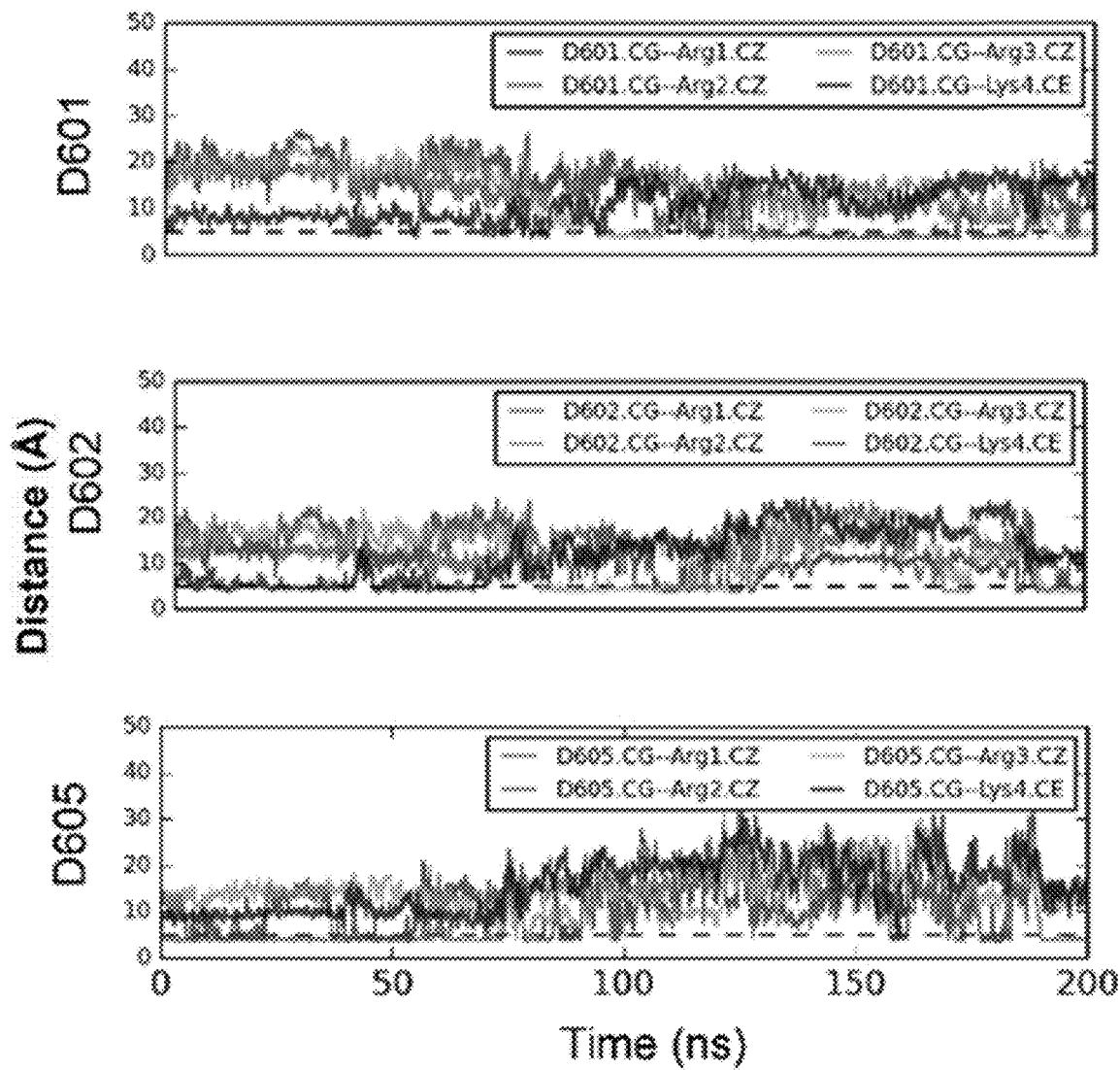
FIG. 21F shows the multiple acid residues at C-terminal of EBNA1 DBD domain ($D_{601}$, $D_{602}$ and $D_{605}$) involved in forming salt bridge (ion bonds) with basic motif (RrRK) in $P_3$ in the MD simulation of $P_3$-EBNA1 complex. Observations are made by measuring the distances between CG atom of $D_{601}/D_{602}/D_{605}$ and CZ/CE atom of arginine/lysine. If the distance is less than 5 Å, it suggests a salt bridge may be formed between the acid-basic residue pair.
Figure 22A:
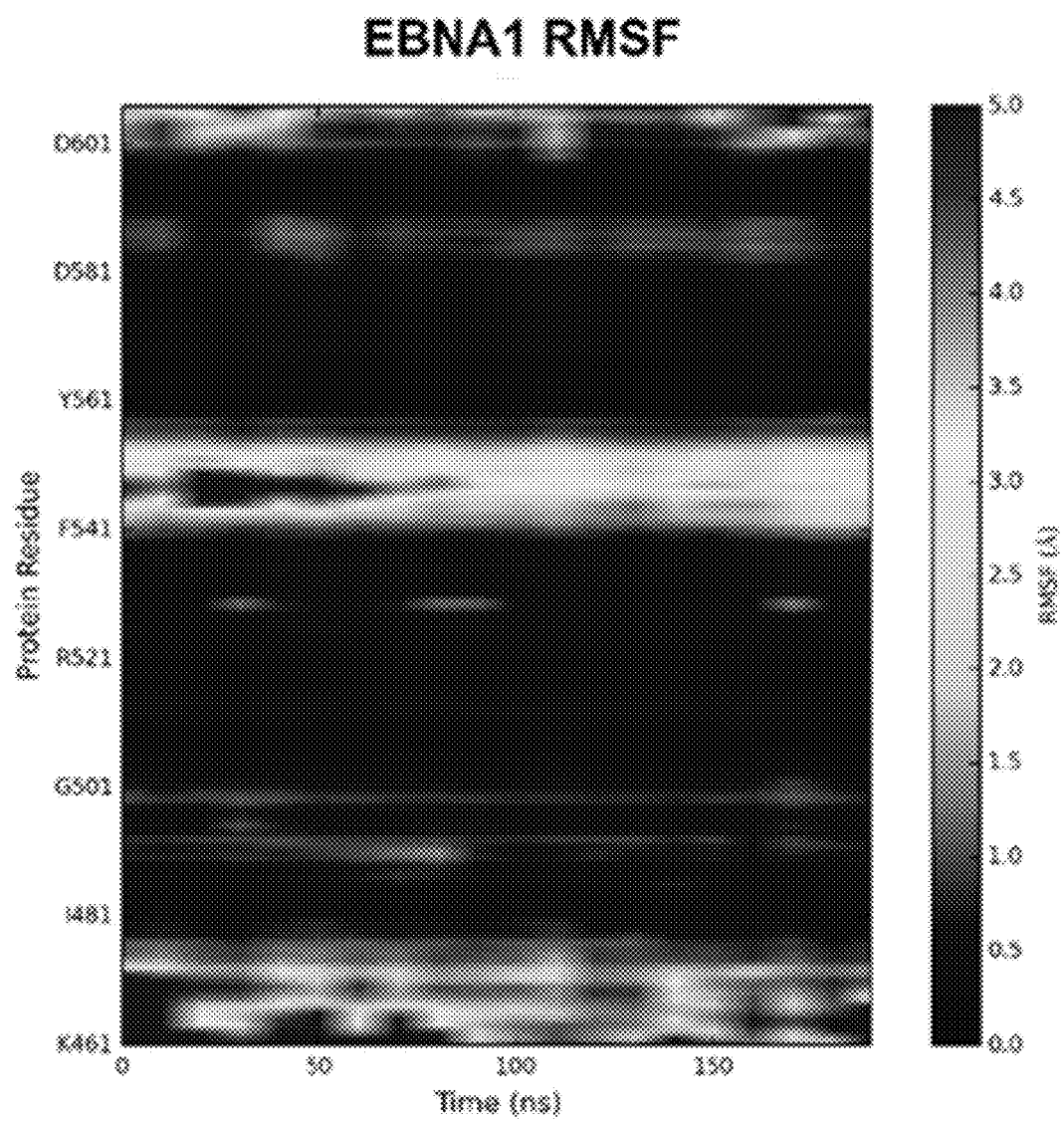
FIG. 22A shows the $C_\alpha$ RMSF of all residues in EBNA1 in the MD simulation of $L_2P_3$-EBNA1 complex.
Figure 22B:
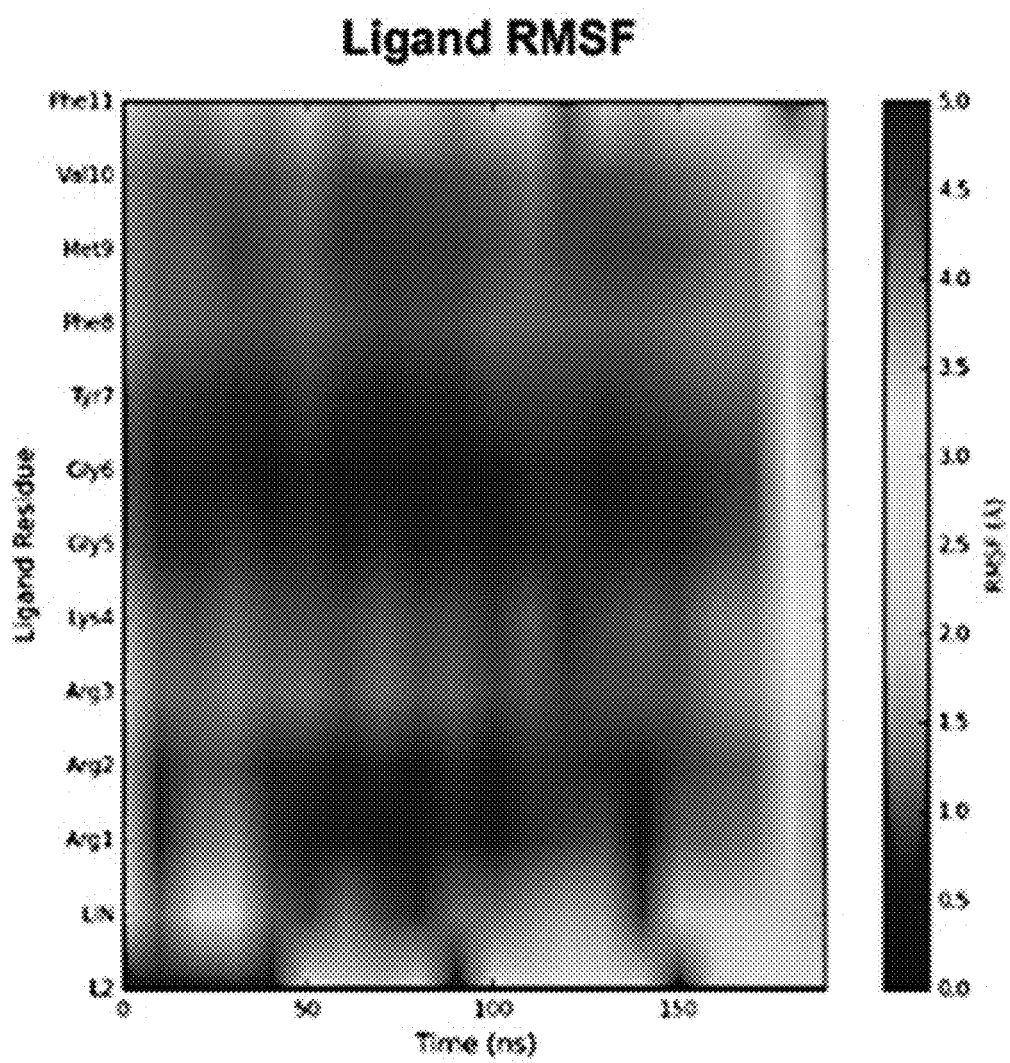
FIG. 22B shows the $C_\alpha$ RMSF of $L_2P_3$-EBNA1 complex.
Figure 22C:
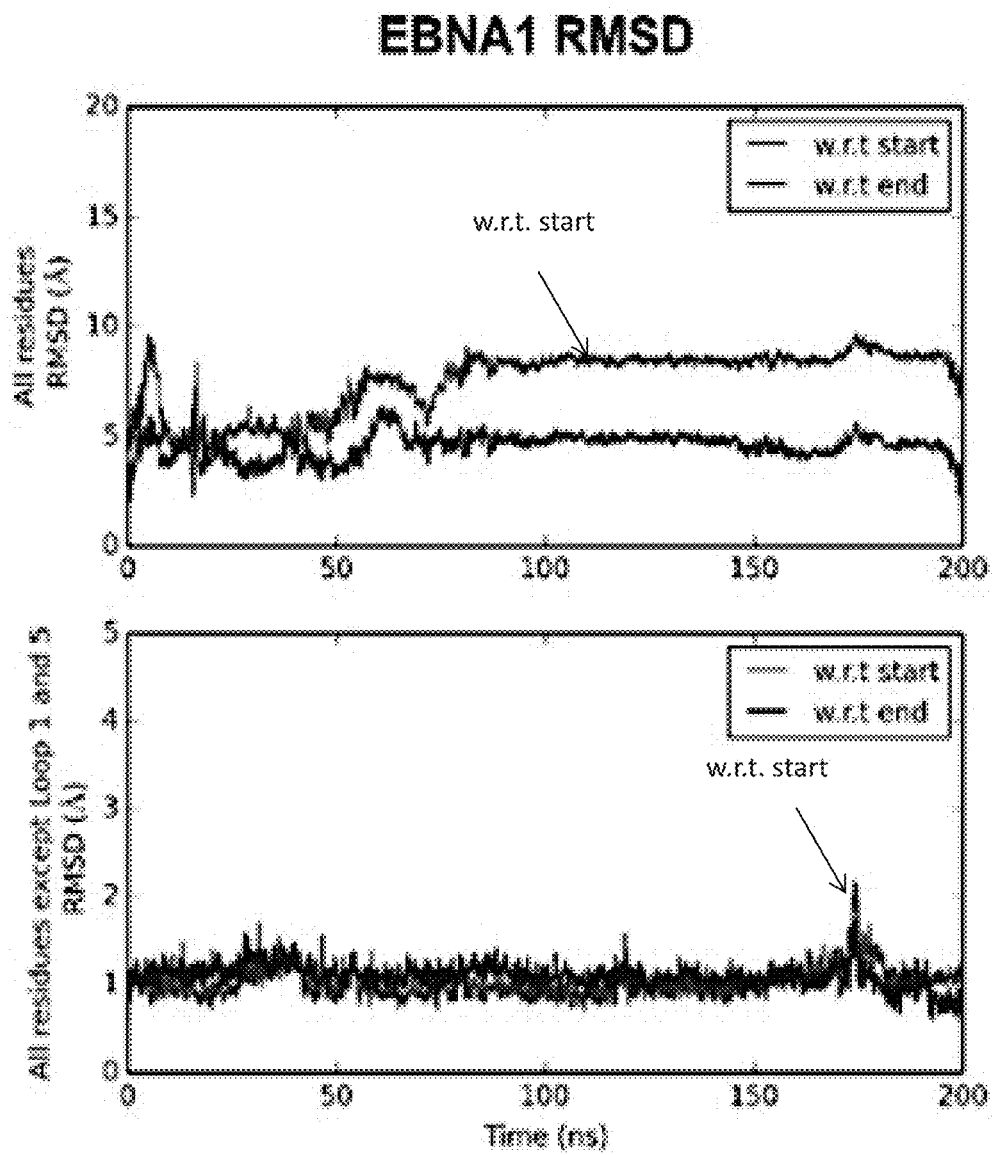
FIG. 22C shows the $C_\alpha$ RMSD of $L_2P_3$ in the MD simulation of $L_2P_3$-EBNA1 complex.
Figure 22D:
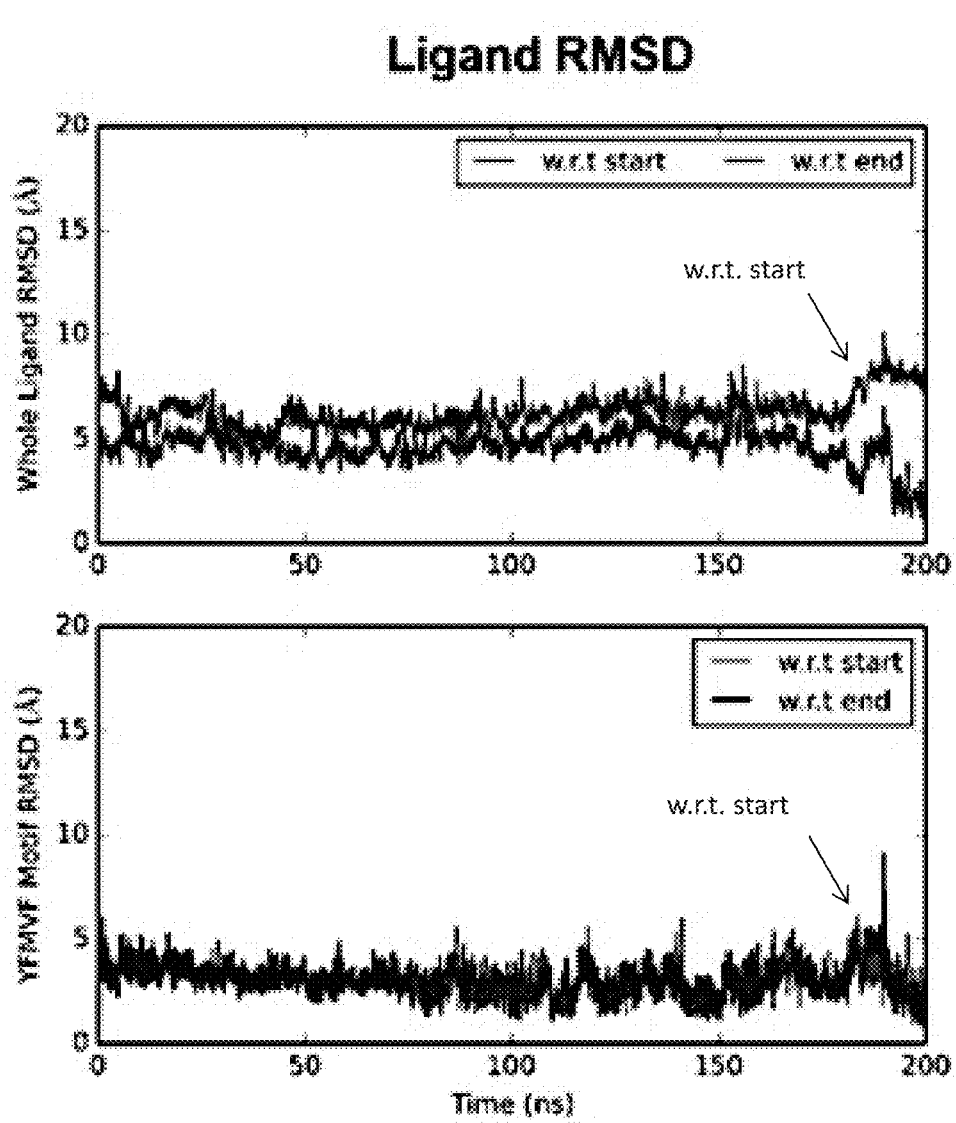
FIG. 22D shows the $C_\alpha$ RMSD evolution of all residues in $L_2P_3$ (upper) and the $C_\alpha$ RMSD for YFMVF motif (lower) with regard to the start or end conformation in the MD simulation of $L_2P_3$-EBNA1 complex.
Figure 22E:
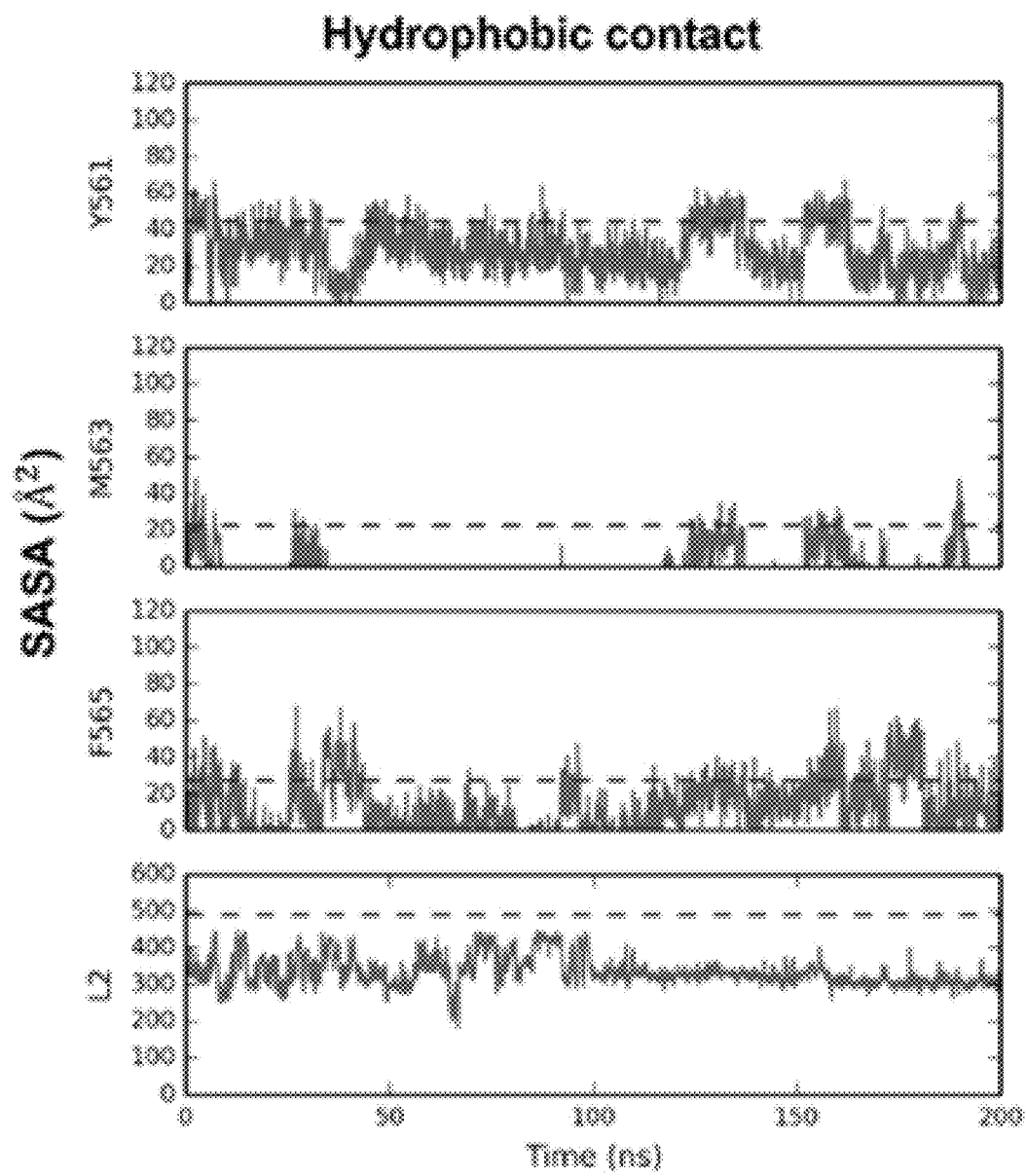
FIG. 22E shows the key residues on dimerization interface ($Y_{561}$, $M_{563}$ and $F_{565}$) involved in probe-receptor hydrophobic contacts in the MD simulation of $L_2P_3$-EBNA1 complex. Observations are made by calculating the SASA of each residue during the simulation and compared with its referential value (dashed line) in free-accessible status. If the SASA is smaller than the referential one, it suggests that the intra- or inter-chain hydrophobic contacts may be formed within that residue.
Figure 22F:
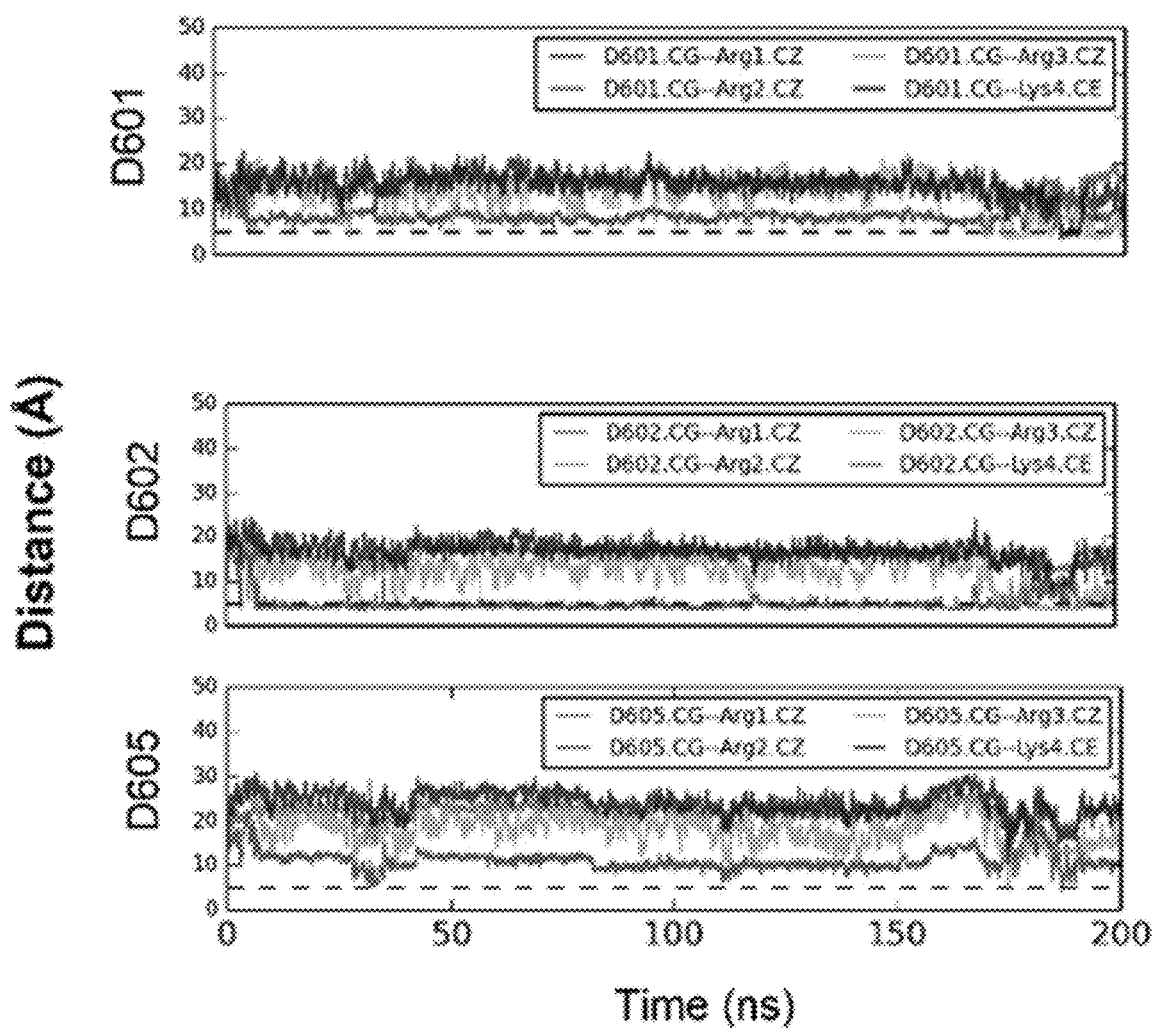
FIG. 22F shows the multiple acid residues at C-terminal of EBNA1 DBD domain ($D_{601}$, $D_{602}$ and $D_{605}$) involved in forming salt bridge (ion bonds) with basic motif (RrRK) in $L_2P_3$ in the MD simulation of $L_2P_3$-EBNA1 complex. Observations are made by measuring the distances between CG atom of $D_{601}/D_{602}/D_{605}$ and CZ/CE atom of aarginine/lysine. If the distance is less than 5 Å, it suggests a salt bridge may be formed between the acid-basic residue pair.
Figure 23A:
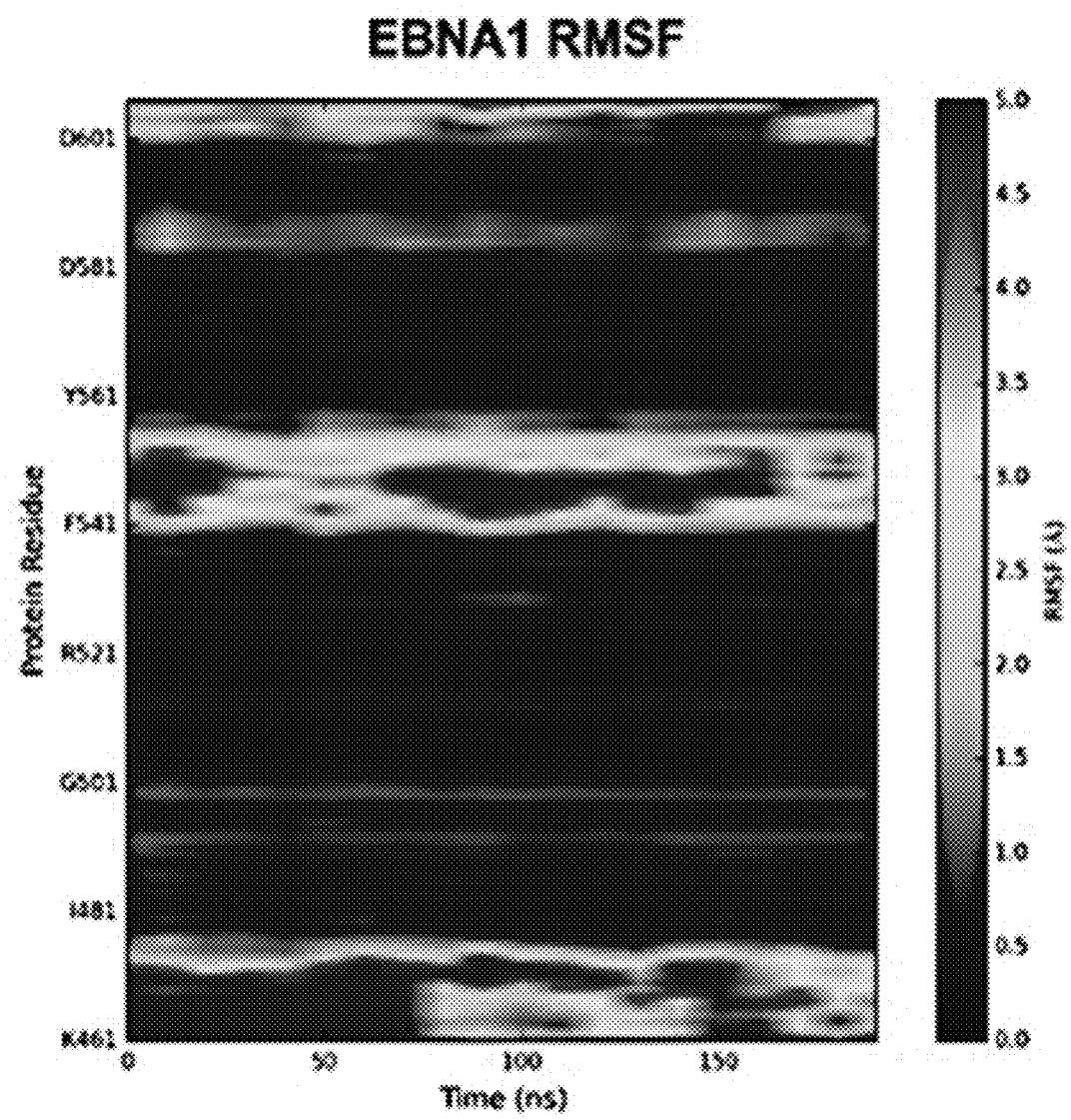
FIG. 23A shows the $C_\alpha$ RMSF of all residues in EBNA1 in the MD simulation of $P_4$-EBNA1 complex.
Figure 23B:
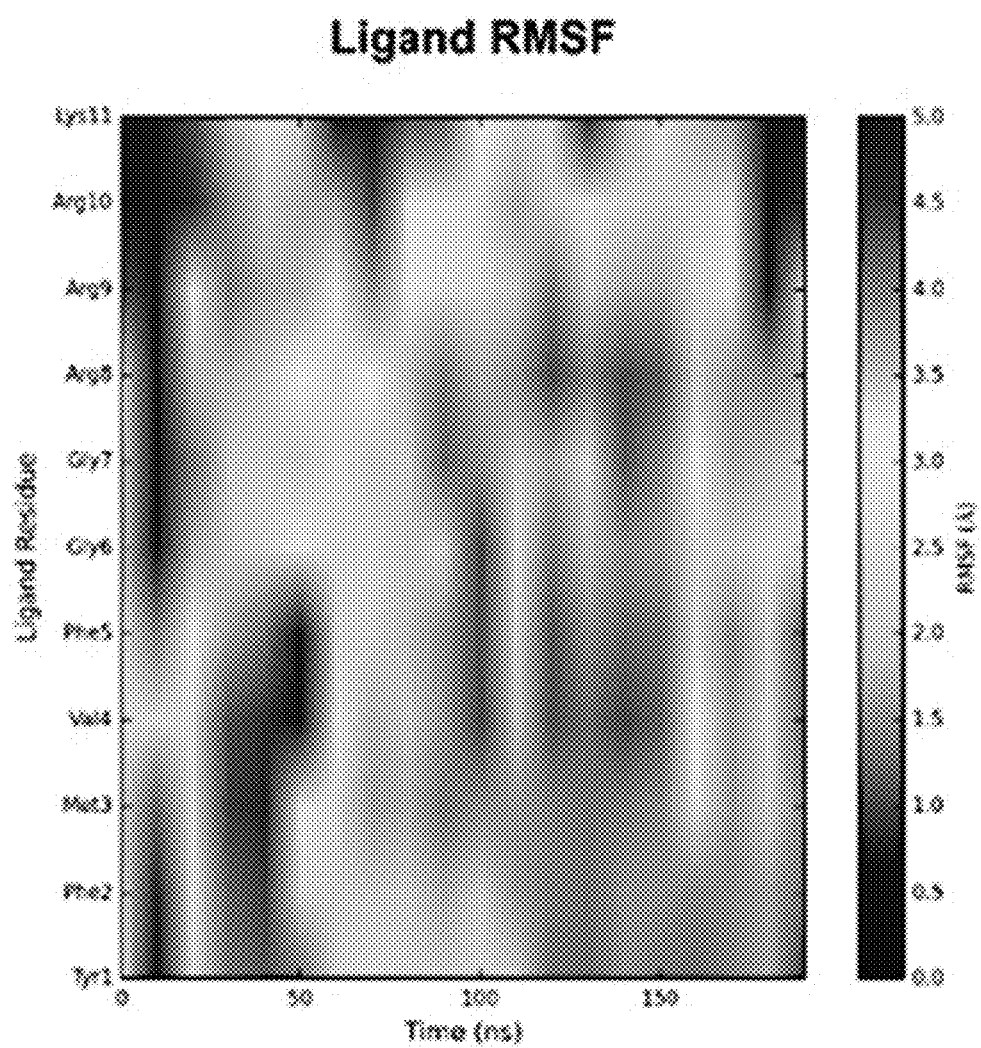
FIG. 23B shows the $C_\alpha$ RMSF of $P_4$ in the MD simulation of $P_4$-EBNA1 complex.
Figure 23C:
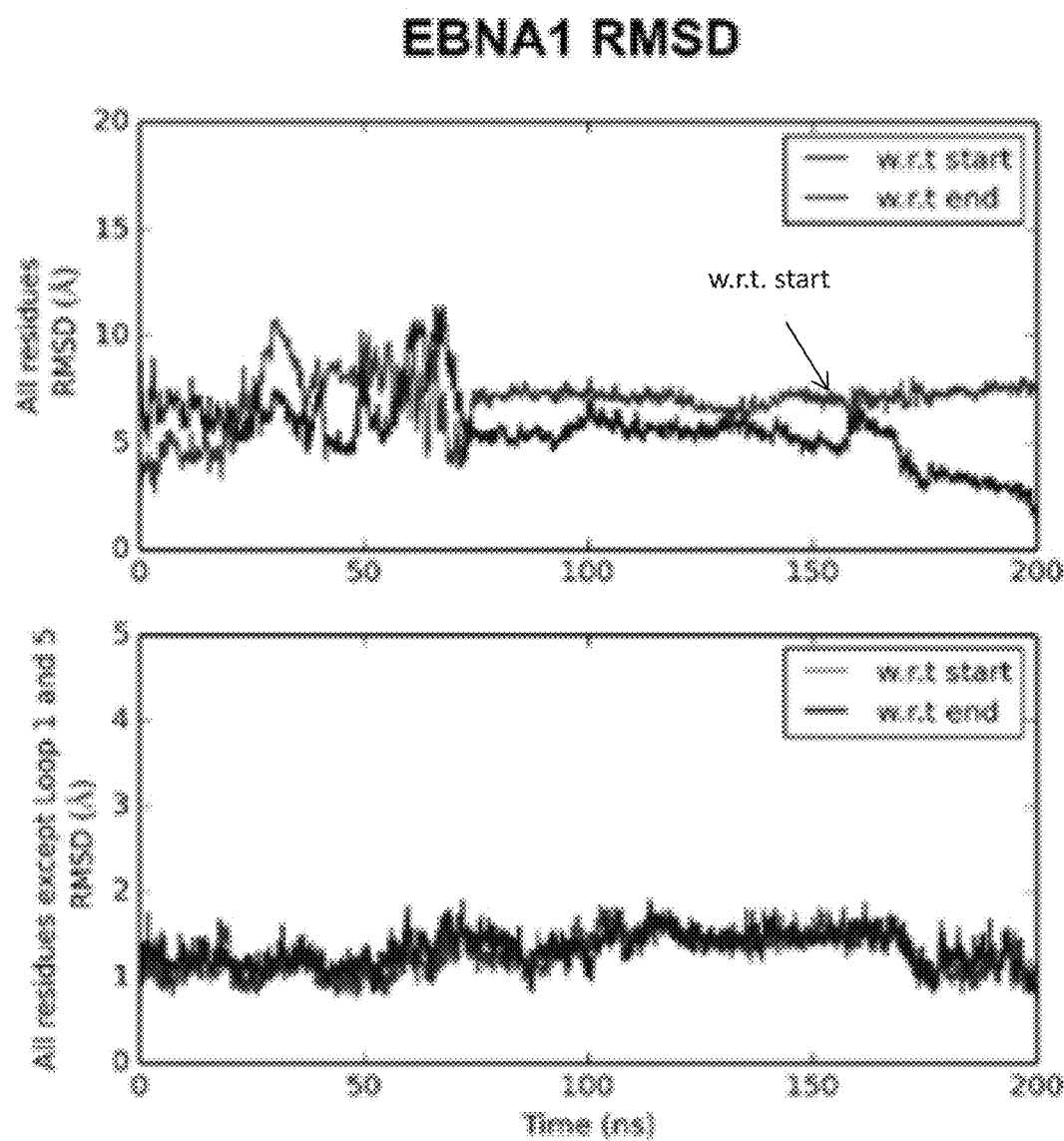
FIG. 23C shows the $C_\alpha$ RMSD evolution with all residues (upper) and all residues except the highly dynamic loop 1 and 5 (lower) of EBNA1 with regard to start or end in the MD simulation of $P_4$-EBNA1 complex.
Figure 23D:
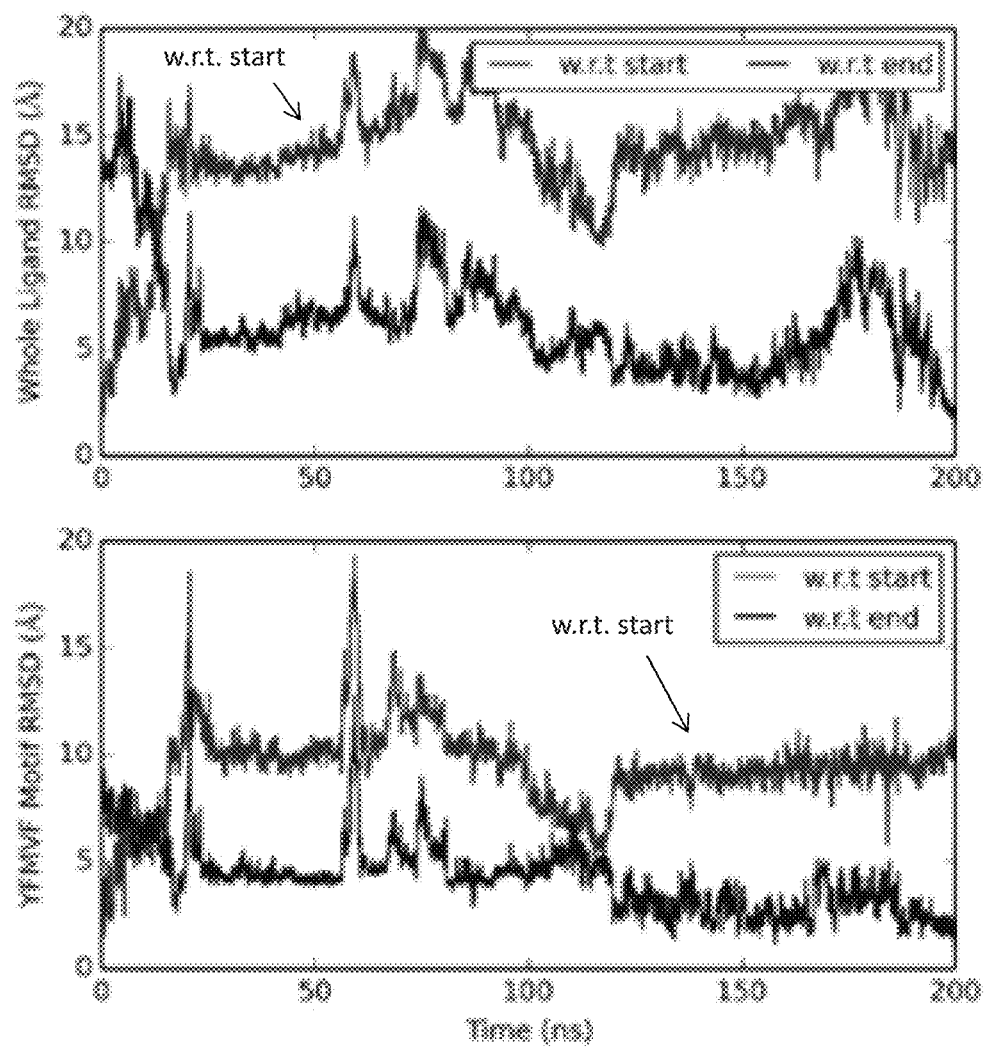
FIG. 23D shows the $C_\alpha$ RMSD evolution of all residues in $P_4$ (upper) and the $C_\alpha$ RMSD for YFMVF motif (lower) with regard to the start or end conformation in the MD simulation of $P_4$-EBNA1 complex.
Figure 23E:
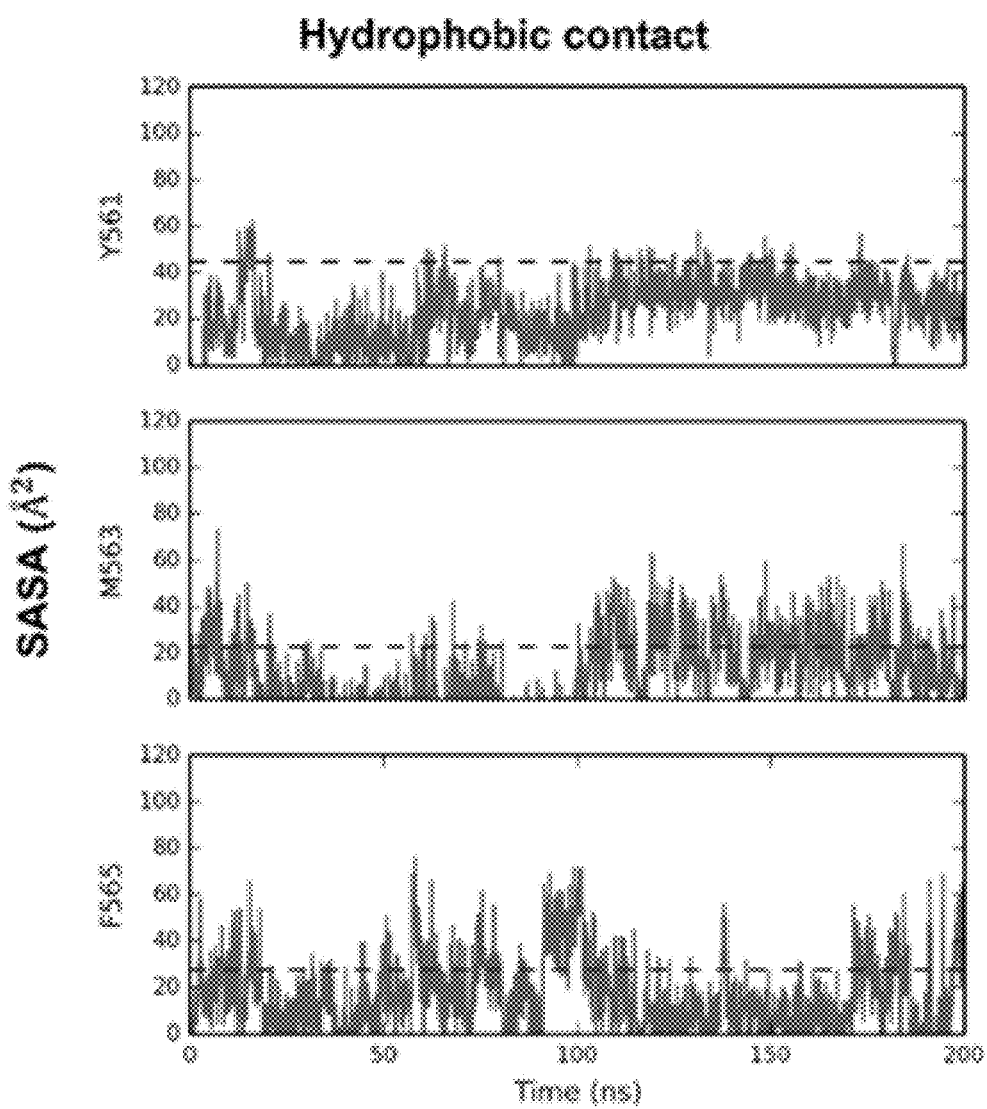
FIG. 23E shows the key residues on dimerization interface ($Y_{561}$, $M_{563}$ and $F_{565}$) involved in probe-receptor hydrophobic contacts in the MD simulation of $P_4$-EBNA1 complex. Observations are made by calculating the SASA of each residue during simulation and compared with its referential value (dashed line) in free-accessible status. If the SASA is smaller than the referential one, it suggests than the intra- or inter-chain hydrophobic contacts may be formed with that residue.
Figure 23F:
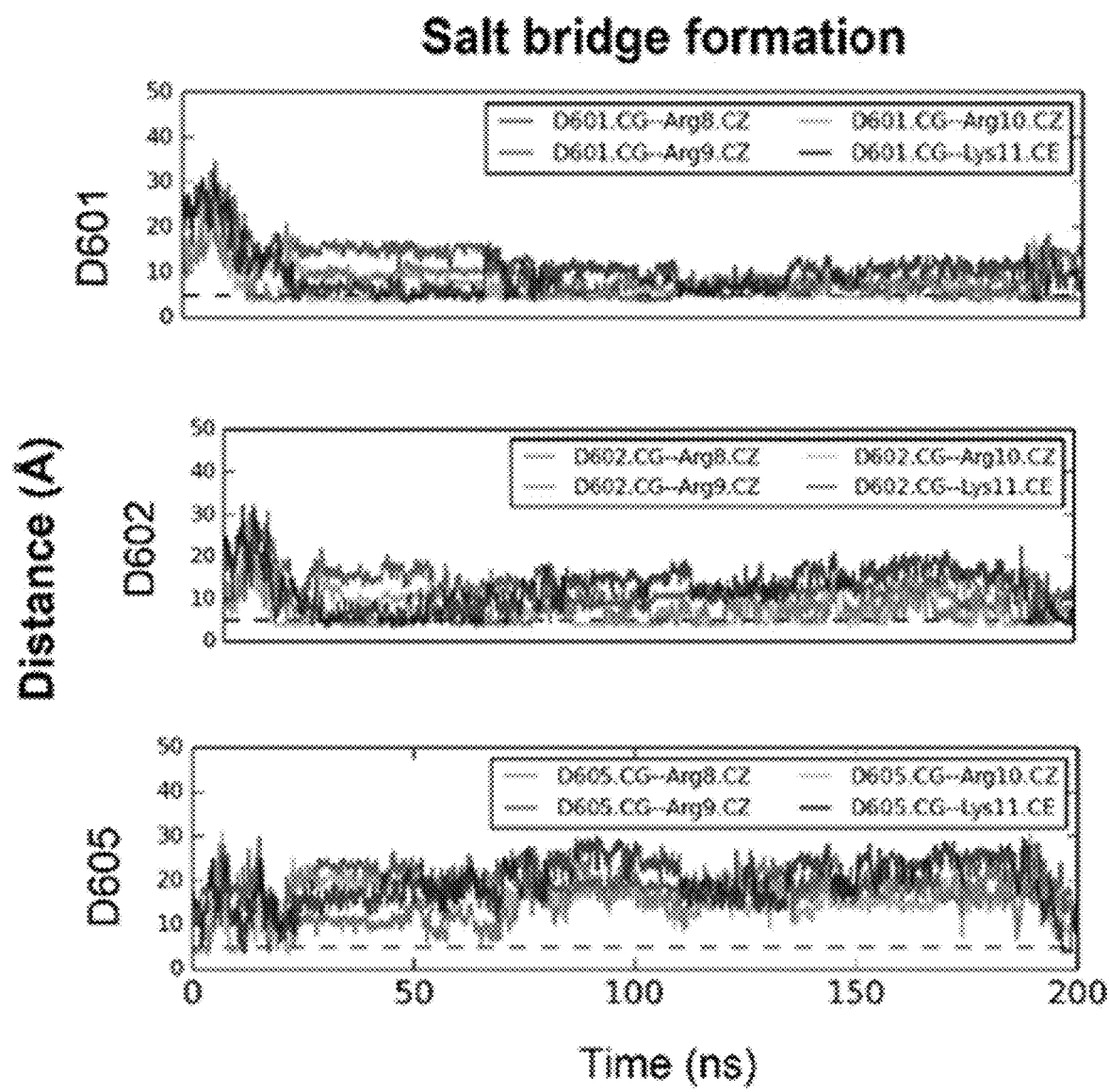
FIG. 23F shows the multiple acid residues at C-terminal of EBNA1 DBD domain ($D_{601}$, $D_{602}$ and $D_{605}$) involved in forming salt bridge (ion bonds) with basic motif (RrRK) in $P_4$ in the MD simulation of $P_4$-EBNA1 complex. Observations were made by measuring the distances between CG atoms of $D_{601}/D_{602}/D_{605}$ and CZ/CE atom of arginine/lysine. If the distance is less than 5 Å, it suggests a salt bridge may be formed between the acid-basic residue pair.
Figure 24A:
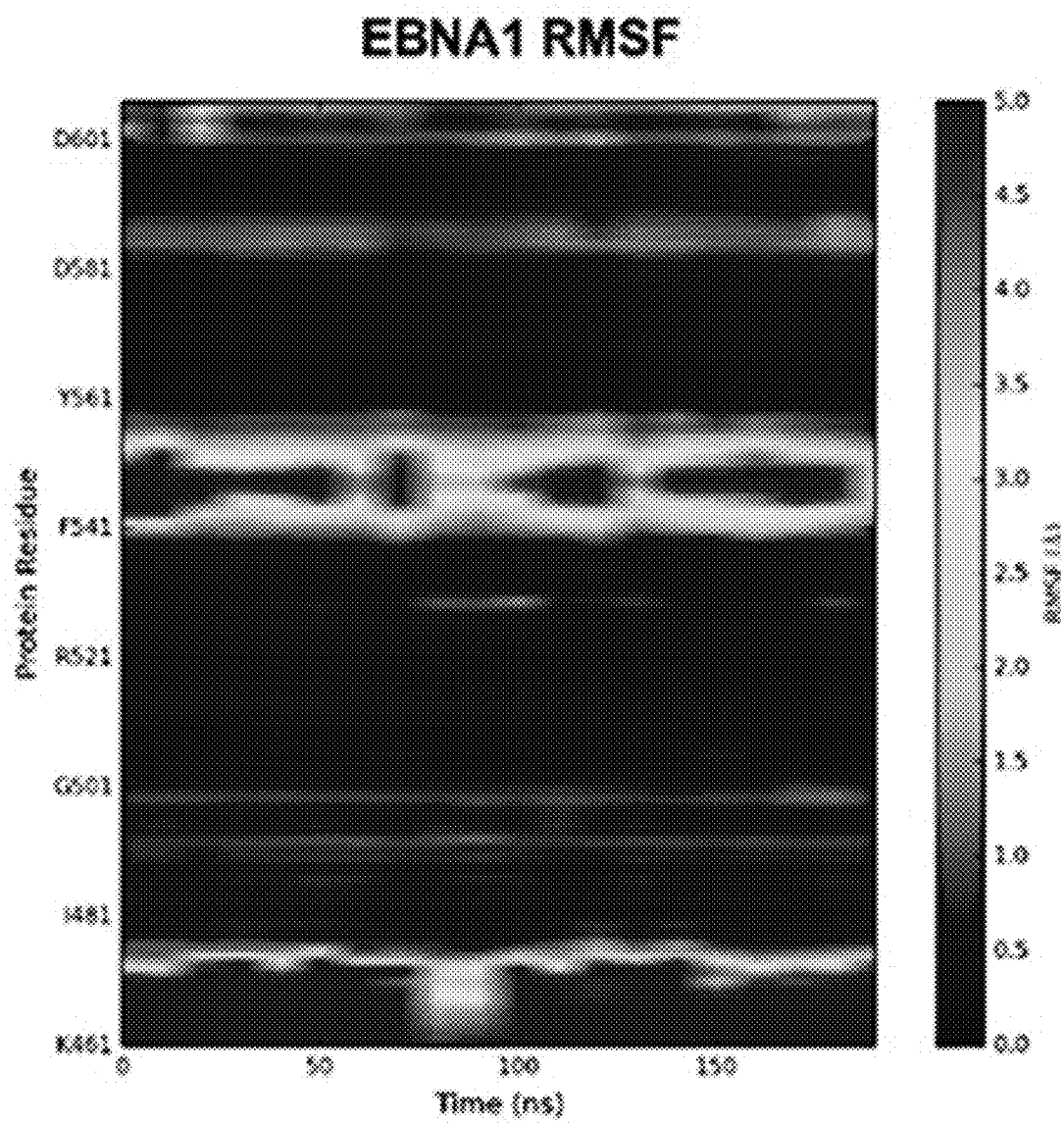
FIG. 24A shows the $C_\alpha$ RMSF of all residues in EBNA1 in the MD simulation of $L_2P_4$-EBNA1 complex.
Figure 24B:
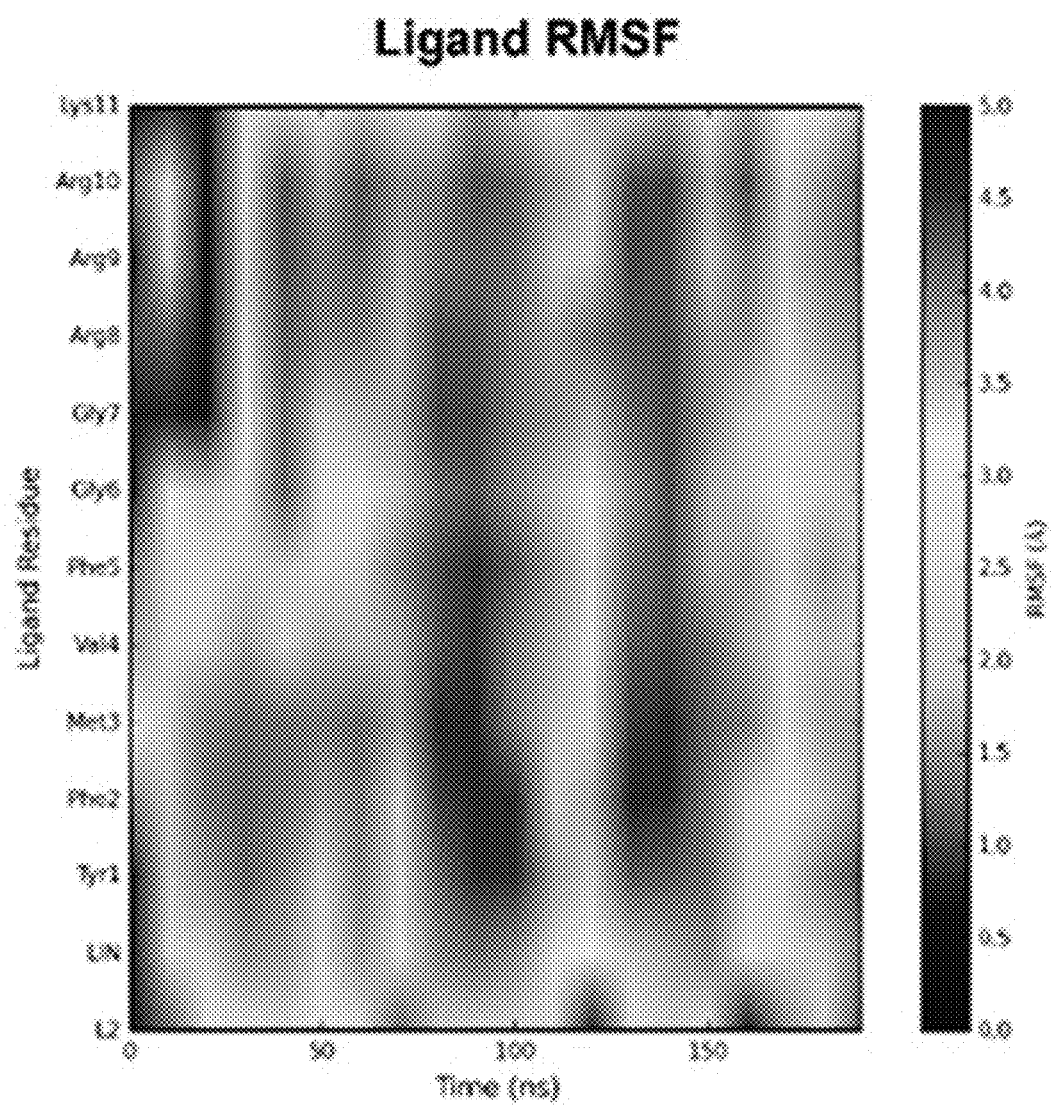
FIG. 24B shows the $C_\alpha$ RMSF of $L_2P_4$ in the MD simulation of $L_2P_4$-EBNA1 complex.
Figure 24C:
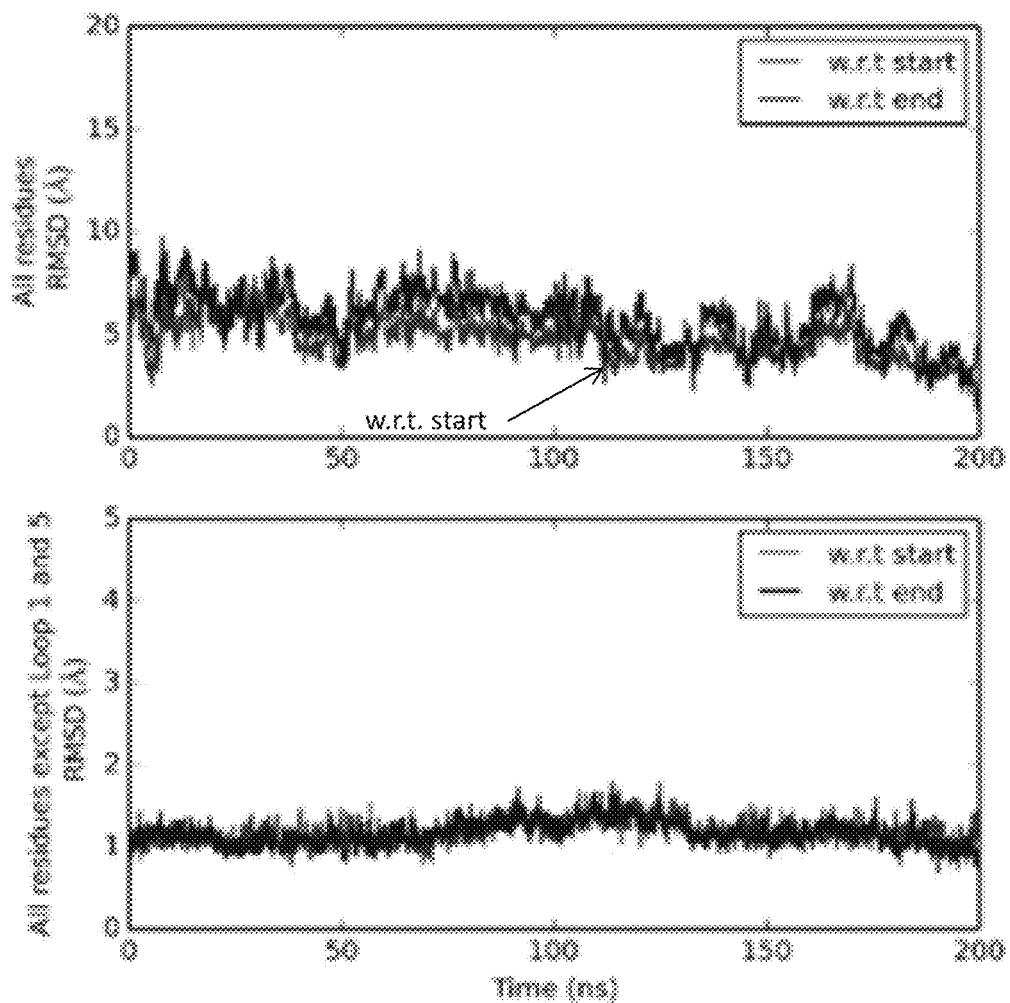
FIG. 24C shows the $C_\alpha$ RMSD evolution with all residues (upper) and all residues except the highly dynamic loop 1 and 5 (lower) of EBNA1 with regard to start or end conformation in the MD simulation in $L_2P_4$-EBNA1 complex.
Figure 24D:
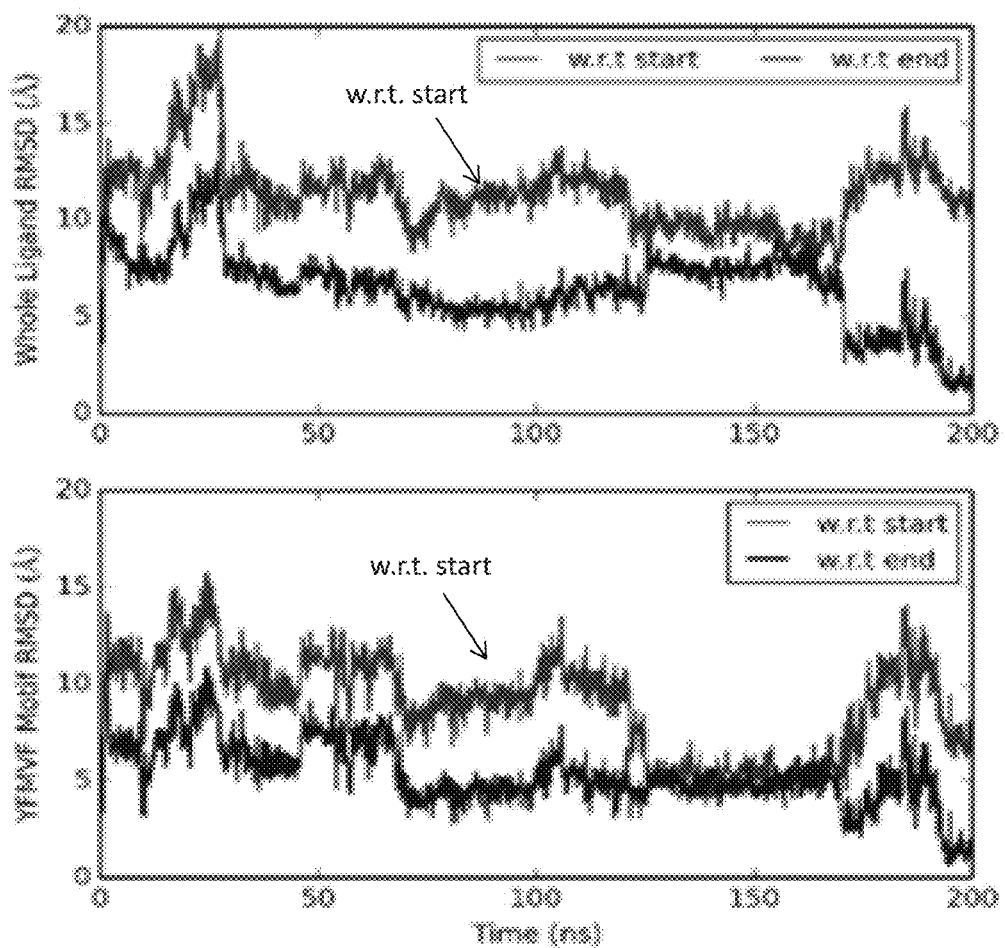
FIG. 24D shows the $C_\alpha$ RMSD evolution of all residues in $L_2P_4$ (upper) and the $C_\alpha$ RMSD for YFMVF (lower) motif with regard to the start or end conformation in the MD simulation of $L_2P_4$-EBNA1 complex.
Figure 24E:
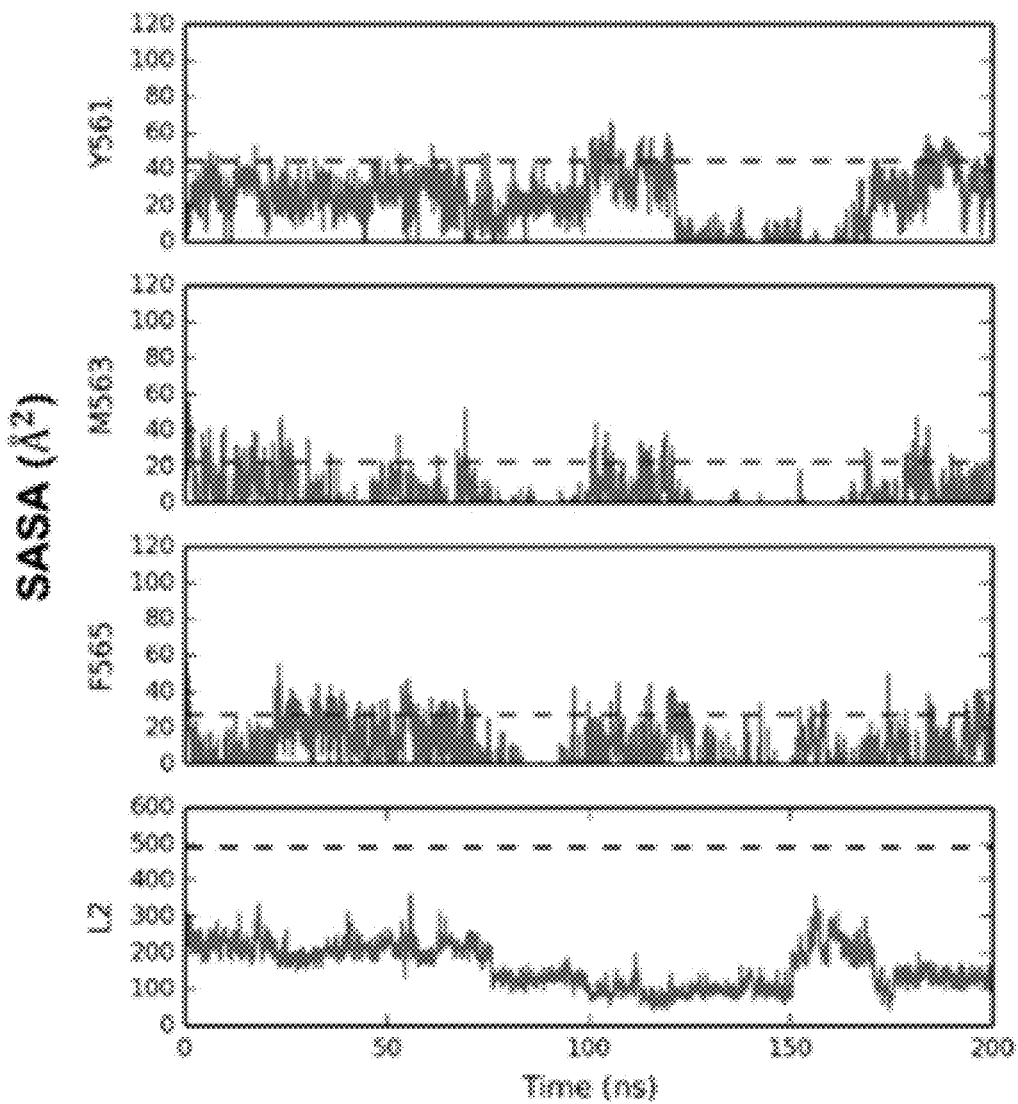
FIG. 24E shows the key residues on dimerization interface ($Y_{561}$, $M_{563}$ and $F_{565}$) involved in probe-receptor hydrophobic contacts in the MD simulation of $L_2P_4$-EBNA1 complex. Observations are made by calculating the SASA of each residue during simulation and compared with its referential value (dashed line) in free-accessible status. If the SASA is smaller than the referential one, it suggests that the intra- or inter-chain hydrophobic contacts may be formed within that residue.
Figure 24F:
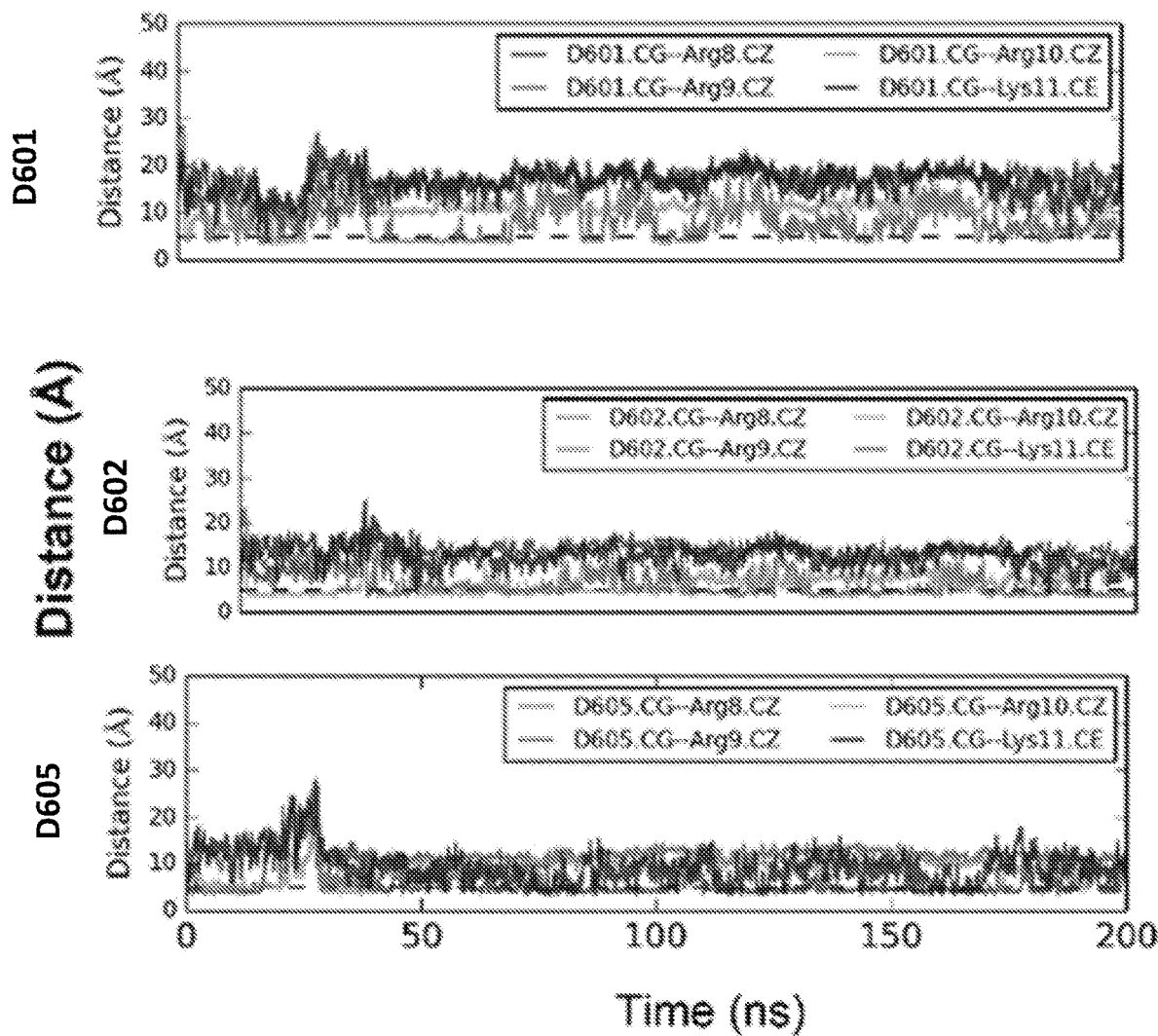
FIG. 24F shows the multiple acid residues at C-terminal of EBNA1 DBD domain ($D_{601}$, $D_{602}$ and $D_{605}$) involved in forming salt bridge (ion bonds) with basic motif (RrRK) in $L_2P_4$ in the MD simulation of $L_2P_4$-EBNA1 complex. Observations are made by measuring the distances between CG atom of $D_{601}/D_{602}/D_{605}$ and CZ/CE atom of arginine/lysine. If the distance is less than 5 Å, it suggests a salt bridge may be formed between the acid-basic residue pair.
Figure 25A:
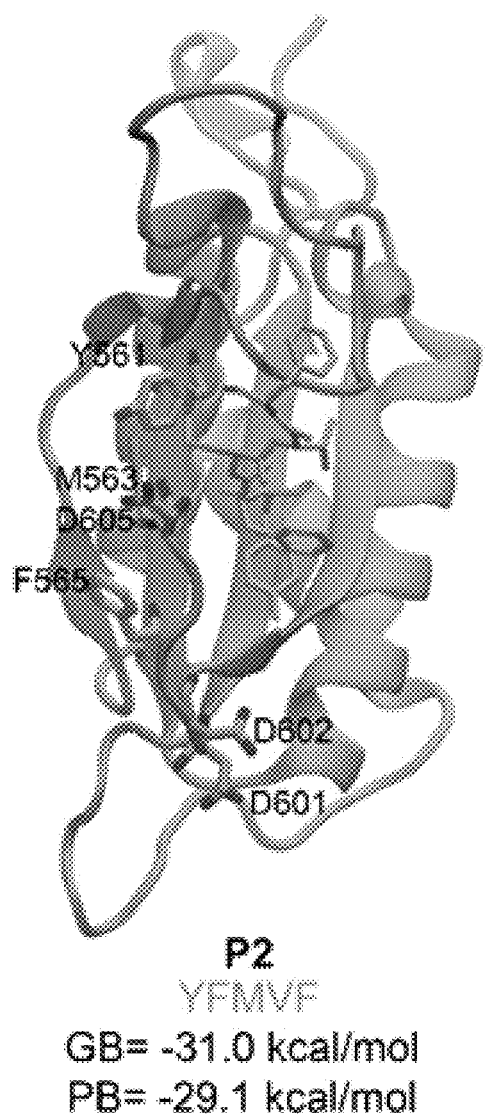
FIG. 25A shows the representative structure resulted from 200 ns MD simulation of $P_2$-EBNA1 complex. The peptide sequence and GB/PB binding free energy has been marked in each complex. EBNA1 is rendered in ribbon, and the major binding sites in EBNA1 are rendered in stick mode in the 3D structure, including the $Y_{561}$, $M_{563}$, $F_{565}$, $D_{601}$, $D_{602}$ and $D_{605}$.
Figure 25B:
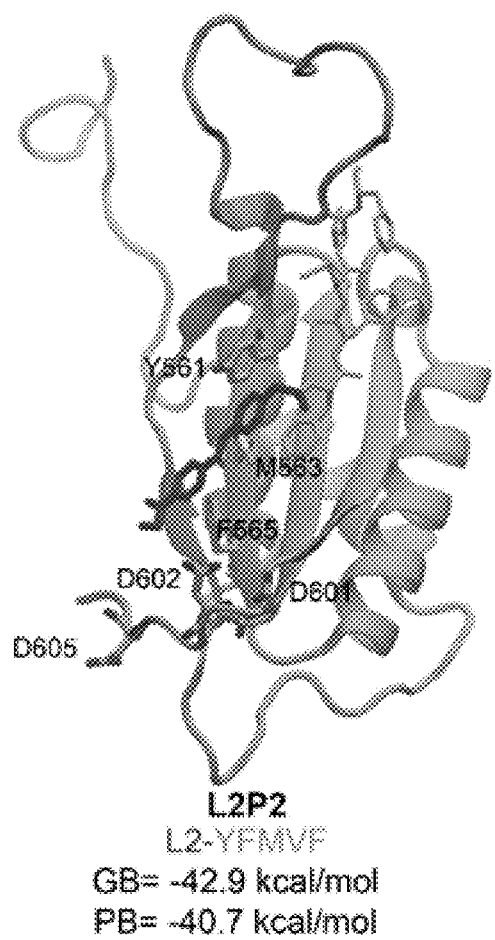
FIG. 25B shows the representative structure resulted from 200 ns MD simulation of $L_2P_2$-EBNA1 complex. The peptide sequence and GB/PB binding free energy has been marked in each complex. EBNA1 is rendered in ribbon, and the major binding sites in EBNA1 are rendered in stick mode in the 3D structure, including the $Y_{561}$, $M_{563}$, $F_{565}$, $D_{601}$, $D_{602}$ and $D_{605}$.
Figure 25C:
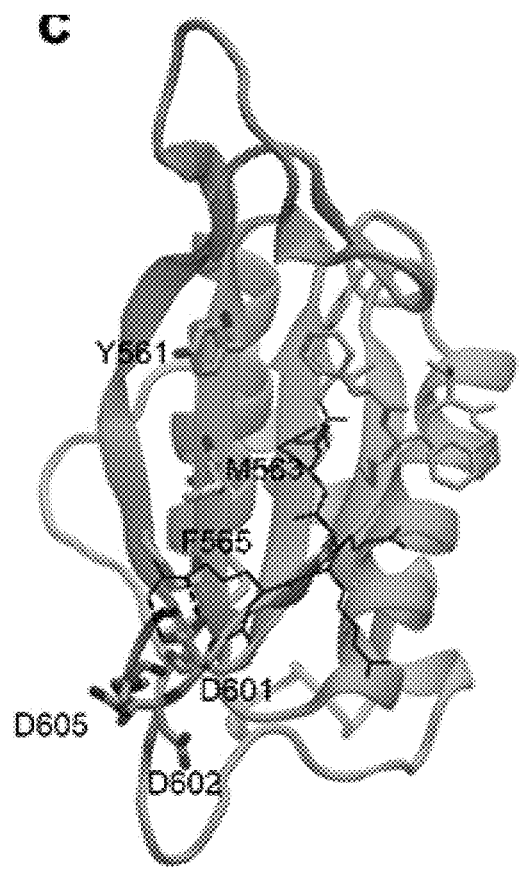
FIG. 25C shows the representative structure resulted from 200 ns MD simulation of $P_3$-EBNA1 complex. The peptide sequence and GB/PB binding free energy has been marked in each complex. EBNA1 is rendered in ribbon, and the major binding sites in EBNA1 are rendered in stick mode in the 3D structure, including the $Y_{561}$, $M_{563}$, $F_{565}$, $D_{601}$, $D_{602}$ and $D_{605}$.
Figure 25D:
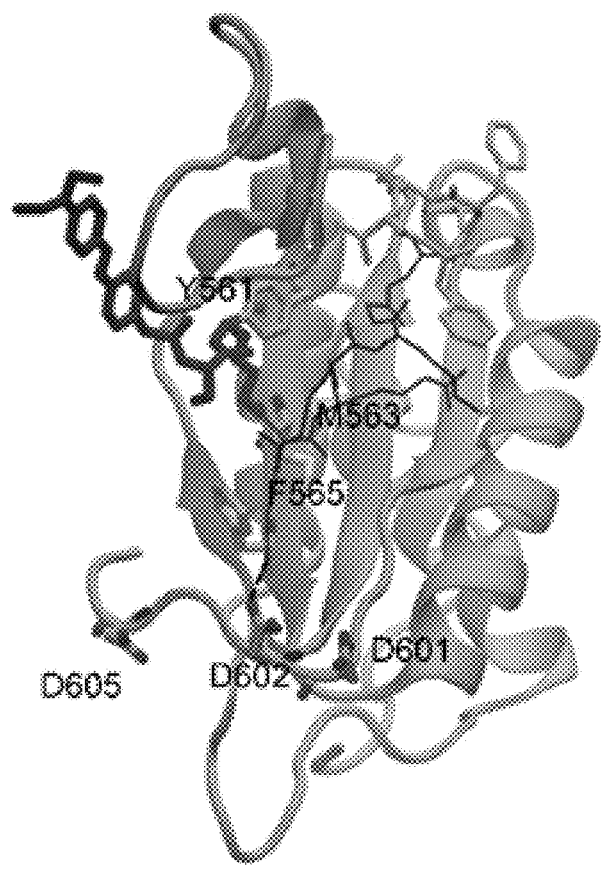
FIG. 25D shows the representative structure resulted from 200 ns MD simulation of $L_2P_3$-EBNA1 complex. The peptide sequence and GB/PB binding free energy has been marked in each complex. EBNA1 is rendered in ribbon, and the major binding sites in EBNA1 are rendered in stick mode in the 3D structure, including the $Y_{561}$, $M_{563}$, $F_{565}$, $D_{601}$, $D_{602}$ and $D_{605}$.
Figure 25E:
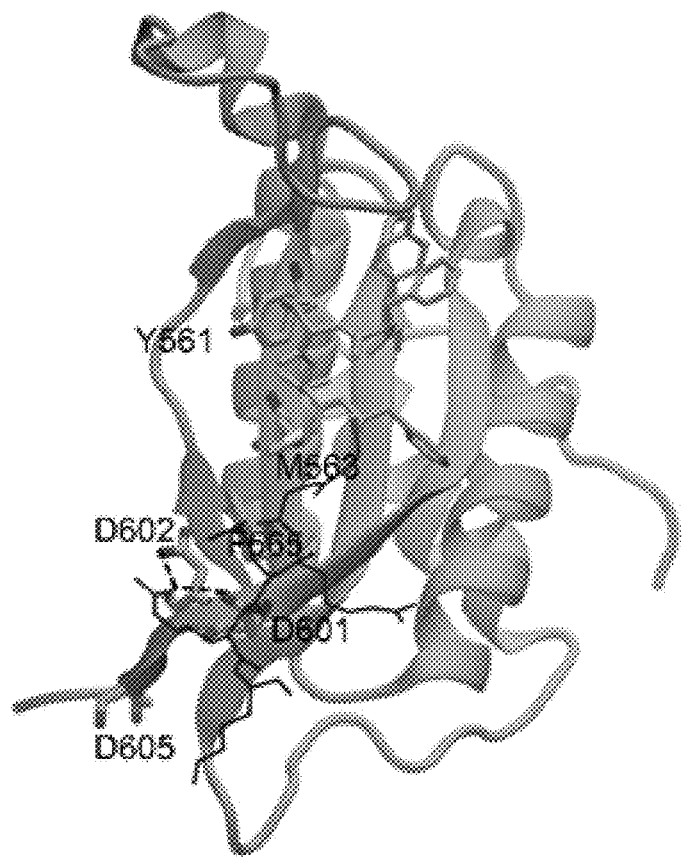
FIG. 25E shows the representative structure resulted from 200 ns MD simulation of $P_4$-EBNA1 complex. The peptide sequence and GB/PB binding free energy has been marked in each complex. EBNA1 is rendered in ribbon, and the major binding sites in EBNA1 are rendered in stick mode in the 3D structure, including the $Y_{561}$, $M_{563}$, $F_{565}$, $D_{601}$, $D_{602}$ and $D_{605}$.
Figure 25F:
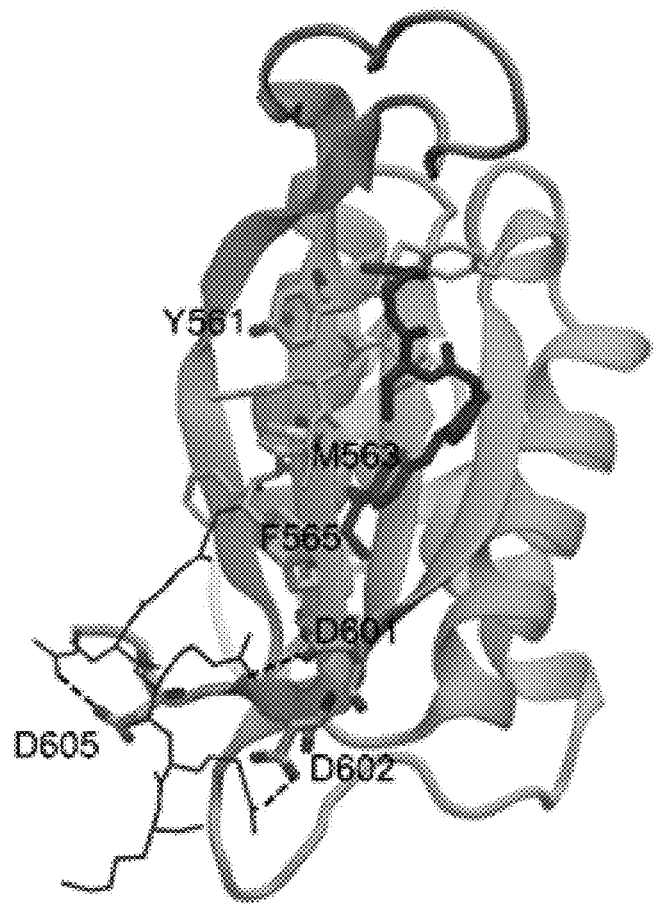
FIG. 25F shows the representative structure resulted from 200 ns MD simulation of $L_2P_4$-EBNA1 complex. The peptide sequence and GB/PB binding free energy has been marked in each complex. EBNA1 is rendered in ribbon, and the major binding sites in EBNA1 are rendered in stick mode in the 3D structure, including the $Y_{561}$, $M_{563}$, $F_{565}$, $D_{601}$, $D_{602}$ and $D_{605}$.

To better characterize the ligand-EBNA1 complex, calculation of the binding energy, 200 ns MD simulations are performed using the selected docked poses to calculate the interaction energy in the complex. The AMBER (assisted model building with energy refinement) types of the non-standard residues are parameterized (FIGS. 18A-18B) and the missing force field parameters are defined before running the MD simulations. All complexes are found to be stable after 50 ns. The salt-bridge interaction appears only in the $P_3$ and $P_4$ containing ligands having the RrRK tetrapeptide. Despite this, the main interactions shown by the MD simulations for each complex are similar (clear hydrophobic contacts and salt-bridging; FIGS. 25A-25F). The hydrophobic interactions are found between the ligands and the key residues on the dimeric interface, while the salt bridging/ionic bonding are found between the RrRK motif and several residues in the aspartate-rich tail in EBNA1 ($D_{602}$, $D_{601}$ and $D_{605}$). In particular, $D_{602}$ demonstrates the strongest salt-bridge interaction and $D_{605}$ shows the weakest (FIGS. 19A-19E, 20A-20E, 21A-21F, 22A-22F, 23A-23F and 24A-24F). Taken together, the MD simulations show two major interaction types, which facilitate the binding of the peptide conjugates of the present invention to EBNA1. They also demonstrated a secondary role for the RrRK sequence in binding to EBNA1, in additional to nuclear localization.

The binding free energy for all complexes is calculated by the Molecular Mechanics Poisson-Boltzmann Surface Area (MMPBSA) method. The calculated generalized Born (GB) and Poisson-Boltzmann (PB) values took the same order, $L_2P_4>L_2P_3>L_2P_2$, indicating that $L_2P_4$ has the strongest binding interaction with EBNA1.

b. Responsive Emission of $L_2P_4$ with EBNA1.—

Figure 26A:
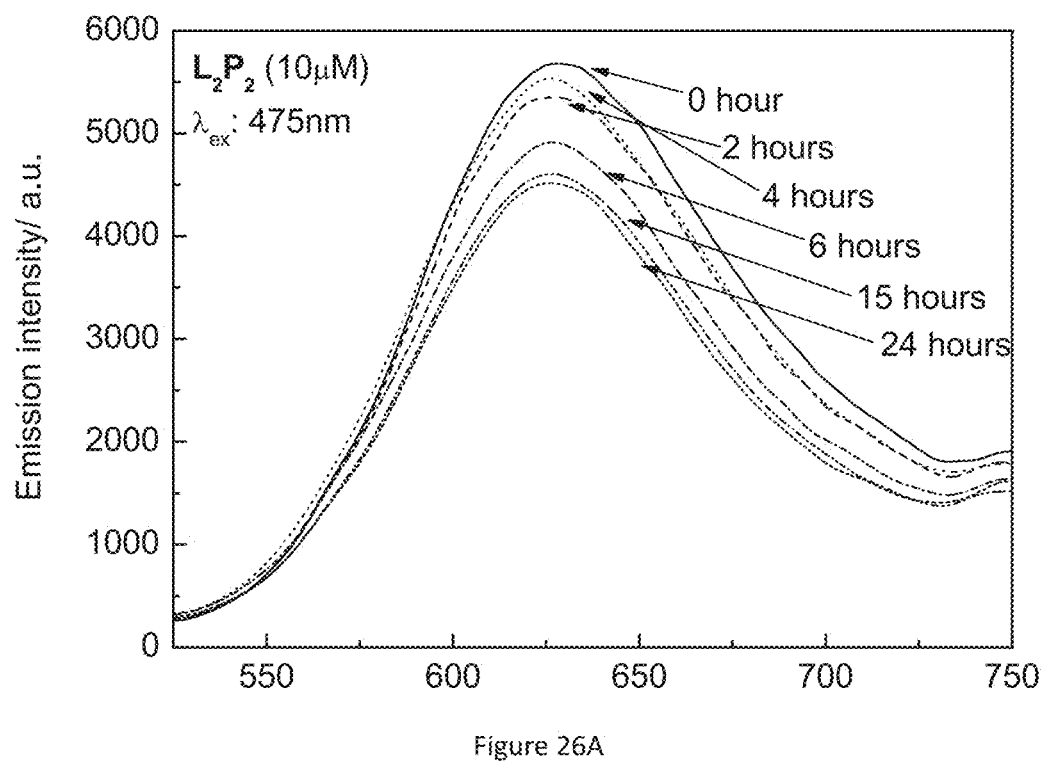
FIG. 26A shows the emission spectra of $L_2P_2$ in PBS buffer at t=0 hour and after incubation for 2, 4, 6, 15 and 24 hours at 37° C. (Concentration: 1 µM, PBS buffer: 8 g NaCl, 0.2 g KCl, 0.2 g $KH_2PO_4$, 3.62 g $Na_2HPO_4 \cdot 12H_2O$).
Figure 26B:
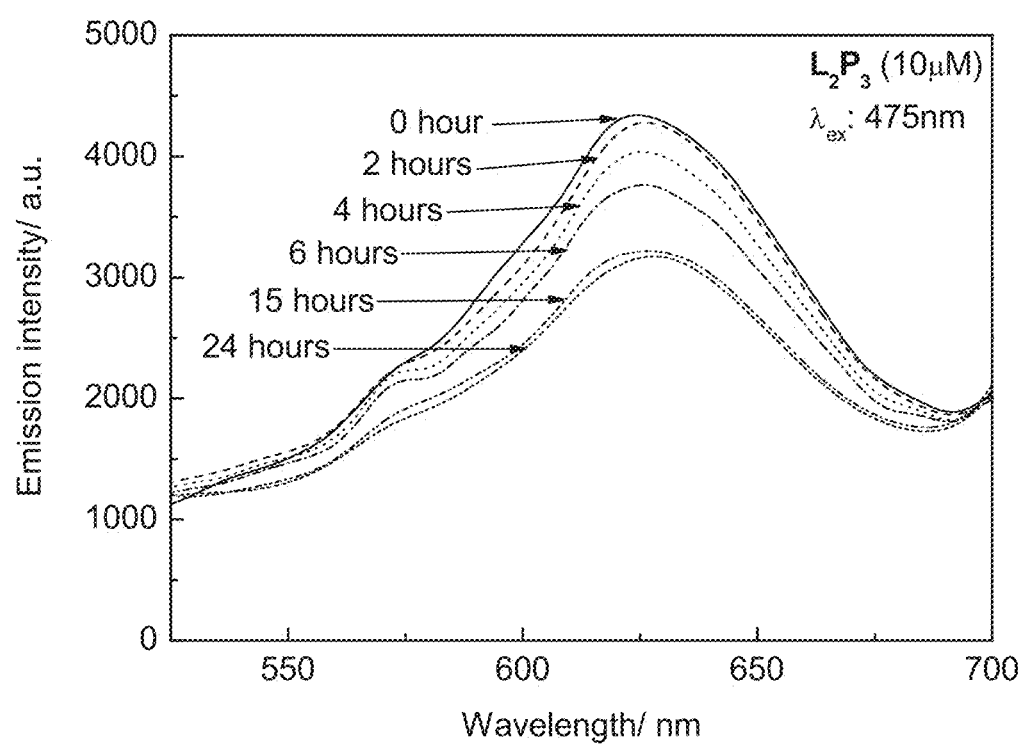
FIG. 26B shows the emission spectra of $L_2P_3$ in PBS buffer at t=0 hour and after incubation for 2, 4, 6, 15 and 24 hours at 37° C. (Concentration: 1 µM in PBS buffer: 8 g NaCl, 0.2 g KCl, 0.2 g $KH_2PO_4$, 3.62 g $Na_2HPO_4 \cdot 12H_2O$).
Figure 26C:
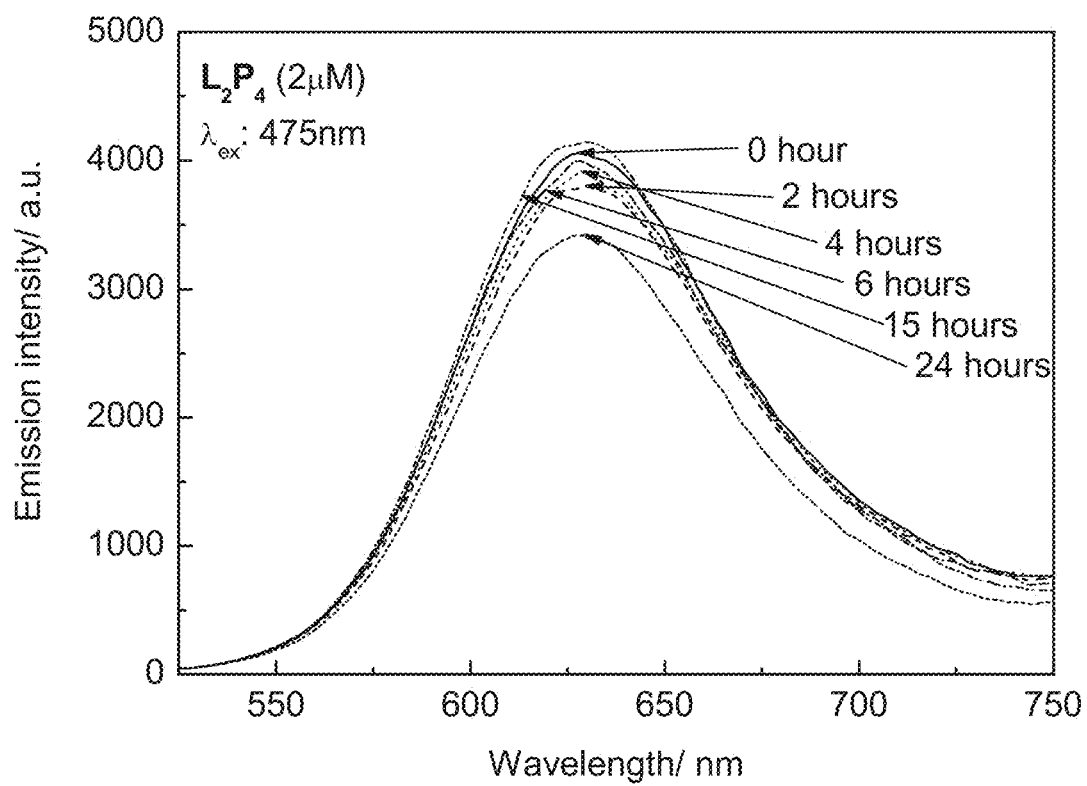
FIG. 26C shows the emission spectra of $L_2P_4$ in PBS buffer at t=0 hour and after incubation for 2, 4, 6, 15 and 24 hours at 37° C. (Concentration: 1 µM in PBS buffer: 8 g NaCl, 0.2 g KCl, 0.2 g $KH_2PO_4$, 3.62 g $Na_2HPO_4 \cdot 12H_2O$).
Figure 27A:
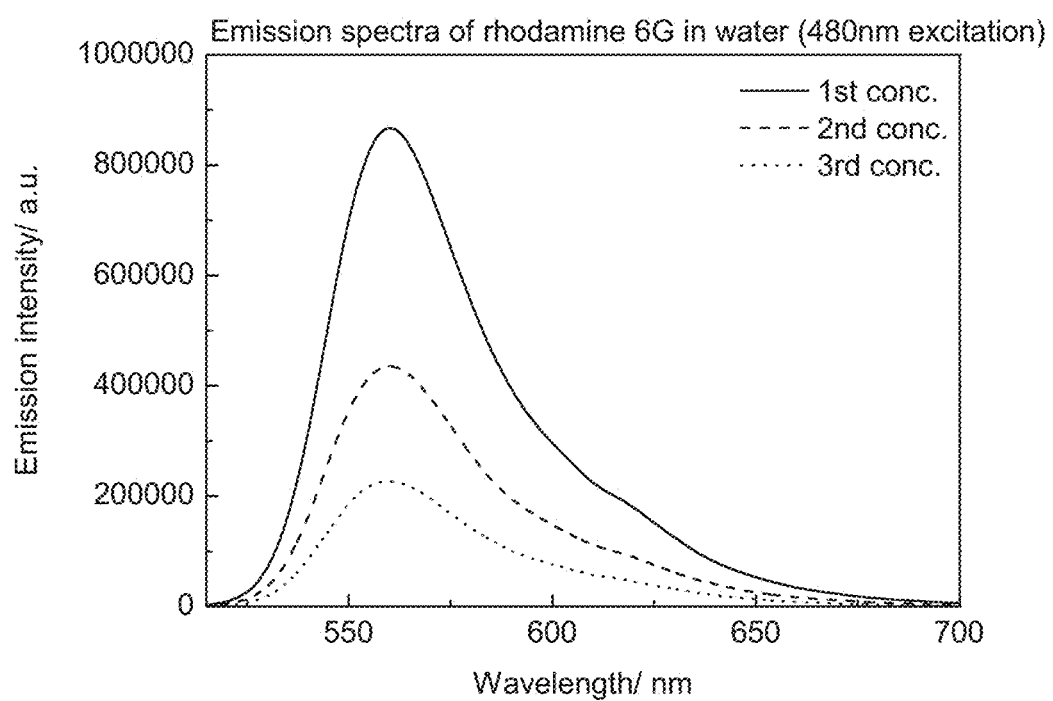
FIG. 27A shows the emission spectra of rhodamine 6G in water for the emission quantum yield determination ($\lambda_{ex}$=480 nm).
Figure 27B:
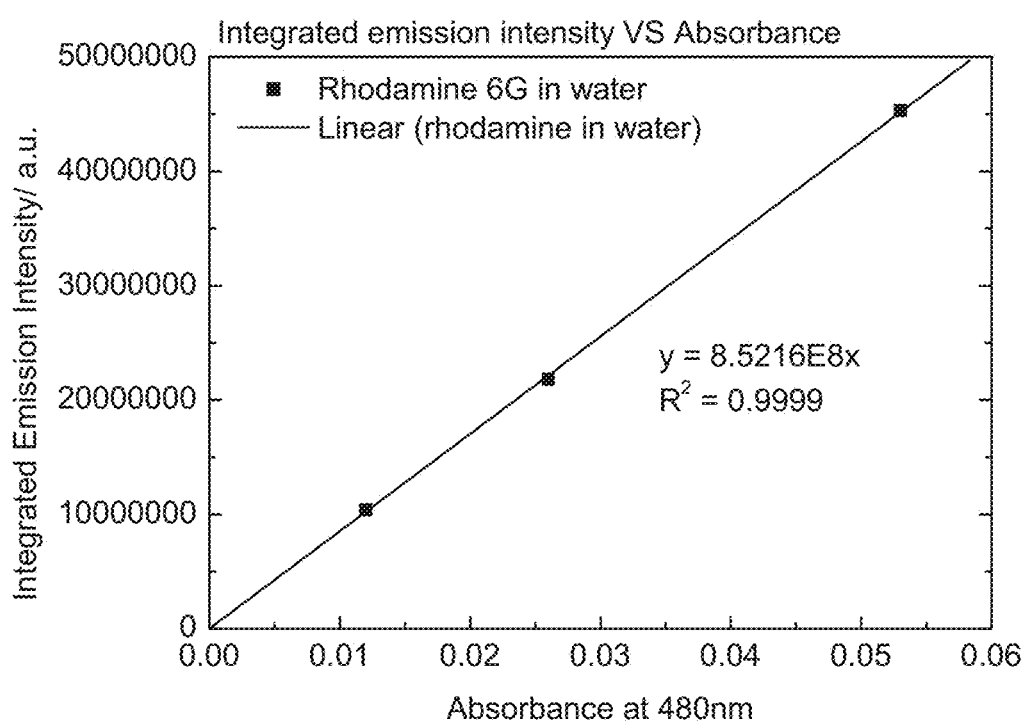
FIG. 27B shows the emission plot (emission vs absorbance) of rhodamine in water for the emission quantum yield determination ($\lambda_{ex}$=480 nm).
Figure 27C:
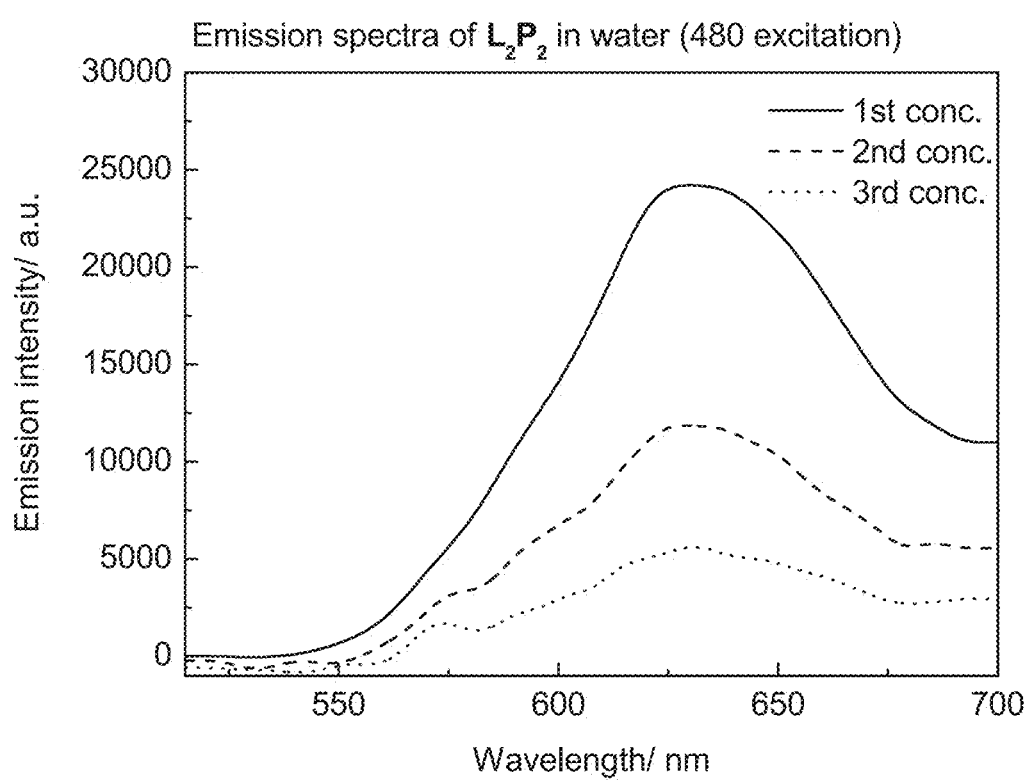
FIG. 27C shows the emission spectra of $L_2P_2$ in water for the emission quantum yield determination ($\lambda_{ex}$=480 nm. By comparative method using rhodamine 6G, the quantum yield of $L_2P_2$ is 4.4%).
Figure 27D:
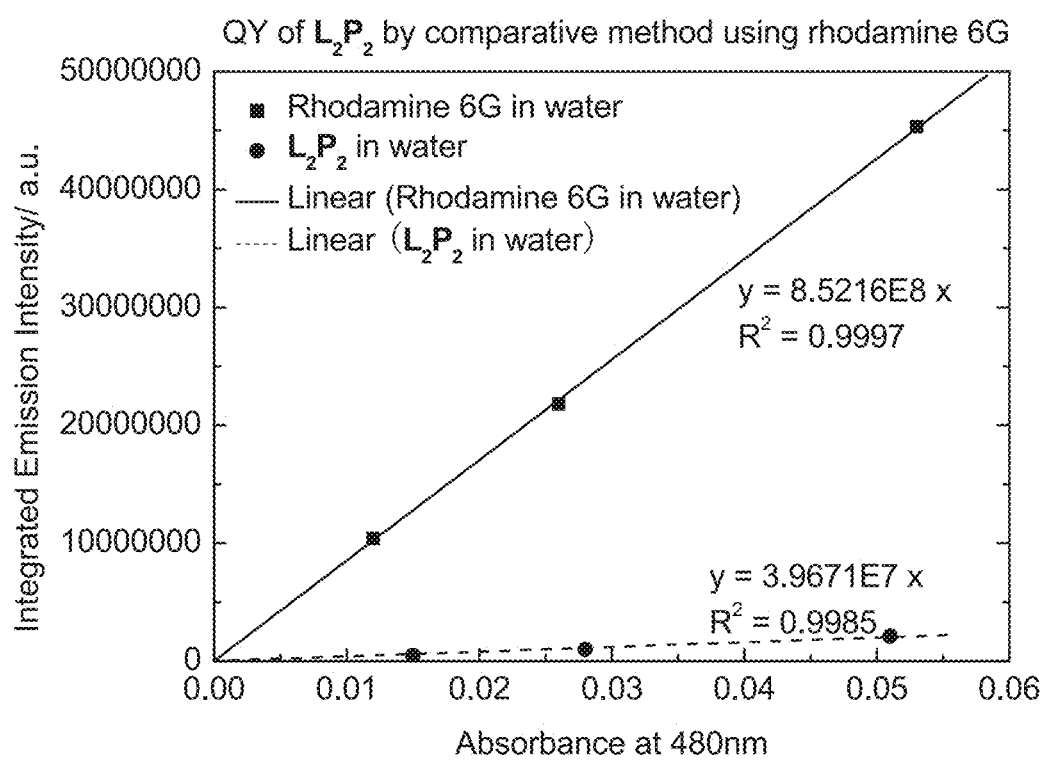
FIG. 27D shows the emission plot (emission vs absorbance) of $L_2P_2$ in water for the emission quantum yield determination ($\lambda_{ex}$=480 nm. By comparative method using rhodamine 6G, the quantum yield of $L_2P_2$ is 4.4%).
Figure 27E:
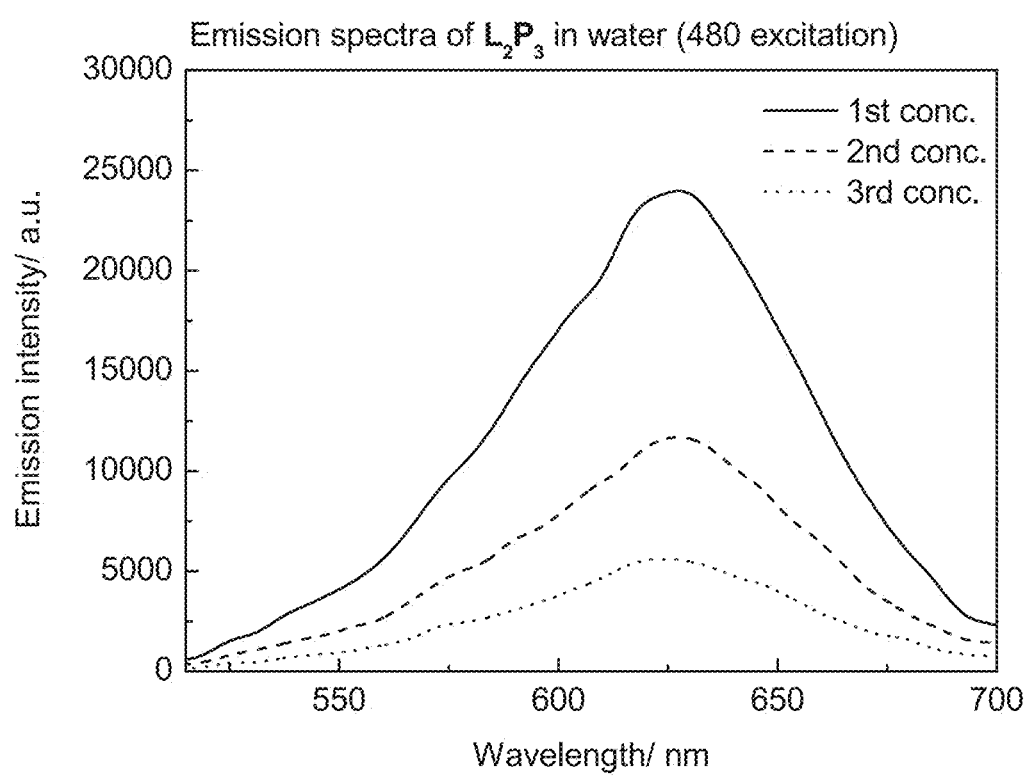
FIG. 27E shows the emission spectra of $L_2P_3$ in water for the emission quantum yield determination ($\lambda_{ex}$=480 nm. By comparative method using rhodamine 6G, the quantum yield of $L_2P_3$ is 4.3%).
Figure 27F:
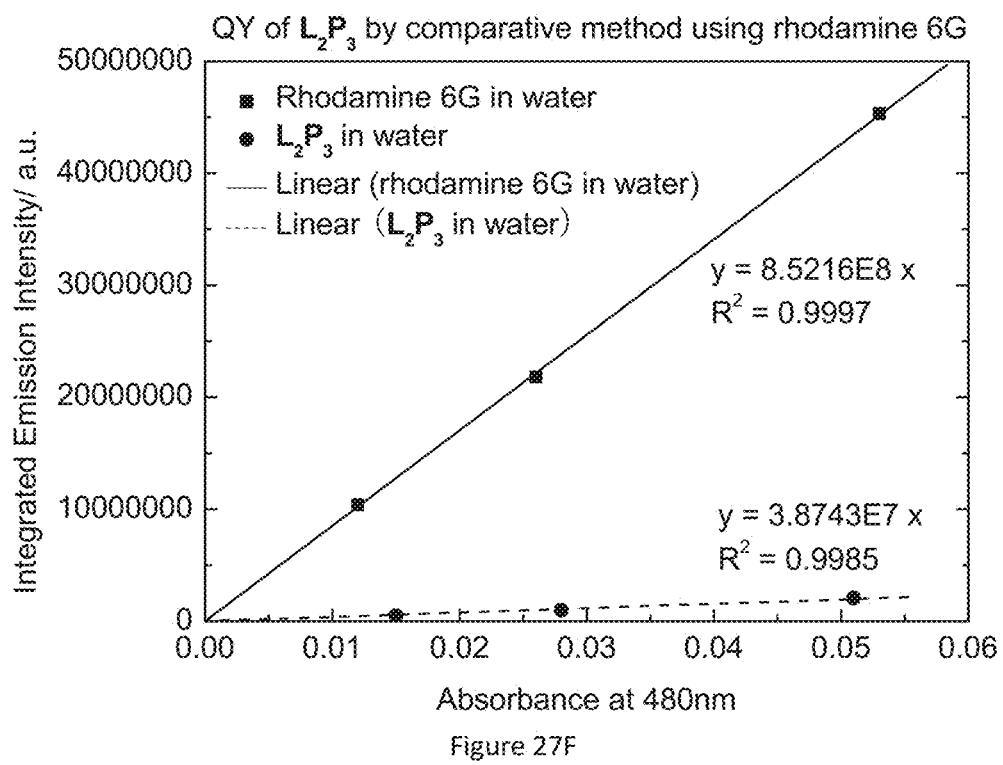
FIG. 27F shows the emission plot (emission vs absorbance) of $L_2P_3$ in water for the emission quantum yield determination ($\lambda_{ex}$=480 nm. By comparative method using rhodamine 6G, the quantum yield of $L_2P_3$ is 4.3%).
Figure 27G:
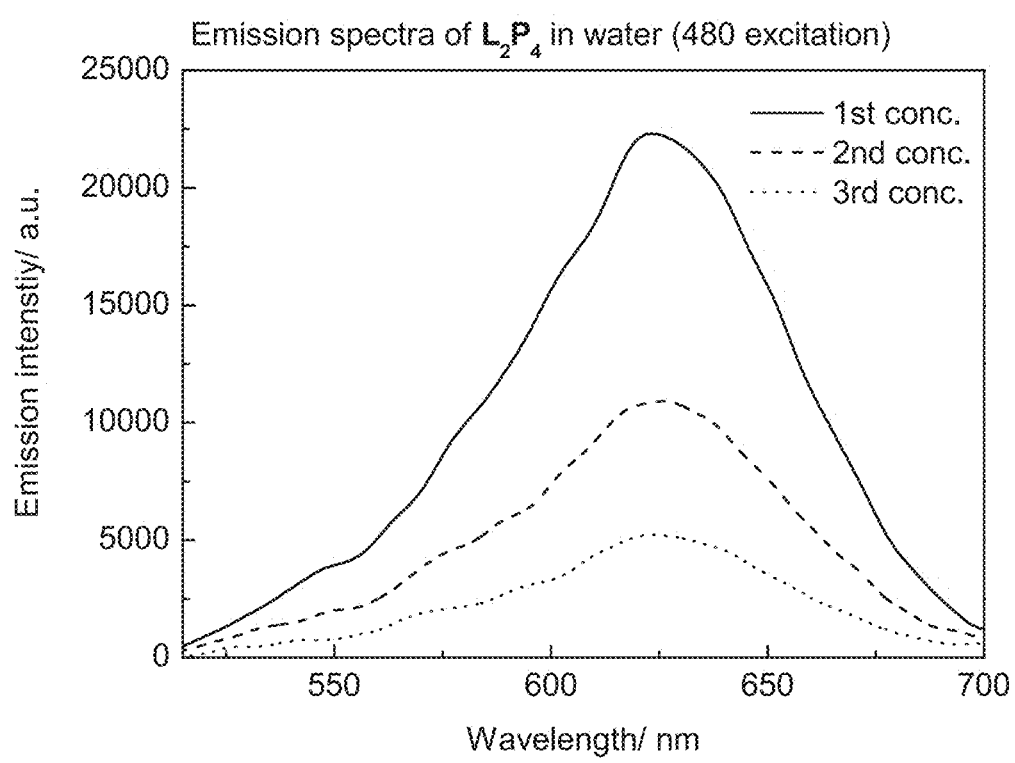
FIG. 27G shows the emission spectra of $L_2P_4$ in water for the emission quantum yield determination ($\lambda_{ex}$=480 nm. By comparative method using rhodamine 6G, the quantum yields of $L_2P_4$ is 3.9%).
Figure 27H:
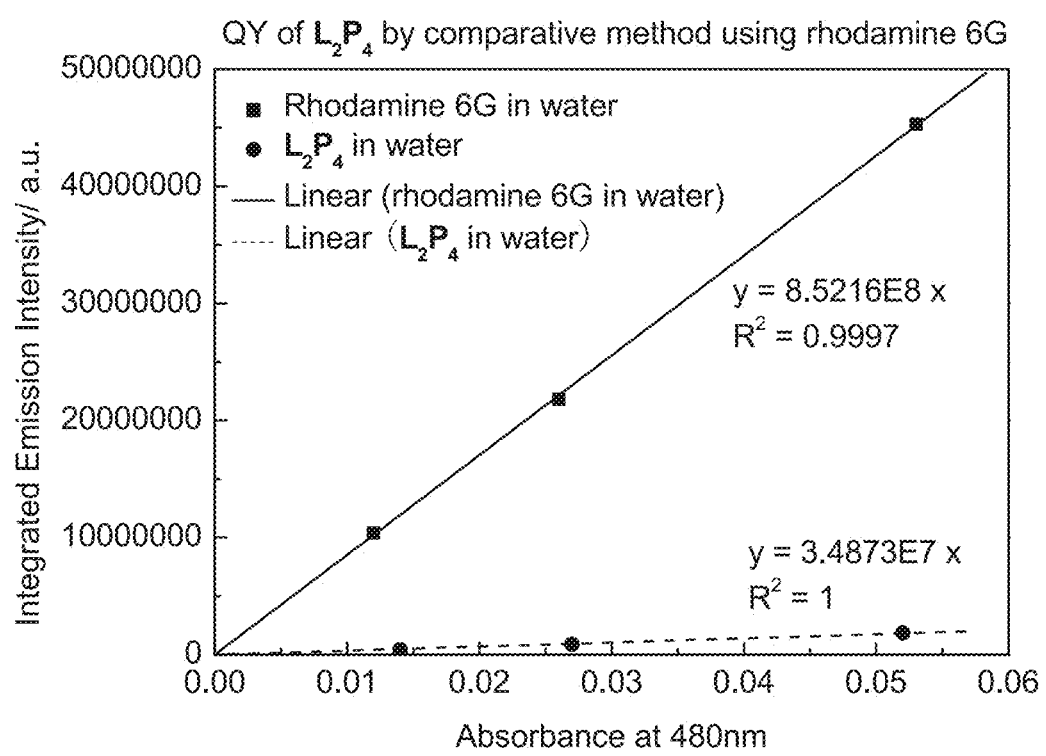
FIG. 27H shows the emission plot (emission vs absorbance) of $L_2P_4$ in water for the emission quantum yield determination ($\lambda_{ex}$=480 nm. By comparative method using rhodamine 6G, the quantum yield of $L_2P_4$ is 3.9%).
Figure 28A:
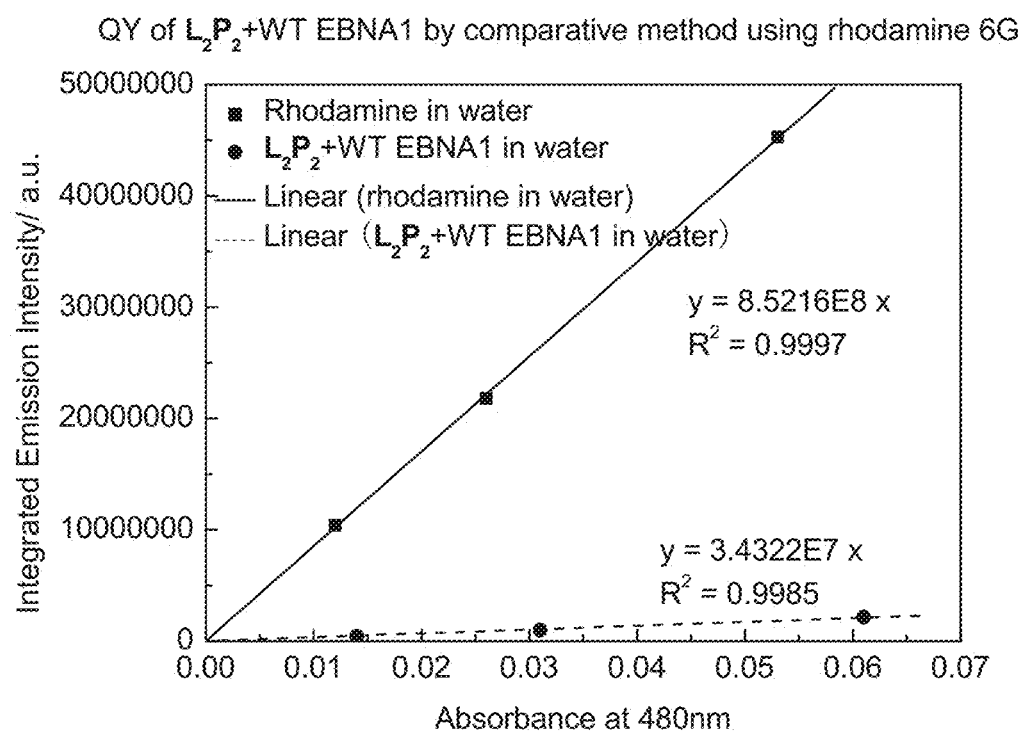
FIG. 28A shows the plot (emission vs absorbance) of $L_2P_2$ in water in the presence of saturated WT-EBNA1 for the emission quantum yield determination ($\lambda_{ex}$=480 nm. By comparative method using rhodamine 6G, the quantum yields of $L_2P_2$+WT EBNA1 is 3.8%).
Figure 28B:
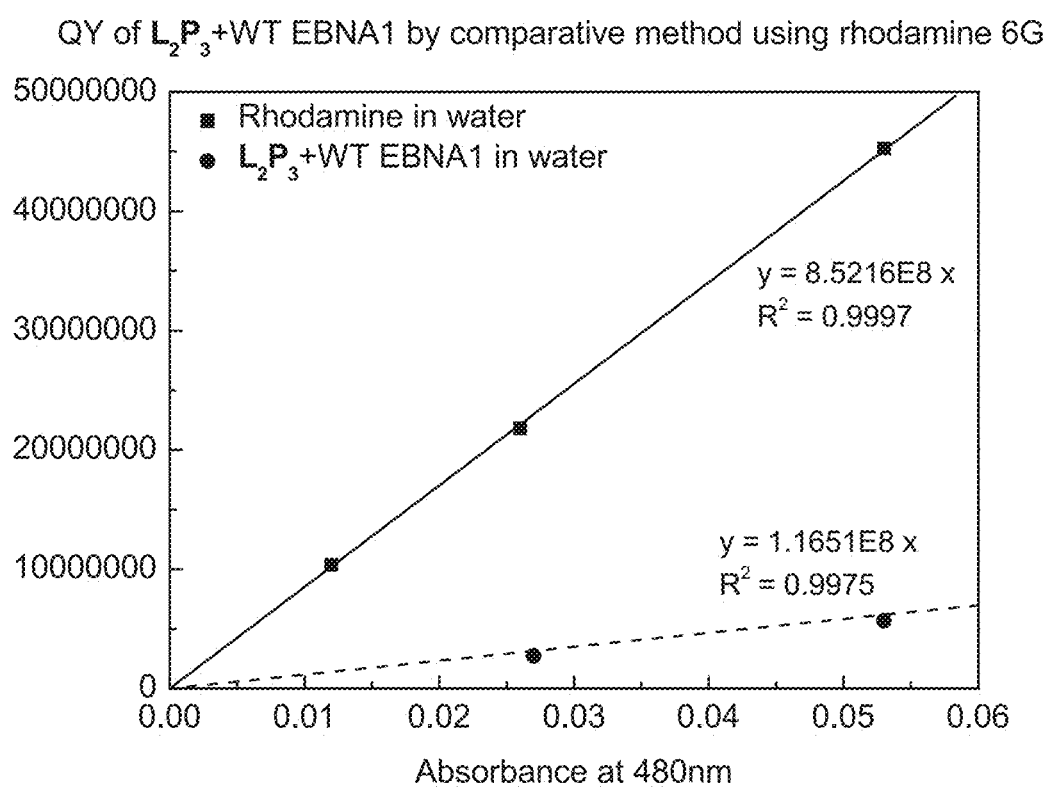
FIG. 28B shows the plot (emission vs absorbance) of $L_2P_3$ in water in the presence of saturated WT-EBNA1 for the emission quantum yield determination ($\lambda_{ex}$=480 nm. By comparative method using rhodamine 6G, the quantum yields of $L_2P_3$+WT EBNA1 is 13.0%).
Figure 28C:
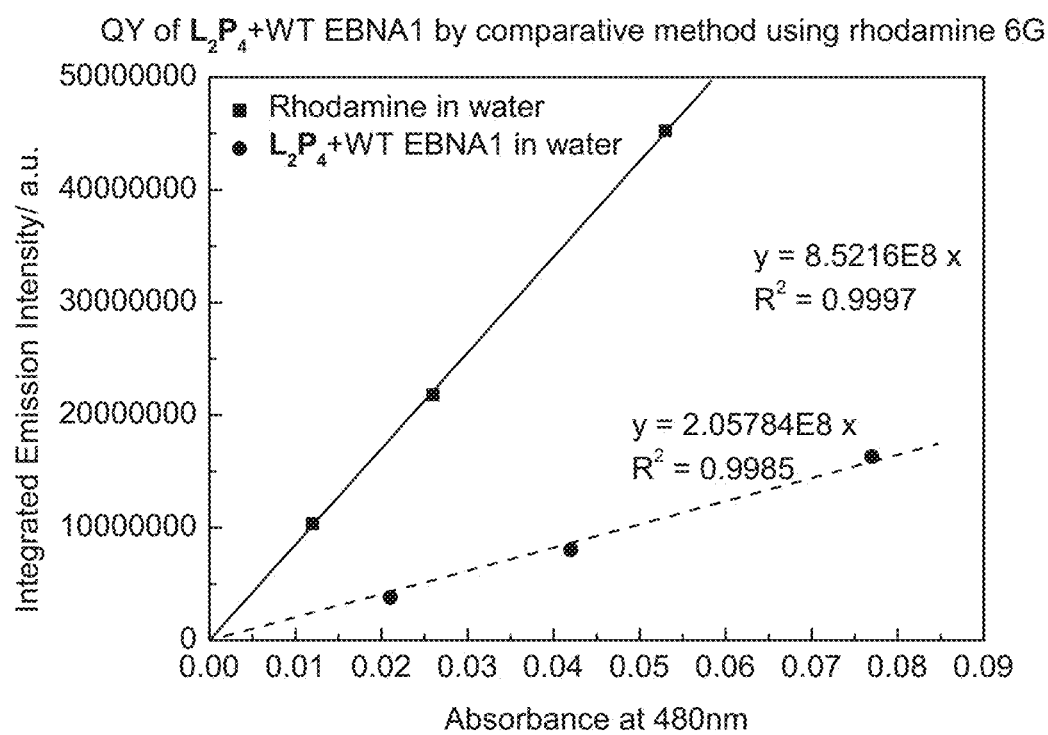
Figure 29A:
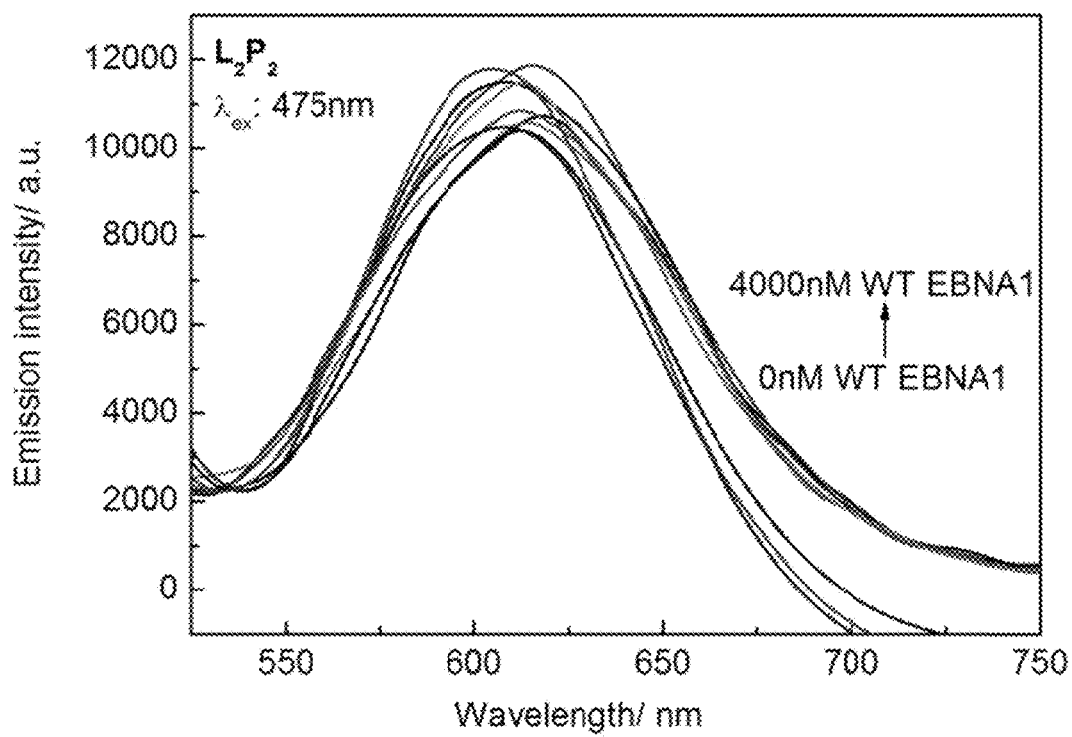
Figure 29B:
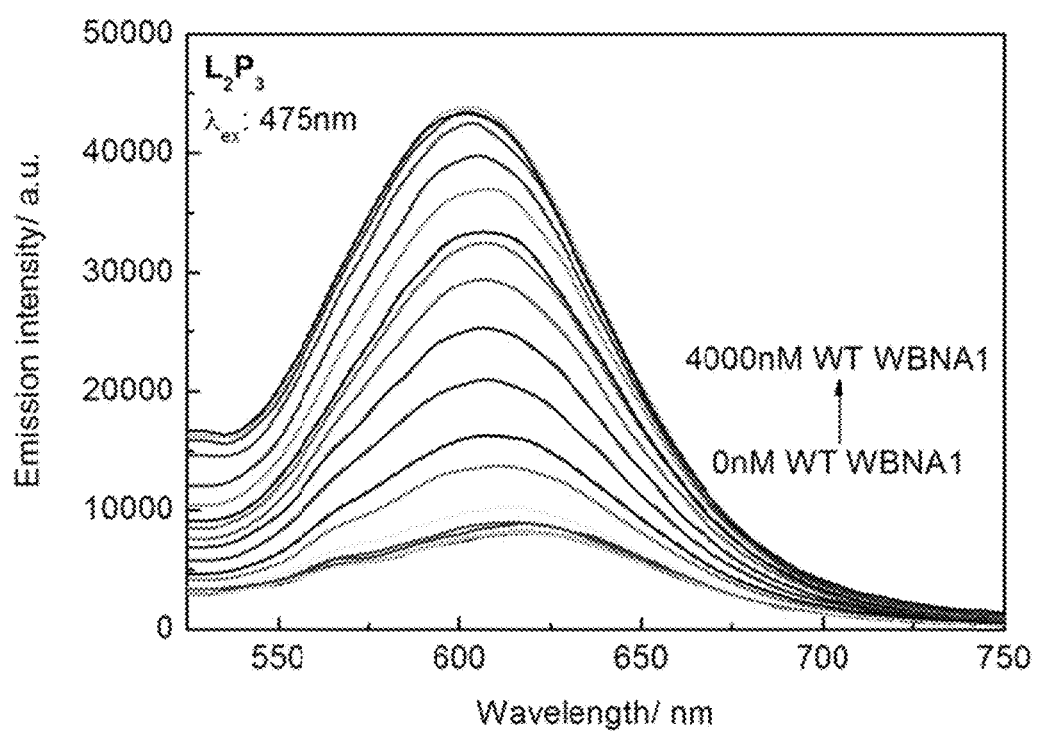
Figure 29C:
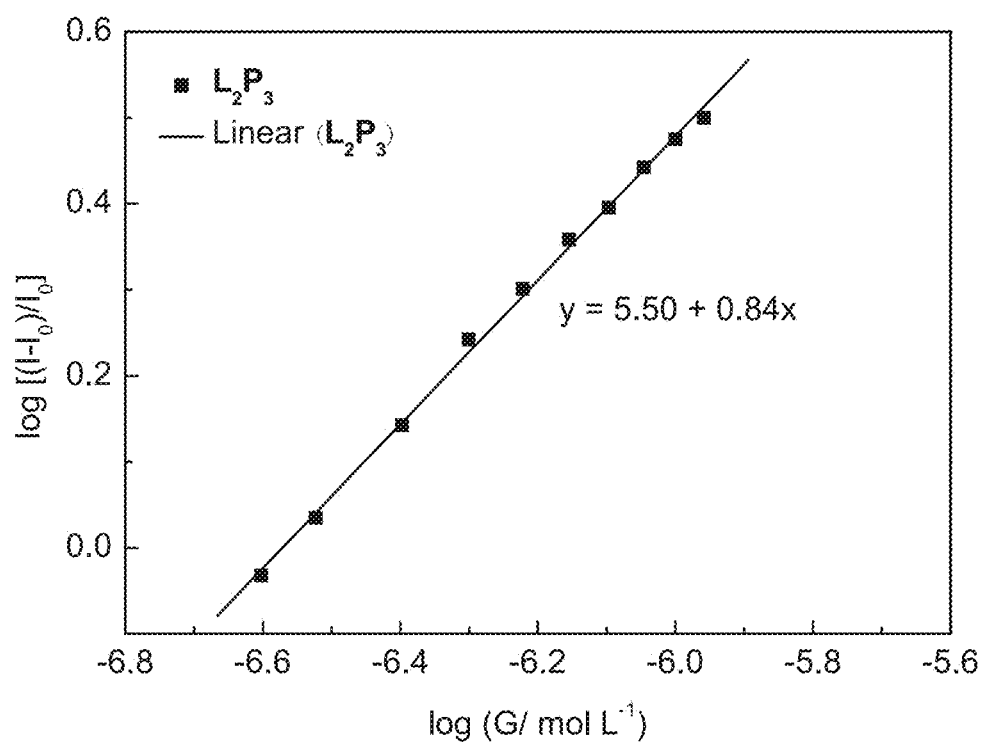
Figure 29D:
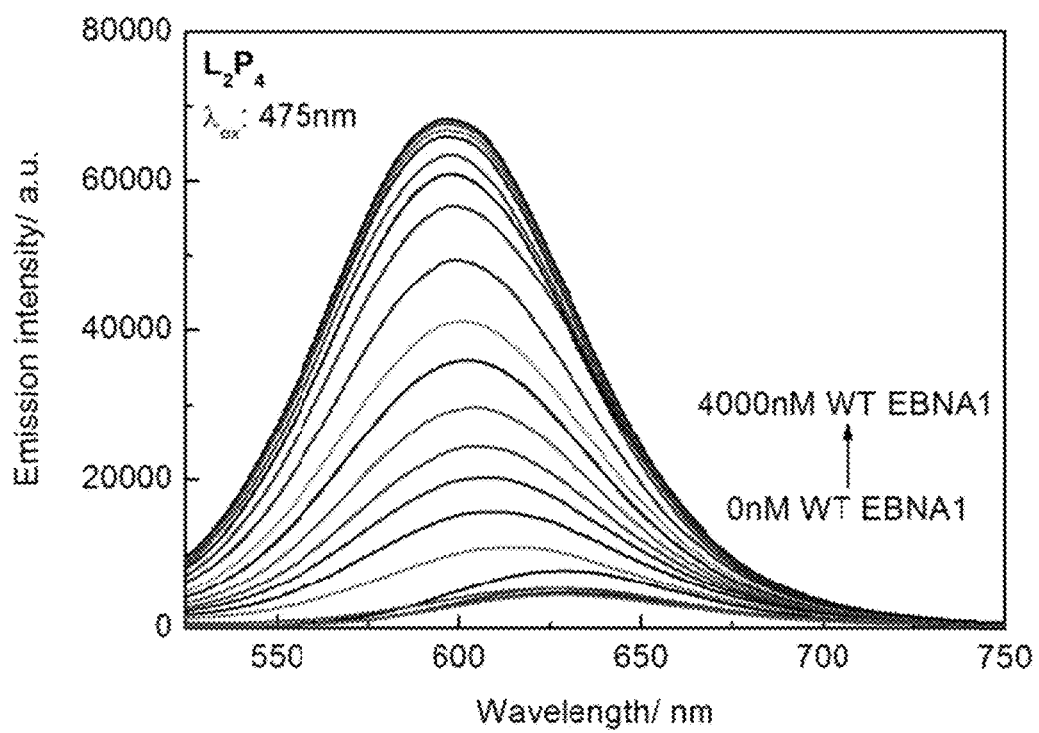
Figure 29E:
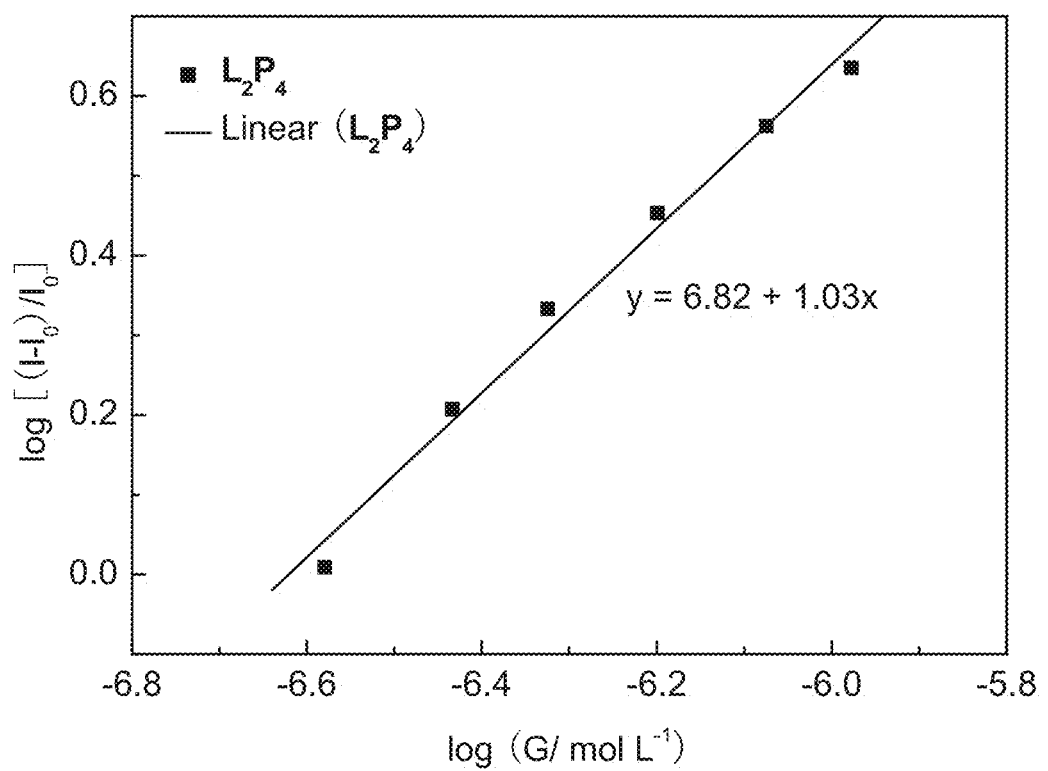
Figure 30A:
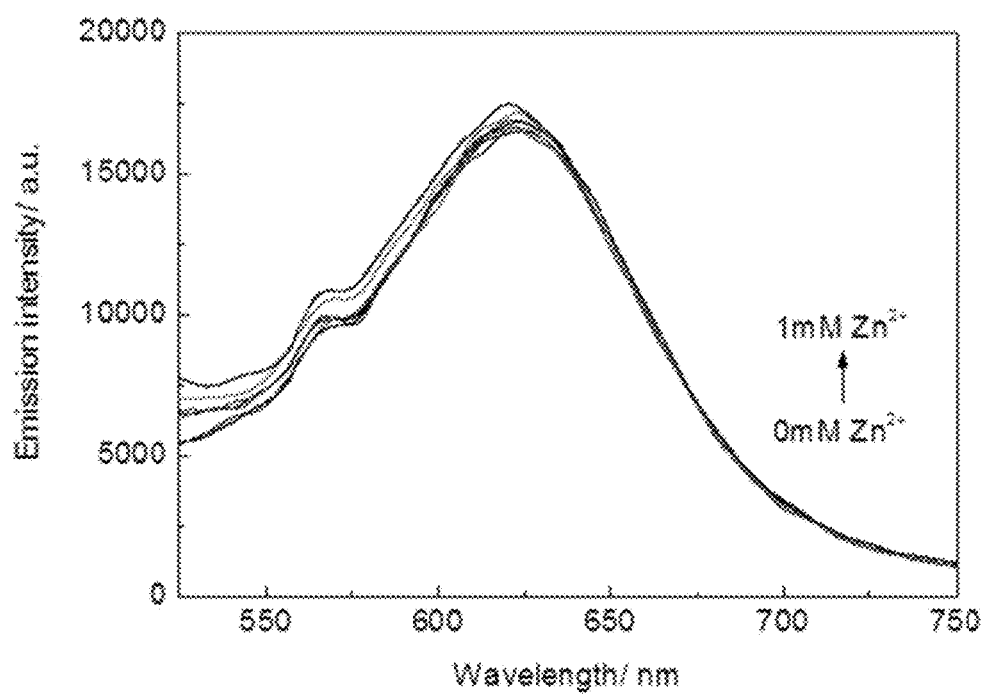
Figure 30B:
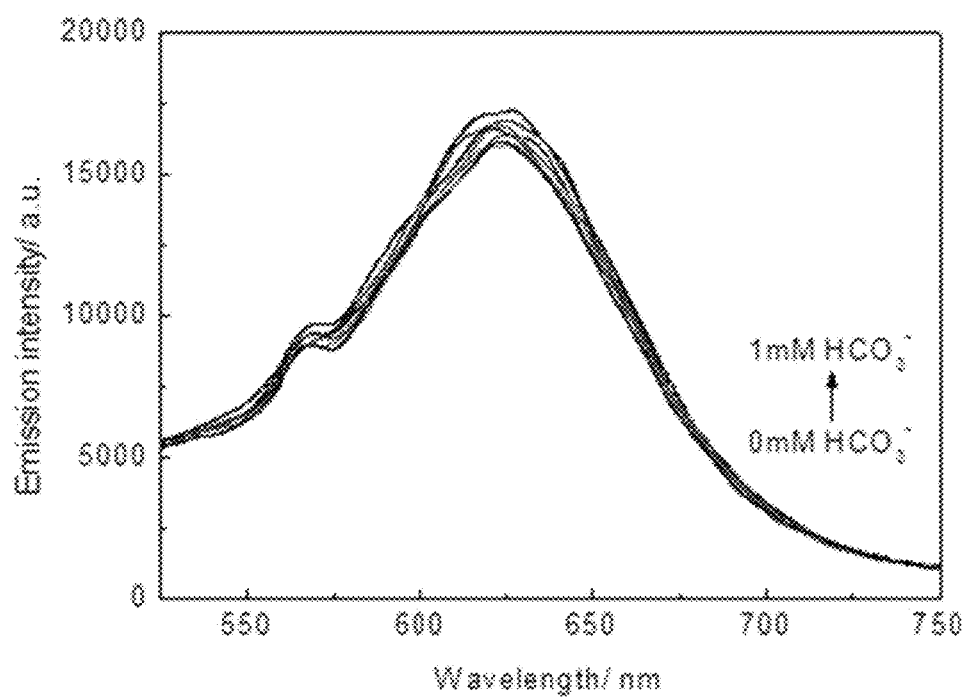
Figure 30C:
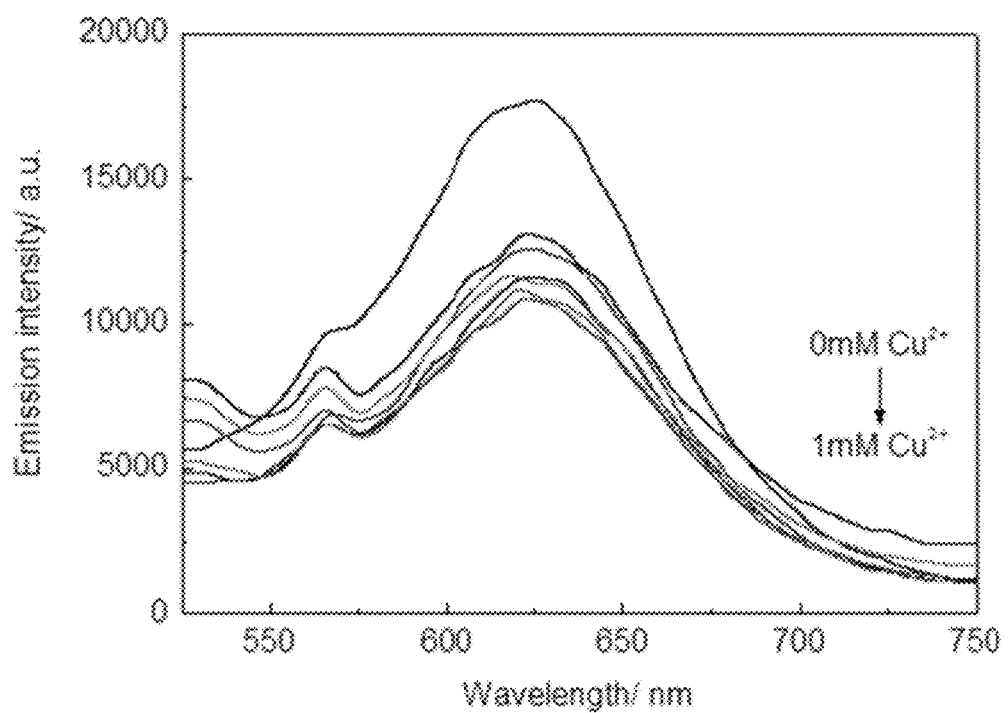
Figure 30D:
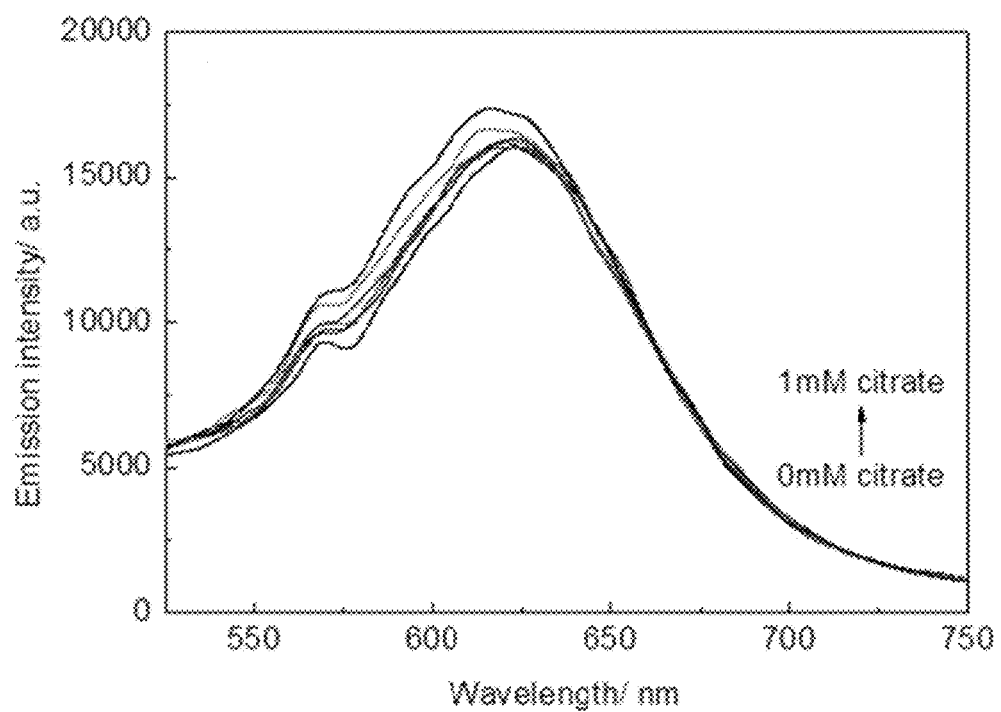
Figure 30E:
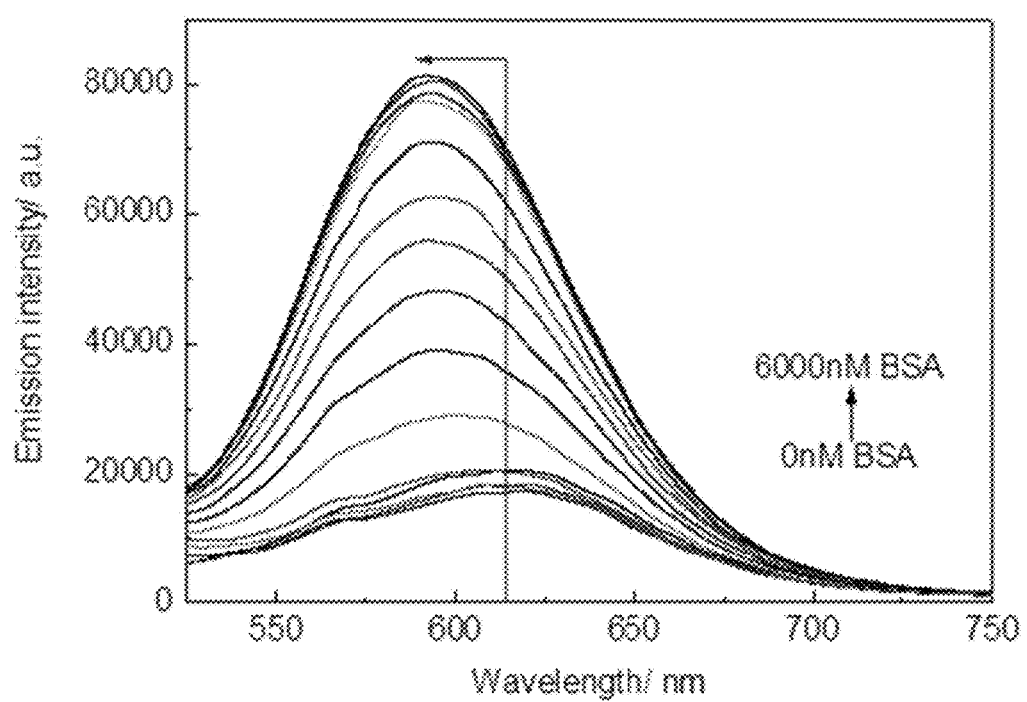
Figure 30F:
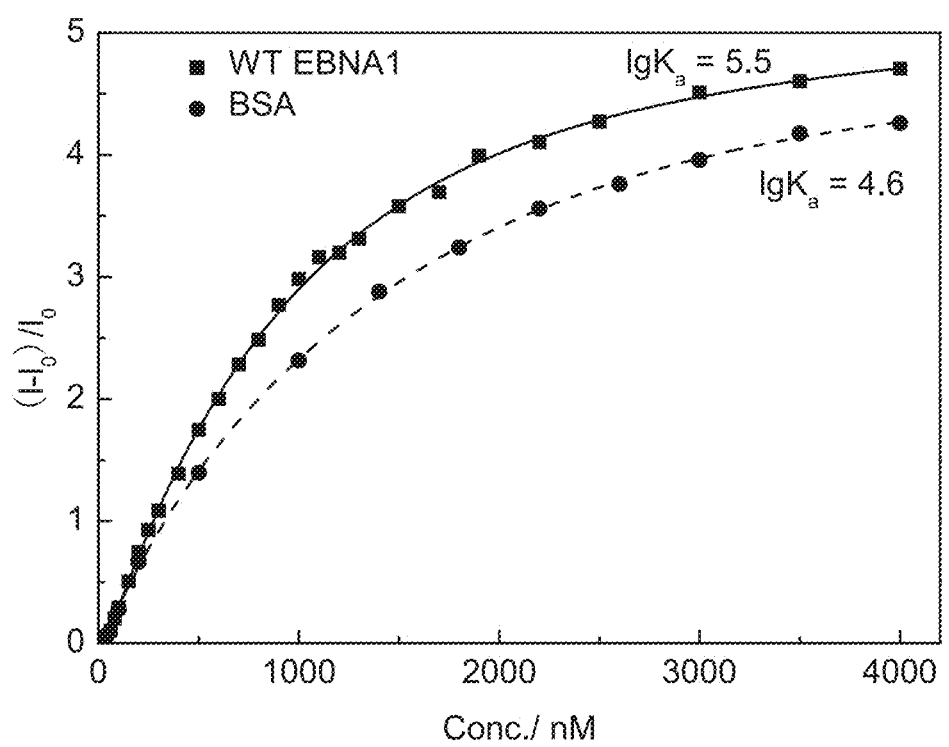

The stability of the peptide conjugates, assessed by monitoring their emission spectra at 37° C. for 24 h, is confirmed in the simulated extracellular anion mixture (PBS buffer) (FIGS. 26A-26C). As discussed in the previous section, the MD simulations and free energy calculations show that $L_2P_4$ has the strongest interaction with WT-EBNA1, and thus it is useful to prevent the homodimerization of EBNA1 and ultimately inhibit the growth of EBV-positive tumors. To access the actual binding affinity of $L_2P_4$ to WT-EBNA1, a luminescence titration experiment is carried out in PBS buffer. The results obtained from the titration experiment aligned well with the calculated data via MMPBSA. $L_2P_4$ is found to have the strongest emission response on addition of 4 μM WT-EBNA1 (FIGS. 2A-2C and FIGS. 29A-29E), an 8.8-fold emission enhancement ($\phi_{initial}$=4%, $\phi_{4 \mu M \, WT\text{-}EBNA1}$=23%) and a 25 nm blue-shift are shown in FIG. 21. The quantum yields for $L_2P_4$ with and without the addition of WT-EBNA1 are calculated as shown in FIGS. 27A-27H and 28A-28C.

Under the same conditions, a 4.7-fold increase in intensity is observed for $L_2P_3$, and no intensity change is observed for $L_2P_2$. The affinity of a probe for a protein can be quantified via the binding constant and the binding ratio. The binding constant (log Kassoc/$K_a$) of the three peptide conjugate to WT-EBNA1 is calculated as shown in FIG. 21. The logarithm of the fluorescence ratio exhibits a linear relationship with respect to the protein concentration. The value of log $K_{assoc}$ calculated are 5.50 and 6.82 for $L_2P_3$ and $L_2P_4$, respectively, and both of the binding ratios are found to be 1:1. On account of $L_2P_4$'s greater binding strength, the binding selectivity of $L_2P_4$ for WT-EBNA1 in the presence of various proteins (FIG. 2C) and biologically relevant metal ions and small molecules, such as $Zn^{2+}$ and citrate (FIGS. 30A-30F & FIGS. 31A-31F), are investigated. The proteins analysed in the selectivity assay included four EBNA1 mutant proteins and bovine serum albumin (BSA). EBNA1 mutant proteins are prepared by mutation of YFMVF to FFAVA (yielding EBNA1-3A) or via conservative point mutation of $Y_{561}$, $M_{563}$ and $F_{565}$ to A (yielding EBNA1-$Y_{561}$A, EBNA1-$M_{563}$A and EBNA1-$F_{565}$A). The selectivity of $L_2P_4$ for each protein is investigated by recording changes in its emission. A relatively small emission enhancement is observed (FIG. 2C) on addition of the four mutant EBNA1 proteins and BSA, showing that the binding of $L_2P_4$ is weaker for these proteins than for WT-EBNA1 (log $K_{assoc}$ values for EBNA1-$Y_{561}$A, EBNA1-$M_{563}$A, EBNA1-$F_{565}$A and EBNA1-3A were 5.1, 3.6, 4.3 and 3.9, respectively; for BSA, log $K_{assoc}$ was 4.7). $L_2P_4$ is shown to be selective for WT-EBNA1.

It is well established that when an environment-sensitive fluorophore is conjugated to peptides with specific targeting, subsequent protein binding will increase the emission intensity and a strong blueshift will occur due to the marked change in excited-state dipole moments. It is well known that the dual fluorescence of 4-(N,N-dimethyl-amino)benzonitrile (DMABN) arises due to an emission from the local excited (LE) state and an "anomalous" redshifted emission from the ICT state. Among the numerous DMABN analogues of this molecule reported to date, pyridine derivatives have been a focus of particular interest, especially in the determination of cell microviscosity. With this in mind, the present invention provides a fluorescent probe consisting of an ICT-state pyridine-derivative fluorophore and a nucleus-permeable EBNA1-specific peptide that generates ICT-based emission after binding EBNA1, can be used to prevent the homodimerization of EBNA1, and be used for simultaneous imaging and inhibition of EBV-positive tumors.

Figure 2A:
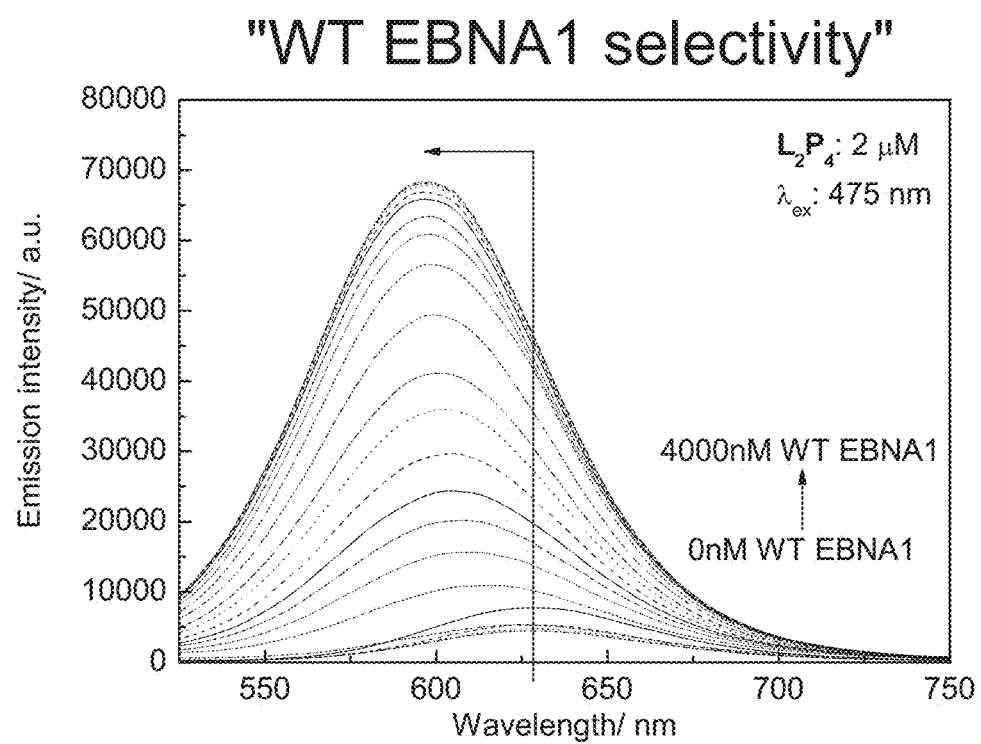
FIG. 2A shows 8.8-fold intensity increase and 25 nm blueshift of $L_2P_4$ in response to the addition of WT-EBNA1 (indicated by the right-angled arrow) $\lambda_{ex}$, excitation wavelength.
Figure 2B:
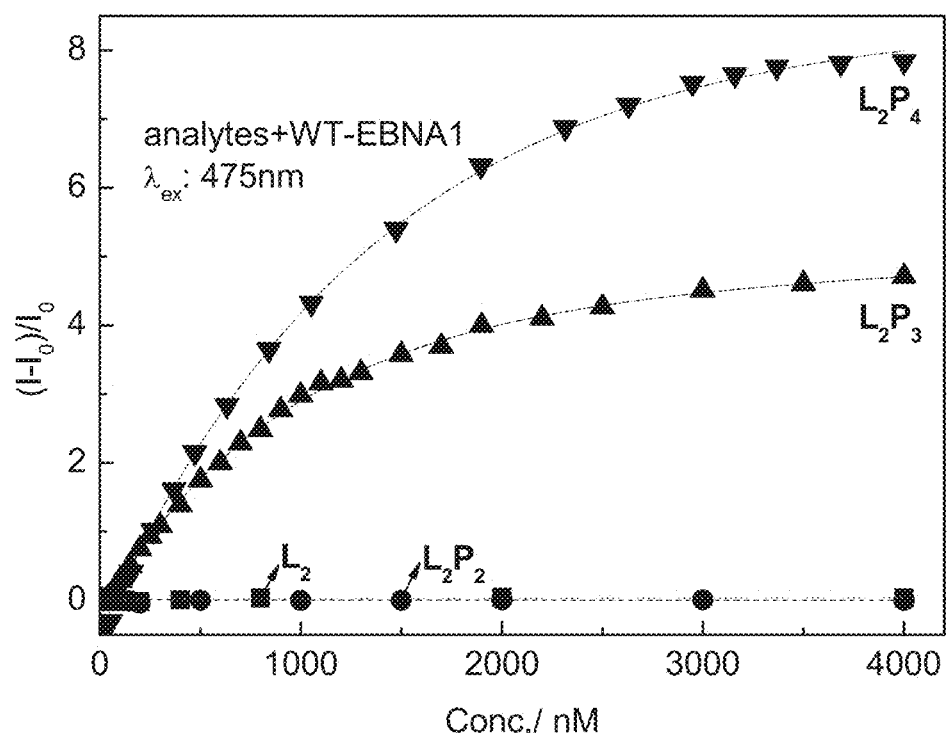
FIG. 2B shows the change in eimission intensity of $L_2$, $L_2P_2$, $L_2P_3$ and $L_2P_4$ on addition of WT-EBNA1.
Figure 2C:
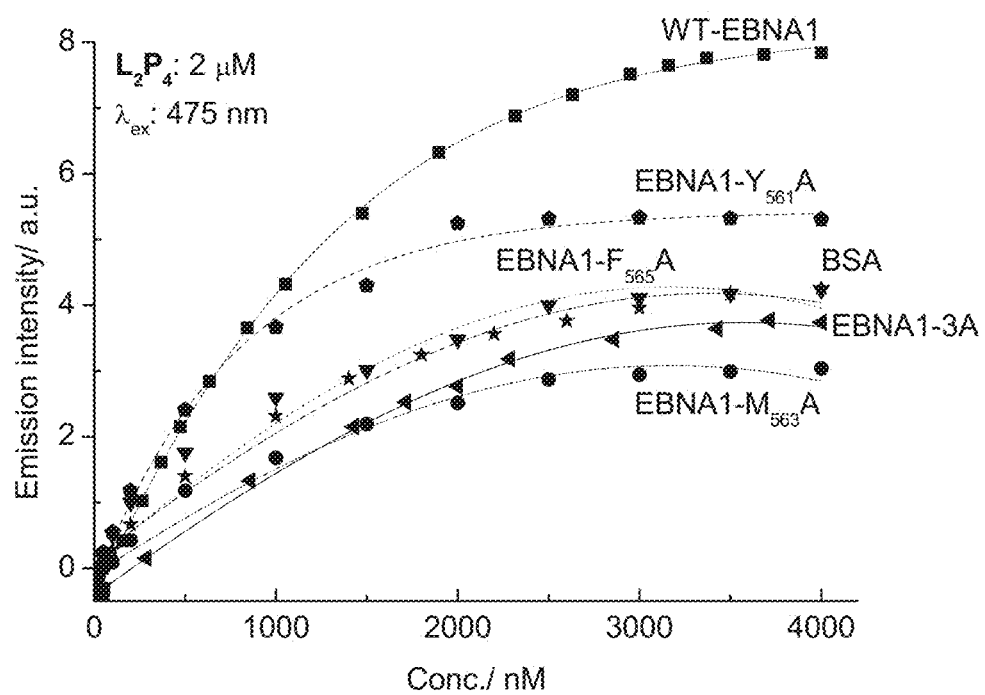
FIG. 2C shows the selectivity of $L_2P_4$ for various proteins; represented by emission in intensity in arbitrary units (a.u.).
Figure 2D:
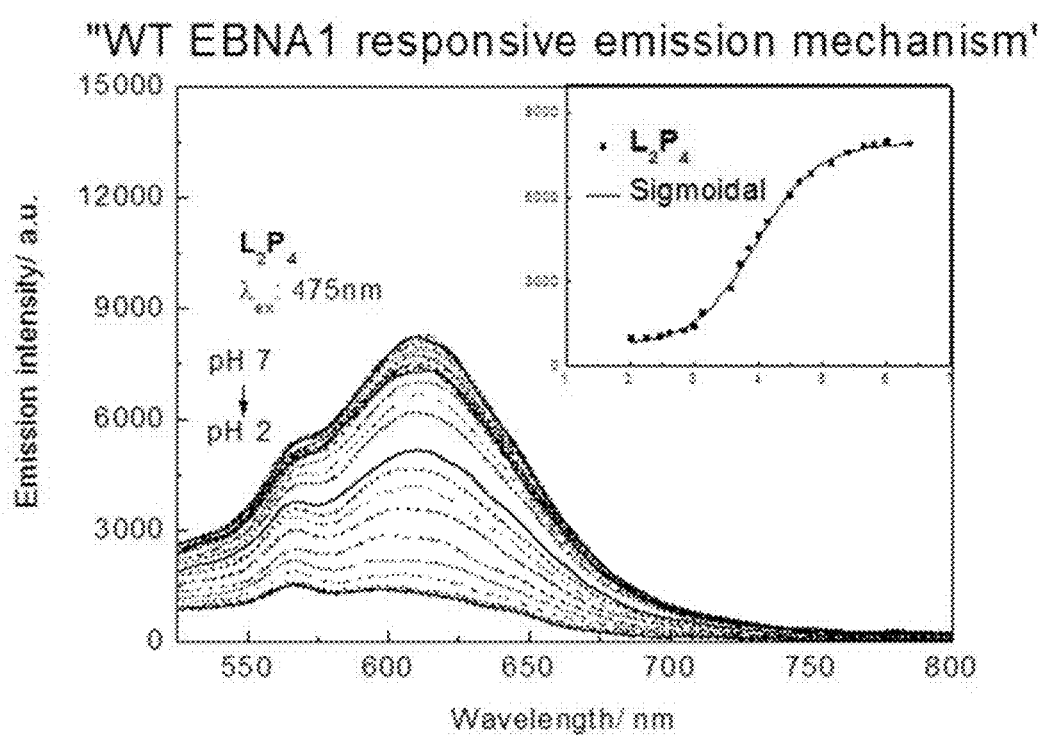
FIG. 2D shows the emission spectra of $L_2P_4$ for various buffer pHvalues; used to confirm the ICT state and determine the $pK_a$ value. The emission band gradually decreases as the pH lowers from 7 to 2, in consistent with the characteristics of ICT emission. ICT emission decreases at lower pH because the nitrogen atoms become protonated, thereby making their lone pairs unavaliable for generation of an ICT excited state. Inset: emission intensity of $L_2P_4$ for various buffer pH values.
Figure 2E:
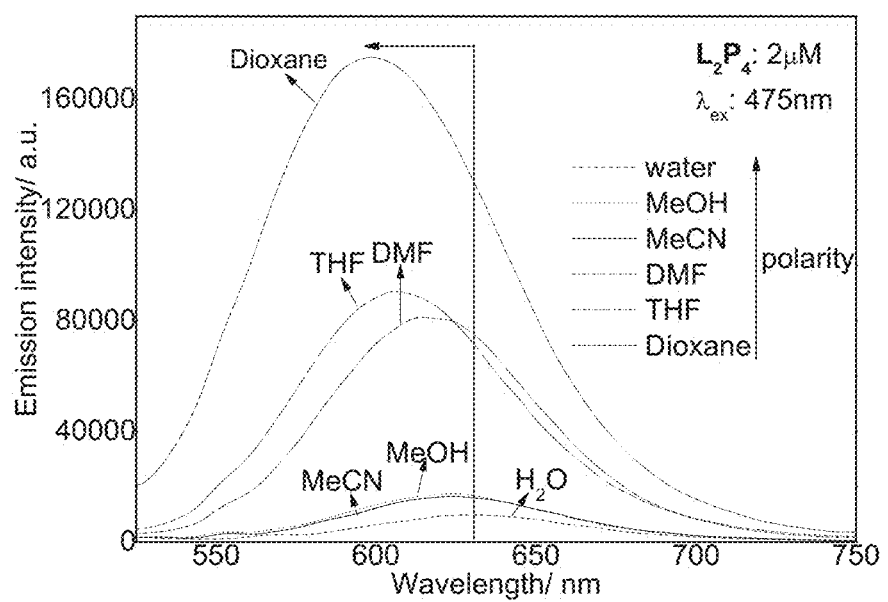
FIG. 2E shows the $L_2P_4$ emission spectra from solvatochromism experiments showing the affect of decreasing solvent polarity.
Figure 2F:
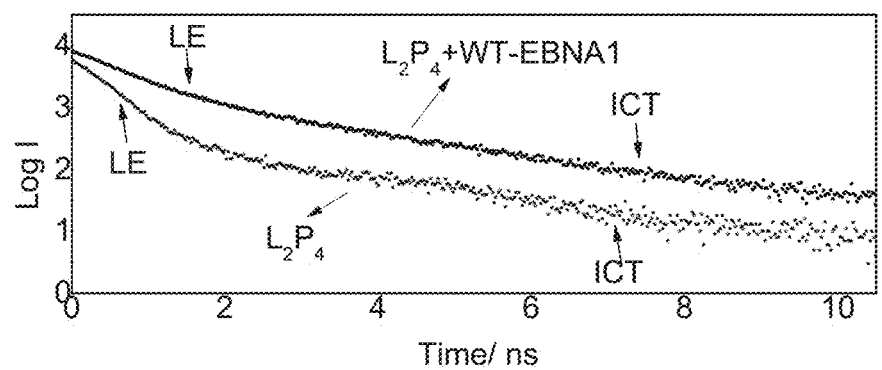
FIG. 2F shows the emission lifetime (decay) of $L_2P_4$ on binding WT-EBNA1.
Figure 2G:
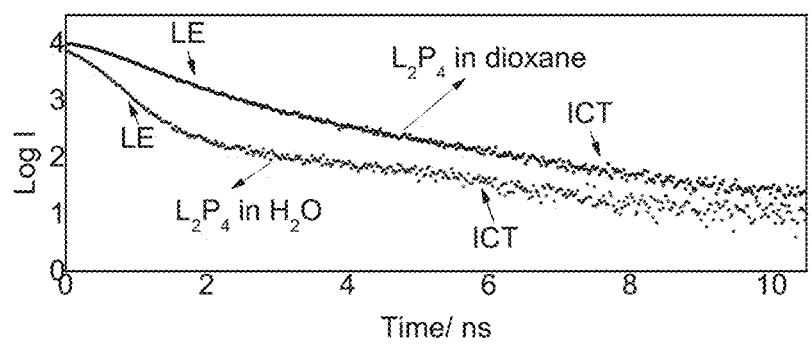
FIG. 2G shows the emission lifetime (decay) of $L_2P_4$ on solvatochromism (lower) with increasing solvent polarity. Comparatively large local excited (LE) emission decays and correspondingly smaller ICT decays are found in less polar solvents, indicating a smaller dipole moment and consequently an upshift of the ICT state. Additionally, the emission lifetime of $L_2P_4$ on binding WT-EBNA1 is found to be similar to that in polar solvents.
Figure 3A:
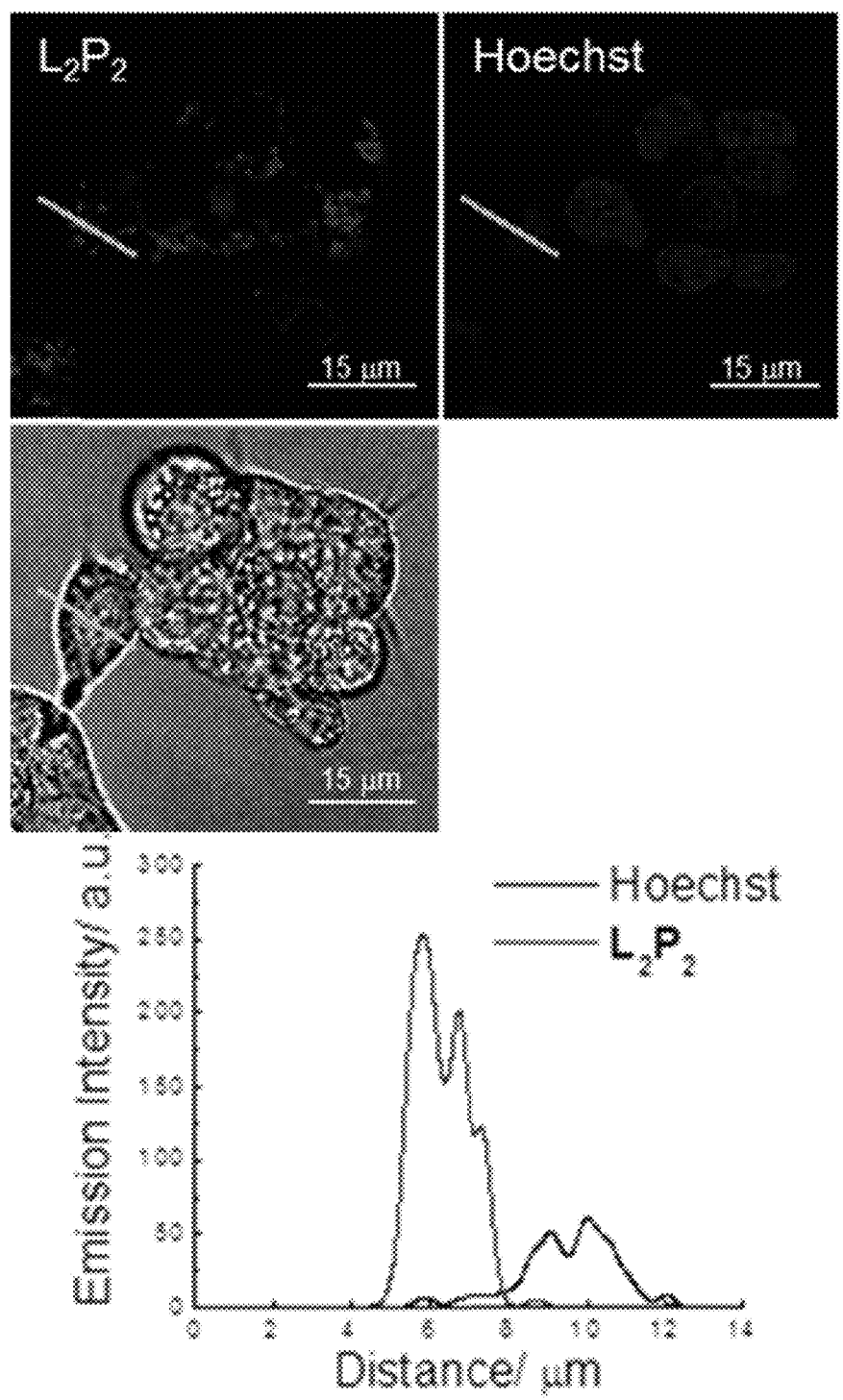
FIG. 3A shows the in vitro confocal microscopy of the $L_2P_2$ probe in EBV-positive C666-1 cells. $\lambda_{ex}$=488 nm; $\lambda_{em}$=500-650 nm; filter, BP500. C666-1 are treated with $L_2P_2$ (10 μM) for 6 h, and then co-stained with the nuclear dye Hoechst 33342 (1 nM) for 1 h. Profiles of the emission intensity of the $L_2P_2$ probe and Hoechst 33342 are plotted along the green line marked on the confocal microscopy images.
Figure 3B:
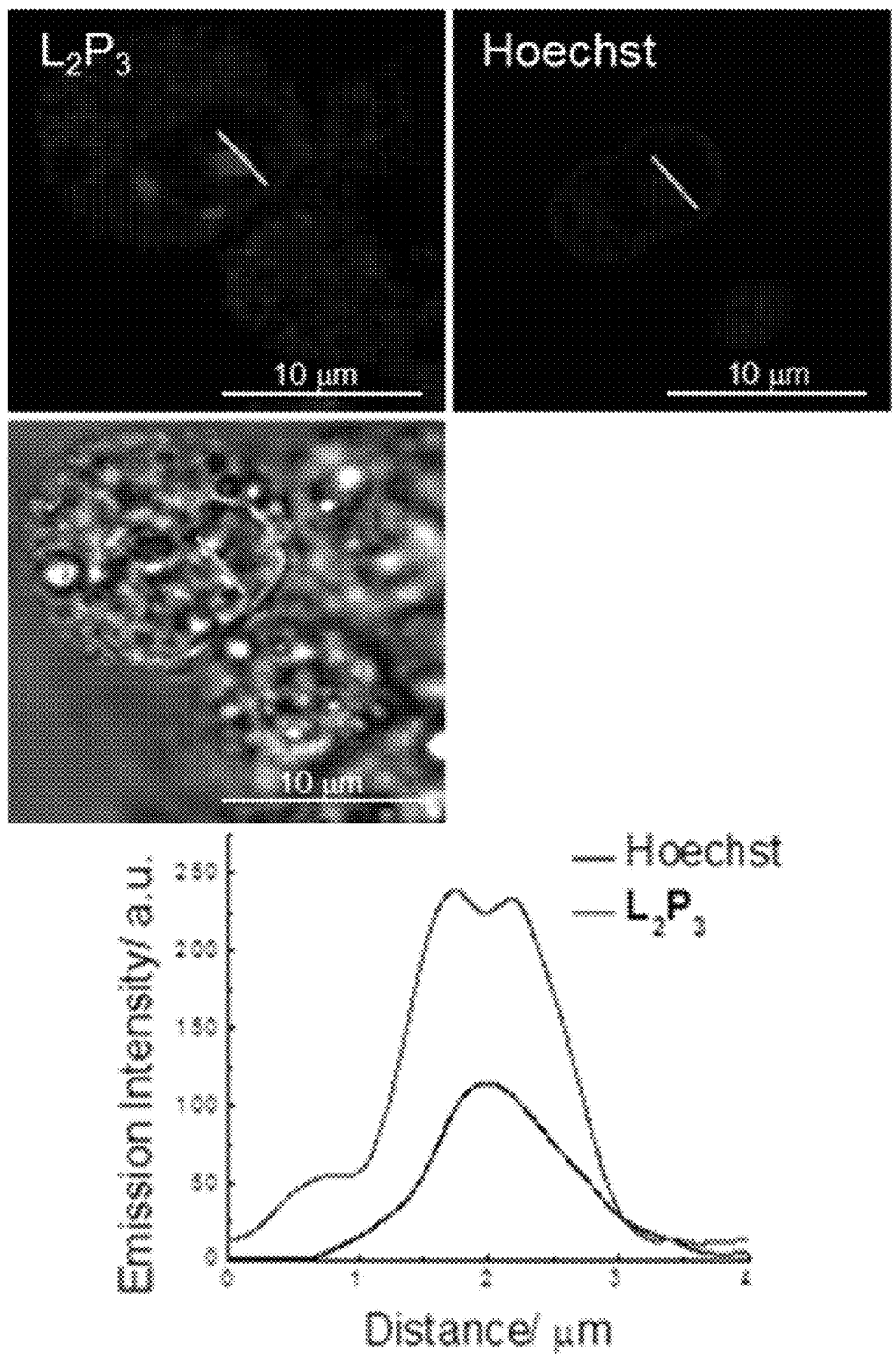
FIG. 3B shows the in vitro confocal microscopy of the $L_2P_3$ probe in EBV-positive C666-1 cells. $\lambda_{ex}$=488 nm; $\lambda_{em}$=500-650 nm, filter, BP500. C666-1 are treated with $L_2P_3$ (10 μM) for 6 h, and then co-stained with the nuclear dye Hoechst 33342 (1 nM) for 1 h. Profiles of the emission intensity of the $L_2P_3$ probe and Hoechst 33342 are plotted along the green line marked on the confocal microscopy images.
Figure 3C:
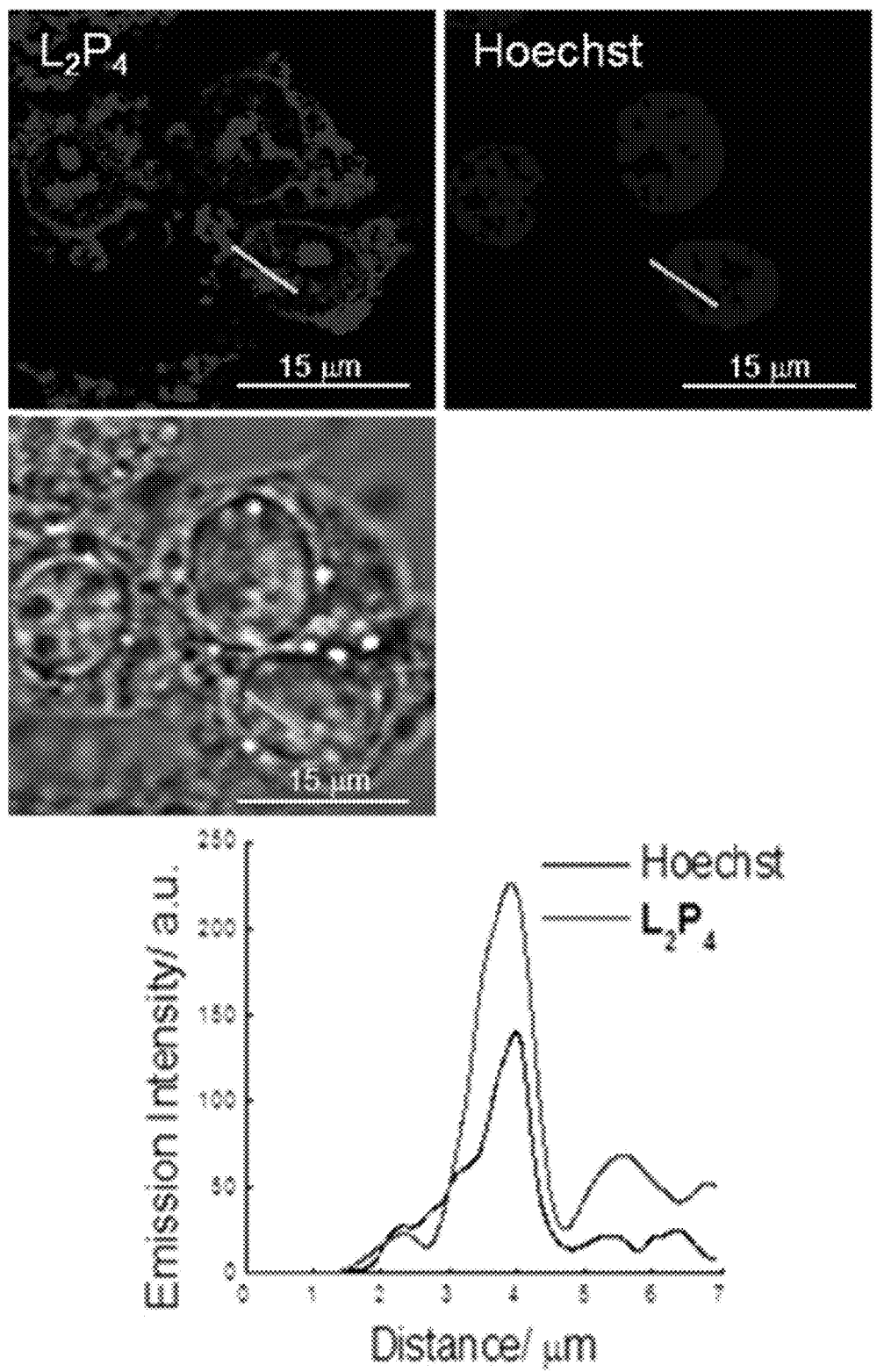
FIG. 3C shows the in vitro confocal microscopy of the $L_2P_4$ probe in EBV-positive C666-1 cells. $\lambda_{ex}$=488 nm; $\lambda_{em}$=500-650 nm; filter, BP500. C666-1 are treated with $L_2P_4$ (10 μM) for 6 h, and then co-stained with the nuclear dye Hoechst 33342 (1 nM) for 1 h. Profiles of the emission intensity of the $L_2P_4$ probe and Hoechst 33342 are plotted along the green line marked on the confocal microscopy images. The $L_2P_4$ found in the nucleus (by the lambda scan), the shape and location of the emission band is similar to the data obtained for the solution under the same excitation.
Figure 3D:
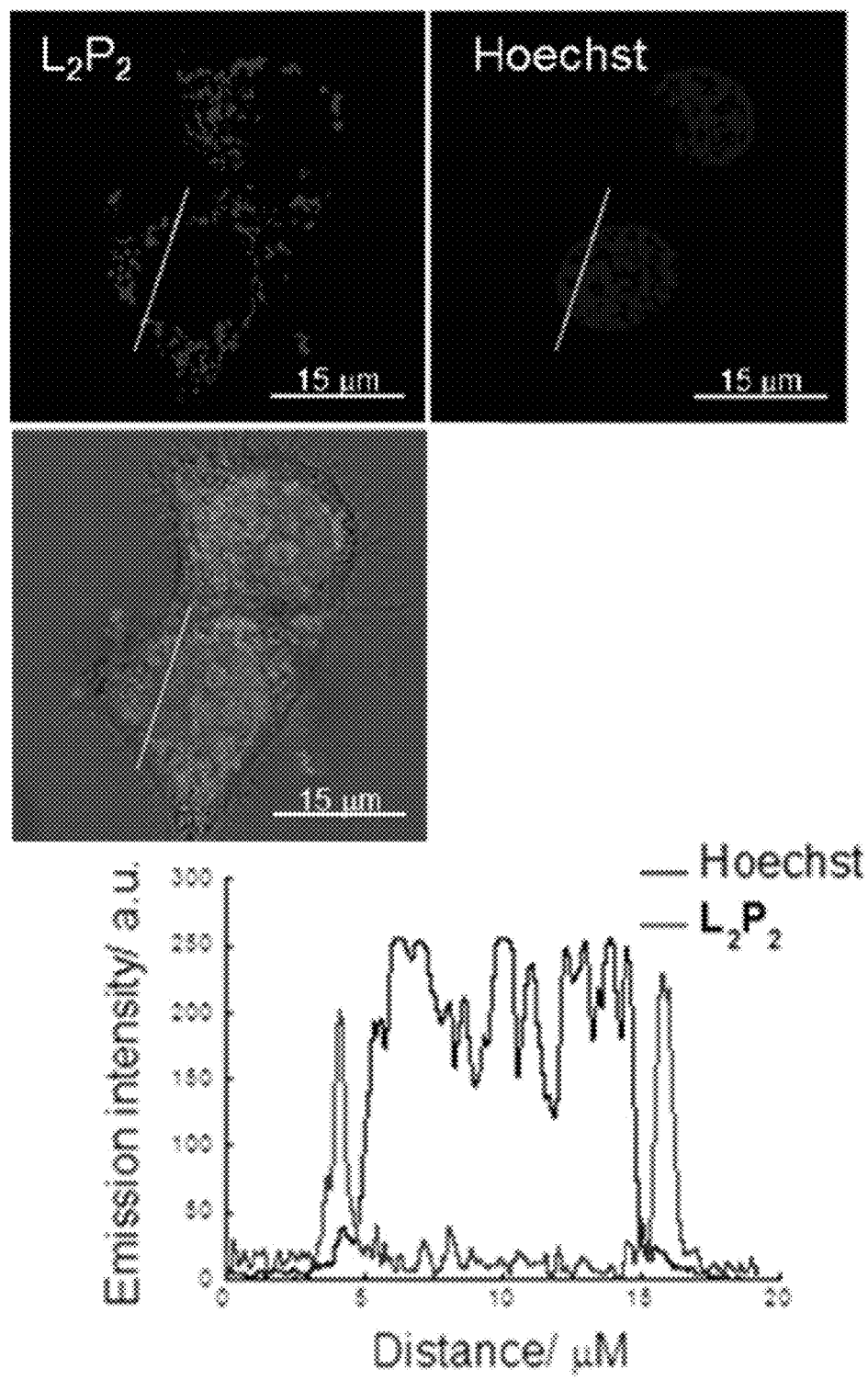
FIG. 3D shows the in vitro confocal microscopy of the $L_2P_2$ probe in EBV-positive NPC43 cells. $\lambda_{ex}$=488 nm; $\lambda_{em}$=500-650 nm; filter, BP500. NPC43 are treated with $L_2P_2$ (10 μM) for 6 h and then co-stained with the nuclear dye Hoechst 33342 (1 nM) for 1 h. Profiles of the emission intensity of the $L_2P_2$ probe and Hoechst 33342 are plotted along the green line marked on the confocal microscopy images.
Figure 3E:
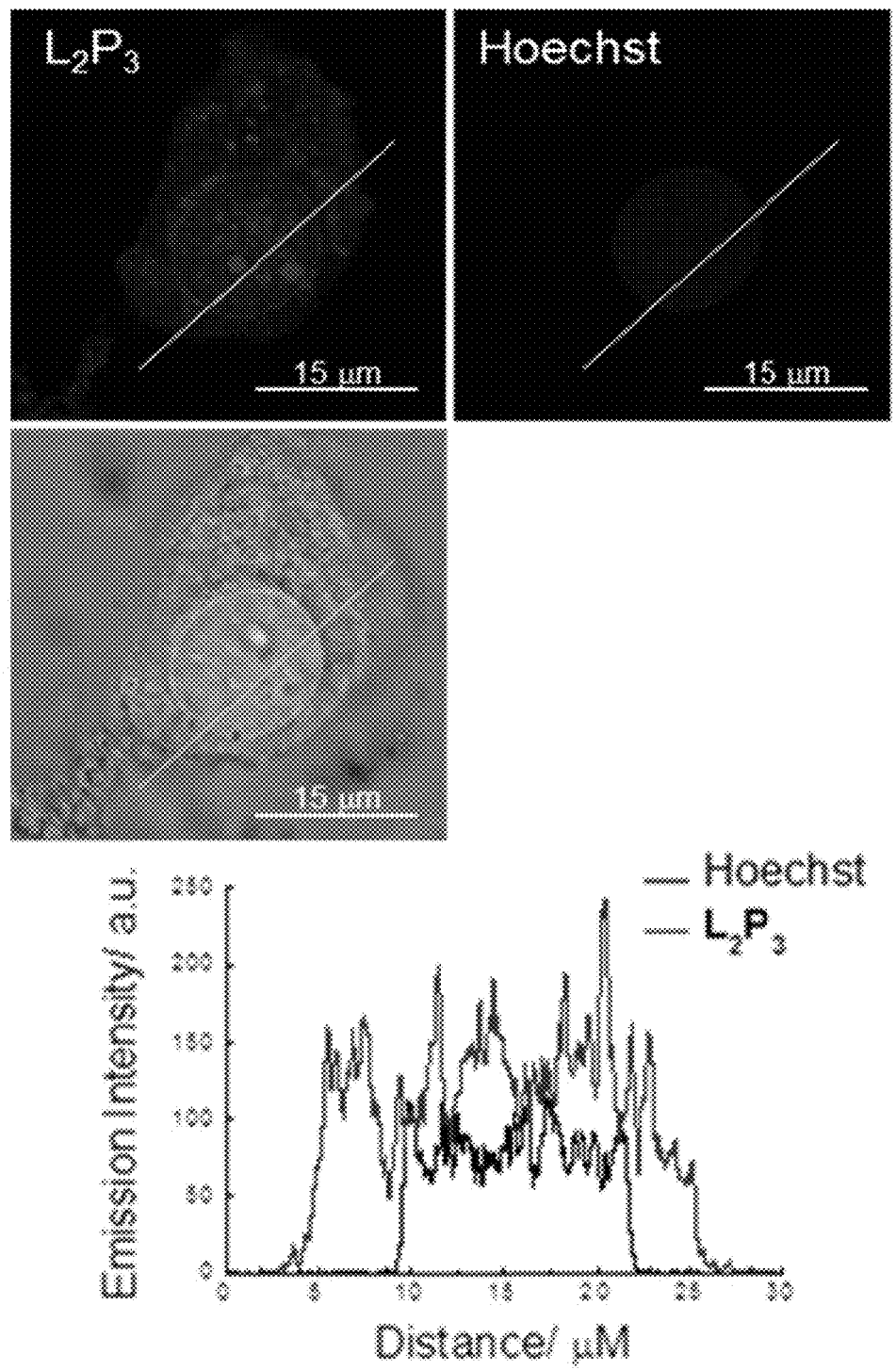
FIG. 3E shows the in vitro confocal microscopy of the $L_2P_3$ probe in EBV-positive NPC43 cells. $\lambda_{ex}$=488 nm; $\lambda_{em}$=500-650 nm; filter, BP500. NPC43 are treated with $L_2P_3$ (10 μM) for 6 h, and then co-stained with the nuclear dye Hoechst 33342 (1 nM) for 1 h. Profiles of the emission intensity of the $L_2P_3$ probe and Hoechst 33342 are plotted along the green line marked on the confocal microscopy images.
Figure 3F:
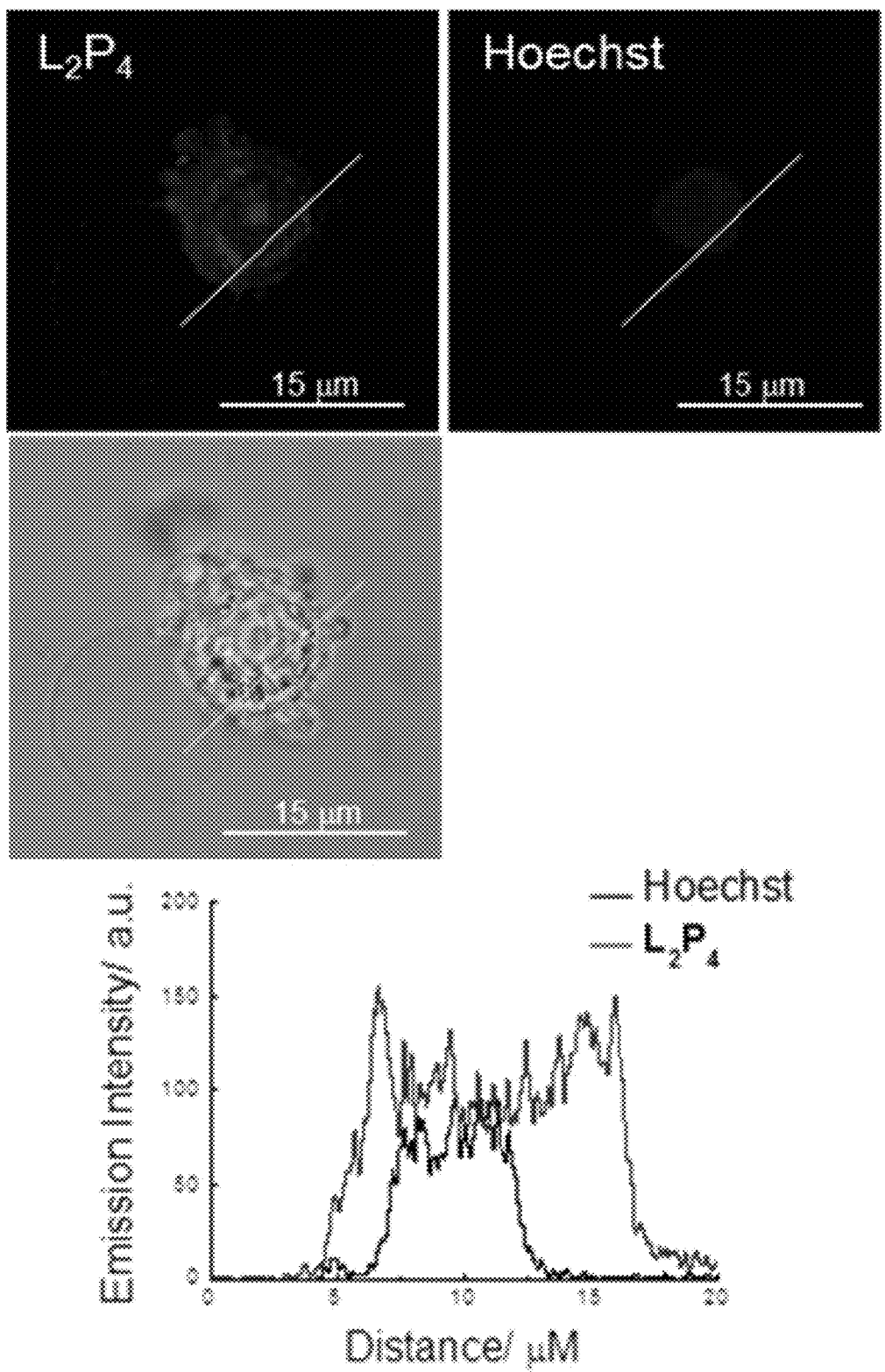
FIG. 3F shows the in vitro confocal microscopy of the $L_2P_4$ probe in EBV-positive NPC43 cells. $\lambda_{ex}$=488 nm; $\lambda_{em}$=500-650 nm; filter, BP500. NPC43 are treated with $L_2P_4$ (10 μM) for 6 h and then co-stained with the nuclear dye Hoechst 33342 (1 nM) for 1 h. Profiles of the emission intensity of the $L_2P_4$ probe and Hoechst 33342 are plotted along the green line marked on the confocal microscopy images. The $L_2P_4$ found in the nucleus (by lambda scan), the shape and location of the emission band is similar to the data obtained for the solution under the same excitation.
Figure 4A:
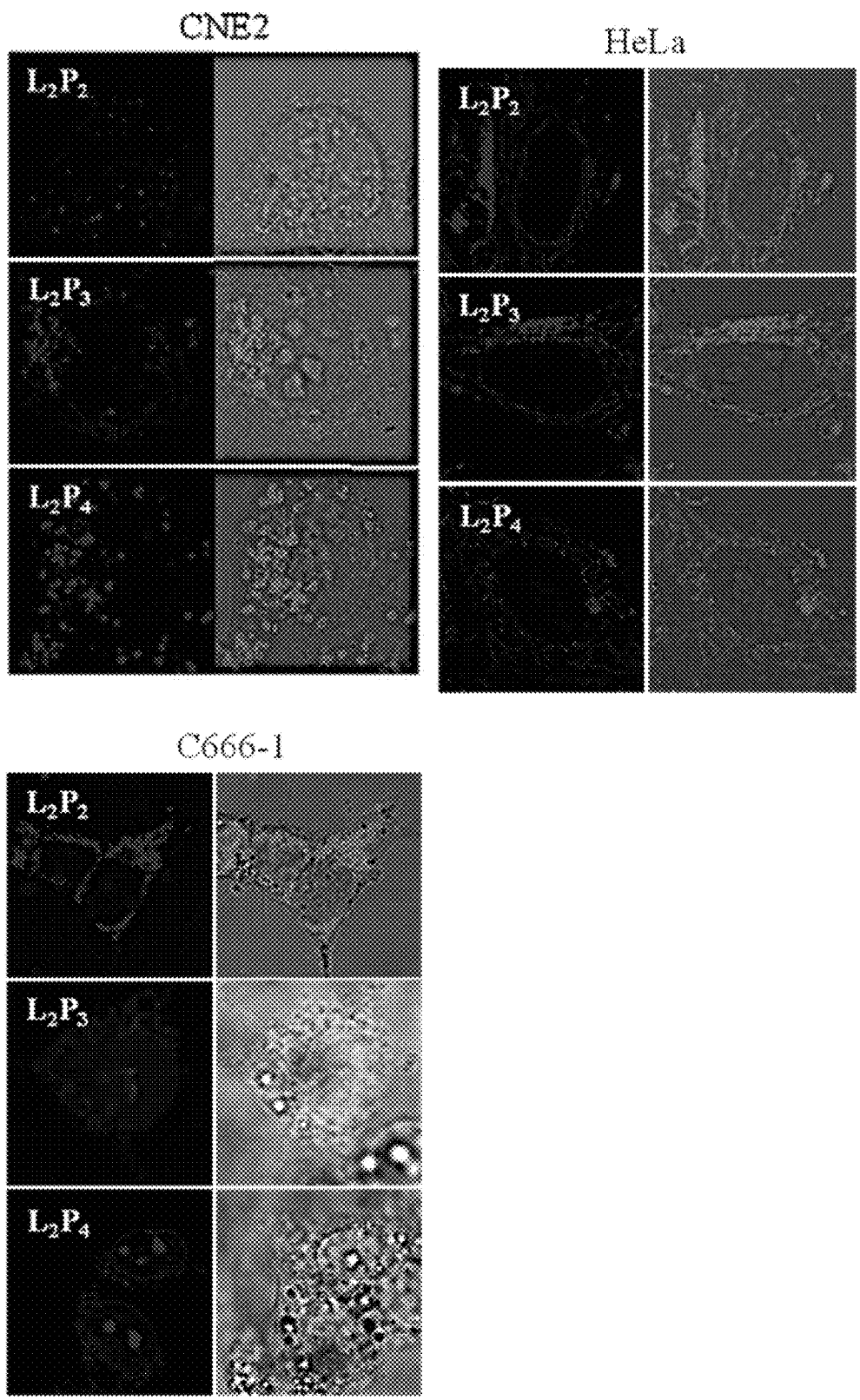
FIG. 4A shows the in vitro confocal imaging of $L_2P_2$, $L_2P_3$ and $L_2P_4$ in EBV-negative (CNE2 and HeLa) and EBV-positive (C666-1) cells. The corresponding bright-field images are shown on the right. The emission of $L_2P_4$ is found to be selective for EBV-positive cells over EBV-negative cells.
Figure 4B:
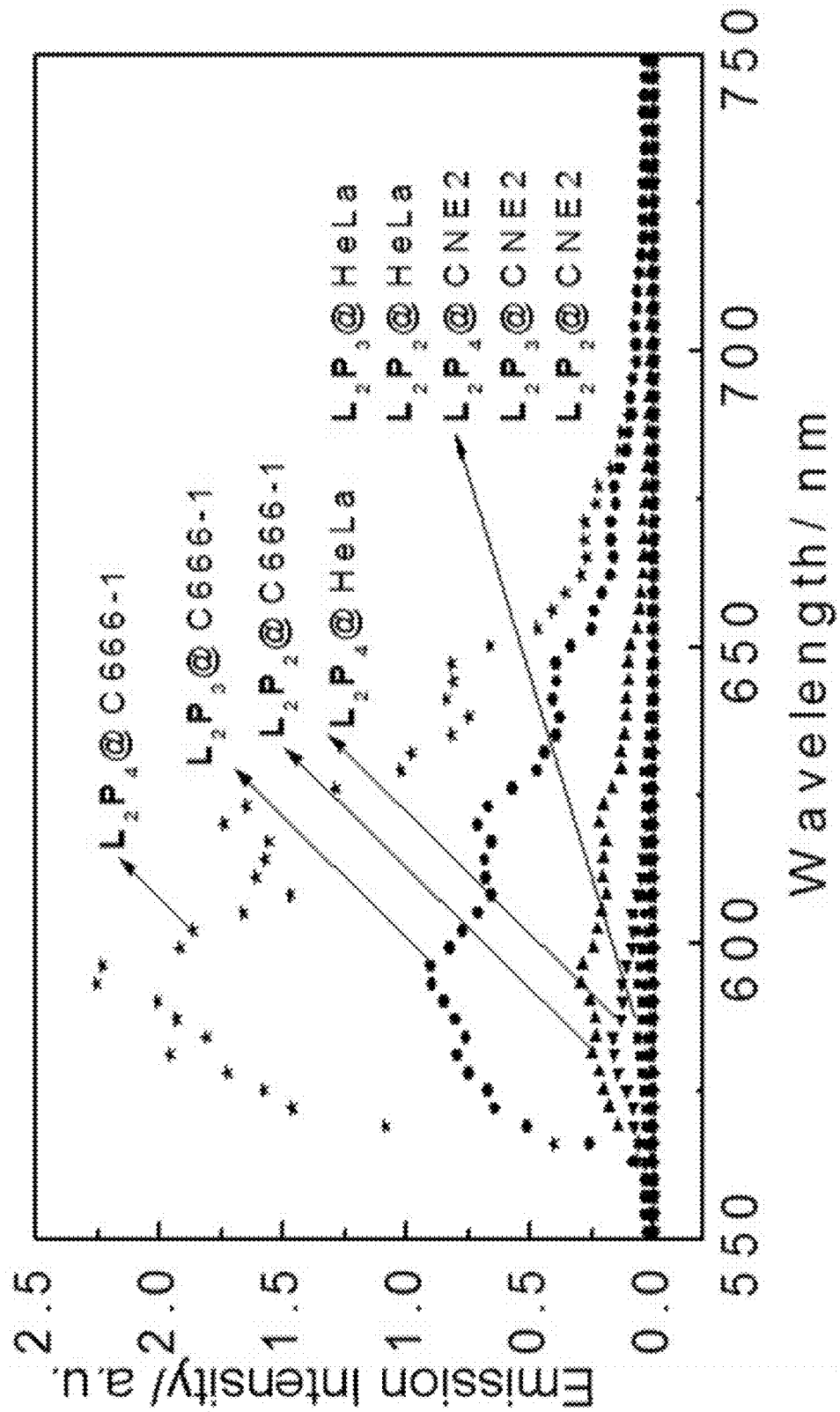
FIG. 4B shows the in vitro emission spectra (from confocal microscopy) of $L_2P_2$, $L_2P_3$ and $L_2P_4$ in the nucleus. Emission intensity was three times greater for $L_2P_4$ than $L_2P_3$ in the EBV-positive C666-1 cells.

The absorption spectra of $L_2P_4$ are measured in various solvents (FIG. 32). The spectra shows two absorption bands at 274 nm and ~500 nm, which corresponded to the transition from ground state to local excited and ICT states, respectively. The maximum absorption band slightly red shifted in polar solvents. $L_2P_4$ demonstrates dual fluorescence on excitation: a weak but higher energy emission at 560 nm arising from the local excited state and a strong emission at ~625 nm from the ICT state are both observed (FIGS. 2A, 2D and 2E). The fluorescence emission of the local excited band is solvent-independent, while the ICT band exhibited a marked dependence on solvent polarity, progressively blue shifted with the decreasing polarity of solvents (FIG. 2E). Additionally, the emission decay of $L_2P_4$ is shown in FIG. 2F, upper ($\lambda_{ex}$=475 nm; monitored at 625 nm), and the emission lifetime of $L_2P_4$ in different solvents is shown in FIG. 34 The observed shorter lifetime (~0.5 ns) corresponded to the local excited emission, and the ICT band exhibited a longer lifetime (3.8 ns).

c. In Vitro Nuclear Imaging of $L_2P_4$.

To demonstrate the selective nuclear localization of $L_2P_4$, EBV-positive (C666-1 and NPC43) and EBV-negative (CNE2 and HeLa) cell lines are imaged for $L_2P_2$, $L_2P_3$ and $L_2P_4$ (FIGS. 3A-3F and 4A-4B). HeLa is EBV-negative human cervical carcinoma cells, CNE2 is EBV-negative nasopharyngeal carcinoma cells, C666-1 is EBV-positive nasopharyngeal carcinoma cells, and NPC 43 is the newly derived EBV-positive nasopharyngeal carcinoma cells. The nuclear localization sequence RrRK is incorporated into $P_3$ and $P_4$ to enhance their nucleus permeability. The cellular uptake and localization of the three probes are evaluated independently using confocal imaging and flow cytometry (FIGS. 3A-3F, 4A-4B, 36A-36C, 37A-37F and 38A-38F). From these experiments, $L_2P_4$ is found to exhibit the highest cellular uptake in both HeLa and C666-1 cells (FIG. 36A-36C). Owing to the contribution of RrRK, nuclear localization of $L_2P_3$ and $L_2P_4$ are observed in the EBV-positive cells (C666-1 and NPC43), whereas $L_2P_2$ is only found in the cytoplasm, demonstrating that $L_2P_3$ and $L_2P_4$ localize in the nuclei of the EBV-positive cells.

d. Selective Toxicity of $L_2P_4$ Towards EBV-Positive Cells.

Figure 5A:
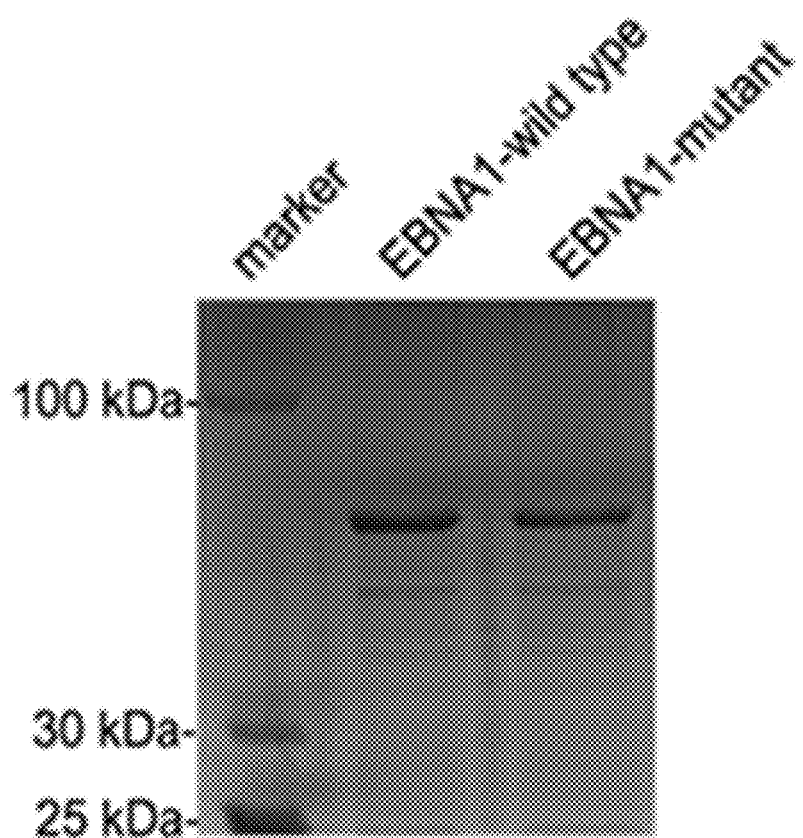
FIG. 5A shows the EBNA1 proteins purification. EBNA1 protein (379-641 a.a.) fusion with glutathione S-transferase (GST) was expressed in *Escherichia coli* (BL21) and purified by glutathione sepharose 4B rinse (GE Healthcare Dharmacon). The residues YFMVF of WT-EBNA1 is mutated to FFAVA yielding the mutant EBNA1 (EBNA1-3A).
Figure 5B:
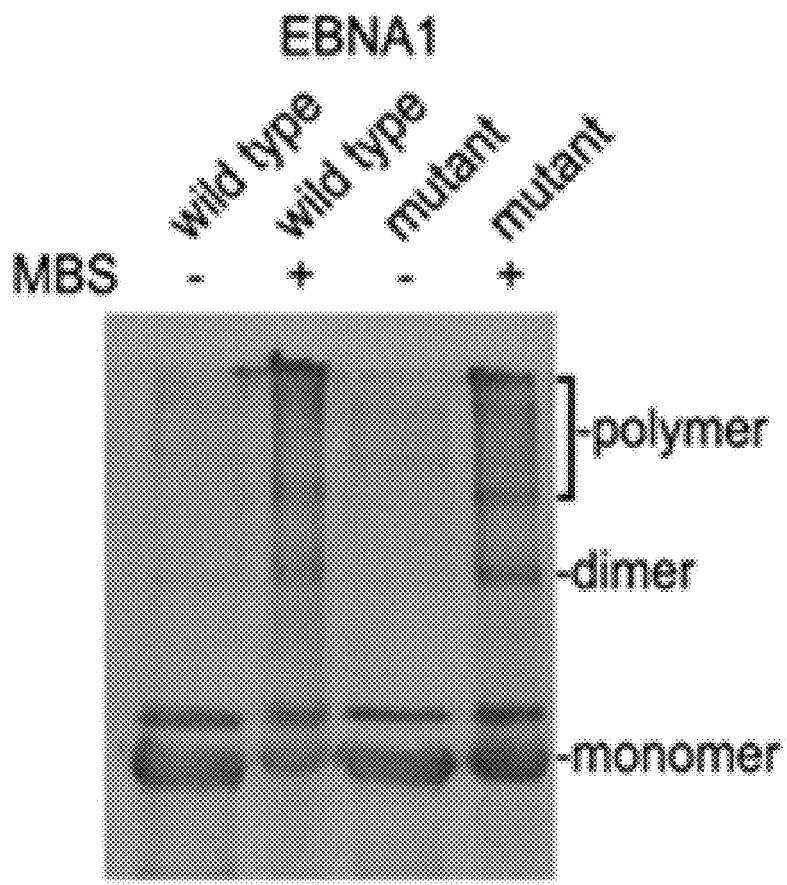
FIG. 5B shows the MBS cross-linked dimerization assay. The WT and mutant EBNA1 (EBNA1-3A) are analyzed for dimerization, which differently impairs the capability of EBNA1 dimerization.
Figure 5C:
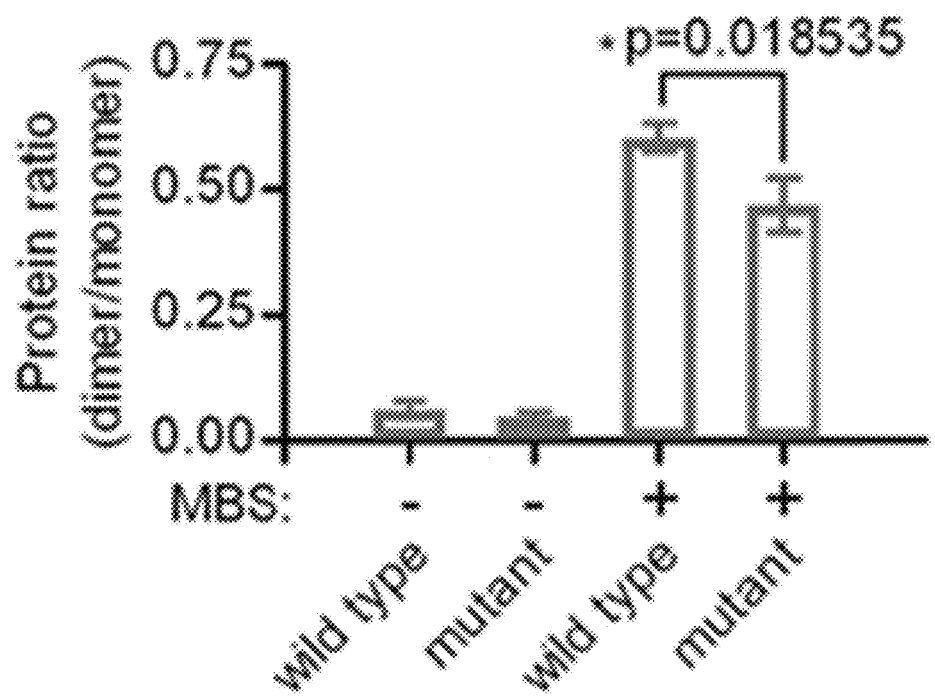
FIG. 5C shows the EBNA1 homodimerization efficiency (**, $P<0.01$). The dimerization efficiency decreases in mutant EBNA1 (EBNA1-3A).
Figure 6A:
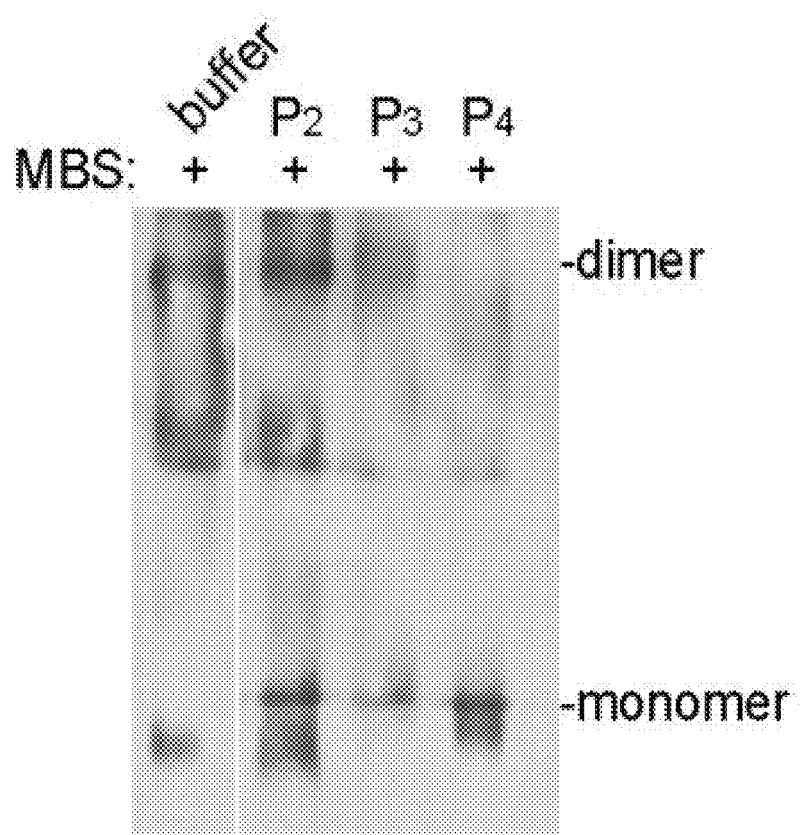
FIG. 6A shows the EBNA1 dimerization assay. WT-EBNA1 is subjected to MBS cross-linked dimerization assay after addition of peptides ($P_2$-$P_4$).
Figure 6B:
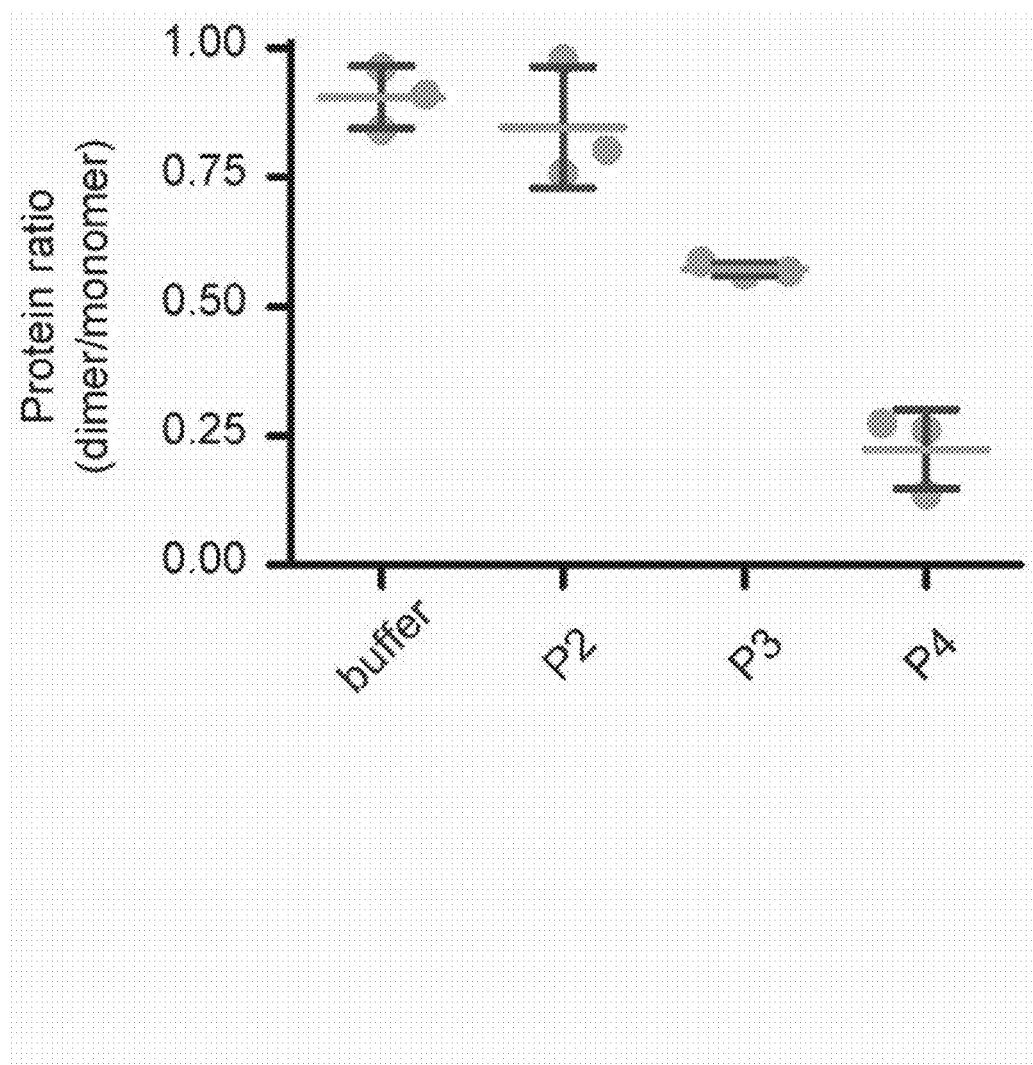
FIG. 6B shows the EBNA1 dimerization assay. The inhibitory efficiency of peptides ($P_2$-$P_4$) is measured as the EBNA1 dimer/monomer ratio; the intensity of each protein band represents the mean±s.d. of three independent experiments.
Figure 6C:
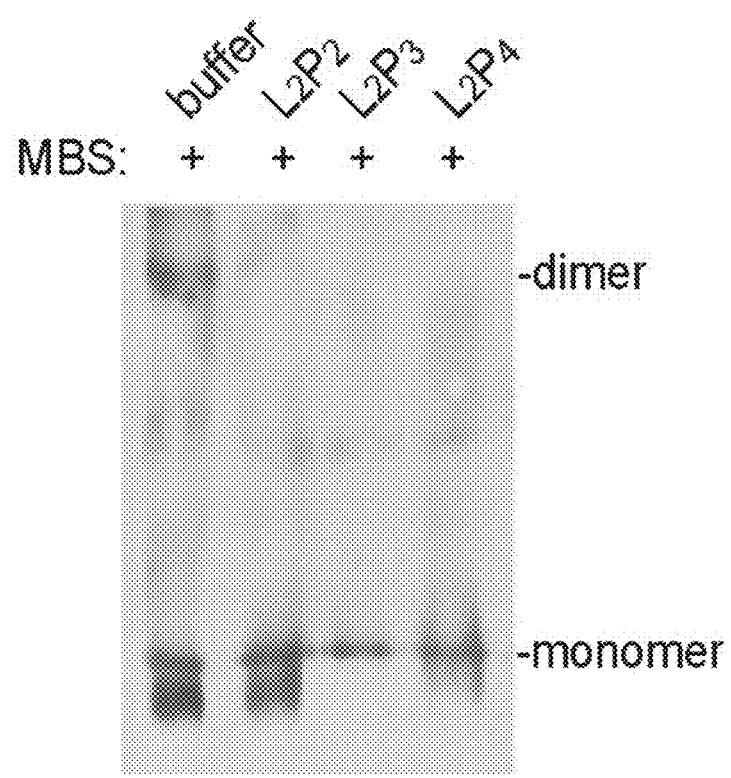
FIG. 6C shows the EBNA1 dimerization assay. WT-EBNA1 is subjected to MBS cross-linked dimerization assay after addition of peptide conjugates ($L_2P_2$-$L_2P_4$).
Figure 6D:
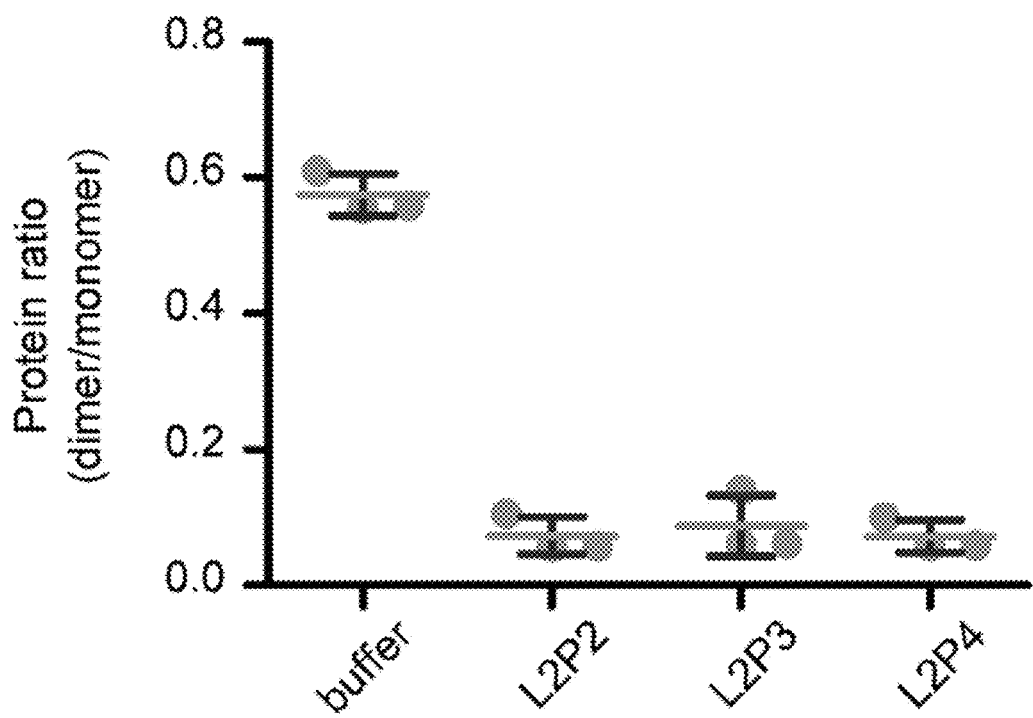
FIG. 6D shows the EBNA1 dimerization assay. The inhibitory efficiency of peptide conjugates ($L_2P_2$-$L_2P_4$) is measured as the EBNA1 dimer/monomer ratio; the intensity of each protein band represents the mean±s.d. of three independent experiments.
Figure 7A:
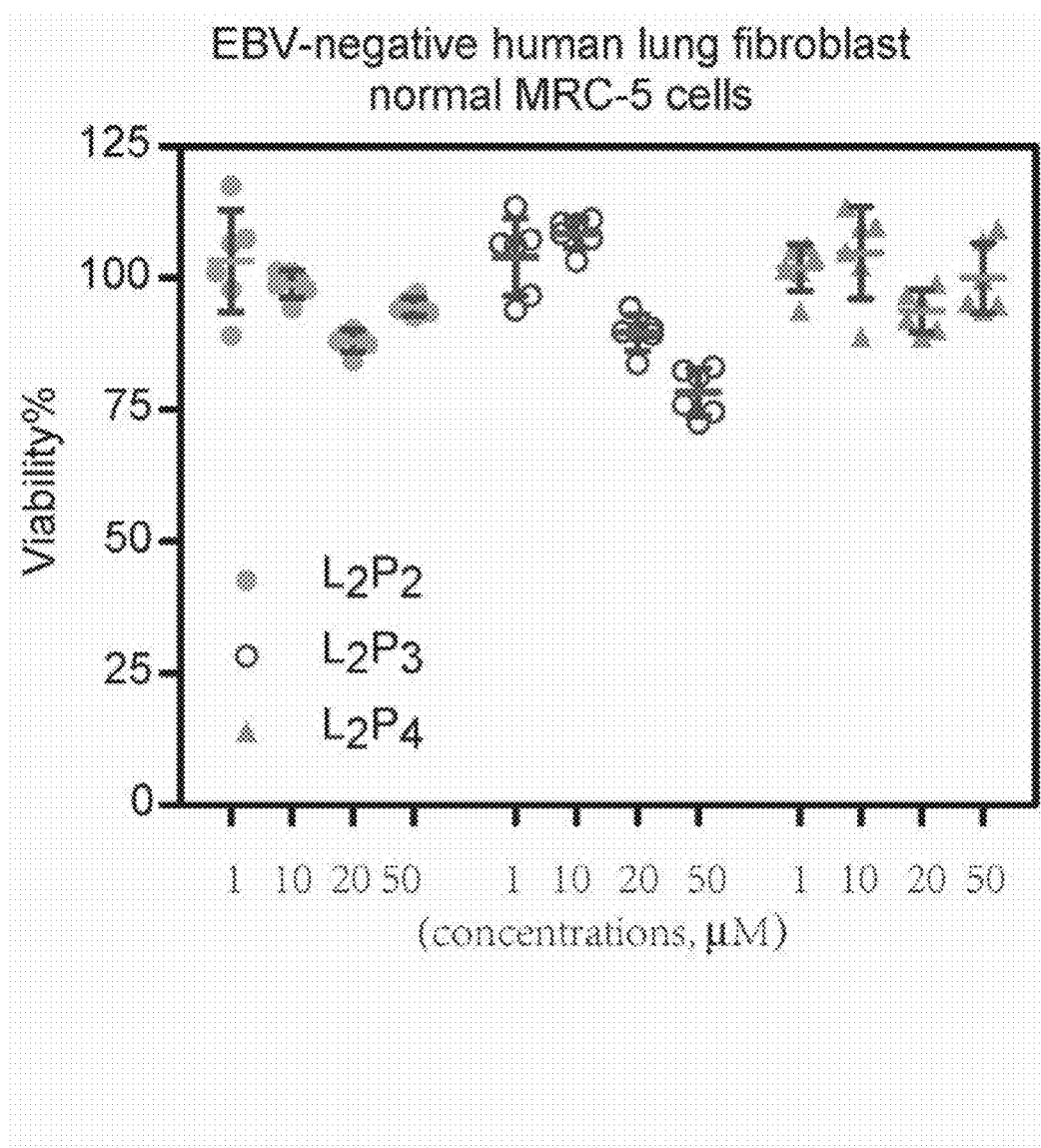
FIG. 7A shows the cytotoxicity (MTT assay) of the conjugate probes to EBV-negative human normal lung fibroblast MRC-5 cells after 24 hours. Each conjugate probe is tested in triplicate, and repeated twice. The data represent the mean±s.d.
Figure 7B:
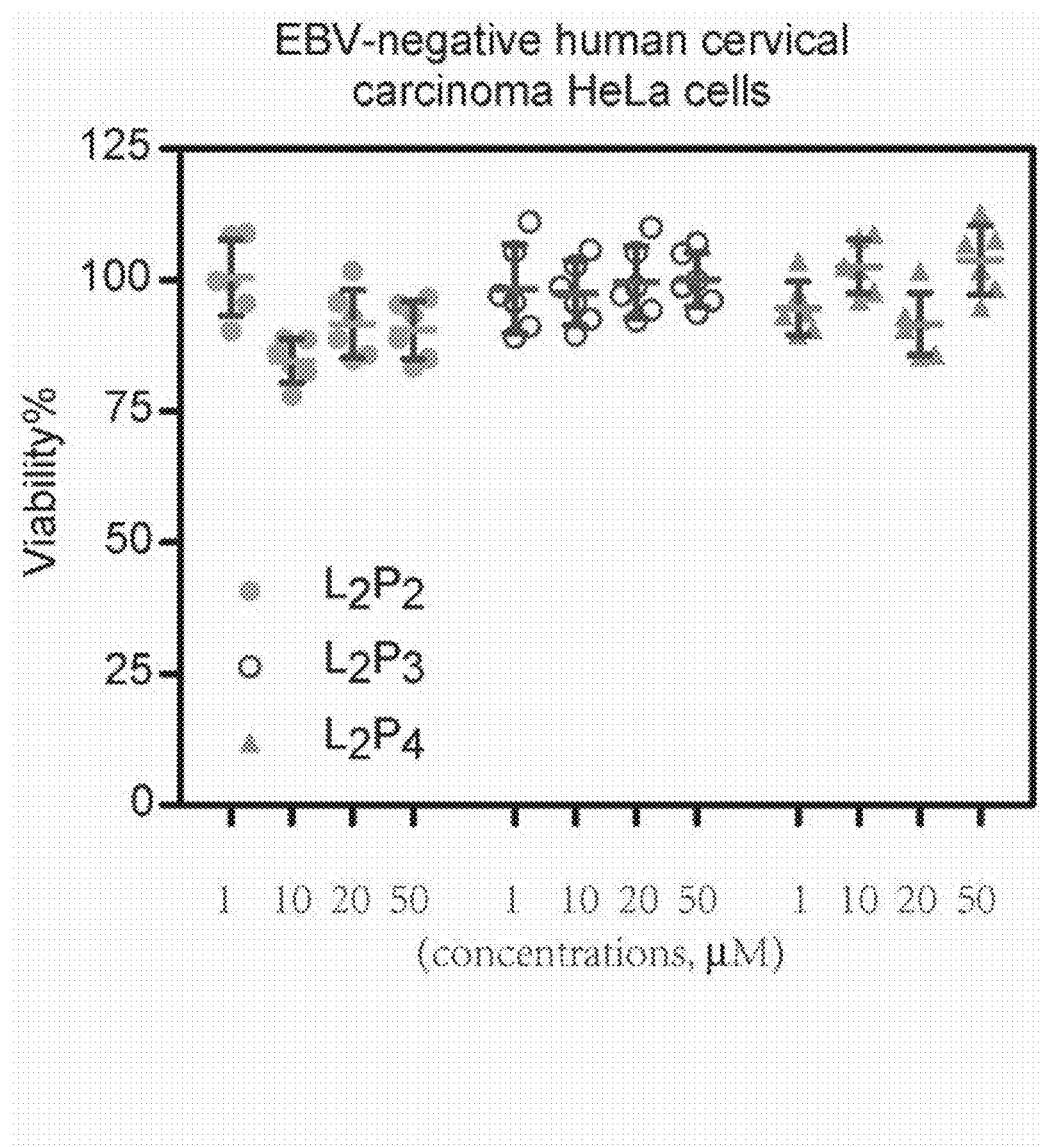
FIG. 7B shows the cytotoxicity (MTT assay) of the conjugate probes to EBV-negative human cervical carcinoma HeLa cells after 24 hours. Each conjugate probe is tested in triplicate, and repeated twice. The data represent the mean±s.d.
Figure 7C:
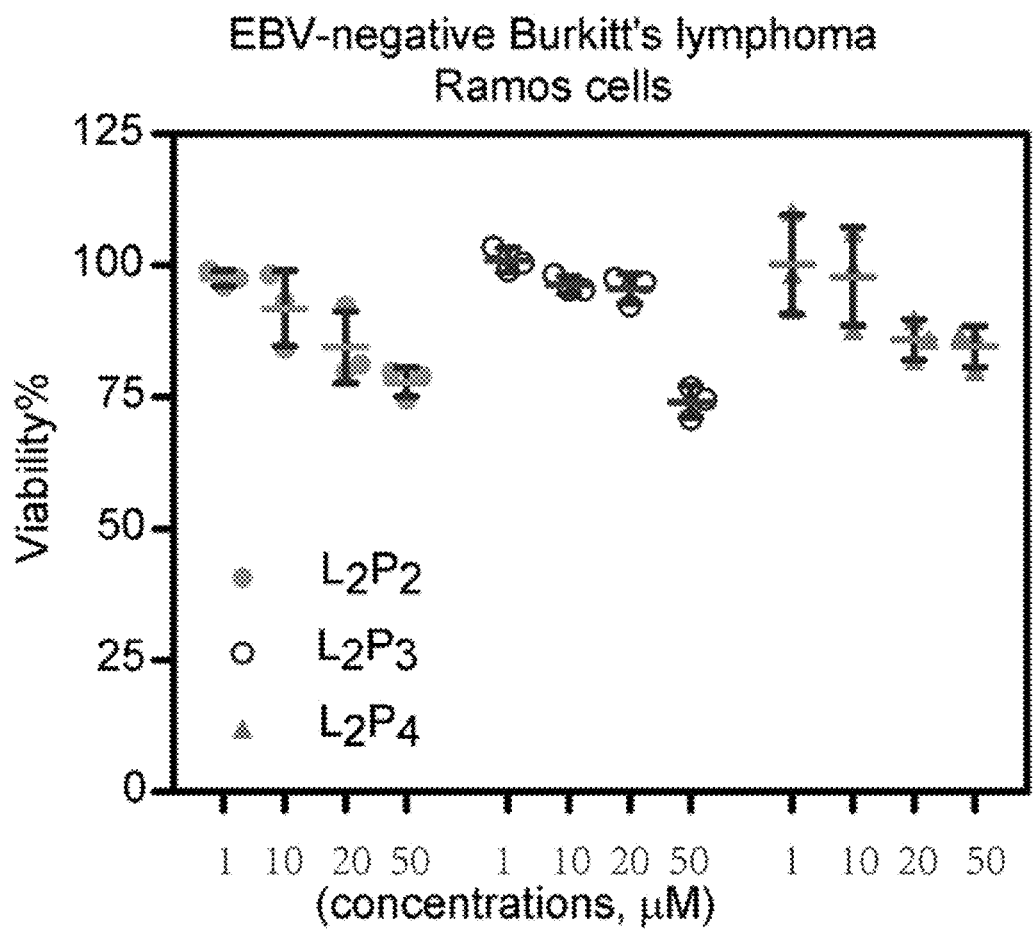
FIG. 7C shows the cytotoxicity (MTT assay) of the conjugate probes to EBV-negative Burkitt's lymphoma Ramos cells after 24 hours. Each conjugate probe is tested in triplicate, and repeated twice. The data represent the mean±s.d.
Figure 7D:
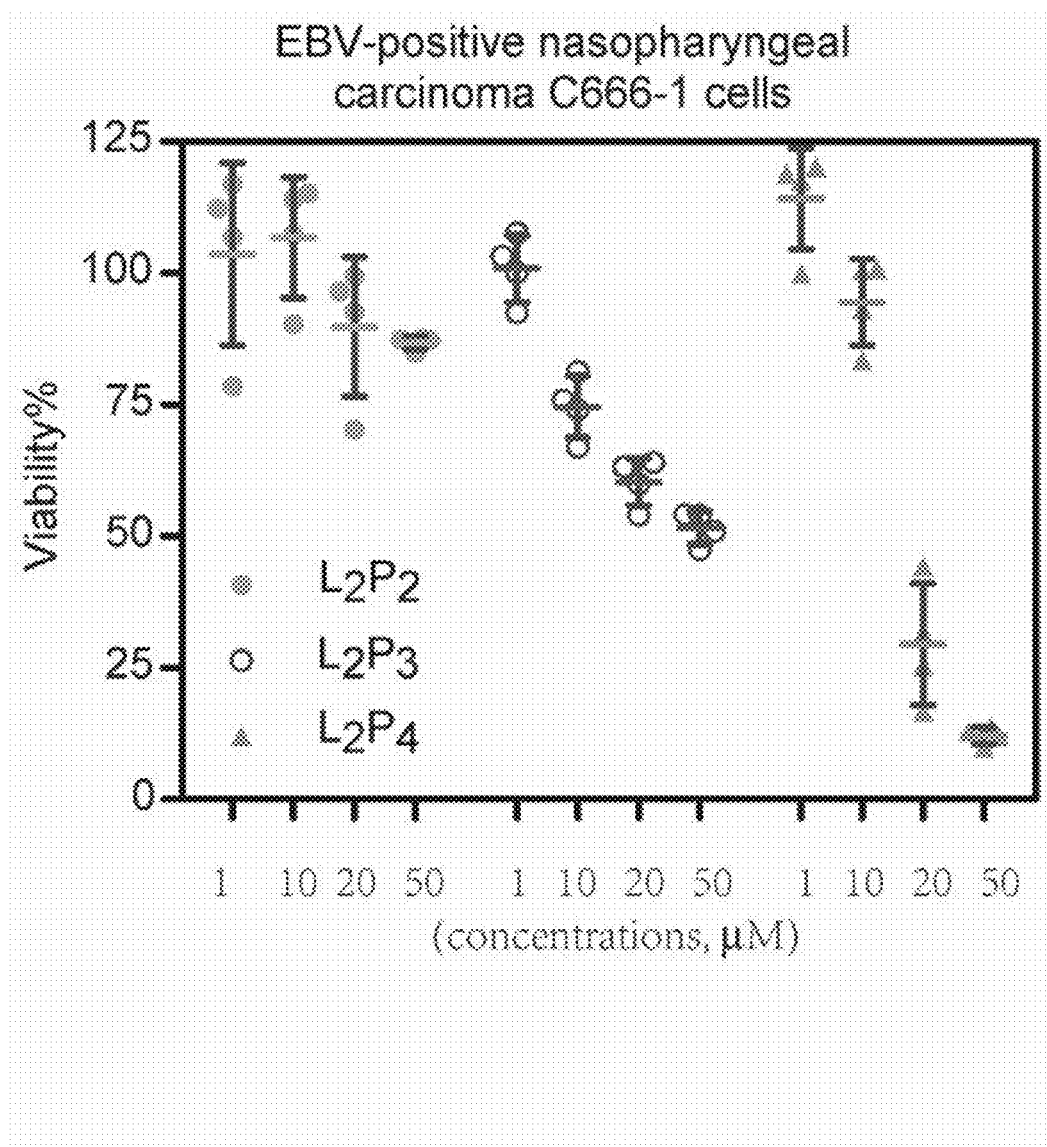
FIG. 7D shows the cytotoxicity (MTT assay) of the conjugate probes to EBV-positive nasopharyngeal carcinoma C666-1 cells after 24 hours. Each conjugate probe is tested in triplicate, and repeated twice. The data represent the mean±s.d.
Figure 7E:
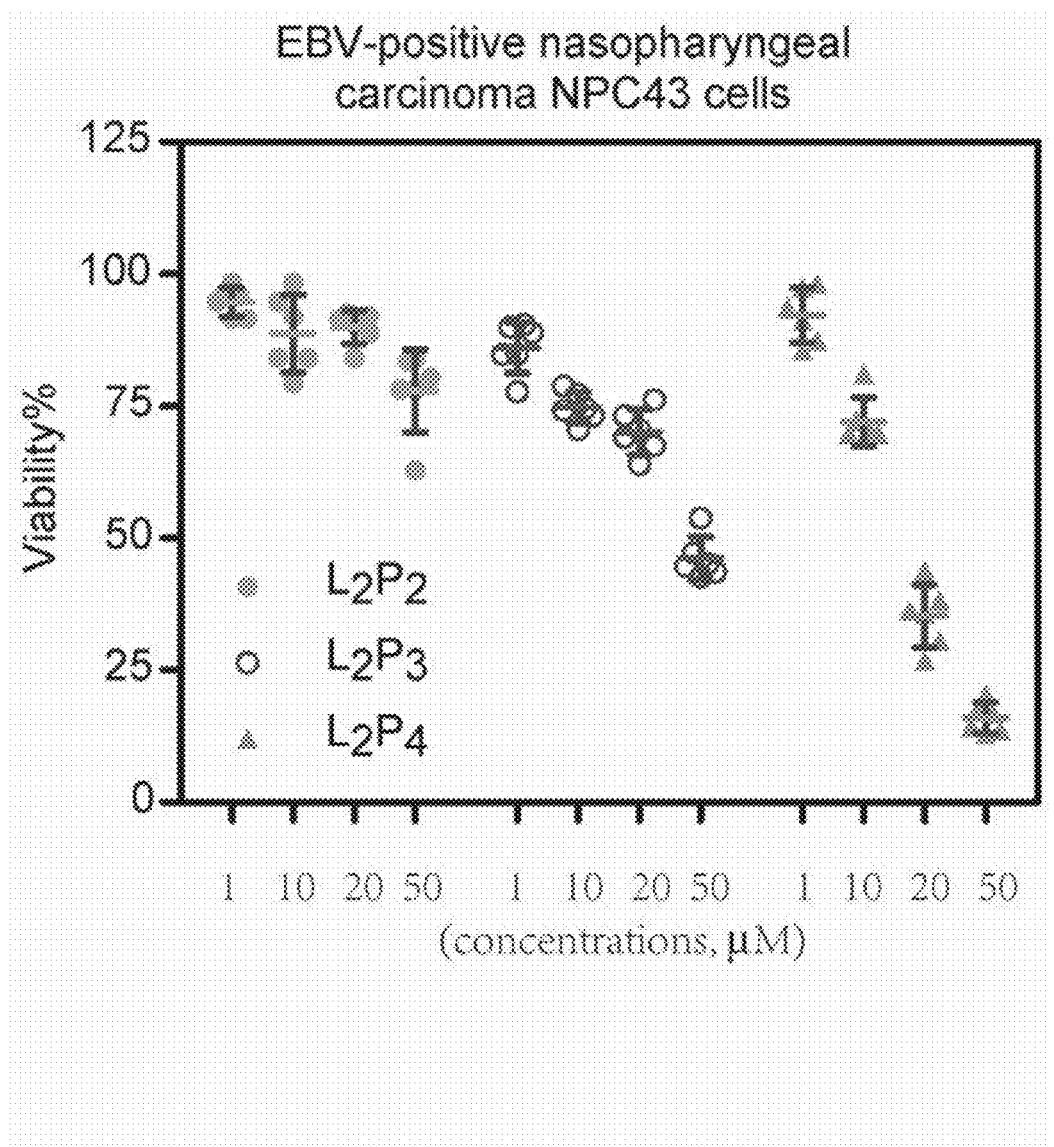
FIG. 7E shows the cytotoxicity (MTT assay) of the conjugate probes to EBV-positive nasopharyngeal carcinoma NPC43 cells after 24 hours. Each conjugate probe is tested in triplicate, and repeated twice. The data represent the mean±s.d.
Figure 7F:
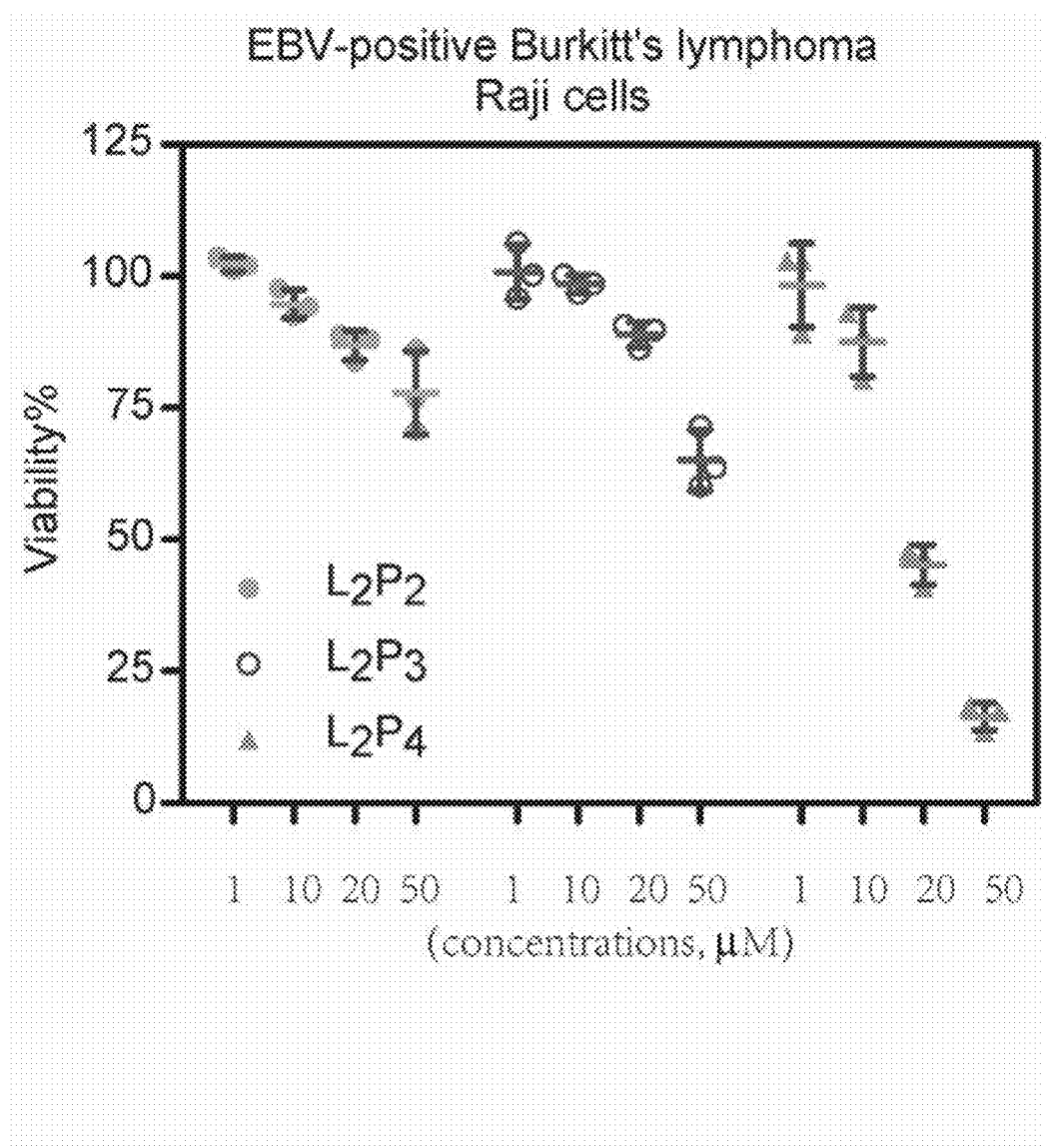
FIG. 7F shows the cytotoxicity (MTT assay) of the conjugate probes to EBV-positive Burkitt's lymphoma Raji cells after 24 hours. Each conjugate probe is tested in triplicate, and repeated twice. The data represent the mean±s.d.

EBNA1 can only facilitate DNA replication of EBV by forming homodimers; therefore, blocking dimer formation provides a route to kill EBV-infected tumor cells. It is well known that EBNA1 dimer is formed through the YFMVF-mediated interface, and this can be examined via a 3-maleimidobenzoyl N-hydroxysuccinimide ester (MBS) cross-linked dimerization assay; MBS is an amine-to-sulfhydryl crosslinker that contains NHS-ester and maleimide reactive groups. The MBS-mediated protein crosslinking effect is represented as the dimer to monomer ratio. The importance of YFMVF for dimerization is further investigated in the WT-EBNA1 and EBNA1 mutants (EBNA1-$Y_{561}$A, EBNA1-$M_{563}$A, EBNA1$F_{565}$A and EBNA1-3A) in their homodimerization efficiency. Prior to that, the purity of the WT-EBNA1 and EBNA1 mutants is checked and their homodimerization efficiency is analyzed as shown in FIGS. 5A-5C. The results showed that the dimerization efficiency is greatly decreased for EBNA1-3A, while a relatively small decrease in the efficiency is observed for the other three point mutants (FIGS. 35A-35C). Consistent with this observation and the luminescence titration experiment, the MBS cross-linked dimerization assay is also inhibited by the peptide conjugates of the present invention, as shown in FIGS. 6A-6D (P<0.001).

Considering the strong binding of $L_2P_4$ to WT-EBNA1 and the selective nuclear in vitro imaging, selective and efficient cytotoxicity towards EBV-positive cells by $L_2P_4$ is shown. An MTT (3-(4,5-dimethylthiazol-2-yl)-2,5-diphenyltetrazolium bromide) cytotoxicity assay is carried out for the three peptides ($P_2$, $P_3$ and Pa; FIGS. 39A-39F) and the three peptide conjugates ($L_2P_2$, $L_2P_3$ and $L_2P_4$; FIGS. 7A-7F) in three EBV-negative cell lines (MRC-5 (normal lung fibroblasts), HeLa and Ramos) and three EBV-positive cell lines (C666-1, NPC43 and Raji). All probes (peptides or peptide conjugates) are found to exhibit low cytotoxicity in EBV-negative cells even at high doses (50 μM), and exhibited dose-dependent cytotoxicity in EBV-positive cells. The degree of cytotoxicity of the peptide conjugate in EBV-positive cells ($L_2P_4$>$L_2P_3$>$L_2P_2$) is the same as that for the MD simulation, luminescence titration and in vitro imaging results.

e. In Vivo Tumor Imaging and Inhibition of $L_2P_4$

Figure 8A:
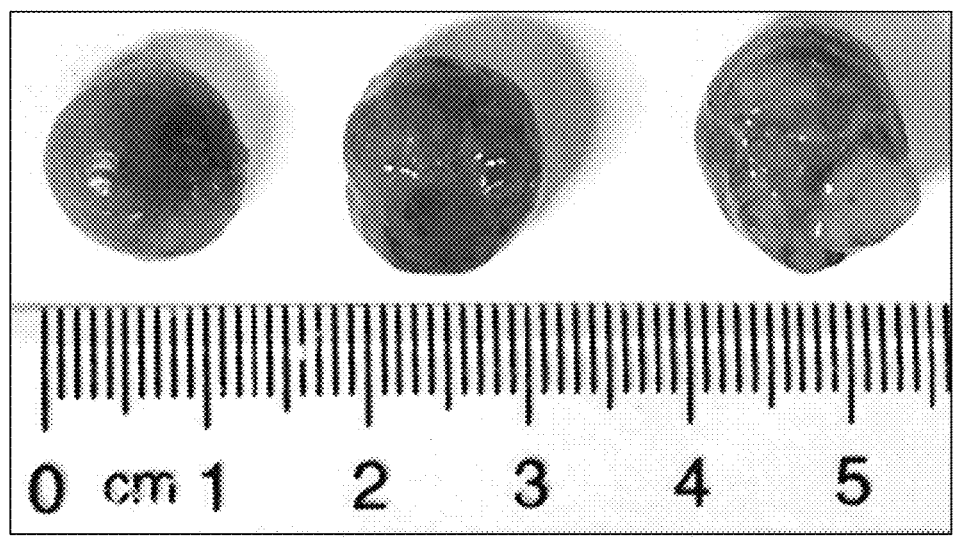
FIG. 8A shows the in vivo tumor inhibition assays. Mice are given intra-tumoral injections of dimethylsulfoxide (DMSO; vehicle and control) twice-weekly for 21 days. At the experimental endpoint, the tumors are excised and photographed.
Figure 8B:
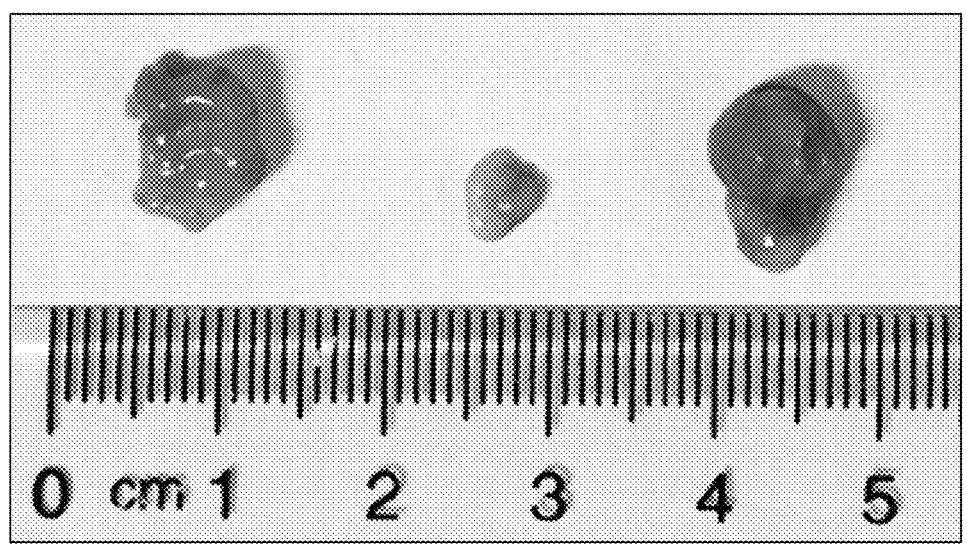
FIG. 8B shows the in vivo tumor inhibition assays for $P_4$ (4 μg per tumor). Mice are given intra-tumoral injections of $P_4$ twice-weekly for 21 days; high (H) and low (L) doses are 4 and 2 μg per tumor, respectively. At the experimental endpoint, the tumors are excised and photographed.
Figure 8C:
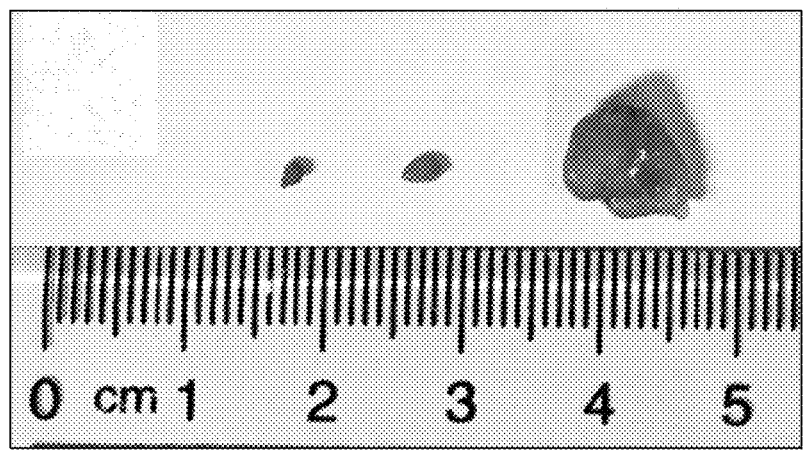
FIG. 8C shows the in vivo tumor inhibition assays for $L_2P_4$ (4 μg per tumor). Mice are given intra-tumoral injections of $L_2P_4$ twice-weekly for 21 days; high (H) and low (L) doses are 4 and 2 μg per tumor, respectively. At the experimental endpoint, the tumors are excised and photographed.
Figure 8D:
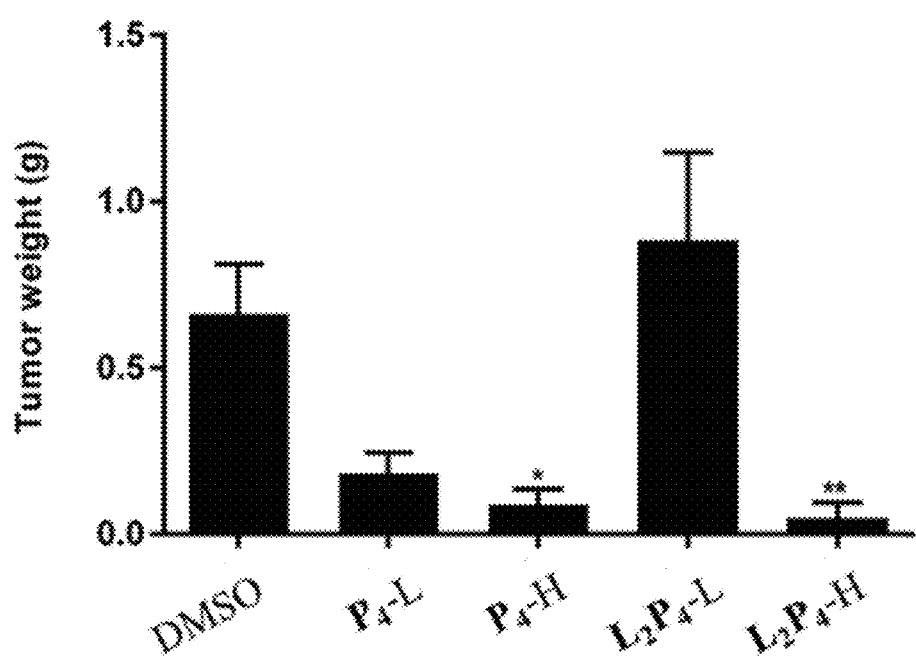
FIG. 8D shows the in vivo studies of $P_4$ and $L_2P_4$ as EBV-specific anti-cancer agents. In vivo tumor inhibition assays for $P_4$ and $L_2P_4$, Mice are given intra-tumoral injections of $P_4$, $L_2P_4$ or dimethylsulfoxide (DMSO; vehicle and control) twice-weekly for 21 days; high (H) and low (L) doses are 4 and 2 μg per tumor, respectively. At the experimental endpoint, the tumors are excised and photographed, and their weights are measured. Data are expressed as the mean±SEM. *$P<0.05$; **$P<0.005$.
Figure 8E:
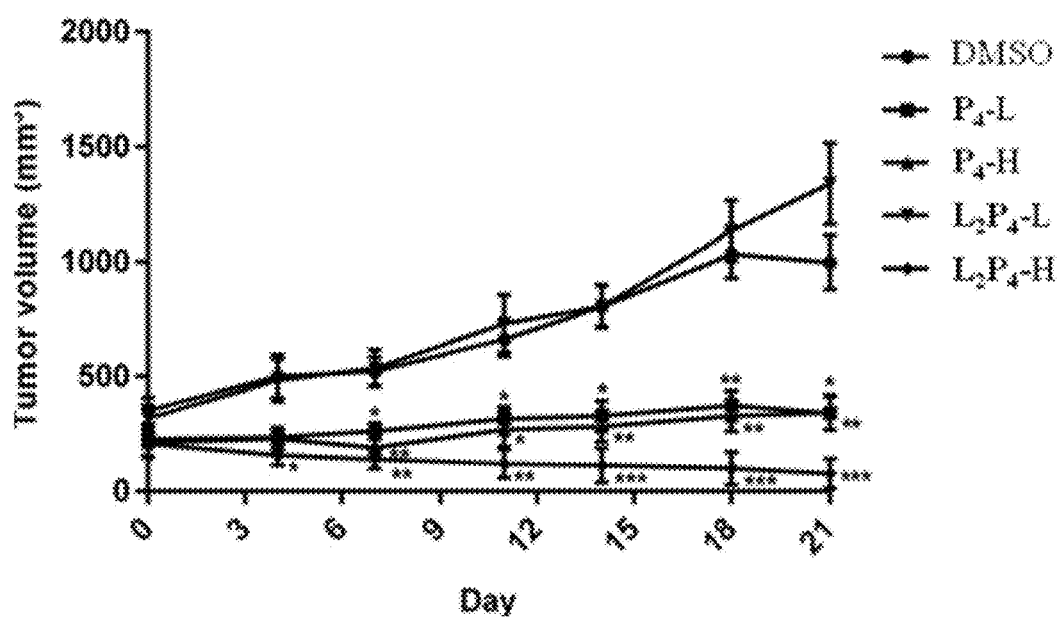
FIG. 8E shows the in vivo studies of $P_4$ and $L_2P_4$ as EBV-specific anti-cancer agents. In vivo tumor inhibition assays for $P_4$ and $L_2P_4$, Mice are given intra-tumoral injections of $P_4$, $L_2P_4$ or dimethylsulfoxide (DMSO; vehicle and control) twice-weekly for 21 days; high (H) and low (L) doses are 4 and 2 μg per tumor, respectively. At the experimental endpoint, the tumors are excised and photographed, and their volumes are measured. Data are expressed as the mean±SEM. *$P<0.05$; **$P<0.005$.

To further evaluate the in vivo performance of $L_2P_4$, intra-tumoral injections of $P_4$ or $L_2P_4$ (low dose (L) of 2 μg or high dose (H) of 4 μg) are administered to C666-1 and HeLa cell xenografts in BALB/c nude mice. The injections are carried out biweekly along with body weight and tumor measurements. Mice carrying HeLa cell xenografts served as controls to confirm the specificity of the in vivo targeting effect of $P_4$ or $L_2P_4$. Treatment with $P_4$ or $L_2P_4$ have no significant effects on the body weights of the mice when compared with controls (FIGS. 40, 41A-41E and 43A-43C), indicating that neither $P_4$ nor $L_2P_4$ exhibited a toxic effect in EBV-negative cancer in vivo. C666-1 cell xenograft growth is effectively inhibited, whereas the growth of HeLa xenografts is unaffected by treatment with $P_4$ or $L_2P_4$ (FIGS. 8D, 56D and 43B). By day 7, treatment of C666-1 cell xenografts with $P_4$-L, $P_4$—H and $L_2P_4$-H have significantly decreased the tumor volumes versus controls, and at the end of the experiment (day 21), the average tumor volumes are decreased by 65.7%, 65.5% and 92.3% ($p<0.05$, $p<0.005$ and $p<0.001$), respectively (FIGS. 6D, 8D and 42A-42B). For the HeLa cell xenografts, there are no significant differences in average tumor volume between control mice and those treated with $P_4$ or $L_2P_4$ (low and high dose) at the end of the experiment (day 18), as shown in FIG. 43B. At the end of the experiment, the mice are killed and the tumors are excised and weighed. For C666-1 cell xenografts, average tumor weights are decreased after treatment with $P_4$-L, $P_4$-H and $L_2P_4$-H by 72.6%, 86.6% and 92.8% (not significant, $p<0.05$ and $p<0.005$), respectively, when compared with controls (FIGS. 8A, 8B, 8C, 8D and 8E). Whereas for the HeLa cell xenografts, there are no significant differences in the averaged tumor weights (FIGS. 43C and 44). The significant and selective inhibition of EBV-positive tumor growth by $P_4$ and $L_2P_4$ confirmed their EBV-targeting specificity and indicated that the conjugation of $L_2$ to $P_4$ does not affect its tumor inhibitory effect.

Figure 8F:
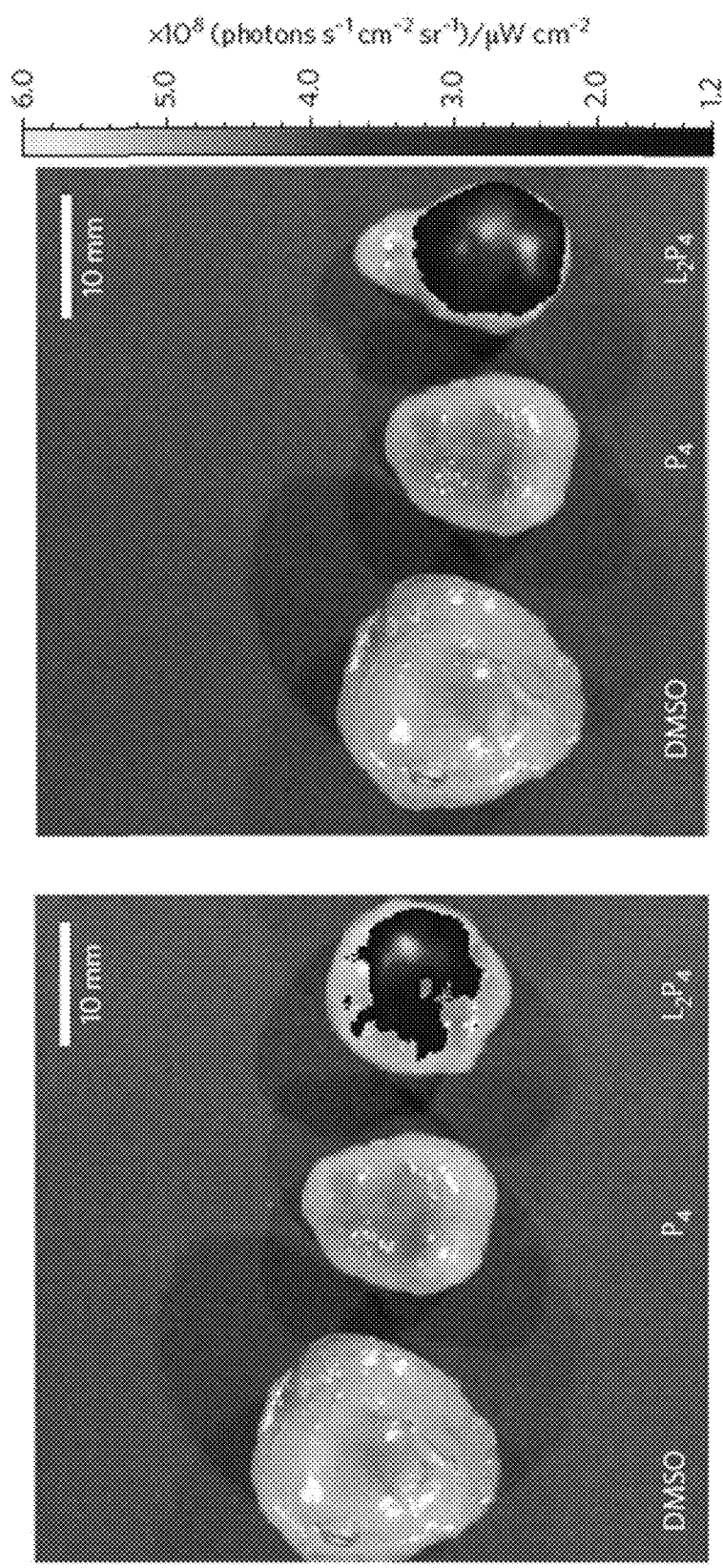
FIG. 8F shows the in vivo studies of $P_4$ and $L_2P_4$ as EBV-specific anti-cancer agents. In vivo tumor inhibition assays for $P_4$ and $L_2P_4$, Mice are given intra-tumoral injections of $P_4$, $L_2P_4$ or dimethylsulfoxide (DMSO; vehicle and control) twice-weekly for 21 days; high (H) and low (L) doses are 4 and 2 μg per tumor, respectively. At the experimental endpoint, the tumors are excised. Representative fluorescence images of excised C666-1 tumors. Tumors are excised directly after the mice are killed and the fluorescence quantified as total radiant efficiency, [photons/s]/[μW/cm$^2$]. Image: min=0.00, max=5.59×10$^8$.

Fluorescence imaging of the excised C666-1 tumors shows that $L_2P_4$ fluorescence signal remains detectable 48 h after the intra-intratumoral injection (FIG. 8F). As expected, no fluorescent signal is detected in control or $P_4$ treated tumors.

Figure 1C:
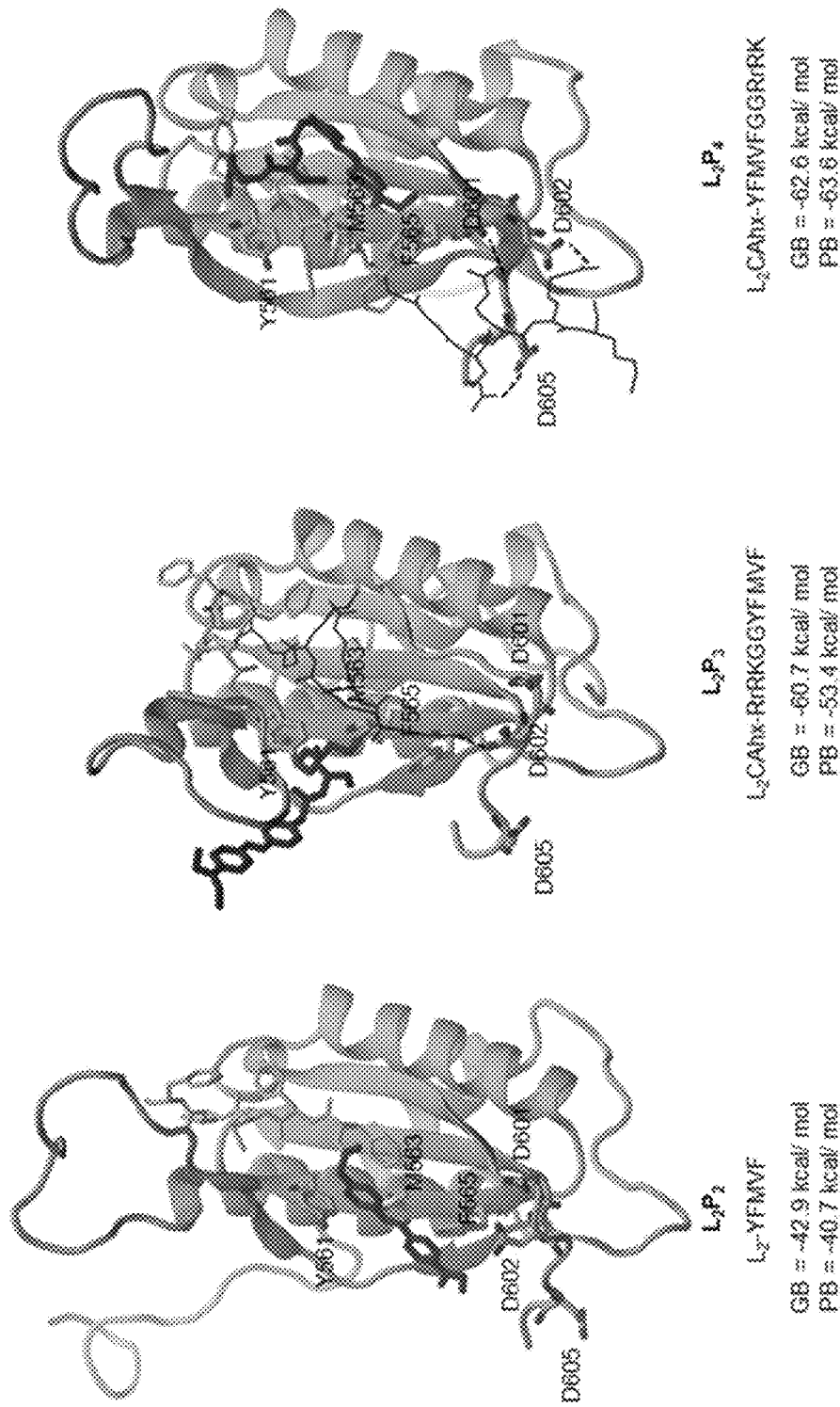
FIG. 1C shows the representative conformations of the probes $L_2P_2$, $L_2P_3$ and $L_2P_4$ and EBNA1 in the MD simulation. The calculated generalized Born (GB) and Poisson-Boltzmann (PB) values represent the binding free energy between the probes of the present invention and EBNA1.

In the present invention, the initial MD studies show that a network of hydrophobic interactions and salt bridging mediates the binding of $L_2P_4$ to the dimeric interface of EBNA1 (FIG. 1). The selective and strong binding of $L_2P_4$ to EBNA1 is further confirmed using luminescence titration experiments (FIG. 2). $L_2P_4$ is found to localize in the nuclei of EBV-positive cells, but not in those of EBV-negative cells. The selective emission of $L_2P_4$ in the nucleus is generated by its binding with EBNA1 (FIGS. 3A-3F).

The present application also provides that EBNA1 mutants (especially EBNA1-3A) are not able to undergo homodimerization (FIGS. 35A-35C), emphasizing the importance of the dimeric interface (YFMVF) in EBNA1 dimer formation. The analysis of the WT-EBNA1 dimerization efficiency on addition of the present peptide conjugates using an MBS cross-linked dimerization assay shows that the present peptide conjugates can significantly interfere with EBNA1 dimer formation (FIGS. 6A-6D). Extensive cytotoxicity assays performed on both EBV-positive and-negative cells demonstrate the significant and selective inhibition of EBV-positive cell growth by $L_2P_4$, and more importantly, revealed that the reason for the selective cytotoxicity is through inhibition of the EBNA1 dimerization process (FIGS. 7A-7F). Finally, experiments investigating the effects of $L_2P_4$ on mice carrying C666-1 and HeLa cell xenografts confirm that $L_2P_4$ specifically targets EBV, and they show the application of the peptide conjugate of the present application in in vivo targeting and inhibiting the growth of EBV-positive tumors (FIGS. 8A-8F) and thus treating EBV associated cancers. The present application shows that $L_2P_4$ can selectively inhibit EBV-positive tumors—in vitro and in vivo—by interfering EBNA1 homodimerization.

Experimental

1) Synthesis and Purification

General Procedures for Peptide Synthesis and Cleavage:

All chemicals used are of reagent-grade and are purchased from Sigma-Aldrich and used without further purification. All analytical-grade solvents are dried by standard procedures, distilled and deaerated before use.

Peptide synthesis: Automated solid-phase peptide synthesis is carried out on Rink amide resin (0.82 mmol/g) at 0.10 mmol scale on a CEM Liberty 1 single-channel microwave (MW) peptide synthesizer equipped with a Discovery microwave unit. Fmoc-protected amino acids are used (5 equiv.) with N, N'-diisopropylcarbodiimide/hydroxybenzotriazole (DIC/HOBt) activation. A 0.8 M solution of DIC in DMSO is used in the 'activator base' position, and a 0.5 M solution of HOBt in DMF is used in the 'activator' position (opposite to default configuration). Amino acid side chain functionality is protected as follows: Fmoc-Arg(Pbf)-OH, Fmoc-Cys (Trt)-OH, Fmoc-Lys(Boc)-OH and Fmoc-Tyt(tBu)-OH. Reactions are carried out using the default 10 minutes MW coupling cycle at 75° C. (25 W), or a 50° C. for Cys residues. The cycle is extended by the addition of 1 hour room temperature (RT) preactivation period at the start. For Arg and Cys residues this cycle is repeated (double couplings). A 2 hours preactivation period is used for Ahx residues. Removal of the Fmoc group is carried out at RT using two successive treatments with 20% (v/v) piperidine solution in DMF (5+10 minutes). Extended Fmoc deprotection reaction times are used for Arg residues (3 min MW+20 minutes). Bubbling with nitrogen gas is used to ensure efficient agitation of the reaction mixture during each step. Preswelling of dry resin is carried out in DMF for a minimum of 1 hour.

Peptide cleavage: Peptide-resin is shrunk in diethyl ether and treated with 3 mL of cleavage cocktail (95% trifluoroacetic acid (TFA), 2.5% deionized water and 2.5% triisopropylsilane) for 3.5 hours at RT. The resin is then removed by filtration and the filtrate is concentrated in vacuo before precipitation using ether and decanting of the liquid (followed by subsequent ether washes). The resulting solid peptide is dissolved in deionized water containing 0.1% TFA and lyophilized.

Synthesis of $L_2P_2$, $L_2P_3$ and $L_2P_4$:

Reactions for each step are monitored by thin-layer chromatography (TLC), which is carried out on silica gel plates (0.25 mm, 60 $F_{254}$) using UV light as visualizing method. Flash column chromatography is carried out on 230-400 mesh silica gel. NMR spectra are recorded on a Bruker Ultrashield 400 Plus NMR spectrometer. The $^1$H NMR chemical shifts are referenced to tetramethylsilane, TMS (d=0.00). The following abbreviations are used to explain the multiplicities: s=singlet, d=doublet, t=triplet, q=quartet, dd=doublet of doublets, m=multiplet, br=broad. High-resolution mass spectra, reported as m/z, are obtained on a Bruker Autoflex MALDI-TOF mass spectrometer. Lowresolution mass spectra are obtained on a TQD mass spectrometer. The synthetic route of $L_2P_2$, $L_2P_3$ and $L_2P_4$ is shown in the FIG. 9. The synthesis starts with the reaction of compound 1 (4-methylpyridine) and compound 2 (4-diethylaminobenzaldehyde) in the presence of sodium hydride (60% dispersion in mineral oil) as base to get the N,N'-diethyl-4-(2-(pyridine-4-yl)vinyl) aniline (reaction condition a, NaH, dimethylformide (DMF), about 60° C.), which is then reacted with ethyl bromoacetate to get compound 4 (4-(4-(diethylamino)styryl)-1-(2-ethoxy-2-oxoethyl)pyridine-1-ium) bromide (reaction condition b, Ethyl bromoacetate, acetonitrile (MeCN), about 85° C.). Compound 4 is then hydrolysed by 0.4M NaOH to get compound 5 (4-(4-(Diethylamino)styryl)-N-carboxymethylpyridinium chloride) (reaction condition c, 0.4M NaOH, dioxane, room temperature), which is then coupled with three kinds of peptide-resin ($P_2$-$P_4$) and followed by the cleavage of the resin to get the crude products (crude $L_2P_2$, $L_2P_3$ and $L_2P_4$) (reaction condition d, Peptide-resin, diisopropylethylamine (DIPEA), benzotriazol-1-yl-oxytripyrrolidinophosphonium hexafluorophosphate (PyBOP), DMF, room temperature; reaction condition e, Trifluoroacetic acid (TFA), triisopropylsiliane (Tis), $H_2O$, room temperature). The crudes are purified through HPLC to get the three compound 7 ($L_2P_2$, $L_2P_3$ and $L_2P_4$).

3: Yield: 62%; $^1$HNMR (FIG. 45) (CDCl$_3$): δ –8.50 (dd, $J_1$=1.6 Hz, $J_2$=4.8 Hz, 2H), 7.41 (d, J=8.8 Hz, 2H), 7.31 (dd, $J_1$=1.2 Hz, $J_2$=4.8 Hz, 2H), 7.23 (d, J=16.4 Hz, 1H), 6.77 (d, J=16 Hz, 1H), 6.67 (d, J=8.8 Hz, 2H), 3.40 (q, J=7.2 Hz, 4H), 1.19 (t, J=7.2 Hz, 6H); $^{13}$CNMR (FIG. 46) (CDCl$_3$): δ 149.91, 148.14, 145.67, 133.37, 128.55, 123.22, 120.30, 111.45, 77.20, 44.41, 12.62;

4: Yield: 90%; $^1$HNMR (FIG. 47) (CDCl$_3$): δ –8.83 (d, J=7.2 Hz, 2H), 7.72 (d, J=6.8 Hz, 2H), 7.59 (d, J=16 Hz, 1H), 7.51 (d, J=8.8 Hz, 2H), 6.82 (d, J=16 Hz, 1H), 6.68 (d, J=9.2 Hz, 2H), 5.89 (s, 2H), 4.30 (q, J=7.2 Hz, 2H), 3.45 (q, J=7.2 Hz, 4H), 1.33 (t, J=7.2 Hz, 3H), 1.23 (t, J=7.2 Hz, 6H); $^{13}$CNMR (FIG. 49) (CDCl$_3$): δ 166.53, 155.02, 150.39, 144.65, 143.74, 131.30, 121.66, 115.73, 111.57, 77.23, 63.10, 59.43, 44.69, 14.08, 12.63; MALDI-TOF MS: calculated for [M$^+$]: 339.2067, found: 339.2046 (FIG. 50);

5: Yield: 67%; $^1$HNMR (FIG. 51) (MeOD): δ –8.33 (d, J=6.8 Hz, 2H), 7.82 (d, J=6.8 Hz, 2H), 7.70 (d, J=16 Hz, 1H), 7.49 (d, J=9.2 Hz, 2H), 6.95 (d, J=16.4 Hz, 1H), 6.66 (d, J=9.2 Hz, 2H), 4.88 (s, 2H), 3.38 (q, J=7.2 Hz, 4H), 1.11 (t, J=7.2 Hz, 6H); $^{13}$CNMR (FIG. 52) (MeOD): δ 154.03, 150.04, 143.89, 142.70, 130.51, 127.22, 122.10, 121.50, 115.91, 111.25, 61.73, 44.11, 11.54; MALDI-TOF MS: calculated for [M$^+$]: 311.1754, found: 311.1662 (FIG. 53);

$L_2P_2$: MALDI-TOF MS: calculated for [M$^+$]: 997.5004, found: 998.5093;

$L_2P_3$: MALDI-TOF MS: calculated for [M$^+$]: 1924.0, found: 1925.0;

$L_2P_4$: MALDI-TOF MS: calculated for [M$^+$]: 1924.0, found: 1926.308.

HPLC Purification:

All peptide conjugates are used after purified by High Performance Liquid Chromatography (HPLC). HPLC is carried out on either a preparative column (C18, 10.0×250 mm, 5 μm particle size), or on a LCT Premier XE mass spectrometer using a BEH analytical column (C18, 2.1×50 mm, 1.7 μm particle size). Peptides/probes are eluted in $H_2O$/MeCN+0.1% TFA. The gradient elution used for purification is 0-55% B in 60 minutes, and it is set at 0-100% B in 30 minutes for the analysis. The mass spectrometry is carried out on a TQD mass spectrometer (Waters Ltd, UK). Peptides/peptide conjugates identities are also confirmed by MALDI-TOF mass spectra analysis (Autoflex II ToF/ToF mass spectrometer Bruker Daltonik GmBH) operating in positive ion mode using the α-cyano-4-hydroxycinnamic acid (CHCA) matrix.

Figure 10A:
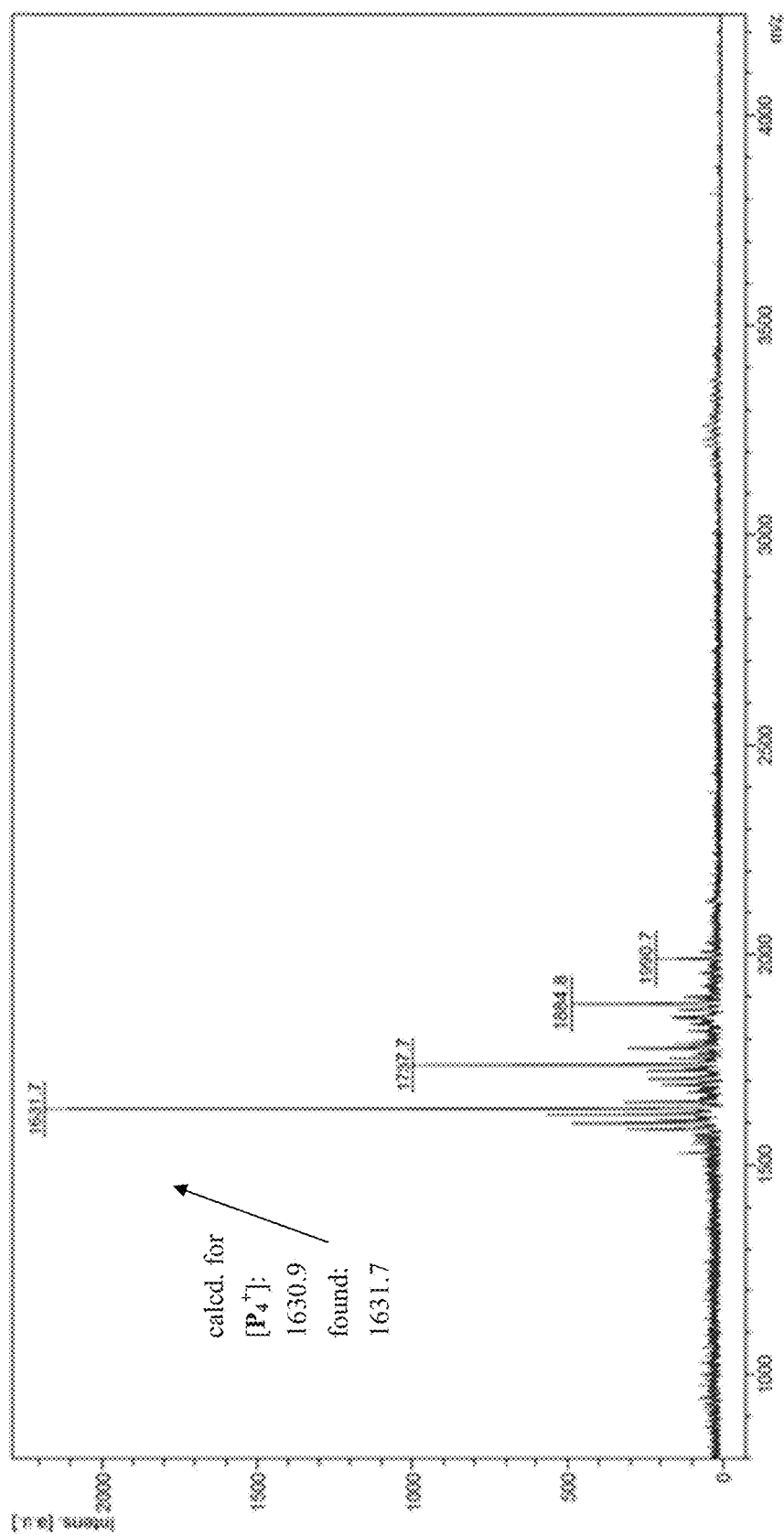
FIG. 10A shows the MALDI-TOF spectrum of the crude $P_4$.
Figure 10B:
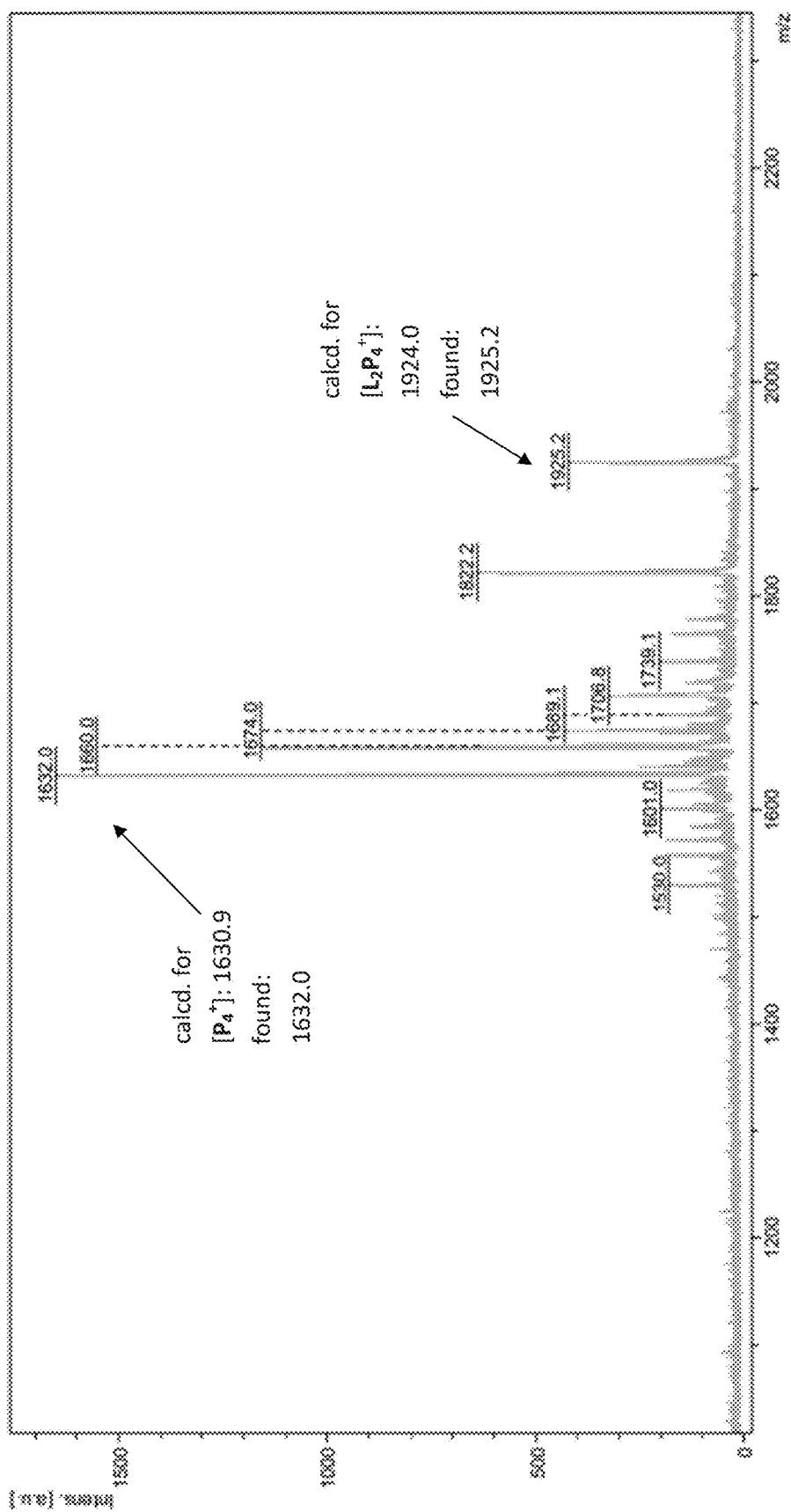
FIG. 10B shows the MALDI-TOF spectrum of the crude $L_2P_4$.
Figure 10C:
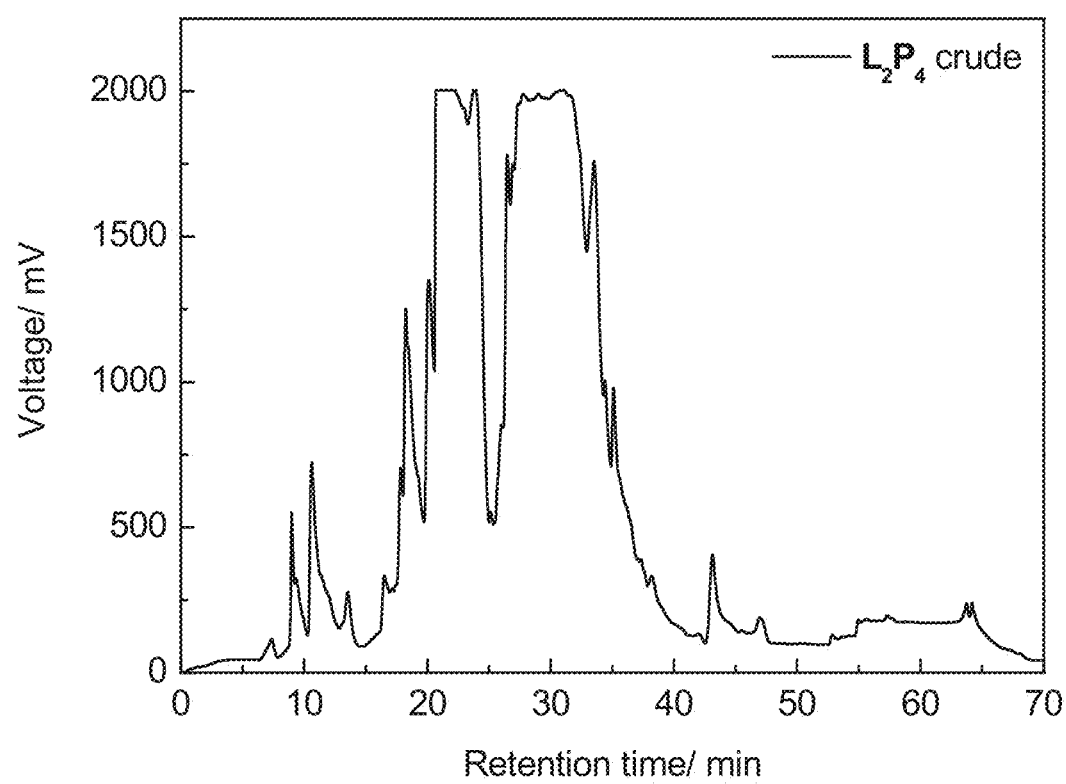
FIG. 10C shows the preparative HPLC spectrum of $L_2P_4$ crude.

$L_2P_4$ is taken as an example to show the detailed purification procedure. Before the preparative HPLC, the MALDI-TOF spectrum of $L_2P_4$ crude is prepared (FIG. 10B). It shows both $L_2P_4$ and $P_4$ identities, and the m/z peak corresponded to $P_4$ is even stronger than $L_2P_4$. Afterwards $L_2P_4$ crude is weighted out to prepare a 5 mg/mL solution in water to perform the preparative HPLC (FIG. 10C).

TABLE 1

Solvent gradient used for preparative HPLC

| STEP | TIME | FLOW | % A | % B | % C | % D | CURV |
|---|---|---|---|---|---|---|---|
| 0 | 3.0 | 2.00 | 100 | 0.0 | 0.0 | 0.0 | |
| 1 | 60.0 | 2.00 | 45.0 | 55.0 | 0.0 | 0.0 | 1.0 |
| 2 | 10.0 | 2.00 | 0.0 | 100 | 0.0 | 0.0 | 1.0 |
| 3 | 10.0 | 2.00 | 0.0 | 100 | 0.0 | 0.0 | |
| 4 | 10.0 | 2.00 | 100 | 0.0 | 0.0 | 0.0 | 1.0 |
| 5 | 5.0 | 2.00 | 100 | 0.0 | 0.0 | 0.0 | |
| 6 | HALT | | | | | | |

Figure 11A:
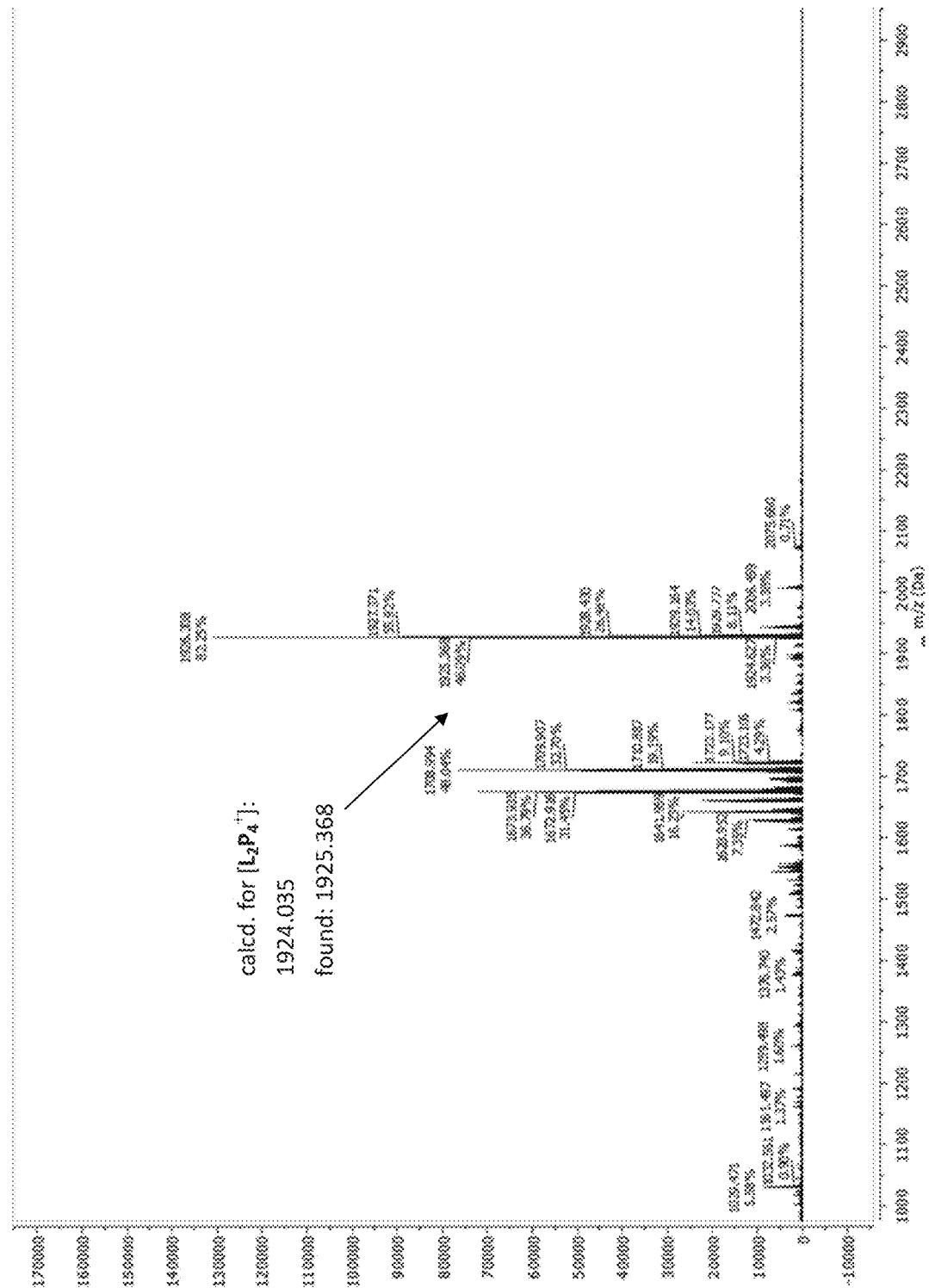
FIG. 11A shows the MALDI-TOF spectrum of purified $L_2P_4$. The strongest peak at 1632.0, which corresponded to $P_4$, has been removed.
Figure 11B:
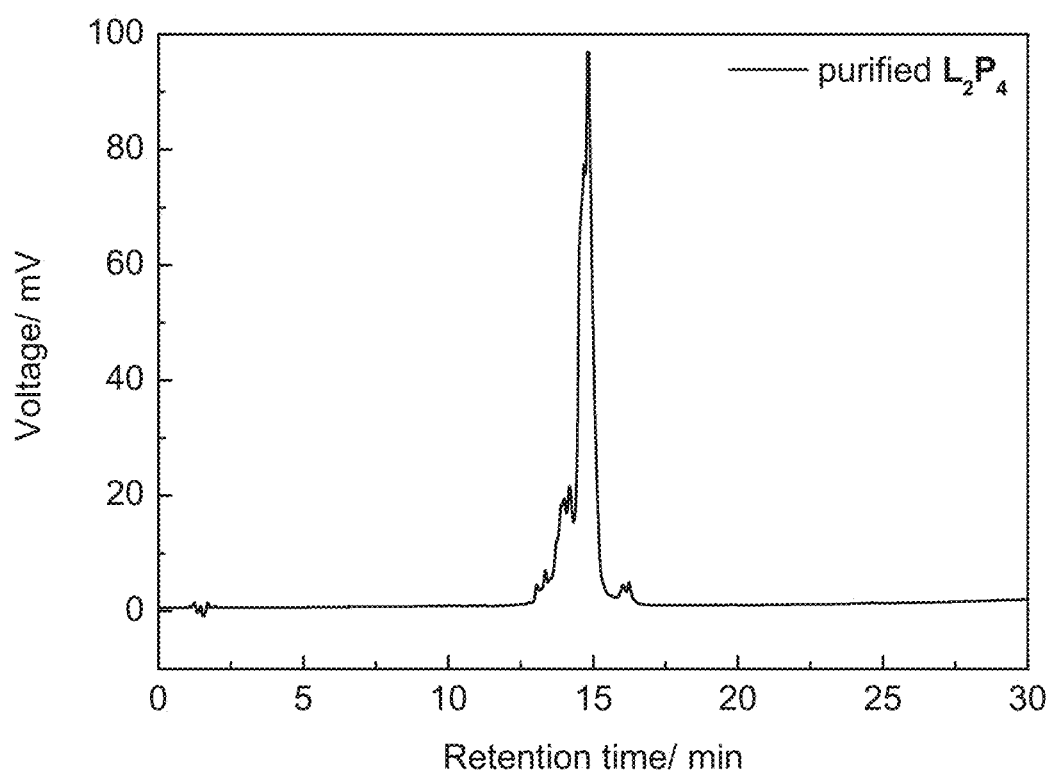
FIG. 11B shows the analytical HPLC spectrum of purified $L_2P_4$.
Figure 12A:
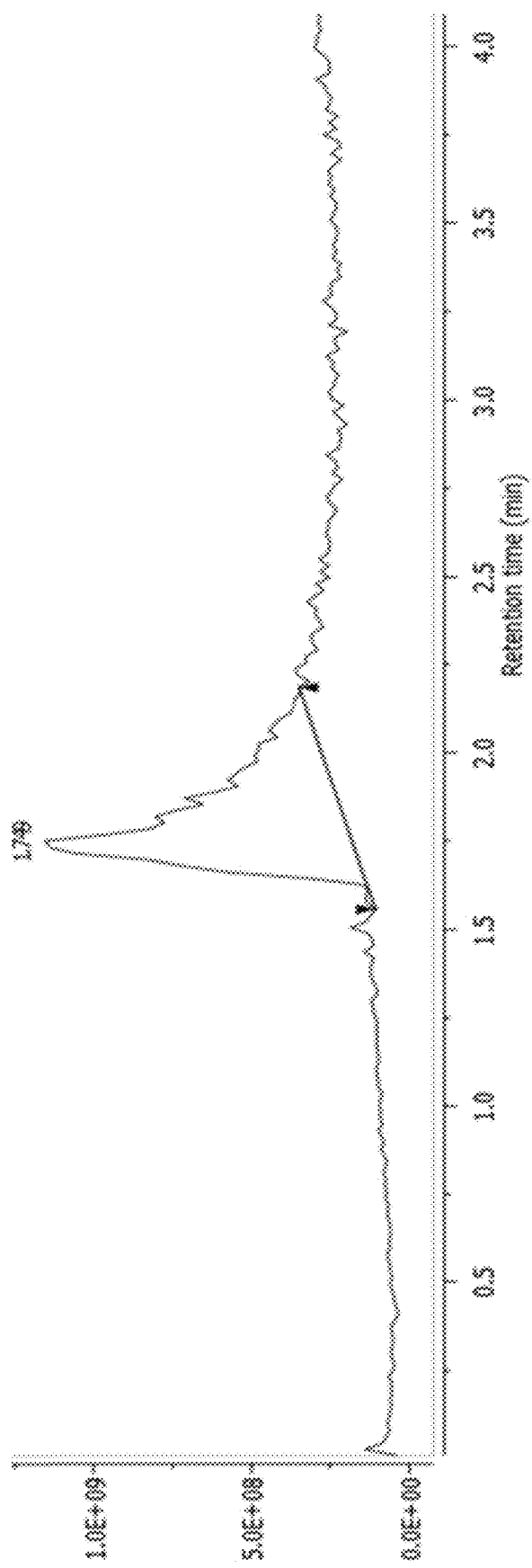
FIG. 12A shows the LCMS spectrum of purified $L_2P_4$.
Figure 12B:
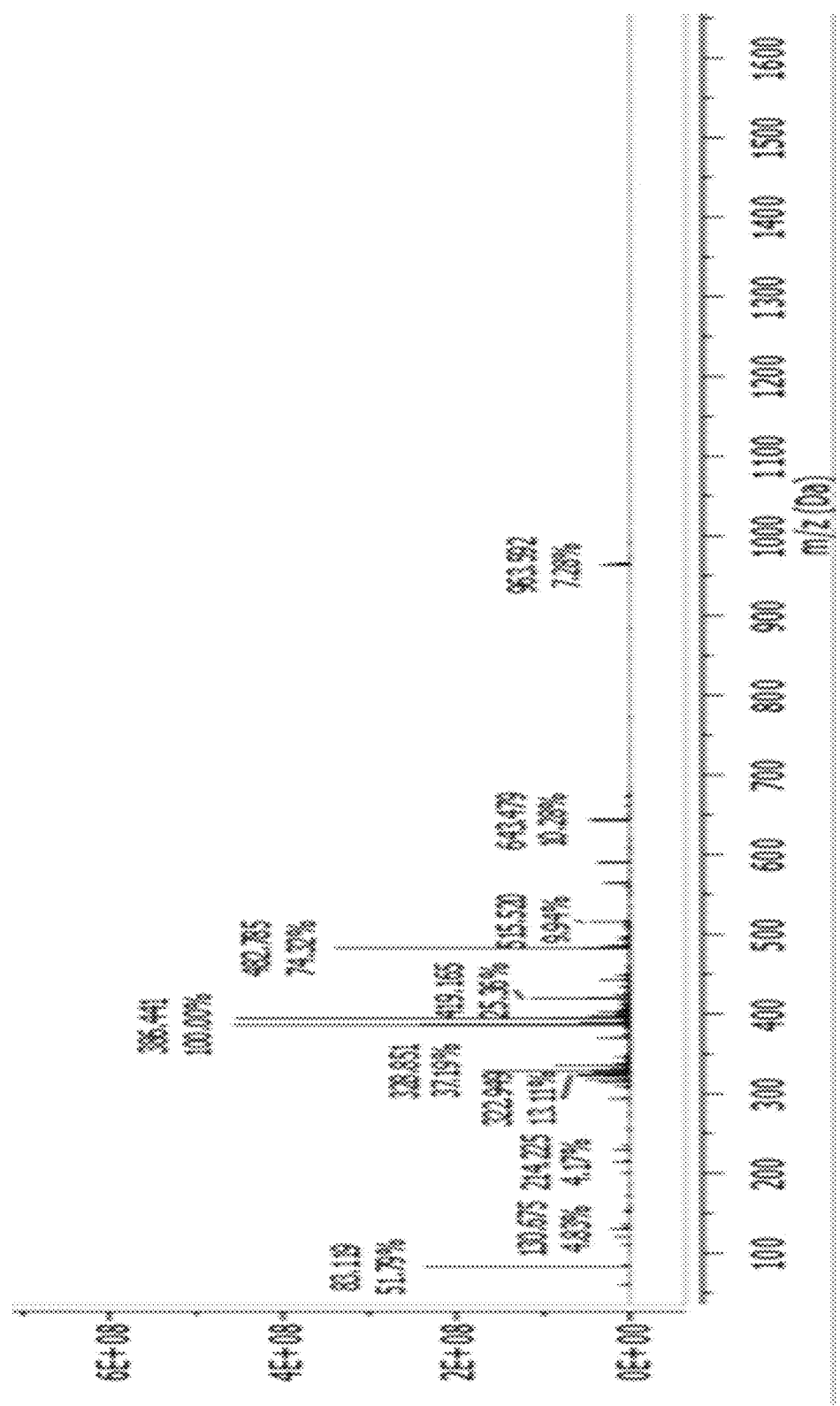
FIG. 12B shows the LCMS analysis of purified $L_2P_4$ (calculated for $[L_2P_4+2H]^{2+}$: 963.025, found: 963.592; calculated for $[L_2P_4+3H]^{3+}$: 642.352, found: 643.479; calculated for $[L_2P_4+4H]^{4+}$: 482.016, found: 482.785; calculated for $[L_2P_4+5H]^{5+}$: 385.814, found: 386.441; calculated for $[L_2P_4+6H]^{6+}$: 321.680, found: 322.949).
Figure 13A:
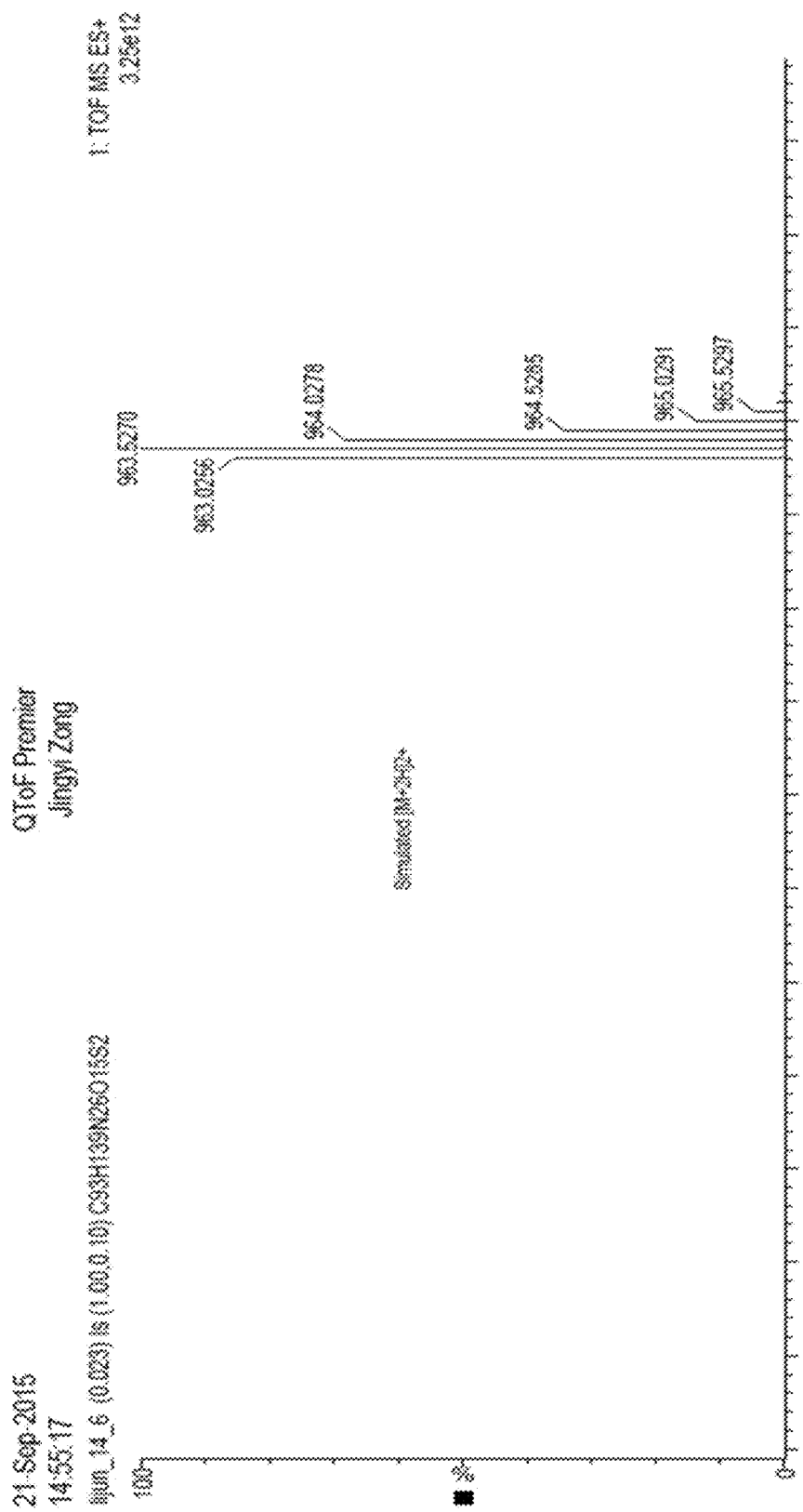
FIG. 13A shows the simulated accurate mass spectrum of purified $L_2P_4$.
Figure 13B:
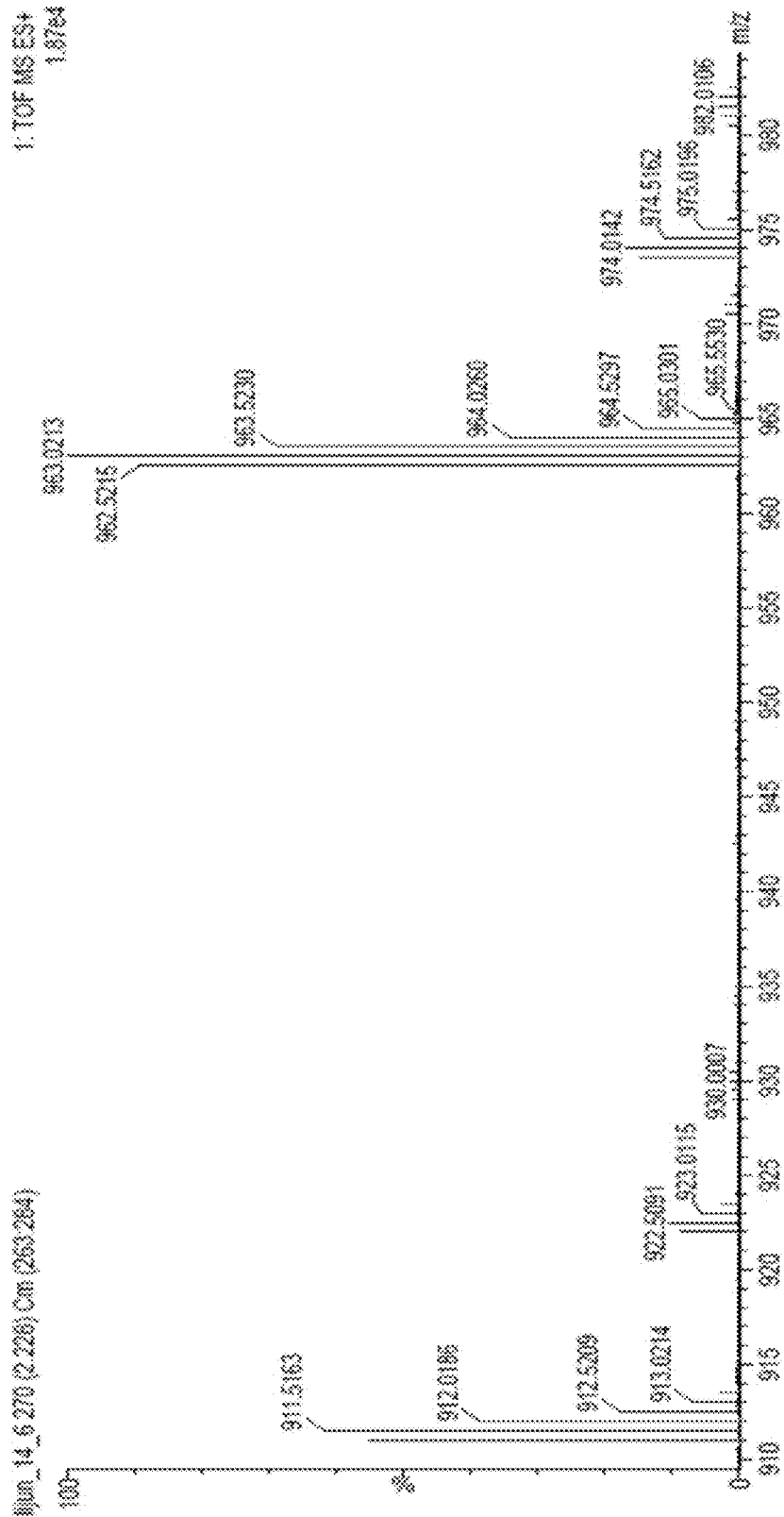
FIG. 13B shows the experimental accurate mass spectra of purified $L_2P_4$.
Figure 14A:
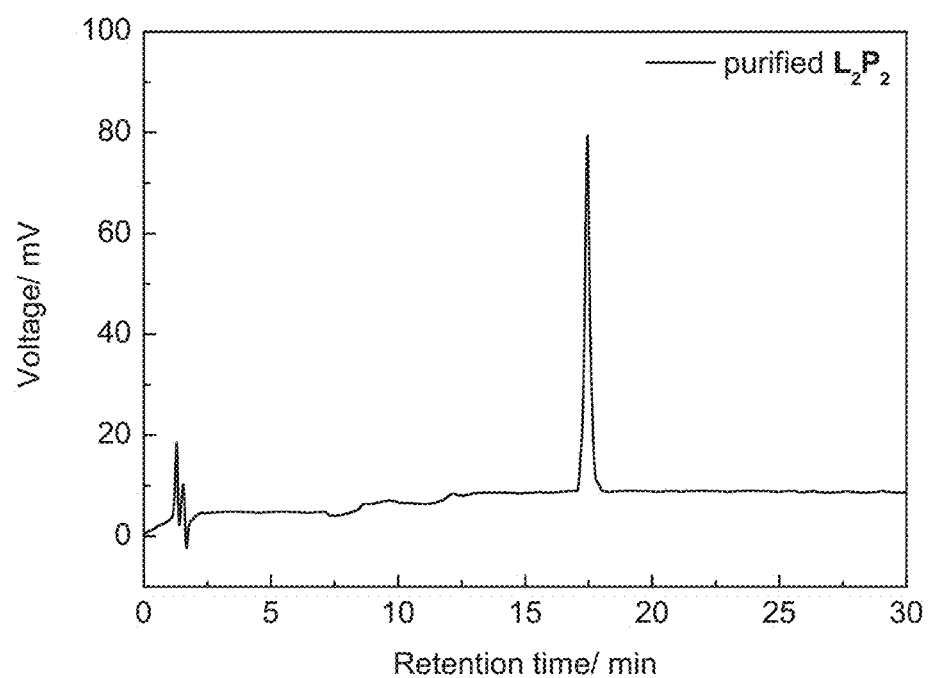
FIG. 14A shows the analytic HPLC spectrum of purified $L_2P_2$.
Figure 14B:
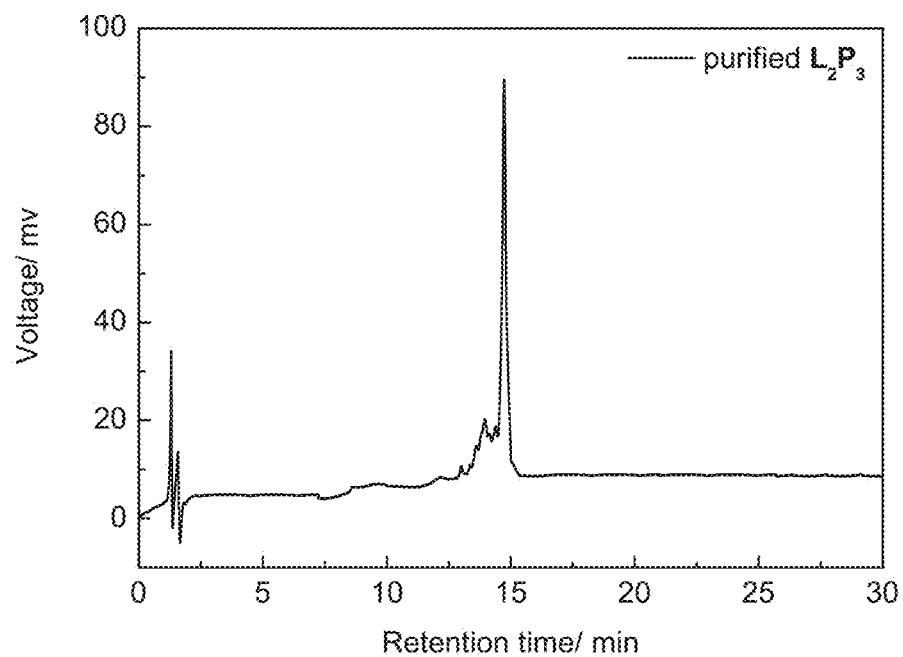
FIG. 14B shows the analytic HPLC spectrum of purified $L_2P_3$.

All peaks appeared in the preparative HPLC has been collected and sent for the MALDI-TOF analysis. The retention time range corresponded to $L_2P_4$ are be collected and prepared for the analytical HPLC. It may be arranged for one more preparative and analytical HPLC until the pure analytical HPLC spectrum with a single peak is obtained (FIGS. 11A-11B). And the inventors also performed the LCMS (FIGS. 12A-12B) and accurate mass (FIGS. 13A-13B) analysis of $L_2P_4$. $L_2P_2$ and $L_2P_3$ are purified in a similar way, and their purified HPLC are shown in FIGS. 14A-14B.

TABLE 2

Solvent gradient used for analytical HPLC

| STEP | TIME | FLOW | % A | % B | % C | % D | CURV |
|---|---|---|---|---|---|---|---|
| 0 | 3.0 | 2.00 | 100 | 0.0 | 0.0 | 0.0 | |
| 1 | 30.0 | 2.00 | 0.0 | 100 | 0.0 | 0.0 | 1.0 |
| 2 | 10.0 | 2.00 | 0.0 | 100 | 0.0 | 0.0 | |
| 3 | 10.0 | 2.00 | 100 | 0.0 | 0.0 | 0.0 | 1.0 |
| 4 | 5.0 | 2.00 | 100 | 0.0 | 0.0 | 0.0 | |
| 5 | HALT | | | | | | |

2) MD Simulation

Figure 15B:
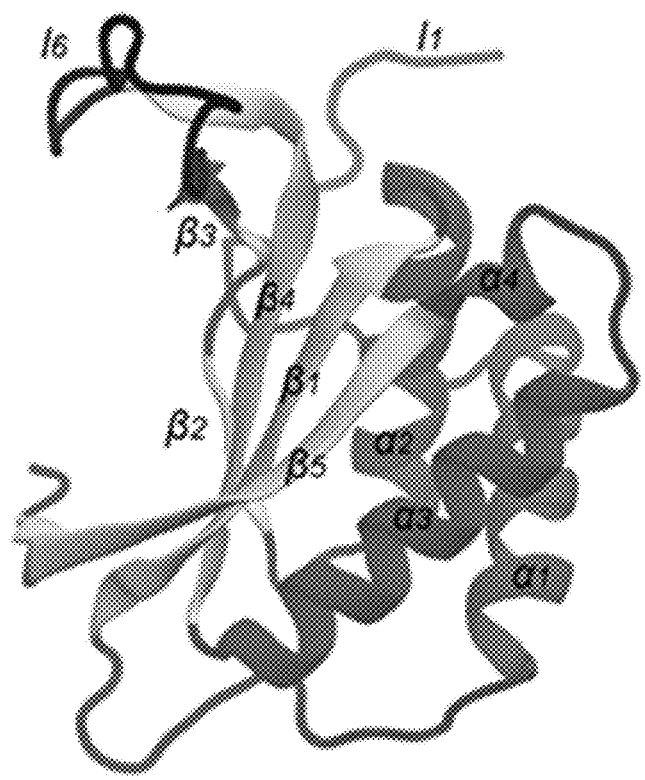
FIG. 15B shows the major structure motifs in the crystal structure of EBNA1 DBD domain (PDB ID: 1B3T, chain A, residue 461-607).

The X-ray crystal structure of DNA binding domain (DBD domain) of EBNA1 is α/β mixed fold, comprising four a helix and five β sheet motifs which are separated by several loops (FIGS. 15A-15B). Each structural motif carries its own function, the five β sheets drive the dimerization through hydrophobic packing, the a helix 1-2 interact with DNA via electrostatic interaction, and the positive charge loop 1 involves in the DNA binding. The present peptide conjugates occupy the dimerization interface of EBNA1 DBD domain. To investigate the interactions between the probes and EBNA1, 200 ns MD simulation is carried out in AMBER 14.

Initial Structural Establishment for Probe-EBNA1 Complexes:

The initial structures of 7 complexes are built in MOE software. $P_2$-EBNA1 complex structure is obtained from EBNA1 dimer by deleting all residues in chain B except residues 561-565 (YFMVF). The N-terminus of the resulted truncated peptide was acetylated and the C-terminus is amidated to generate the aforementioned complex structure. The initial structure of $L_2P_2$-EBNA1 is established based on the $P_2$-EBNA1 structure by adding $L_2$ into N-terminus. $P_3$-EBNA1 structure is also obtained through modification of $P_2$-EBNA1 structure by appending the RrRKGG-sequence into $P_2$. Structures of the remaining complexes are gained in a similar way.

Modification of Force Field Parameters for Non-Standard Residues:

There still contained several non-standard residues in the simulated system, such as $L_2$ and linker (LIN), which should be parameterized prior to MD simulation. The putative structure of $L_2$-NME (FIG. 18A) is uploaded to R.E.D. development Server to calculate the RESP partial charge of $L_2$ moiety by restraining the whole charge of NME into zero. The missing force field parameters are defined by compared with similar atoms in PARM99 or GAFF force field (Table 3). The putative structure and AMBER atom types of LIN (FIG. 18B) are obtained similarly, no missing force field parameters are found.

MD simulation: Unbiased 200 ns MD simulation is carried out for all systems in Amber 14 with ff99SBildn force field. The system is solvated into a periodic boundary, cubic, and TIP3 explicit water box with a 10 Å buffer distance by LEaP module in Amber tools 14. The whole system charge is neutralized by adding counter ions. The established system is minimized and equilibrated. For each of the simulations, the peptide is solvated in a periodic truncated cubic box with TIP3[22] water molecules, providing 10 Å buffer distance between the peptide surface and the periodic box edge. The peptide is then heated from 100 K to 300 K in 20 ps. 200 ps of equilibration with constant pressure and temperature (NPT) of the system is performed prior to the production run in order to ensure correct density. The production runs are performed with constant volume and energy (NVE) with a 2 fs time step, using SHAKE constraints on hydrogen-heavy atom bonds.

RMSD and RMSF Calculation:

All the trajectories in the production stage are analyzed by cpp trajectory. The residue 16-144 of EBNA1 is used for structural alignment, while the flexible N-terminus and C-terminus loops are excluded for the calculation of RMSD. The $C_\alpha$ RMSD are obtained with regarding to the start and end for all snapshots during the production stage. Per residue $C_\alpha$ RMSF is calculated in time window of 5 ns. Seven clusters peptide/peptide conjugates-EBNA1 are generated by using default settings with distance defined by $C_\alpha$ RMSD.

Binding Free Energy Calculation:

The binding free energies for all the peptides/peptide conjugates to EBNA1 are calculated by Molecular Mechanics/Poisson-Boltzmann Surface Area (MMPBSA). Time intervals are adjusted to make sure that at least 100 frames are included in the calculation. For Generalized Born (GB) calculation, the mbondi2 is used and the salt concentration is set to 0.1 M. The ionic strength is set to 0.1 mM and the radius from Parameter/topology (prmtop) file is used for Poisson Boltzmann (PB) calculation.

TABLE 3

The modified force field parameters of $L_2$

| Non-standard residues | Type | Item | Parameters |
|---|---|---|---|
| $L_2$ | Bonded | CA-N* | k = 425.0 kcal/(mol*Å$^2$), $d_0$ = 1.381 Å |
| | Angle | CA-CA-CM | k = 64.880 kcal/(mol*rad$^{-2}$), $\theta_0$ = 120.660 |
| | | CA-CA-N* | k = 70.210 kcal/(mol*rad$^{-2}$), $\theta_0$ = 118.340 |
| | | CA-CA-N2 | k = 69.340 kcal/(mol*rad$^{-2}$), $\theta_0$ = 120.130 |
| | | HA-CA-N* | k = 51.210 kcal/(mol*rad$^{-2}$), $\theta_0$ = 118.340 |
| | | C-CT-N* | k = 66.810 kcal/(mol*rad$^{-2}$), $\theta_0$ = 111.370 |
| | | CA-N*-CA | k = 66.980 kcal/(mol*rad$^{-2}$), $\theta_0$ = 120.090 |
| | | CA-N*-CT | k = 63.150 kcal/(mol*rad$^{-2}$), $\theta_0$ = 124.360 |
| | | CT-N2-CT | k = 63.530 kcal/(mol*rad$^{-2}$), $\theta_0$ = 114.440 |
| | Dihedral | CA-CA-N*-CA | v = 0.3 kcal/(mol*rad$^{-2}$), phase = 180.0, period = 2 |
| | | CA-CA-N*-CT | v = 0.3 kcal/(mol*rad$^{-2}$), phase = 180.0, period = 2 |
| | | HA-CA-N*-CA | v = 0.3 kcal/(mol*rad$^{-2}$), phase = 180.0, period = 2 |
| | | HA-CA-N*-CT | v = 0.3 kcal/(mol*rad$^{-2}$), phase = 180.0, period = 2 |
| | | CA-CT-N2-CT | v = 0.0 kcal/(mol*rad$^{-2}$), phase = 0.0, period = 2 |
| | | CA-CA-N*-CT | v = 0.3 kcal/(mol*rad$^{-2}$), phase = 180.0, period = 2 |
| | | HA-CA-N*-CA | v = 0.3 kcal/(mol*rad$^{-2}$), phase = 180.0, period = 2 |
| | | HA-CA-N*-CT | v = 0.3 kcal/(mol*rad$^{-2}$), phase = 180.0, period = 2 |
| | | CA-CT-N2-CT | v = 0.0 kcal/(mol*rad$^{-2}$), phase = 0.0, period = 2 |

TABLE 4

Binding free energy calculated by MMPBSA from 200 ns MD simulation

| Complex | Full | | | | Top 1 Cluster | | | |
|---|---|---|---|---|---|---|---|---|
| | GB (kcal/mol) | | PB(kcal/mol) | | GB(kcal/mol) | | PB(kcal/mol) | |
| $P_2$-EBNA1 | −38.1608 | 0.6215 | −35.7065 | 0.5404 | −40.9697 | 0.3721 | −37.7606 | 0.3598 |
| $L_2P_2$-EBNA1 | −49.5919 | 0.8907 | −45.2472 | 0.7118 | −55.9281 | 0.6226 | −50.2469 | 0.5831 |
| $P_3$-EBNA1 | −65.8822 | 1.2335 | −69.8883 | 1.3585 | −75.6087 | 0.8403 | −80.5365 | 1.0445 |
| $L_2P_3$-EBNA1 | −52.8775 | 0.8201 | −55.9332 | 0.8776 | −58.1618 | 0.9997 | −60.6310 | 1.1798 |
| $P_4$-EBNA1 | −71.6019 | 1.2261 | −65.8096 | 1.1299 | −77.6491 | 0.8228 | −71.0914 | 0.8797 |
| $L_2P_4$-EBNA1 | −56.8395 | 0.8842 | −58.0182 | 0.9026 | −57.5039 | 1.1218 | −56.8983 | 0.8997 |

3) Photophysical Measurement

UV-visible absorption spectra in the spectral range 200 to 800 nm are recorded by an HP UV-8453 spectrometer. Emission spectra are recorded using a Fluorolog-3 Combined Fluorescence Lifetime and Steady state spectrofluorometer. This is equipped with a NL-C2 Pulsed Diode Controller NanoLED, which is a cost-effective source of picoseconds and nanosecond optical pulses at a wide range of wavelengths from ultraviolet to NIR.

Stability Test of $L_2P_2$, $L_2P_3$ and $L_2P_4$:

The stability of $L_2P_2$, $L_2P_3$ and $L_2P_4$ are evaluated at 37° C. for 24 hours via emission spectrum due to most in vitro tests (such as flow cytometry, confocal imaging & co-staining and toxicity test) are conducted before incubated within 24 hours (FIGS. 26A-26C).

Emission Quantum Yield of $L_2P_2$, $L_2P_3$ and $L_2P_4$:

The quantum yields of $L_2P_2$, $L_2P_3$ and $L_2P_4$ with and without WT (wild type) EBNA1, are measured by the comparative method using rhodamine 6G ($\phi$=95%) in water with excitation at 480 nm as references. Quantum yields of $L_2P_n$ are evaluated by the following equation 1:

$$\phi_s = \left(\frac{G_s}{G_r}\right)\left(\frac{\eta_s}{\eta_r}\right)^2 \phi_r \quad \text{equation 1}$$

Where the subscripts r and s denote reference and sample respectively, $\phi$ is the quantum yield, G is the slope from the plot integrated emission intensity vs absorbance, and $\eta$ is the refractive index of the solvent. The correction curve is obtained by comparing the experimentally recorded spectrum of the standard rhodamine 6G with the published data.

The enhancement on quantum yields can be achieved for $L_2P_3$ and $L_2P_4$ in the presence of WT EBNA1. $L_2P_4$ demonstrated a greater enhancement with a smaller concentration of EBNA1 compared to $L_2P_3$ ($\phi_{initial}$=4%, $\phi_{5\,\mu M}$ EBNA1=23%, FIGS. 27A-27H and FIGS. 28A-28C), which illustrate a stronger binding affinity between $L_2P_4$ and WT EBNA1.

Bind Constant Via Luminescence Titration:

Luminescence titration analysis is conducted with gradually addition of WT EBNA1 to evaluate the binding constants between the three peptide conjugates and WT EBNA1. Addition of WT EBNA1 stops either when the volume of added anion is 5% of the peptide conjugate solution or the influence on luminescence is saturated. The binding constants for $K_a$ are obtained from the double logarithm regression curve:

$$lg[(I-I_0)/I_0] = lg\,K_a + n\,lg[G] \quad \text{equation 2}$$

Where I and $I_0$ are current and initial fluorescence, respectively, $K_a$ is the binding constant, n is the number of binding sites per WT EBNA1, and [G] is total concentration of WT EBNA1.

Selectivity Test Via Luminescence Titration:

Titration experiments are prepared to investigate the effect of several common biological anions and bull serum albumin (BSA) on the $L_2P_3$ and $L_2P_4$ (The selectivity of $L_2P_2$ to different biological anions and proteins are not measured due to the titration to WT EBNA1 did not show any enhancements, demonstrating an extremely weak or even no binding between $L_2P_2$ and WT EBNA1). Liquid concentrated stock solutions of each anion, as well as BSA, are added individually and gradually to a solution of the probes concerned. Addition stops either when the volume of added anion is 5% of the peptide conjugate solution or the influence on probe luminescence is saturated. Luminescent emission spectra are determined via aforementioned procedure.

Absorption Spectrum in Different Solvents:

The absorption spectra of $L_2P_4$ in polar and non-polar solvents have been measured to further investigate the intermolecular charge transfer (ICT) state. As can be seen in the spectra, two absorption bands appeared at 274 nm and ~500 nm, which corresponded to the transition from ground state to local excited (LE) state and ICT state, respectively, as is assigned in the similar molecules. The maximum absorption band slightly red-shift in polar solvent. This phenomenon indicated that the ICT state is more polar than the ground state which was consistent with the ICT characteristics as a result of donation of electron from —N(Et)$_2$ group to the $\pi^*$ system of the acceptor connected through benzene ring.

pH-Dependent Emission:

The emission of $L_2P_4$ in different pH has also been measured to further confirm the existence of ICT state. pH effects on emission spectra of $L_2P_4$ and $L_2P_3$ in PBS buffer are shown in FIGS. 33A-33D. The emission band at 614 nm gradually decreases with pH changing from 7 to 2, this observation well consistent with the characteristic of ICT emission, as the nitrogen lone pair bound to H$^+$, so it is not available to generate ICT state, and hence for the decreasing in the ICT state emission. In the meanwhile, the $pK_a$ value has been calculated through the Henderson-Hosslbalch equation:

$$pH = pK_a + \log\frac{[A^-]}{HA} \quad \text{equation 3}$$

Lifetime Decay in Different Solvents:

The emission lifetime decays of $L_2P_4$ (monitored at 625 nm) in polar and non-polar solvents are determined on a Fluorolog-3 spectrofluorometer with the NanoLED by using a 460 spectral LED source (HKBU, Department of Chemistry) (FIG. 34). The emission decay showed two components as recorded in Table 5. Comparatively large LE emission decay and corresponding smaller ICT decay can be concluded in less polar solvents, which can be interpreted a less dipole moment for ICT state in solvents with small polarity and consequently an upshift of the ICT state.

TABLE 5

Emission lifetime of $L_2P_4$ in different solvents

| Solvent | Decay times (ns) | |
|---|---|---|
|  | LE emission | ICT emission |
| Water | 0.47 | 4.01 |
| MeOH | 0.46 | 4.60 |
| MeCN | 0.49 | 4.45 |
| DMF | 0.53 | 3.22 |
| THF | 0.84 | 2.49 |
| Dioxane | 0.99 | 2.81 |

4) In-Vitro Imaging, Tissue Culture and MTT Assay

Protein Samples Preparation.

Five protein samples are used. Wild type EBNA1 protein (379-641 a.a.) fusing with glutathione S-transferase is expressed in *Escherichia coli* and purified by glutathione sepharose 4B rinse (GE Healthcare Dharmacon), afterwards 5 µg EBNA1 is prepared and incubated with MBS at 37° C.

for 10 minutes. The protein is separated on an SDS-PAGE gel, transferred onto the nitrocellulose membrane and blotted by antibodies. The intensity of the protein bands is measured by Gel-Pro Analyzer and plotted by GraphPad Prism 5.0 software. EBNA1 mutation proteins are prepared by mutation of YFMVF to FFAVA (yielding EBNA1-3A mutant) or conservative point mutation of $Y_{561}$, $M_{563}$, $F_{565}$ to A (yielding EBNA1-$Y_{561}$A, EBNA1-$M_{563}$A and EBNA1-$F_{565}$A) through site-directed mutagenesis.

EBNA1 Protein and In Vitro MBS Cross-Linker Mediated Dimerization Assay:

For MBS (3-maleimidobenzoyl N-hydroxysuccinimide) cross-linked dimerization assay, 5 µg WT and mutant EBNA1 are incubated with MBS at 37° C. for 10 minutes. It is then separated on an SDS-PAGE gel, transferred onto the nitrocellular membrane and blotted by antibodies. The intensity of the western blotting bands is measured using GraphPad Prism 5.0 software. The MBS mediated protein crosslinking effect is represented as ratio of dimer/monomer.

Cell Culture:

MRC-5 (normal lung fibroblasts) cells are grown in Minimum Essential Medium (MEM); HeLa (cervical carcinoma) cells are grown in Dulbecco's Modified Eagle Medium (DMEM); CNE2, Ramos, C666-1 and Raji (nasopharyngeal carcinoma) cells are grown in Roswell Park Memorial Institute (RPMI)-1640 medium, all the medium used is supplemented with 10% fetal bovine serum (FBS), 1% penicillin and streptomycin at 37° C. and 5% CO2.

NPC 43 cells is established from a surgical resected NPV tissues from a male patient, 64 years old with Stage III recurrent NPC. The NPC 43 cell harbour EBV virus and is kept in RPMI supplemented with 10% FBS and 4 µM of a Rho kinase inhibitor, Y27632 over 200 population doublings. The NPC 43 is tumorigenic when injected at subcutaneous site (10 million cells) of NOD/SCID mice. STR profiling confirms its origin from the NPV patients. The NPC 43 cells is induced to under lytic reactivation of EBV by treatment with TPA/sodium butyrate and infectious EBV harvested from supernatant of NPC 43 cells.

Flow Cytometry Analysis on Cellular Uptake:

HeLa and C666-1 cells ($10^5$ per sample) are seeded to 35 m Petri dish overnight. Afterwards, cells are incubated with peptide conjugates, trypsinized and washed with phosphate-buffered saline (PBS) for several times. Cellular uptake is evaluated with flow cytometry under 488 nm excitation generated by argon laser. The emission is obtained by using FL-3 equipped with 650 nm long pass filter. 10000 events are analyzed to get the cellular uptake.

In Vitro Imaging and Co-Staining:

To study the in vitro behavior and location of the $L_2P_n$, 10 µM $L_2P_n$ are dosed into C666-1 cells in 2 mL of tissue culture medium. The cells are incubated with 6 hours before monitoring imaging. It is further treated with 1 nM nucleus lyso tracker/mito tracker/Hoechst 33342 for 1 hour in co-staining experiment. Imaging is conducted with a commercial multi-photon Leica TCS SP5 (upright configuration) confocal microscope equipped with a coherent femto-second laser (680 nm to 1050 nm), argon laser (432 nm, 457 nm and 488 nm), He—Ne laser (632 nm), UV-lamp and controlled CO2 content stage-top tissue culture chamber (2-7% CO2, 37° C.).

Toxicity Test:

The MTT viability assay is performed according to standard methods. In brief, $3\times10^3$ cells are seeded in 96-well plates 24 hours prior to exposure to peptide conjugates. The cells are treated with the peptide conjugate at the dark for another 24 hours. The cell monolayers are rinsed with phosphate-buffered saline (PBS) and then incubated with 50 uL MTT [3-(4,5-dimethylthiazol-2-yl)-2,5-diphenyltetrazolium bromide] solution (0.5 mg/mL) at 37° C. for 3 hours. Then the media are removed, and 100 uL of DMSO solubilizing reagent is added and shaked for 30 minutes to dissolve the formed formazan crystals in living cells. The absorbance is measured at dual wavelength, 540 nm and 690 nm, on a Labsystem Multiskan microplate reader (Merck Eurolab, Switzerland). Each dosed concentration is performed in triplicate wells, and repeated twice for the MTT assay. The MTT cytotoxicity of $P_2$, $P_3$ and $P_4$ is shown in FIGS. 39A-39F.

5) Animal Study

Intra-Tumoral Injection of Nude Mice:

C666-1 cells ($8\times10^6$) suspended in 110 µL serum free Roswell Park Memorial Institute (RPMI) media 1640 are mixed 1:1 with Matrigel to a final volume of 150 µl and are injected into the right flanks of male 6- to 8-week-old BALB/c nude mice. 18 days after inoculation, when tumors grew to an average volume of 200-300 $mm^3$, mice are randomized into experimental groups (n=3 or 4 per group). $P_4$ and $L_2P_4$ are diluted to the desired concentrations (2 µg, $P_4$-L and $L_2P_4$-L; 4 µg, $P_4$-H and $L_2P_4$-H) in 0.1% DMSO and injected directly into the tumor using a 29 gauge syringe. Mice receiving an equivalent volume of 0.1% DMSO alone served as controls. Body weight and tumor volumes are measured twice weekly. Tumor volumes were calculated as (length× $width^2$)/2. Intra-tumoral tumor injections are repeated twice weekly for 3 weeks, after which time the mice are sacrificed and their internal organs and tumors harvested and weighed.

TABLE 6

The drug treatments and number of mice for animal study

| Treatment | Number of mice |
|---|---|
| Control (0.1% DMSO in PBS buffer) | 3 |
| $P_4$-L (2 µg/tumor) | 3 |
| $P_4$-H (4 µg/tumor) | 3 |
| $L_2P_4$-L (2 µg/tumor) | 2 |
| $L_2P_4$-H (4 µg/tumor) | 3 |

Targeting of EBNA1 Viral Protein as a Therapeutic Approach for EBV-Associated Tumour with Positron Emission Tomography Imaging In another embodiment of the present invention there is presented a therapeutic approach for EBV-associated tumor with positron emission tomography imaging using a nucleus-permeable small-molecule inhibitor from the same $L_2$ structure family group as $L_2P_4$. FIG. 58 shows an illustration on how different ligands synthesis for the same $L_2$ structure family can result in $L_2P_4$ and $L_2$ for PET imaging.

An imaging technique gaining attention is positron emission tomography (PET), in which radioactive elements are introduced to give an analog of a small molecule involved in physiological processes as a tracer. The clinically used tracer is 18F-fluorodeoxyglucose (FDG), a glucose analog that is heavily involved in tumor development. However, intake of FDG by normal tissues creates interference that limits the sensitivity. The selectivity must be significantly improved.

This embodiment of the present provides dual-modality imaging techniques (Optical and PET) for EBV-associated cancers. Multiple studies have suggested a correlation between EBNA1 and the tumorigenesis of EBV-related malignancies, it would be beneficial to visualize the role of EBNA1 in the various processes and design appropriate inhibiting agents. In literature, to improve the efficacy of T-cell-directed therapy against EBV diseases, the therapeutic site must be in the cytoplasm. Imaging agents used in this therapy should be designed to 1) specifically localized in the cytoplasm to achieve maximum treatment efficacy and 2) visualize the cytoplasm so that the progress of the treatment could be monitored. On the other hand, some research suggests that EBNA1 is critical during cell division, and is responsible for activating the transcription of other viral transforming proteins in cells with type III latency. Imaging agents focusing on this approach would then need to be alternatively designed to be nucleus-permeable so to be of imaging interests. Challenges are common in creating nucleus-permeable molecules, not to mention nucleus-permeable fluorescent compounds. Therefore, the present invention further provides imaging agents specific for EBNA1 while simultaneously demonstrating cellular localization.

The inventors have designed and synthesized functional selective peptides to be conjugated onto small molecules for optical imaging and also applied gallium labelling to produce dual-modality probes more suitable for imaging of the nuclei. Areas in the selectivity and binding affinity towards EBNA1 and cancer inhibition is also investigated for improvement. The inventors have recently achieved a monumental breakthrough in interfering with the growth of EBV-associated cancers at a highly effective dosage (<4 □mol/kg, ~92% cancer inhibition) and EBNA1 can be visualized in nucleus with embodiments of the present invention as bio probes.

Significance

The inventors have selected to focus our dual-mode probes on performing PET and optical imaging in vitro and in vivo. The inventors made and introduced various peptides to optimizing the target specificity towards EBNA1 for feasible clinical use, which is not available currently in clinical practice. The inventors also studied the underlying mechanism to specifically inhibit the dimerization of EBNA1 which is believed to be crucial in tumorigenesis. The outcome of this collaboration provided an in-depth proof-of-principle investigation on targeting and monitoring EBV-associated cancers in vitro and in vivo, and control the growth of EBV latently infect tumors (e.g. nasopharyngeal carcinoma).

Design and Synthesis of the EBNA1 Specific PET Imaging Agents, and Study of the Binding Mechanism Between EBNA1 and Proposed Cold Labelling Agents Synthesis of the EBNA1 Specific PET (Cold Labelling) Available Imaging Agent There are two major problems associated with commercially or literature available PET agents—(i) the recognition of cancer cells and (ii) the coordination time between radiometal and ligand. For rapid radiolabelling, the inventors recently reported Ga porphyrin-ruthenium complexes via new and fast microwave methodology as well as radiolabelling in high yields (~60%). In one embodiment of the present invention, the inventors have generated numerous EBNA1-specific dual-functional probes to carry out the PET imaging as well as the inhibition of EBNA1 function which can then be applied in EBV related disease therapy. Twenty cold gallium labelling complexes ligated with EBNA1 specific peptides have been synthesized. The inventors' publication showed that the novel lanthanide complexes conjugated with an EBNA1-specific peptide demonstrates selective imaging of EBNA1 in vitro, however, the subcellular localization (cytoplasm only) limits its therapeutic value. EBNA1 is mainly localized in the nucleus. The inventors have previously identified nucleus permeable-EBNA1 permeable peptides and successful synthesis of the peptide conjugated with particular PET available ligands (FIG. 59). This makes great advances in the investigation of EBNA1 inhibitory functions. Significant changes could be brought to commercial or recent researched anticancer agents in terms of improving their cell permeability and effectively monitoring their therapeutic effects. A range of newly designed peptides for EBNA1 specific binding has also been applied. Some other embodiments of the present invention wherein MRI imaging ligands are synthesized are shown in FIG. 60. FIG. 61 shows embodiments of the present invention wherein ligands for PET imaging are also synthesized.

Evaluation of the Binding Affinity Via Isothermal Titration Calorimetric and Protein NMR The binding and selectivity of the complexes to EBNA1 have been examined by the binding affinities of the complexes with EBNA1, via isothermal titration calorimetry (ITC). ITC is a standard for the measurement of interactions in solution, especially macromolecular proteins with its ligands. It provides real-time and accurate solution observation of molecule-molecule interactions, with advantages of being label-free, having no molecular weight/types limitation and, above all, being non-destructive.

In Vivo Biodistribution Evaluation of Proposed Cold Gallium Complexes—

All the proposed complexes are injected intravenously to BALB/c athymic mice bearing xenografted tumors (EBV-positive or-negative tumors). The gallium content, reflective of the quantity of the complexes, are determined by ICP-MS. The gallium content in urine of the mouse are be evaluated to confirm the metabolism of these complexes in vivo. In addition, the in vivo emission of the proposed cold gallium complexes areee monitored. The whole body in vivo imaging of mice are carried out by an in vivo imaging box with a 457/800/980 nm excitation source and the xenografts are surgically extracted for two-photon confocal microscopy, with the peritumor cells extracted being the control. The in vivo optical imaging will be carried out in the PI's institute. Five gallium complexes will be selected and carried on for in vivo micro-PET imaging.

In Vivo PET Imaging in Various Mouse Models (9 Months)—

Five gallium complexes are selected and radiolabelling of the complexes are carried out $^{68}$GaCl$_3$ are produced by using an Eckert & Ziegler IGG100 $^{68}$Ge/$^{68}$Ga-Generator in a fully-automated Modular-Lab system. As with the in vivo study with cold complexes, the hot complexes are injected intravenously to BALB/c athymic mice bearing EBV-positive or EBV-negative tumors. These results are correlated with the PET imaging. In addition, the in vitro imaging of radiolabelled gallium complexes with EBNA1 are monitored in EBV-positive and EBV-negative cell lines and the results compared with the data obtained.

68Ge/68Ga-Generator in a fully-automated Modular-Lab system. As with the in vivo study with cold complexes, the hot complexes are injected intravenously to BALB/c athymic mice bearing EBV-positive or EBV-negative tumors. The results obtained are correlated with the PET imaging. In addition, the in vitro imaging of radiolabelled gallium complexes with EBNA1 are monitored in EBV-positive and EBV-negative cell lines and the results compared with the data obtained.

Biological and Pharmacokinetic Studies of the Complexes in Phase 1 (9 Months)

Evaluation of the Cytotoxicity and Subcellular Localization of the Synthesized Probes in EBV-Positive and Negative NPC Cells by Flow Cytometry and Confocal Microscopy—

Tumor sphere formation assays are used to evaluate the anti-tumor activity of the synthesized probes. EBV-positive cell lines (e.g. C666-1, MKN28, LCL(GT)-B cells, LCL(GS)-B cells) and EBV-negative cell lines (e.g. MKN1, Akata B cells, Awaia B cells and HeLa) are treated with our proposed complexes in section 1.1 at various concentrations. The size/number of tumor spheres formed in each of the culture are determined. Results are expressed as a size distribution profile and the total number of tumor spheres per treatment. Cytotoxicity are monitored by flow cytometry and the subcellular localization of the probes are determined using confocal microscopy. $IC_{50}$ values of the proposed cold gallium complexes in EBV-positive/-negative cell lines are assessed.

Pharmacokinetic Study—

Plasma and urine pharmacokinetic study of the gallium-based EBNA1 labelling agent are performed in mice. The pharmacokinetic assays are carried out in PI and NKM laboratories. Animals are fasted overnight before i.p. injection with a single dose of gallium labelling agent (Regan-Shaw, FASEBJ 2008). Mice are housed individually in metabolic cages and urine and blood samples are collected from 8 mice per group at time 0 (as a blank) and at every 24 hours after drug treatment, until disappearance of signal. Urine samples are filtered and stored at −80° C. until analysis. Blood samples from tail veins are collected. Plasma samples collected after centrifugation are stored at −80° C. until analysis. The samples are analyzed using ICP-MS of the gallium compound. Using pharmacokinetic analysis software, pharmacokinetic parameters of gallium-based labelling agent re determined by non-compartmental methods.

The invention claimed is:

1. A peptide comprising the sequence CAhxRrRKGGYF-MVF (SEQ ID NO. 2) or the sequence CAhxYFMVFGGR-rRK (SEQ ID NO. 3), wherein Ahx is 6-aminohexanoic acid.

2. The peptide of claim 1, wherein the peptide comprises SEQ ID NO. 2.

3. The peptide of claim 1, wherein the peptide consists of SEQ ID NO. 2.

4. The peptide of claim 1, wherein the peptide comprises SEQ ID NO. 3.

5. The peptide of claim 1, wherein the peptide consists of SEQ ID NO. 3.

6. A peptide conjugate comprising 4-(4-(diethylamino)styryl)-N-carboxymethylpyridinium coupled to the peptide of claim 1 through an amide bond as shown below:

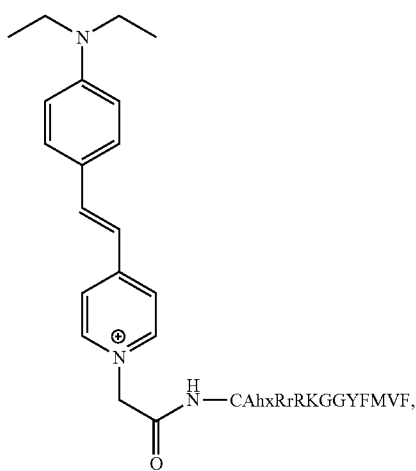

wherein Ahx is 6- aminohexanoic acid.

7. A method for imaging Epstein-Barr virus-infected cells comprising contacting the peptide conjugate of claim 6 to the Epstein-Barr virus-infected cells; radiating the Epstein-Barr virus-infected cells at an appropriate absorption band; and detecting resulting emission bands from the radiated Epstein-Barr virus-infected cells using fluorescence imaging.

8. The method of claim 7, wherein the appropriate absorption bands of the Epstein-Barr virus-infected cells are at 274 nm and 500 nm.

9. The method of claim 7, wherein the fluorescence imaging detects resulting emission bands at 560 nm and 625 nm.

10. A method for treating Epstein-Barr virus-infected cancer cells in a subject in need thereof comprising the step of administering the peptide conjugate of claim 6 to the subject.

11. The method of claim 10, wherein the peptide conjugate is administered by intra-tumoral injection.

12. A method of preparing the peptide conjugate of claim 6, wherein the method comprises the steps:

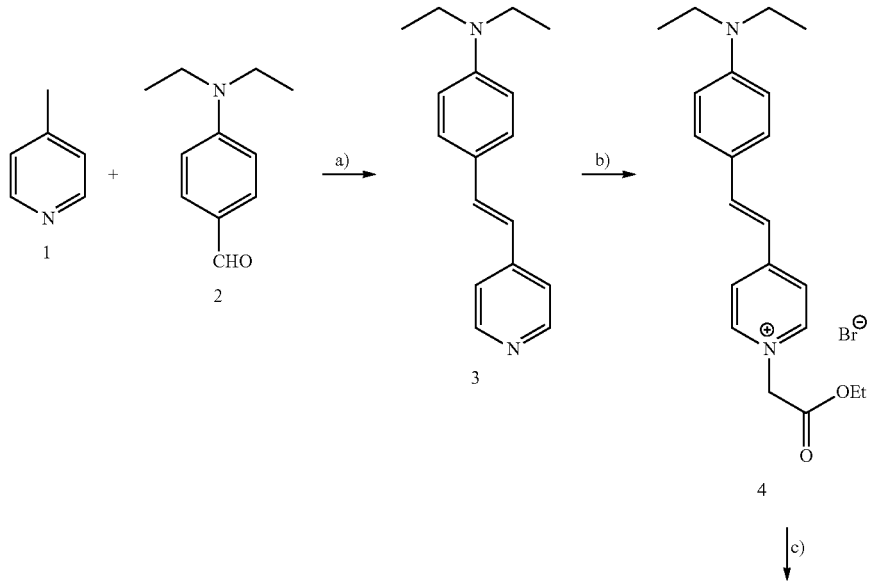

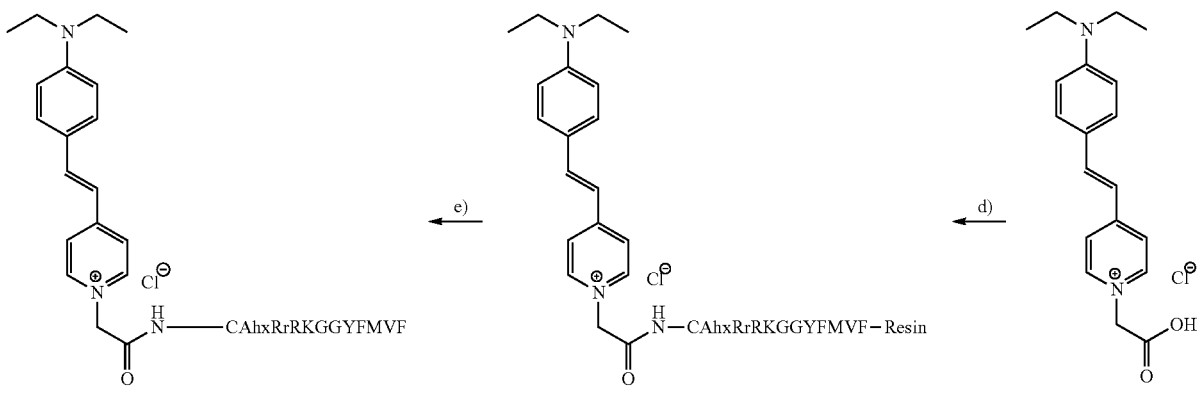

a) reacting compound 1 (4-methylpyridine) and compound 2 (4-diethylaminobenzaldehyde) in the presence of NaH dispersed in mineral oil and dimethylformide (DMF) at about 60° C. to produce compound 3 (N,N'-diethyl-4-(2-(pyridine-4-yl)vinyl) aniline);
b) reacting compound 3 with ethyl bromoacetate in the presence of acetonitrile (MeCN) at about 85° C. to obtain compound 4 (4-(4-(diethylamino)styryl)-1-(2-ethoxy-2-oxoethyl)pyridine-1-ium bromide);
c) hydrolyzing compound 4 with 0.4M NaOH in the presence of dioxane at room temperature to obtain compound 5 (4-(4-(diethylamino)styryl)-N-carboxymethylpyridinium chloride);
d) coupling compound 5 with CAhxRrRKGGYFMVF-resin in the presence of diisopropylethylamine (DIPEA), benzotriazol-1-yl-oxytri pyrrolidinophosphonium hexafluorophosphate (PyBOP) and DMF at room temperature to obtain compound 10; and
e) cleaving the resin of compound 10 in the presence of trifluoroacetic acid (TFA), triisopropylsilane (TIS) and water at room temperature to obtain the peptide of claim 6, wherein the resin is Rink amide resin.

\* \* \* \* \*